US011572398B2

(12) United States Patent
Sauerberg et al.

(10) Patent No.: US 11,572,398 B2
(45) Date of Patent: Feb. 7, 2023

(54) GLP-1 DERIVATIVES AND USES THEREOF

(71) Applicant: Novo Nordisk A/S, Bagsvaerd (DK)

(72) Inventors: Per Sauerberg, Farum (DK); Jacob Kofoed, Vaerloese (DK)

(73) Assignee: Novo Nordisk A/S, Bagsvaerd (DK)

( * ) Notice: Subject to any disclaimer, the term of this patent is extended or adjusted under 35 U.S.C. 154(b) by 86 days.

(21) Appl. No.: 15/531,105

(22) PCT Filed: Nov. 26, 2015

(86) PCT No.: PCT/EP2015/077757
§ 371 (c)(1),
(2) Date: May 26, 2017

(87) PCT Pub. No.: WO2016/083499
PCT Pub. Date: Jun. 2, 2016

(65) Prior Publication Data
US 2017/0320927 A1 Nov. 9, 2017

(30) Foreign Application Priority Data
Nov. 27, 2014 (EP) ..................................... 14195172

(51) Int. Cl.
*C07K 14/605* (2006.01)
*A61K 47/54* (2017.01)
(Continued)

(52) U.S. Cl.
CPC .......... *C07K 14/605* (2013.01); *A61K 47/542* (2017.08); *A61K 47/59* (2017.08); *A61K 38/00* (2013.01)

(58) Field of Classification Search
CPC ...... A61K 38/00; A61K 47/542; A61K 47/59; C07K 14/605; A61P 3/04; A61P 3/10
See application file for complete search history.

(56) References Cited

U.S. PATENT DOCUMENTS

| 6,268,343 B1 | 7/2001 | Knudsen et al. |
| 9,006,178 B2 | 4/2015 | Kofoed et al. |
| (Continued) | | |

FOREIGN PATENT DOCUMENTS

| EP | 1060191 A1 | 12/2000 |
| JP | 2000500505 A | 1/2000 |
| (Continued) | | |

OTHER PUBLICATIONS

Fischer et al., Molecules, vol. 19:6952-6974 (2014) (Year: 2014).*
(Continued)

*Primary Examiner* — Randall L Beane
(74) *Attorney, Agent, or Firm* — Jianjie Hu

(57) ABSTRACT

The invention relates to a derivative of a GLP-1 analogue of a general Formula I, which derivative comprises a side chain attached to a Lys residue at position 34, 35, 36, 37, or 38 of the GLP-1 analogue, which side chain comprises a Branched linker, a $1^{st}$ and a $2^{nd}$ Protractor selected from C18 diacid, C20 diacid, and sulfonic acid C16, and at least one Linker element-1 incorporating ethylene glycol units. Linker element-1 may be incorporated in an optional Pre-linker, and/or in a $1^{st}$ or $2^{nd}$ Post-linker. The invention also relates to novel GLP-1 analogues, novel side chain intermediate products and their manufacture and use to prepare derivatives of biologically active peptides and proteins, as well as pharmaceutical compositions and medical uses of the analogues and derivatives. The derivatives have very long half-lives while maintaining a satisfactory potency, which makes them potentially suitable for once-monthly administration.

2 Claims, 1 Drawing Sheet
Specification includes a Sequence Listing.

(51) Int. Cl.
*A61K 47/59* (2017.01)
*A61K 38/00* (2006.01)

(56) References Cited

U.S. PATENT DOCUMENTS

| | | | |
|---|---|---|---|
| 10,195,255 B2 | 2/2019 | Reedtz-Runge et al. | |
| 10,392,428 B2 | 8/2019 | Kofoed | |
| 2006/0014241 A1 | 1/2006 | Glaesner et al. | |
| 2008/0207507 A1 | 8/2008 | Lau et al. | |
| 2010/0261637 A1 | 10/2010 | Spetzler et al. | |
| 2011/0166321 A1 | 7/2011 | Garibay et al. | |
| 2013/0116173 A1* | 5/2013 | DiMarchi | C07K 14/605 514/5.3 |
| 2013/0143798 A1 | 6/2013 | Lau et al. | |
| 2013/0244931 A1 | 9/2013 | Lau et al. | |
| 2013/0288958 A1 | 10/2013 | Lau et al. | |
| 2013/0288960 A1 | 10/2013 | Madsen et al. | |
| 2014/0088005 A1 | 3/2014 | Wieczorek et al. | |
| 2014/0179899 A1 | 6/2014 | Garibay et al. | |
| 2016/0143998 A1 | 5/2016 | Reedtz-Runge et al. | |
| 2018/0258153 A1 | 9/2018 | Kofoed | |

FOREIGN PATENT DOCUMENTS

| | | | | |
|---|---|---|---|---|
| JP | 2002512175 A | | 4/2002 | |
| JP | 2018505859 A | | 3/2018 | |
| WO | 9943706 | | 9/1999 | |
| WO | 200055119 A1 | | 9/2000 | |
| WO | 200135988 A1 | | 5/2001 | |
| WO | 0215981 A1 | | 2/2002 | |
| WO | 2004/093823 A2 | | 11/2004 | |
| WO | WO-2004101739 A2 * | | 11/2004 | C07K 14/475 |
| WO | 2005/027978 A2 | | 3/2005 | |
| WO | 2006/037810 | | 4/2006 | |
| WO | 2006097537 A2 | | 9/2006 | |
| WO | 2006124529 A1 | | 11/2006 | |
| WO | 2009/030771 A1 | | 3/2009 | |
| WO | 2009030738 A1 | | 3/2009 | |
| WO | 2010/142665 A1 | | 12/2010 | |
| WO | 2011/080103 A1 | | 7/2011 | |
| WO | 2012/012352 A2 | | 1/2012 | |
| WO | 2012062803 A1 | | 5/2012 | |
| WO | 2012140117 A1 | | 10/2012 | |
| WO | 2012177929 A2 | | 12/2012 | |
| WO | 2013/167454 A1 | | 11/2013 | |
| WO | 2014202727 A1 | | 12/2014 | |
| WO | 2015000942 A1 | | 1/2015 | |

OTHER PUBLICATIONS

Fischer et al., Molecules, vol. 19:6952-6974 (May 27, 2014) (Year: 2014).*
Pratesi et al., J. Med. Chem., vol. 53:432-440 (2010) (Year: 2010).*
Tanada et al., J. Org. Chem., vol. 71:125-134 (online Nov. 25, 2005) (Year: 2005).*
Bambino et al., Synthesis of a Symmetrically Branched Template for Parallel α-Helix Dimers, Tetrahedron Letters, vol. 35(26):4619-4622 (1994) (Year: 1994).*
"Critical", merriam-webster.com, 7 pages, attached as pdf, also available at https://www.merriam-webster.com/dictionary/critical (last visited Mar. 18, 2021) (Year: 2021).*
Deacon, C F et al., "Dipeptidyl Peptidase IV Resistant Analouges of Glucagon-Like Peptide-1 Which Have Extended Metabolic Stability and Improved Biological Activity," Diabetologia, 1998, vol. 41, pp. 271-278.
Knudsen L. B. et al., Potent Derivatives of Glucagon-like Peptide-1 with Pharmacokinetic Properties Suitable for Once Daily Administration, Journal of Medical Chemistry, 2000, vol. 43, No. 9, 1664-1669.
Li et al.,"Insulin and Orally Hypoglycemic Agent" Nov. 2012, The Fourth Military Medical University Press, p. 373.

* cited by examiner

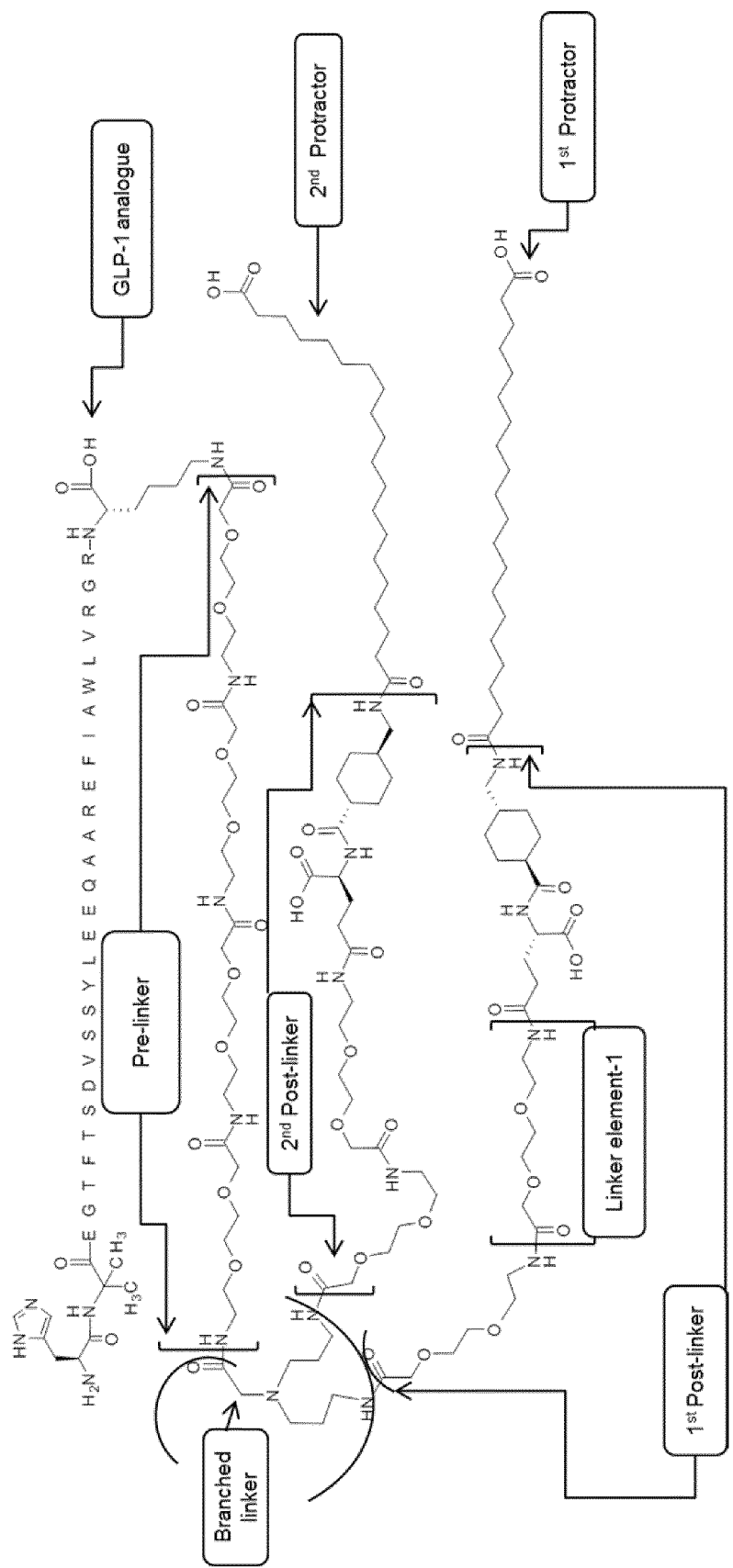

GLP-1 DERIVATIVES AND USES THEREOF

CROSS-REFERENCE TO RELATED APPLICATIONS

This application is a 35 U.S.C. § 371 National Stage application of International Application PCT/EP2015/077757 (WO 2016/083499), filed Nov. 26, 2015, which claims priority to European Patent Application 14195172.3, filed Nov. 27, 2014; the contents of all above-named applications are incorporated herein by reference.

In accordance with 37 C.F.R. § 1.52(e)(5), Applicants enclose herewith the Sequence Listing for the above-captioned application entitled "140101US01_Corr_Sequence_Listing_ST25", created on May 25, 2017. The Sequence Listing is made up of 6 kilobytes, and the information contained in the attached "SEQUENCE LISTING" is identical to the information in the specification as originally filed. No new matter is added.

TECHNICAL FIELD

The present invention relates to derivatives of analogues of glucagon-like peptide 1 (GLP-1), more in particular to GLP-1 derivatives with a branched acylation, and their pharmaceutical use.

INCORPORATION-BY-REFERENCE OF THE SEQUENCE LISTING

The Sequence Listing, entitled "SEQUENCE LISTING", is 3822 bytes, was created on 29 Sep. 2015 and is incorporated herein by reference.

BACKGROUND

WO 2005/027978 A2 discloses a number of GLP-1 derivatives including some with a branched acylation of C12 or C14 fatty acids.

Patent application no. PCT/EP2014/062952 which was filed 19 Jun. 2014 and claims a first priority date of 20 Jun. 2013 (WO 2014/202727 A1, publication date 24 Dec. 2014) discloses a number of GLP-1 derivatives with branched acylation.

SUMMARY

Semaglutide is a GLP-1 derivative for once weekly administration which is under development by Novo Nordisk A/S. This compound is disclosed in WO 2006/097537 A2, Example 4.

The invention relates to novel GLP-1 derivatives which have potential for once-monthly administration.

In one aspect the invention relates to a derivative of a GLP-1 analogue which is acylated at a Lys residue corresponding to position 34, 35, 36, 37, or 38 of human native GLP-1(7-37) with two acyl chains, via one and the same Branched linker, which may be referred to as a tri-radical of Gly((N)-bis-amino-C2/C4). Each of the acyl chains is made up of two long fatty diacids or sulfonic acids that are connected to the Branched linker via a so-called Post-linker. The Branched linker is connected to the Lys$^{34}$, Lys$^{35}$, Lys$^{36}$, Lys$^{37}$, or Lys$^{38}$ residue of the GLP-1 analogue via an optional Pre-linker. The derivative furthermore comprises at least one linker element incorporating ethylene glycol units and optionally additional linker elements, in the Pre- and/or Post-linker parts thereof.

In a second aspect the invention relates to novel GLP-1 analogues which comprise the following changes when compared to native GLP-1(7-37): (7Imp, 8Aib, 22E, 26R, 34R, 37K), (8Aib, 22E, 26R, 34R, 37P), or (8Aib, 22E, 26R, 34R, 37P, 38K); such as the analogues of SEQ ID NO: 3, SEQ ID NO: 4, SEQ ID NO: 6, SEQ ID NO: 7, and SEQ ID NO: 8. These analogues are novel peptide intermediates of the GLP-1 derivatives of the invention.

In a third aspect the invention relates to novel side chain intermediate products relating to the GLP-1 derivatives of the invention. These compounds are defined by formula II:

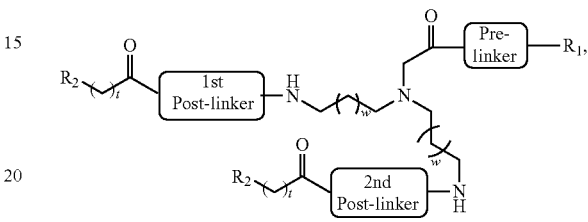

where w is 0-2, t is 15, 16, or 18, $R_1$ is —OH or a or a suitable activation group, $R_2$ is —COOH, —SO$_3$H, a suitable protective group for —COOH, or a suitable protective group for —SO$_3$H. The $R_1$ group may for example be —OPfp or a similar leaving group forming an active ester together with the —CO group of the Pre-linker. The $R_2$ group may for example be —COOtBu, —COSC(CH$_3$)$_3$, or similar protective groups for carboxylic acid and sulfonic acid groups. The Pre-linker may or may not be present. The formula II compound comprises at least one Linker element-1 of Chem. 1:

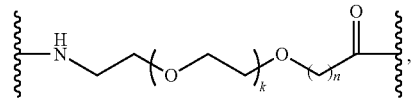

wherein k is an integer in the range of 1-23, and n is an integer in the range of 1-5. The invention also relates to the use of such compound for attachment to a biologically active peptide or protein.

In a fourth aspect the invention relates to pharmaceutical compositions comprising such derivatives or analogues and pharmaceutically acceptable excipients, as well as the medical use thereof.

The amino acid sequence of native human GLP-1(7-37) is included in the sequence listing as SEQ ID NO: 1. SEQ ID NO's 2-4 and 6-8 are specific GLP-1 analogues of the GLP-1 derivatives of the invention, and SEQ ID NO: 5 is a GLP-1 analogue which is incorporated in two comparative compounds.

The derivatives of the invention have very long half-lives and still a very good potency.

BRIEF DESCRIPTION OF DRAWINGS

The structure of the derivatives of the invention is explained in more detail in the drawings, where FIG. 1 shows the structure of the derivative of Example 12 with added boxes and lines showing the terminology used herein for the various parts of the molecule.

DESCRIPTION

In what follows, Greek letters may be represented by their symbol or the corresponding written name, for example: α=alpha; β=beta; ε=epsilon; γ=gamma; δ=delta; ω=omega; etc. Also, the Greek letter of may be represented by "u", e.g. in μl=ul, or in μM=uM.

An asterisk (*) or a waved line in a chemical formula designates i) a point of attachment, ii) a radical, and/or iii) an unshared electron.

In its first aspect the invention relates to a derivative of a GLP-1 analogue of the general Formula I:

Xaa$_7$-Xaa$_8$-Glu-Gly-Thr-Xaa$_{12}$-Thr-Ser-Asp-Xaa$_{16}$-Ser-Xaa$_{18}$-Xaa$_{19}$-Xaa$_{20}$-Glu-Xaa$_{22}$-Xaa$_{23}$-Ala-Xaa$_{26}$-Xaa$_{26}$-Xaa$_{27}$-Phe-Ile-Xaa$_{30}$-Xaa$_{31}$-Leu-Xaa$_{33}$-Xaa$_{34}$-Xaa$_{35}$-Xaa$_{36}$-Xaa$_{37}$-Xaa$_{38}$ (SEQ ID NO:9), wherein Xaa$_7$ is L-histidine, (S)-2-Hydroxy-3-(1H-imidazol-4-yl)-propionic acid, D-histidine, deamino-histidine, homohistidine, N$^α$-acetyl-histidine, N$^α$-formyl-histidine, N$^α$-methyl-histidine, 3-pyridylalanine, 2-pyridylalanine, or 4-pyridylalanine; Xaa$_8$ is Ala, Gly, Ser, Aib, (1-aminocyclopropyl) carboxylic acid, or (1-aminocyclobutyl) carboxylic acid; Xaa$_{12}$ is Phe or Leu; Xaa$_{16}$ is Val or Leu; Xaa$_{18}$ is Ser, Val, Arg, or Leu; Xaa$_{19}$ is Tyr or Gln; Xaa$_{20}$ is Leu or Met; Xaa$_{22}$ is Gly or Glu; Xaa$_{23}$ is Gln, Glu, or Arg; Xaa$_{25}$ is Ala or Val; Xaa$_{26}$ is Arg; Xaa$_{27}$ is Glu or Leu; Xaa$_{30}$ is Ala, Glu, or Arg; Xaa$_{31}$ is Trp or His; Xaa$_{33}$ is Val; Xaa$_{34}$ is Arg, His, Asn, Gln, or Lys; Xaa$_{35}$ is Gly, Ala, or Lys; Xaa$_{36}$ is Arg, Gly, or Lys; Xaa$_{37}$ is Gly, Pro, or Lys; Xaa$_{38}$ is Lys, or absent; wherein at least one of Xaa$_{34}$, Xaa$_{35}$, Xaa$_{36}$, Xaa$_{37}$, and Xaa$_{38}$ is Lys; which derivative comprises a side chain that is attached to the Lys residue of Xaa$_{34}$, Xaa$_{35}$, Xaa$_{36}$, Xaa$_{37}$, or Xaa$_{38}$, which side chain comprises:

(i) a Branched linker of formula Chem. 11:

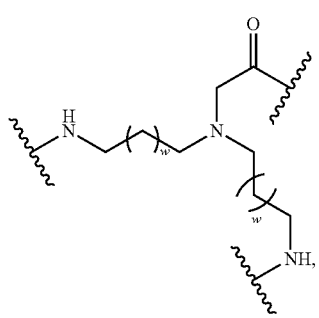

Chem. 11 wherein w is an integer in the range of 0-2;
(ii) a 1$^{st}$ and a 2$^{nd}$ Protractor selected from Chem. 12, Chem. 12a, and Chem. 13:

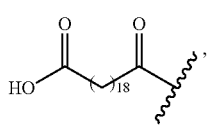

Chem. 12

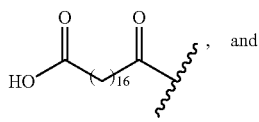, and

Chem. 12a

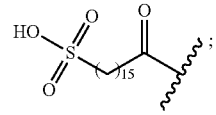

Chem. 13 and
(iii) at least one Linker element-1 of Chem. 1:

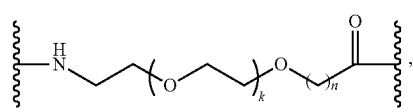

Chem. 1 wherein k is an integer in the range of 1-23, and n is an integer in the range of 1-5; wherein the Branched linker is connected a) at its —CO end to the epsilon amino group of the Lys residue of Xaa$_{34}$, Xaa$_{35}$, Xaa$_{36}$, Xaa$_{37}$, or Xaa$_{38}$, via an optional Pre-linker, and b) at each of its two —NH ends to the —CO end of each of the 1$^{st}$ and 2$^{nd}$ Protractor, respectively, via a 1$^{st}$ and a 2$^{nd}$ Post-linker, respectively; and wherein if the Pre-linker is present it comprises the Linker element-1, or if the Pre-linker is absent, each of the 1$^{st}$ Post-linker and the 2$^{nd}$ Post-linker comprises the Linker element-1; or a pharmaceutically acceptable salt, amide, or ester thereof.

In its second aspect the invention relates to a GLP-1 analogue which comprises the following changes when compared to GLP-1(7-37) (SEQ ID NO: 1): (7Imp, 8Aib, 22E, 26R, 34R, 37K), (8Aib, 22E, 26R, 34R, 37P), or (8Aib, 22E, 26R, 34R, 37P, 38K); or a pharmaceutically acceptable salt, amide, or ester thereof.

In its third aspect the invention relates to a compound of formula II:

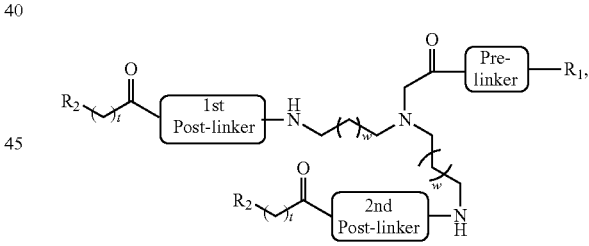

wherein w is an integer in the range of 0-2, t is 15, 16, or 18, R$_1$ is —OH or a suitable activation group, R$_2$ is —COOH, —SO$_3$H, a suitable protective group for —COOH, or a suitable protective group for —SO$_3$H, the Pre-linker is optional; which side chain moiety comprises at least one Linker element-1 of Chem. 1:

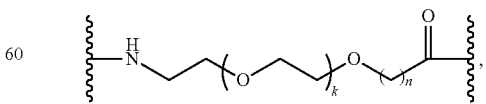

wherein k is an integer in the range of 1-23, and n is an integer in the range of 1-5; with the proviso that if the Pre-linker is present it comprises a Linker element-1 and R$_1$ is attached to the —CO group thereof, or if the Pre-linker is absent, each of the 1$^{st}$ Post-linker and the 2$^{nd}$ Post-linker comprises a Linker element-1, and R$_1$ is attached to the —CO group shown on the left-hand side of the Pre-linker in formula II; or a pharmaceutically acceptable salt, amide, or ester thereof. The invention also relates to the manufacture of this compound, and its use for attachment to a biologically active peptide or protein.

In its fourth aspect the invention relates to a pharmaceutical composition comprising a derivative or an analogue of the invention, and a pharmaceutically acceptable excipient; and the use of a derivative or analogue of the invention as a medicament, in particular for use in (i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C; (ii) delaying or preventing diabetic disease progression, such as progression in type 2 diabetes, delaying the progression of impaired glucose tolerance (IGT) to insulin requiring type 2 diabetes, delaying or preventing insulin resistance, and/or delaying the progression of non-insulin requiring type 2 diabetes to insulin requiring type 2 diabetes; (iii) improving β-cell function, such as decreasing β-cell apoptosis, increasing β-cell function and/or β-cell mass, and/or for restoring glucose sensitivity to β-cells; (iv) prevention and/or treatment of cognitive disorders and/or neurodegenerative disorders, such as Alzheimer's disease, Parkinson's disease, and/or multiple sclerosis; (v) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, such as osteoarthritis and/or urine incontinence; (vi) prevention and/or treatment of diabetic complications, such as angiopathy; neuropathy, including peripheral neuropathy; nephropathy; and/or retinopathy; (vii) improving lipid parameters, such as prevention and/or treatment of dyslipidemia, lowering total serum lipids; increasing HDL; lowering small, dense LDL; lowering VLDL; lowering triglycerides; lowering cholesterol; lowering plasma levels of lipoprotein a (Lp(a)) in a human; inhibiting generation of apolipoprotein a (apo(a)) in vitro and/or in vivo; (viii) prevention and/or treatment of cardiovascular diseases, such as syndrome X, atherosclerosis, myocardial infarction, coronary heart disease, reperfusion injury, stroke, cerebral ischemia, an early cardiac or early cardiovascular disease, left ventricular hypertrophy, coronary artery disease, hypertension, essential hypertension, acute hypertensive emergency, cardiomyopathy, heart insufficiency, exercise intolerance, acute and/or chronic heart failure, arrhythmia, cardiac dysrhythmia, syncopy, angina pectoris, cardiac bypass and/or stent reocclusion, intermittent claudication (atheroschlerosis obliterens), diastolic dysfunction, and/or systolic dysfunction; and/or reduction of blood pressure, such as reduction of systolic blood pressure; (ix) prevention and/or treatment of gastrointestinal diseases, such as inflammatory bowel disease, short bowel syndrome, or Crohn's disease or colitis; dyspepsia, and/or gastric ulcers; and/or inflammation, such as psoriasis, psoriactic arthritis, rheumatoid arthritis, and/or systemic lupus erythematosus; (x) prevention and/or treatment of critical illness, such as treatment of a critically ill patient, a critical illness poly-nephropathy (CIPNP) patient, and/or a potential CIPNP patient; prevention of development of critical illness or CIPNP; prevention, treatment and/or cure of systemic inflammatory response syndrome (SIRS) in a patient; prevention or reduction of the likelihood of a patient suffering from bacteraemia, septicaemia, and/or septic shock during hospitalisation; and/or stabilising blood glucose, insulin balance and optionally metabolism in intensive care unit patients with acute illness; (xi) prevention and/or treatment of polycystic ovary syndrome (PCOS); (xii) prevention and/or treatment of cerebral disease, such as cerebral ischemia, cerebral haemorrhage, and/or traumatic brain injury; (xiii) prevention and/or treatment of sleep apnoea; and/or (xiv) prevention and/or treatment of abuse, such as alcohol abuse and/or drug abuse.

The invention also relates to GLP-1 derivatives, GLP-1 analogues, side chain intermediate products and pharmaceutical compositions and uses as disclosed herein, wherein open ended terms like "comprises" and "comprising" used for defining these inventions are replaced with closed terms such as "consists of", "consisting of", and the like.

GLP-1 Receptor Agonist

A receptor agonist may be defined as an analogue that binds to a receptor and elicits a response typical of the natural ligand. A full agonist may be defined as one that elicits a response of the same magnitude as the natural ligand (see e.g. "Principles of Biochemistry", A L Lehninger, D L Nelson, M M Cox, Second Edition, Worth Publishers, 1993, page 763).

Thus, for example, a "GLP-1 receptor agonist" may be defined as a compound which is capable of binding to the GLP-1 receptor and capable of activating it. And a "full" GLP-1 receptor agonist may be defined as a GLP-1 receptor agonist which is capable of eliciting a magnitude of GLP-1 receptor response that is similar to native GLP-1.

Structural Features

GLP-1 Analogues

The term "GLP-1 analogue" as used herein refers to an analogue (or variant) of the human glucagon-like peptide-1 (GLP-1(7-37)), the sequence of which is included in the sequence listing as SEQ ID NO: 1. The peptide having the sequence of SEQ ID NO: 1 may also be designated "native" GLP-1.

The GLP-1 analogue incorporated in the GLP-1 derivative of the invention may be defined by the following formula I:

Xaa$_7$-Xaa$_8$-Glu-Gly-Thr-Xaa$_{12}$-Thr-Ser-Asp-Xaa$_{16}$-Ser-Xaa$_{18}$-Xaa$_{19}$-Xaa$_{20}$-Glu-Xaa$_{22}$-Xaa$_{23}$-Ala-Xaa$_{25}$-Xaa$_{26}$-Xaa$_{27}$-Phe-Ile-Xaa$_{30}$-Xaa$_{31}$-Leu-Xaa$_{33}$-Xaa$_{34}$-Xaa$_{35}$-Xaa$_{36}$-Xaa$_{37}$-Xaa$_{38}$ (SEQ ID NO:9), wherein Xaa$_7$ is L-histidine, (S)-2-Hydroxy-3-(1H-imidazol-4-yl)-propionic acid, D-histidine, deamino-histidine, homohistidine, N$^\alpha$-acetyl-histidine, N$^\alpha$-formyl-histidine, N$^\alpha$-methyl-histidine, 3-pyridylalanine, 2-pyridylalanine, or 4-pyridylalanine; Xaa$_8$ is Ala, Gly, Ser, Aib, (1-aminocyclopropyl) carboxylic acid, or (1-aminocyclobutyl) carboxylic acid; Xaa$_{12}$ is Phe or Leu; Xaa$_{16}$ is Val or Leu; Xaa$_{18}$ is Ser, Val, Arg, or Leu; Xaa$_{19}$ is Tyr or Gln; Xaa$_{20}$ is Leu or Met; Xaa$_{22}$ is Gly or Glu; Xaa$_{23}$ is Gln, Glu, or Arg; Xaa$_{25}$ is Ala or Val; Xaa$_{26}$ is Arg; Xaa$_{27}$ is Glu or Leu; Xaa$_{30}$ is Ala, Glu, or Arg; Xaa$_{31}$ is Trp or His; Xaa$_{33}$ is Val; Xaa$_{34}$ is Arg, His, Asn, Gln, or Lys; Xaa$_{35}$ is Gly, Ala, or Lys; Xaa$_{36}$ is Arg, Gly, or Lys; Xaa$_{37}$ is Gly, Pro, or Lys; Xaa$_{38}$ is Lys, or absent; wherein at least one of Xaa$_{34}$, Xaa$_{35}$, Xaa$_{36}$, Xaa$_{37}$, and Xaa$_{38}$ is Lys.

In this formula, the numbering of the amino acid residues follows the established practice in the art for native GLP-1, namely that the first (N-terminal) amino acid residue is numbered or accorded position no. 7, and the subsequent amino acid residues downstream towards the C-terminus are numbered 8, 9, 10, and so on, until the last (C-terminal) amino acid residue. In native GLP-1 the C-terminal amino acid residue is Gly, with number 37. However, as it appears from the above formula, in the peptide of Formula I the C-terminal amino acid may be either $Xaa_{37}$ or $Xaa_{38}$ i.e. have number 37 or 38, respectively. GLP-1 analogues of the invention where the C-terminal amino acid $Xaa_{38}$ is present may be said to comprise an extension of one amino acid, as compared to native GLP-1.

The numbering is done differently in the sequence listing, where the first amino acid residue of SEQ ID NO: 1 (His) is assigned no. 1, and the last (Gly) no. 31. However, herein we follow the established numbering practice in the art, as explained above.

Each of the GLP-1 analogues of the derivatives of the invention may be described by reference to i) the number of the amino acid residue in native GLP-1(7-37) which corresponds to the amino acid residue which is changed (i.e., the corresponding position in native GLP-1), and to ii) the actual change.

In other words, the GLP-1 analogue of the invention may be described by reference to the native GLP-1(7-37) peptide, namely as a variant thereof in which a number of amino acid residues have been changed when compared to native GLP-1(7-37) (SEQ ID NO: 1). These changes may represent, independently, one or more amino acid substitutions, additions, and/or deletions.

The following are non-limiting examples of suitable analogue nomenclature.

The GLP-1 analogue incorporated in the derivative of Example 1 herein may be referred to as (8Aib, 22E, 26R, 34R, 37K) GLP-1(7-37). When this Example 1 analogue is aligned with native GLP-1, the amino acid at the position in the analogue which corresponds, according to the alignment, to position 8 in native GLP-1 is Aib, the amino acid at the position in the analogue which corresponds to position 22 in native GLP-1 is E, the amino acid at the position in the analogue which corresponds to position 26 in native GLP-1 is R, the amino acid at the position in the analogue which corresponds to position 34 in native GLP-1 is R, and the amino acid at the position in the analogue which corresponds to position 37 in native GLP-1 is K. All other amino acids in this analogue are identical to the corresponding amino acid in native GLP-1.

As another example the GLP-1 analogue which is incorporated in the derivative of Example 10 herein may be referred to as (8Aib, 22E, 26R, 34R, 37P, 38K) GLP-1(7-37). When this Example 10 analogue is aligned with native GLP-1, the amino acid at the position in the analogue which corresponds, according to the alignment, to position 8 in native GLP-1 is Aib, the amino acid at the position in the analogue which corresponds to position 22 in native GLP-1 is E, the amino acid at the position in the analogue which corresponds to position 26 in native GLP-1 is R, the amino acid at the position in the analogue which corresponds to position 34 in native GLP-1 is R, the amino acid at the position in the analogue which corresponds to position 37 in native GLP-1 is P, and then the Example 10 analogue includes a K as the C-terminal amino acid, which for the present purposes is said to correspond to position 38 in native GLP-1. Each of the other amino acids in this analogue is identical to the corresponding amino acid in native GLP-1.

The general formula I is to be understood in a similar manner.

Analogues "comprising" certain specified changes may comprise further changes, when compared to SEQ ID NO: 1. In a particular embodiment, the analogue "has" the specified changes.

As is apparent from above, amino acid residues may be identified by their full name, their one-letter code, and/or their three-letter code. These three ways are fully equivalent.

The expressions "a position equivalent to" or "corresponding position" may be used to characterise the site of change in a variant GLP-1(7-37) sequence by reference to a reference sequence such as native GLP-1(7-37) (SEQ ID NO: 1). Equivalent or corresponding positions, as well as the number of changes, are easily deduced, e.g. by simple handwriting and eyeballing (visual inspection); and/or a standard protein or peptide alignment program may be used, such as "align" which is based on a Needleman-Wunsch algorithm. This algorithm is described in Needleman, S. B. and Wunsch, C. D., (1970), Journal of Molecular Biology, 48: 443-453, and the align program by Myers and W. Miller in "Optimal Alignments in Linear Space" CABIOS (computer applications in the biosciences) (1988) 4:11-17. For the alignment, the default scoring matrix BLOSUM62 and the default identity matrix may be used, and the penalty for the first residue in a gap may be set at −12, or preferably at −10, and the penalties for additional residues in a gap at −2, or preferably at −0.5.

An example of such alignment is inserted below, in which sequence no. 1 is native GLP-1 of SEQ ID NO: 1, and sequence no. 2 is the analogue (8Aib, 22E, 26R, 34R, 37P, 38K) thereof (SEQ ID NO: 4):

```
#    Aligned_sequences:    2

1:                    1

2:                    2

Matrix:               EBLOSUM62

Gap penalty:          10.0

Extend_penalty:       0.5

Length:               32

#    Identity:             26/32 (81.2%)
```

```
#    Similarity:          28/32  (87.5%)

Gaps:                 1/32  ( 3.1%)

Score:               135.0

1          1         HAEGTFTSDVSSYLEGQAAKEFIAWLVKGRG-  31
                          |.||||||||||||.|||:||||||||:||.
     2          1         HXEGTFTSDVSSYLEEQAAREFIAWLVRGRPK  32
```

When 6 is added to the position numbers shown in this alignment (e.g. to "1" and "31" in sequence 1, and to "1" and "32" in sequence 2) one gets the position numbering as used herein. For example, in sequence 1 (which is identical to SEQ ID NO: 1), the N-terminal amino acid (H) has position number 7, and the C-terminal amino acid (G) has number 37. Regarding sequence 2, the N-terminal amino acid (H) has number 7 and the C-terminal amino acid (K) has number 38.

In case specific amino acid residues or the like with no one-letter codon (such as Aib) are included in the sequence these may, for alignment purposes, be replaced with, e.g., X, as shown in the above alignment. If desired, X can later be manually corrected.

The following are non-limiting examples of what can be inferred from the above alignment:

As one example it can be inferred that sequence 2 has 6 amino acid changes as compared to sequence 1 (namely at all those positions where a full stop ("."), a colon (":"), or a horizontal hyphen ("-") is shown in the alignment).

As another example it can be inferred that, e.g., sequence no. 2 comprises 38K, since it has a K at the position which corresponds, according to the alignment, to position 38 in the reference sequence (sequence 1, SEQ ID NO: 1).

And similarly all other changes in sequence 2 as compared to sequence 1 can be deduced from the alignment.

In what follows, all amino acids of the GLP-1 analogue of the invention for which the optical isomer is not stated is to be understood to mean the L-isomer (unless otherwise specified).

Preferred GLP-1 analogues of the invention, and for incorporation in the GLP-1 derivatives of the invention, are disclosed in the sections headed PARTICULAR EMBODIMENTS, ADDITIONAL PARTICULAR EMBODIMENTS, and STILL FURTHER PARTICULAR EMBODIMENTS.

GLP-1 Derivatives

The term "derivative" as used herein in the context of a GLP-1 analogue means a chemically modified GLP-1 analogue, in which one or more substituents have been covalently attached to the analogue.

The GLP-1 derivative of the invention is a derivative of a GLP-1 analogue of Formula I, as defined in the above section headed GLP-1 analogues.

The GLP-1 derivative of the invention comprises a substituent in the form of a side chain that is attached to the Lys residue at position 34, 35, 36, 37, or 38 of the GLP-1 analogue (i.e., to $Xaa_{34}$, $Xaa_{35}$, $Xaa_{36}$, $Xaa_{37}$, or $Xaa_{38}$ in Formula I).

The side chain is capable of forming non-covalent complexes with albumin, thereby promoting the circulation of the derivative with the blood stream, and also having the effect of protracting the time of action of the derivative, due to the fact that the complex of the GLP-1-derivative and albumin is only slowly disintegrated to release the active pharmaceutical ingredient.

The side chain comprises a Branched linker of formula

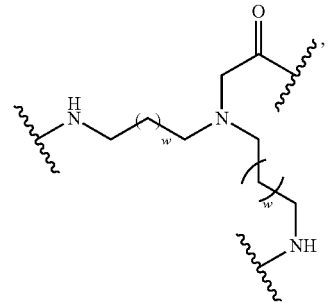

Chem. 11 wherein w is an integer in the range of 0-2.

In a particular embodiment where w is 1 the Branched linker may be referred to as Amino-C3-(Gly(Bis)).

The side chain also comprises a $1^{st}$ and a $2^{nd}$ Protractor selected from

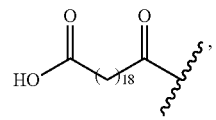

Chem. 12

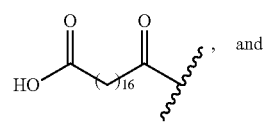

Chem. 12a

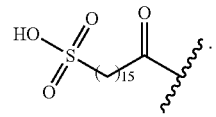

Chem. 13

Chem. 12 may be referred to as C20 diacid. Chem. 12a may be referred to as C18 diacid. Chem. 13 may be referred to as Sulfonic acid-C16.

The Branched linker is a tri-radical, thus it serves to provide a side chain with a two-leg structure. The —CO end of the Branched linker is covalently bound to the Lys residue at position 34, 35, 36, 37, or 38 of the GLP-1 analogue, optionally via a so-called Pre-linker. At each of its two —NH ends the Branched linker is connected to the —CO end of each of the $1^{st}$ and $2^{nd}$ Protractor, respectively, via a $1^{st}$ and a $2^{nd}$ so-called Post-linker, respectively.

The side chain furthermore comprises at least one Linker element-1 of

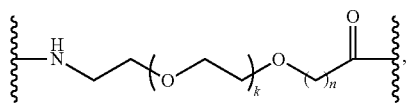

wherein k is an integer in the range of 1-23, and n is an integer in the range of 1-5.

In a particular embodiment the Linker element-1 may form part of the Pre-linker, the $1^{st}$ Post-linker, and/or the $2^{nd}$ Post-linker.

In other particular embodiments, if the Pre-linker is present it comprises the Linker element-1, or if the Pre-linker is absent, each of the $1^{st}$ Post-linker and the $2^{nd}$ Post-linker comprises the Linker element-1.

In a still further particular embodiment, the total number of Linker element-1 structures (in the entire GLP-1 derivative molecule) is at least two. In further particular embodiments, the entire derivative comprises m Linker element-1 structures, where m ranges from 2 to 12.

A number of q Linker element-1 structures may be juxtaposed (mutually connected, in a row), where q ranges from 1 to 6. The derivative of the invention may comprise, preferably has, one, two, or three such blocks of juxtaposed Linker element-1 structures. As a non-limiting example, there may be one block of juxtaposed Linker element-1 structures in the Pre-linker, and one in each of the $1^{st}$ and the $2^{nd}$ Post-linker.

In particular embodiments, Linker element-1 represents the following structures: 8-amino-3,6-dioxaoctanoic acid, abbreviated Ado (when k=1, and n=1), dPEG4 (when k=3, and n=2), dPEG12 (when k=11, and n=2), dPEG16 (when k=15, and n=2), or dPEG24 (when k=23, and n=2).

A number of additional linker elements may be incorporated in the derivatives of the invention (possibly in more copies), such as Linker element-2 (Chem. 2, also referred to as epsilon Lys, abbreviated eps-Lys), Linker element-3 (Chem. 3, also referred to as tranexamic acid, abbreviated Trx), Linker element-4 (Chem. 4, also referred to as gamma Glu, abbreviated gGlu), Linker element-5 (Chem. 5, also referred to as 4-amino butanoic acid, abbreviated Abu), and/or Linker element-6 (Chem. 6, also referred to as serine, abbreviated Ser).

In one embodiment, a Pre-linker is incorporated in the derivative of the invention, which means that the Branched linker is attached to the GLP-1 analogue via such Pre-linker.

In another embodiment, no Pre-linker is incorporated in the derivative of the invention, which means that the Branched linker is attached directly to the Lys residue at position 34, 35, 36, 37, or 38 of the GLP-1 analogue.

Preferred GLP-1 derivatives, e.g. some with particular combinations of linker elements in the various linker parts (Pre-linker, $1^{st}$ and $2^{nd}$ Post-linker), are disclosed in the sections headed PARTICULAR EMBODIMENTS, ADDITIONAL PARTICULAR EMBODIMENTS, and STILL FURTHER PARTICULAR EMBODIMENTS.

In a particular embodiment all connections between the various linker elements, the GLP-1 analogue, the $1^{st}$ and $2^{nd}$ Protractor and the Branched linker are amide bonds.

Each of the specific GLP-1 derivatives of Examples 1-32 are particularly preferred GLP-1 derivatives of the invention, together with their pharmaceutically acceptable salts, amides or esters.

As explained above, the side chain of the GLP-1 derivatives and the compounds of formula II (side chain intermediates) of the invention can be referred to as being branched, with two legs.

In a particular embodiment, the two legs are similar, preferably substantially identical, or, most preferably, identical.

In another particular embodiment, the $1^{st}$ and the $2^{nd}$ Protractor are similar, preferably substantially identical, or, most preferably, identical.

In a still further particular embodiment, the $1^{st}$ and the $2^{nd}$ Post-linker are similar, preferably substantially identical, or, most preferably identical.

The term "substantially identical" includes differences from identity which are due to formation of one or more esters and/or amides; preferably formation of one or more methyl esters, and simple amides; more preferably formation of no more than two methyl esters, and/or simple amides; or most preferably formation of no more than one methyl ester, and/or simple amide.

In the context of chemical compounds such as the Protractors and Post-linkers, similarity and/or identity may be determined using any suitable computer program and/or algorithm known in the art.

For example, the similarity of two Protractors, two Post-linkers, or of the two branches or legs in their entirety (consisting of Protractor plus Post-linker) may suitably be determined using molecular fingerprints, which refers to a mathematical method of representing a chemical structure (see e.g. Chemoinformatics: A textbook, Johann Gasteiger and Thomas Engel (Eds), Wiley-VCH Verlag, 2003).

Examples of suitable fingerprints include, without limitation, UNITY fingerprints, MDL fingerprints, and/or ECFP fingerprints, such as ECFP_6 fingerprints (ECFP stands for extended-connectivity fingerprints).

In particular embodiments, the two protracting moieties, the two linkers, and/or the two entire side chains are represented as a) ECFP_6 fingerprints; b) UNITY fingerprints; and/or c) MDL fingerprints.

The Tanimoto coefficient is preferably used for calculating the similarity of the two fingerprints, whether a), b), or c) is used.

In particular embodiments, whether a), b), or c) is used, the two protracting moieties, the two linkers, and/or the two entire side chains, respectively, have a similarity of at least 0.5 (50%); preferably at least 0.6 (60%); more preferably at least 0.7 (70%), or at least 0.8 (80%); even more preferably at least 0.9 (90%); or most preferably at least 0.99 (99%), such as a similarity of 1.0 (100%).

UNITY fingerprints may be calculated using the programme SYBYL (available from Tripos, 1699 South Hanley Road, St. Louis, Mo. 63144-2319 USA). ECFP_6 and MDL fingerprints may be calculated using the programme Pipeline Pilot (available from Accelrys Inc., 10188 Telesis Court, Suite 100, San Diego, Calif. 92121, USA).

For more details, see for example J. Chem. Inf. Model. 2008, 48, 542-549; J. Chem. Inf. Comput. Sci. 2004, 44, 170-178; J. Med. Chem. 2004, 47, 2743-2749; J. Chem. Inf. Model. 2010, 50, 742-754; as well as SciTegic Pipeline Pilot Chemistry Collection: Basic Chemistry User Guide, March 2008, SciTegic Pipeline Pilot Data Modeling Collection, 2008—both from Accelrys Software Inc., San Diego, US, and the guides http://www.tripos.com/tripos_resources/fileroot/pdfs/Unity_111408.pdf, and http://www.tripos.com/data/SYBYL/SYBYL_072505.pdf.

An example of a similarity calculation is inserted hereinbelow, in which a known entire side chain of a known GLP-1 derivative was compared with a methyl ester thereof:

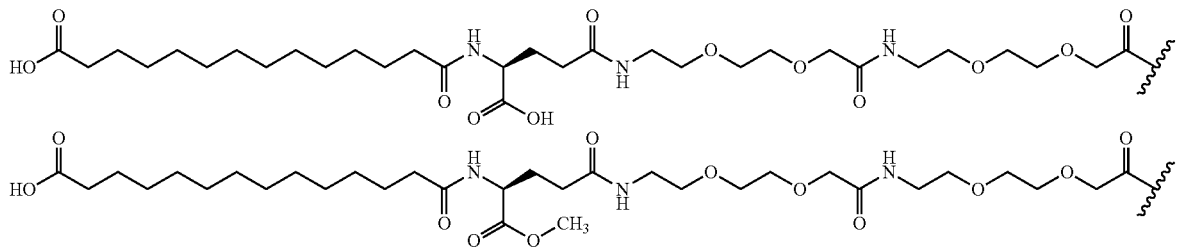

Using a) ECFP_6 fingerprints the similarity is 0.798, using b) UNITY fingerprints the similarity is 0.957; and using MDL fingerprints the similarity is 0.905.

In case of two identical side chains (albumin binding moieties) the derivative may be designated symmetrical.

In particular embodiments, the similarity coefficient is at least 0.80, preferably at least 0.85, more preferably at least 0.90, even more preferably at least 0.95, or most preferably at least 0.99.

The derivatives and compounds of formula II (side chain intermediates) of the invention may exist in different stereoisomeric forms having the same molecular formula and sequence of bonded atoms, but differing only in the three-dimensional orientation of their atoms in space. The stereoisomerism of the exemplified derivatives and compounds of formula II of the invention is indicated in the experimental section, in the names as well as the structures, using standard nomenclature. Unless otherwise stated the invention relates to all stereoisomeric forms of the claimed derivative/compound of formula II.

The concentration in plasma of the GLP-1 derivatives of the invention may be determined using any suitable method. For example, LC-MS (Liquid Chromatography Mass Spectroscopy) may be used, or immunoassays such as RIA (Radio Immuno Assay), ELISA (Enzyme-Linked Immuno Sorbent Assay), and LOCI (Luminescence Oxygen Channeling Immunoasssay). General protocols for suitable RIA and ELISA assays are found in, e.g., WO 2009/030738 on p. 116-118. A preferred assay is the LOCI assay, where LOCI refers to Luminescence Oxygen Channeling Immunoasssay, which is generally described for the determination of insulin by Poulsen and Jensen in Journal of Biomolecular Screening 2007, vol. 12, p. 240-247. The donor beads were coated with streptavidin, while acceptor beads were conjugated with a monoclonal antibody recognising a mid-/C-terminal epitope of the peptide. Another monoclonal antibody, specific for the N-terminus, was biotinylated. The three reactants were combined with the analyte and formed a two-sited immunocomplex. Illumination of the complex released singlet oxygen atoms from the donor beads, which were channeled into the acceptor beads and triggered chemiluminescence which was measured in an Envision plate reader. The amount of light was proportional to the concentration of the compound.

The GLP-1 derivatives and analogues of the invention have GLP-1 activity. This term refers to the ability to bind to the GLP-1 receptor and initiate a signal transduction pathway resulting in insulinotropic action or other physiological effects as is known in the art. For example, the analogues and derivatives of the invention can be tested for GLP-1 activity using the assays described in Examples 33, 34, and/or 36 herein.

Side Chain Intermediate Products

The invention also relates to a compound of formula II:

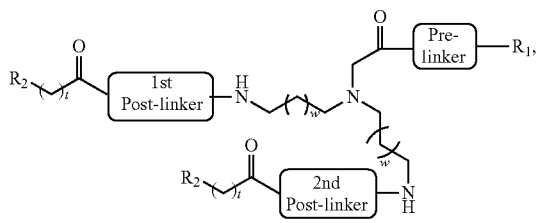

wherein w is an integer in the range of 0-2, t is 15, 16, or 18, $R_1$ is —OH or a suitable activation group, $R_2$ is —COOH, —SO$_3$H, a suitable protective group for —COOH, or a suitable protective group for —SO$_3$H, the Pre-linker is optional; which compound comprises at least one Linker element-1 of Chem. 1:

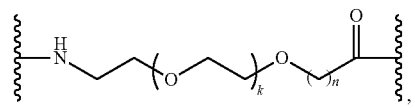

wherein k is an integer in the range of 1-23, and n is an integer in the range of 1-5; with the proviso that if the Pre-linker is present it comprises a Linker element-1 and $R_1$ is attached to the —CO group thereof, or if the Pre-linker is absent, each of the $1^{st}$ Post-linker and the $2^{nd}$ Post-linker comprises a Linker element-1, and $R_1$ is attached to the —CO group shown on the left-hand side of the Pre-linker in formula II; or a pharmaceutically acceptable salt, amide, or ester thereof.

This compound is an intermediate product in the sense that it constitutes the non-peptide part (or the side chain part) of the GLP-1 derivative of the invention.

The side chain part of the GLP-1 derivatives of the invention can be prepared and attached to the peptide part thereof as described in the experimental part, stepwise directly on solid support during peptide synthesis.

Alternatively, the side chain part can be prepared directly on solid support and subsequently be attached to the peptide part using appropriate activation and protective groups. As a non-limiting example the side-chain part of Chem. 98 of the derivative of Example 11 (Chem. 31) can be prepared on 2-cholorotrityl resin by coupling of Fmoc-8-amino-3,6-dioxaoctanoic acid (2 equivalents) in dichloromethane/N-methyl pyrrolidine (1:1) using diisopropylethylamine (6 equivalents) as the first residue. The resin is then washed with dichloromethane/methanol/diisopropylethylamine (85:10:5) twice, dichloromethane, N-methylpyrrolidone. The Fmoc group is then removed by treatment with 20% piperidine in N-methylpyrrolidine (two treatments each for four minutes). Subsequently the resin is washed with NMP, DCM three times each and another coupling of Fmoc-8-amino-3,6-dioxaoctanoic acid (8 equivalents) in N-methyl pyrrolidone using diisopropylcarbodiimide, collidine, and Oxyma-Pure® (each 8 equivalents). Subsequently the resin is washed with NMP, DCM three times each and the Fmoc group removed as outlined above. The following building blocks can then be coupled using the repetitive cycle of coupling, washing, Fmoc removal and washing; N,N-bis(N'-Fmoc-3-aminopropyl)-glycine potassium hemisulfate, Fmoc-8-amino-3,6-dioxaoctanoic acid, Fmoc-8-amino-3,6-dioxaoctanoic acid, Fmoc-8-amino-3,6-dioxaoctanoic acid, Fmoc-8-amino-3,6-dioxaoctanoic acid, Fmoc-Glu-OtBu, Fmoc-tranexamic acid, and icosanedioic acid mono-tert-butyl ester. The crude side-chain part can then be liberated from the resin using trifluroethanol/dichloromethane (20:80) and concentrated to dryness in vacuo. If desired the side-chain part can be purified using flash chromatography as known in the art. The tert-butyl protected side chain part (1.25 equivalents) can then be activated for coupling to the peptide part of the Example 11 compound (1.0 equivalent) of interest by dissolving the side-chain part in dimethylformamide:tetrahydrofurane (1:1). Then O—(N-succinimidyl)-N,N,N',N'-tetramethyluronium tetrafluoroborate (1.4 equivalents) is added followed by diisopropylethylamide (2.5 equivalents) and stirring for 1 h. The peptide part (1.0 equivalent) is dissolved in 200 mM $Na_2CO_3$(aq)/tetrahydrofuran (5:2) pH 10.6. The above prepared OSuc ester of the side chain part is added dropwise to the dissolved peptide under stirring and the pH kept at 10.6-10.8 with 1N NaOH. Stands to react 1 h. The pH is lowered to the isoelectric point of the peptide-sidechain conjugate and the precipitate centrifuged down. The dried precipitate is treated with triflouroacetic acid/water (95:5) for 30 min, and poured into diethyl ether. The finalized product is isolated by centrifugation.

Alternatively, the side chain part can be prepared by solution phase chemistry and subsequently be attached to the peptide part using suitable activation and protective groups such as those discussed in the following.

Alternatively, the side chain part can be attached in several steps using suitable protective groups. As a non-limiting example, the Branched linker of Chem. 11 and the Pre-linker, linked together with amide bonds and suitable protective groups, can be attached to a lysine epsilon amino group of the peptide part by forming an amide bond, using a suitable activation group such as an active ester. Subsequently the 1$^{st}$ and the 2$^{nd}$ Post-linker and the 1$^{st}$ and the 2$^{nd}$ Protractor of Chem. 12, linked together with amide bonds and suitable protective groups, can be attached to the distal amino groups of the Branched linker of Chem. 11.

Non-limiting examples of $R_1$ functional groups are —OH and other suitable activation groups, for example, without limitation, activation groups in the form of suitable leaving groups, for example, without limitation, suitable leaving groups forming an active ester together with a carbonyl group (such as the proximal carbonyl group) of the Pre-linker, such as, without limitation:

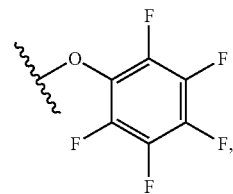

Chem. 120 which may also be designated —OPfp (2,3,4,5,6-pentafluorophenoxy),

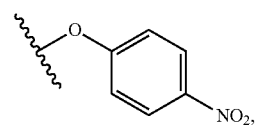

Chem. 121 which may also be designated —OPnp (4-nitrophenoxy), and

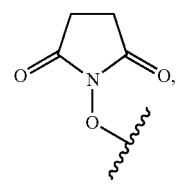

Chem. 122 which may also be designated —OSuc ((2,5-dioxopyrrolidin-1-yl)oxy), and the like. Other suitable activation groups may be selected, e.g., without limitation, according to the teaching of M. Bodanszky, "Principles of Peptide Synthesis", 2nd ed., Springer Verlag, 1993.

Non-limiting examples of $R_2$ functional groups are —COOH, —$SO_3H$, and suitable carboxylic acid or sulfonic acid protective groups, for example, without limitation, suitable non-reactive esters or sulfonic esters, such as, without limitation:

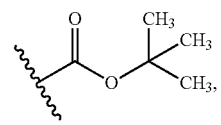

Chem. 123 which may also be designated —COOtBu (tert-butoxycarbonyl),

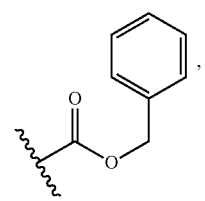

Chem. 124 which may also be designated —COOBz (benzyloxycarbonyl),

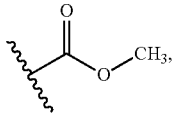
Chem. 125 which may also be designated —COOMe (methoxycarbonyl),

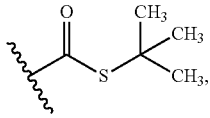
Chem. 126 which may also be designated —COSC(CH$_3$)$_3$(tert-butylsulfanylcarbonyl),

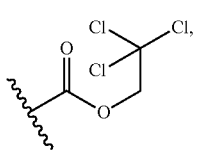
Chem. 127 which may also be designated —COCH$_2$CCl$_3$ (2, 2,2-trichloroethoxycarbonyl), and

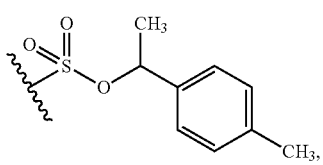
Chem. 128 which may also be designated —SO$_3$CH(CH$_3$)C$_7$H$_7$ (1-(p-tolyl)ethoxysulfonyl), and the like. Other suitable non-reactive esters, sulfonic esters, and other carboxylic acid or sulfonic acid protective groups may be selected, e.g., without limitation, according to the teaching of P. G. M. Wuts, T. W. Greene, "Greene's Protective Groups in Organic Synthesis", 4th ed., John Wiley & Sons, Inc, 2007.

In one embodiment of the side chain intermediate compound of the invention the 1$^{st}$ and the 2$^{nd}$ Post-linker each comprises s times the Linker element-1 of Chem. 1, where s is 0 or an integer in the range of 1-6, and at least one further linker element selected from Linker element-2 of Chem. 2, Linker element-3 of Chem. 3, Linker element-4 of Chem. 4, Linker element-5 of Chem. 5, and Linker element-6 of Chem. 6; wherein in Chem. 4 the free acid group (—COOH) is substituted with R$_3$, in Chem. 2 the free amino group (—NH$_2$) is substituted with R$_5$, and in Chem. 6 the free hydroxyl group (—OH) is substituted with R$_4$, wherein R$_3$ is —COOH or a suitable protective group for a carboxylic acid group; R$_4$ is —OH or a suitable protective group for a hydroxy group; and R$_5$ is —NH$_2$ or a suitable protective group for an amino group.

Non-limiting examples of R$_3$ functional groups are —COOH and suitable protective groups for carboxylic acid groups, for example, without limitation, suitable ester groups, such as, without limitation, —COOtBu (Chem. 123), —COOBz (Chem. 124), —COOMe (Chem. 125), —COSC(CH$_3$)$_3$ (Chem. 126), and —COCH$_2$CCl$_3$ (Chem. 127), and the like. Other suitable esters and protective groups for carboxylic acid groups may be selected, e.g., without limitation, according to the teaching of P. G. M. Wuts, T. W. Greene, "Greene's Protective Groups in Organic Synthesis", 4th ed., John Wiley & Sons, Inc, 2007.

Non-limiting examples of R$_4$ functional groups are —OH and suitable protective groups for hydroxy groups, for example, without limitation, suitable ether groups or suitable ester groups, such as, without limitation:

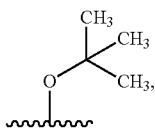
Chem. 129 which may also be designated as —OtBu (tert-butoxy),

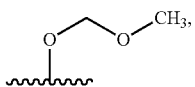
Chem. 130 which may also be designated as —OCH$_2$OCH$_3$ (methoxymethoxy),

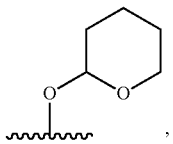
Chem. 131 which may also be designated as tetrahydropyran-2-yloxy,

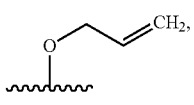
Chem. 132 which may also be designated as —OCH$_2$CHCH$_2$ (allyl ether),

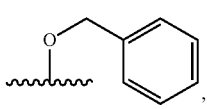
Chem. 133 which may also be designated as —OBz (benzyloxy),

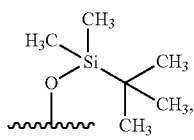
Chem. 134 which may also be designated as —OSi(CH$_3$)$_2$C(CH$_3$)$_3$ (tert. butyldimethylsilyl ether),

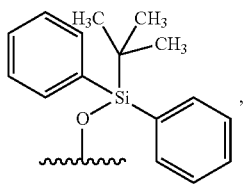
Chem. 135 which may also be designated as —OSi(C$_6$H$_5$)C(CH$_3$)$_3$ (tert. butyldiphenylsilyl ether),

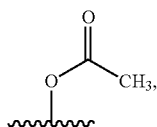
Chem. 136 which may also be designated as —OCOCH$_3$ (acetic acid ester), and

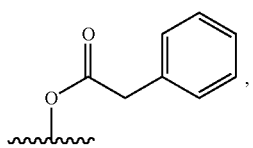
Chem. 137 which may also be designated as —OCOC$_6$H$_5$ (benzoic acid ester), and the like. Other suitable ethers, esters and other protective groups for hydroxy groups may be selected, e.g., without limitation, according to the teaching of P. G. M. Wuts, T. W. Greene, "Greene's Protective Groups in Organic Synthesis", 4th ed., John Wiley & Sons, Inc, 2007.

Non-limiting examples of R$_5$ functional groups are —NH$_2$ and suitable protective groups for amino groups, for example, without limitation, suitable carbamates, such as, without limitation:

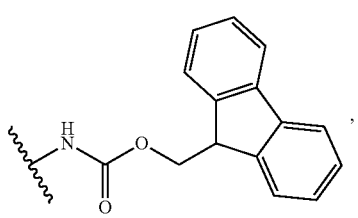
Chem. 138 which may also be designated as —NHFmoc (9H-fluoren-9-ylmethoxycarbonylamino),

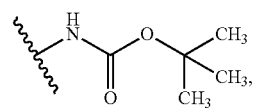
Chem. 139 which may also be designated as —NHBoc (tert-butoxycarbonylamino), and

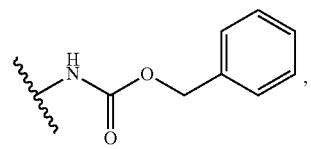
Chem. 140 which may also be designated as —NHCbz (benzyloxycarbonylamino), and the like. Other suitable carbamates and other protective groups for amino groups may be selected, e.g., without limitation, according to the teaching of P. G. M. Wuts, T. W. Greene, "Greene's Protective Groups in Organic Synthesis", 4th ed., John Wiley & Sons, Inc, 2007.

A number of particular side chain intermediate compounds of the invention are disclosed in the section headed PARTICULAR EMBODIMENTS.

Of particular interest are the side chain intermediate compounds of Chem. 90 to Chem. 116 listed in Table A below. Please note that Table A refers to Table B further below for definition of the structure of the 1$^{st}$ Post-linker, the 2$^{nd}$ Post-linker, and the Pre-linker. Table A also shows the Chem. no. of the particular GLP-1 derivative of the invention that incorporates the particular side chain intermediate compound of the invention.

TABLE A

Some specific side chain intermediate compounds of the invention

| Intermediate Chem. No. | Corresponding Derivative Chem. No. | t | 1$^{st}$ Post-linker & 2$^{nd}$ Post-linker | Pre-Linker |
|---|---|---|---|---|
| Chem. 90 | Chem. 21 | 18 | Chem. 80 | |
| Chem. 91 | Chem. 22 | 18 | Chem. 81 | |
| | Chem. 24 | | | |
| Chem. 92. | Chem. 23 | 18 | Chem. 63 | |
| | Chem. 30 | | | |
| Chem. 93 | Chem. 25 | 18 | Chem. 82 | |
| Chem. 94 | Chem. 26 | 18 | Chem. 77 | |
| Chem. 95 | Chem. 27 | 18 | Chem. 78 | |
| Chem. 96 | Chem. 28 | 18 | Chem. 79 | |
| Chem. 97 | Chem. 29 | 15 | Chem. 69 | |
| Chem. 98 | Chem. 31 | 18 | Chem. 65 | Chem. 83 |
| Chem. 99 | Chem. 32 | 18 | Chem. 66 | Chem. 84 |
| Chem. 100 | Chem. 33 | 18 | Chem. 60 | Chem. 85 |
| | Chem. 50 | | | |
| | Chem. 51 | | | |
| | Chem. 52 | | | |
| Chem. 101 | Chem. 34 | 15 | Chem. 76 | |
| Chem. 102 | Chem. 35 | 15 | Chem. 74 | |
| Chem. 103 | Chem. 36 | 15 | Chem. 73 | |
| Chem. 104 | Chem. 37 | 15 | Chem. 72 | |
| Chem. 105 | Chem. 38 | 15 | Chem. 71 | |
| Chem. 106 | Chem. 39 | 15 | Chem. 70 | |
| Chem. 107 | Chem. 40 | 15 | Chem. 69 | |
| Chem. 108 | Chem. 41 | 15 | Chem. 68 | |

TABLE A-continued

Some specific side chain intermediate compounds of the invention

| Intermediate Chem. No. | Corresponding Derivative Chem. No. | t | 1st Post-linker & 2nd Post-linker | Pre-Linker |
| --- | --- | --- | --- | --- |
| Chem. 109 | Chem. 42 | 15 | Chem. 65 | |
| Chem. 110 | Chem. 43 | 15 | Chem. 64 | |
| Chem. 111 | Chem. 44 | 18 | Chem. 63 | |
| Chem. 112 | Chem. 45 | 18 | Chem. 61 | Chem. 85 |
| Chem. 113 | Chem. 46 | 18 | Chem. 62 | Chem. 85 |
| Chem. 114 | Chem. 47 | 18 | Chem. 60 | Chem. 84 |
| Chem. 115 | Chem. 48 | 16 | Chem. 67 | |
| Chem. 116 | Chem. 49 | 16 | Chem. 62 | Chem. 84 |

TABLE B

Combinations of linker elements

| Linker-element | Designation | Structure |
| --- | --- | --- |
| Chem. 60 | Trx-gGlu | 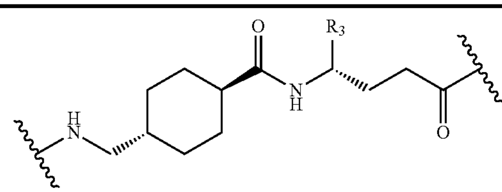 |
| Chem. 61 | Trx-gGlu-Ser | 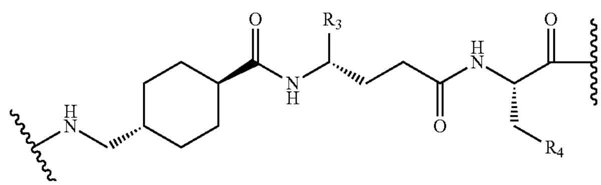 |
| Chem. 62 | gGlu | 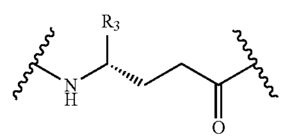 |
| Chem. 63 | Trx-gGlu-6xAdo | 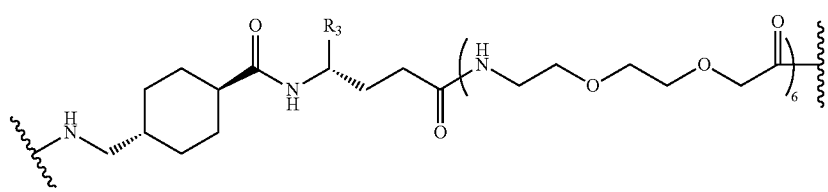 |
| Chem. 64 | Trx-gGlu-5xAdo | 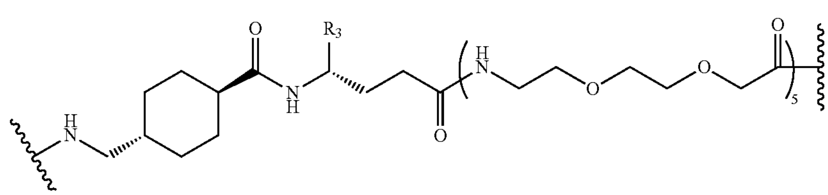 |
| Chem. 65 | Trx-gGlu-4xAdo | 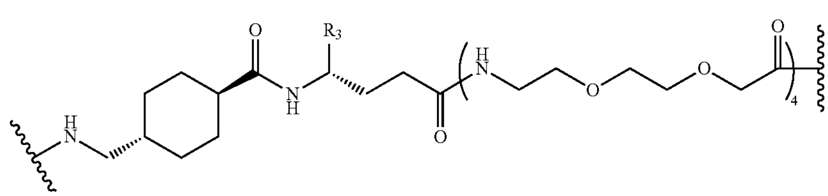 |

TABLE B-continued
Combinations of linker elements
| Linker-element | Designation | Structure |
|---|---|---|
| Chem. 66 | Trx-gGlu-2xAdo | 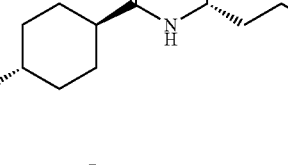 |
| Chem. 67 | gGlu-4xAdo | 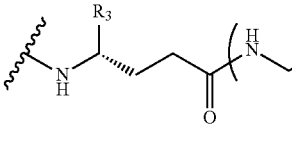 |
| Chem. 68 | Abu-Trx-gGlu-6xAdo | 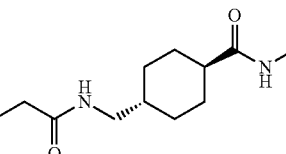 |
| Chem. 69 | Abu-Trx-gGlu-5xAdo | 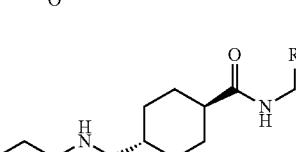 |
| Chem. 70 | Abu-Trx-gGlu-4xAdo | 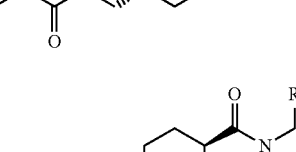 |
| Chem. 71 | Abu-gGlu-6xAdo | 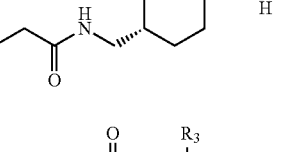 |
| Chem. 72 | Abu-gGlu-5xAdo | 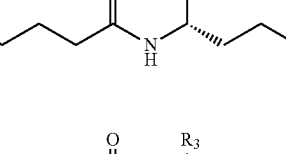 |
| Chem. 73 | Abu-gGlu-4xAdo | 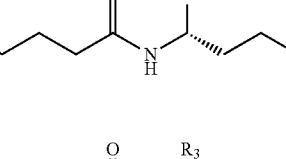 |
| Chem. 74 | Abu-2xeps-Lys-6xAdo | 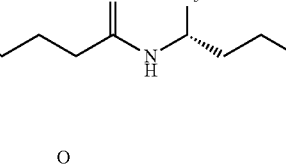 |

TABLE B-continued

Combinations of linker elements

| Linker-element | Designation | Structure |
|---|---|---|
| Chem. 75 | Abu-2xeps-Lys-5xAdo | 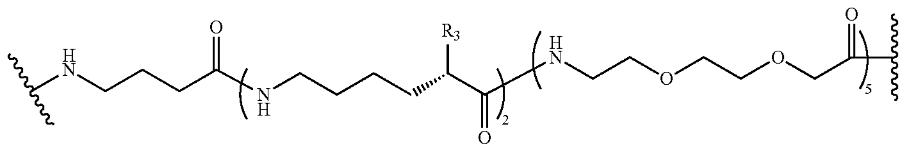 |
| Chem. 76 | Abu-2xeps-Lys-4xAdo | 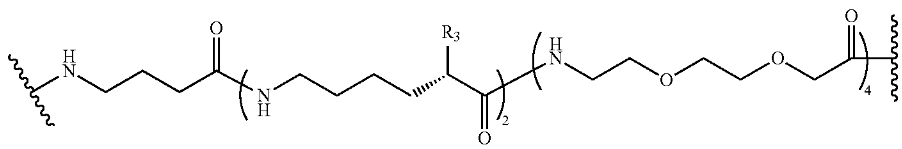 |
| Chem. 77 | 2xeps-Lys-dPEG24 | 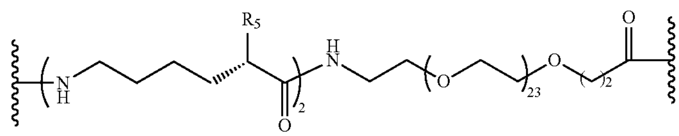 |
| Chem. 78 | 2xeps-Lys-dPEG16 | 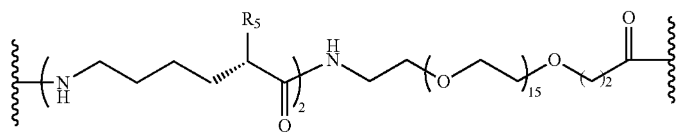 |
| Chem. 79 | 2xeps-Lys-dPEG12 | 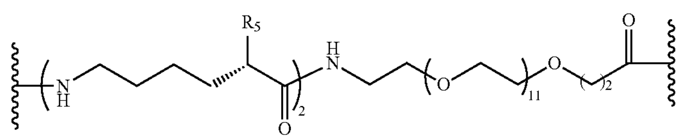 |
| Chem. 80 | 2xeps-Lys-5xAdo | 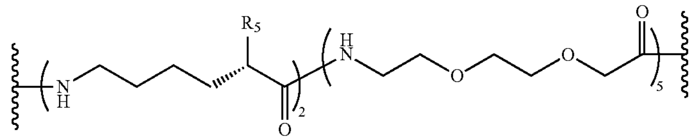 |
| Chem. 81 | 2xeps-Lys-4xAdo | 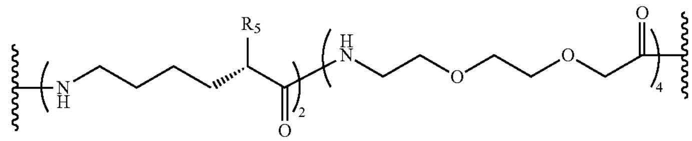 |
| Chem. 82 | 2xeps-Lys-3xdPEG4 | 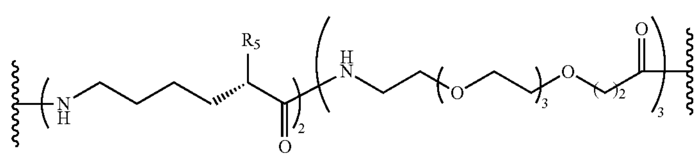 |
| Chem. 83 | 2xAdo | 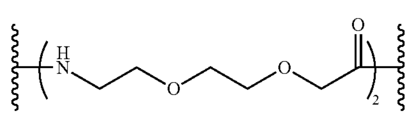 |
| Chem. 84 | 4xAdo | 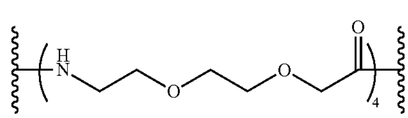 |

TABLE B-continued

Combinations of linker elements

| Linker-element | Designation | Structure |
|---|---|---|
| Chem. 85 | 6xAdo | 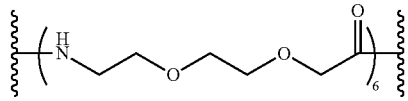 |

The invention also relates to the preparation of the intermediate side chain compound of the invention as well as its use for attachment to a biologically active peptide or protein under the formation of a derivative thereof. Non-limiting examples of how this can be done are outlined above. Additional particular embodiments are disclosed in the section headed PARTICULAR EMBODIMENTS.

In some embodiments the intermediate side chain compound of the invention is capable of forming non-covalent complexes with albumin. In some embodiments, when attached to a biologically active peptide or protein this effect is carried over to the final peptide or protein derivative which accordingly exhibits a prolonged duration of action in vivo.

Pharmaceutically Acceptable Salt, Amide, or Ester

The derivatives, analogues, and side chain intermediate compounds of the invention may be in the form of a pharmaceutically acceptable salt, amide, or ester.

Salts are e.g. formed by a chemical reaction between a base and an acid, e.g.: $2NH_3 + H_2SO_4 \rightarrow (NH_4)_2SO_4$.

The salt may be a basic salt, an acid salt, or it may be neither nor (i.e. a neutral salt). Basic salts produce hydroxide ions and acid salts hydronium ions in water.

The salts of the derivatives of the invention may be formed with added cations or anions between anionic or cationic groups, respectively. These groups may be situated in the peptide moiety, and/or in the side chain of the derivatives of the invention.

Non-limiting examples of anionic groups of the derivatives of the invention include free carboxylic groups in the side chain, if any, as well as in the peptide moiety. The peptide moiety often includes a free carboxylic acid group at the C-terminus, and it may also include free carboxylic groups at internal acid amino acid residues such as Asp and Glu.

Non-limiting examples of cationic groups in the peptide moiety include the free amino group at the N-terminus, if present, as well as any free amino group of internal basic amino acid residues such as His, Arg, and Lys.

The ester of the derivatives of the invention may, e.g., be formed by the reaction of a free carboxylic acid group with an alcohol or a phenol, which leads to replacement of at least one hydroxyl group by an alkoxy or aryloxy group The ester formation may involve the free carboxylic group at the C-terminus of the peptide, and/or any free carboxylic group in the side chain.

The amide of the derivatives of the invention may, e.g., be formed by the reaction of a free carboxylic acid group with an amine or a substituted amine, or by reaction of a free or substituted amino group with a carboxylic acid.

The amide formation may involve the free carboxylic group at the C-terminus of the peptide, any free carboxylic group in the side chain, the free amino group at the N-terminus of the peptide, and/or any free or substituted amino group of the peptide in the peptide and/or the side chain.

In a particular embodiment, the peptide or derivative is in the form of a pharmaceutically acceptable salt. In another particular embodiment, the derivative is in the form of a pharmaceutically acceptable amide, preferably with an amide group at the C-terminus of the peptide. In a still further particular embodiment, the peptide or derivative is in the form a pharmaceutically acceptable ester.

Functional Properties

In a particular embodiment the derivatives of the invention have a very long half-life and at the same time a very good potency in vitro and in vivo, which makes them potentially suitable for once-monthly administration.

Thus, in a first functional aspect, the derivatives of the invention have a good potency. Also, or alternatively, in a second aspect, they bind very well to the GLP-1 receptor, e.g. at a high concentration of albumin. Preferably they are full GLP-1 receptor agonists as is reflected by their ability to bind strongly to the GLP-1 receptor combined with the capacity to activate the receptor. Also, or alternatively, in a third functional aspect, they have improved pharmacokinetic properties.

Biological Activity—In Vitro Potency

The GLP-1 analogue of the derivative of the invention is one non-limiting example of a biologically active peptide or protein.

According to the first functional aspect, the derivatives of the invention, as well as the constituent GLP-1 analogues as such, are biologically active, or potent.

In a particular embodiment, potency and/or activity refers to in vitro potency, i.e. performance in a functional GLP-1 receptor assay, more in particular to the capability of activating the human GLP-1 receptor.

The in vitro potency may, e.g., be determined in a medium containing membranes expressing the human GLP-1 receptor, and/or in an assay with whole cells expressing the human GLP-1 receptor.

For example, the response of the human GLP-1 receptor may be measured in a reporter gene assay, e.g. in a stably transfected BHK cell line that expresses the human GLP-1 receptor and contains the DNA for the cAMP response element (CRE) coupled to a promoter and the gene for firefly luciferase (CRE luciferase). When cAMP is produced as a result of activation of the GLP-1 receptor this in turn results in the luciferase being expressed. Luciferase may be determined by adding luciferin, which by the enzyme is converted to oxyluciferin and produces bioluminescence, which is measured and is a measure of the in vitro potency. One non-limiting example of such an assay is described in Example 33.

The term half maximal effective concentration ($EC_{50}$) generally refers to the concentration which induces a response halfway between the baseline and maximum, by reference to the dose response curve. $EC_{50}$ is used as a measure of the potency of a compound and represents the concentration where 50% of its maximal effect is observed.

The in vitro potency of the derivatives of the invention may be determined as described above, and the $EC_{50}$ of the derivative in question determined. The lower the $EC_{50}$ value, the better the potency.

In a particular embodiment, the derivatives of the invention are very potent, despite the fact that they have very long half-lives. In a particular embodiment, the derivative of the invention has an in vitro potency determined using the method of Example 33 corresponding to an $EC_{50}$ at or below 300 pM.

Additional particular embodiments are disclosed in the sections headed PARTICULAR EMBODIMENTS, ADDITIONAL PARTICULAR EMBODIMENTS, and STILL FURTHER PARTICULAR EMBODIMENTS.

Biological Activity—In Vivo Pharmacology

In another particular embodiment the derivatives of the invention as well as the constituent GLP-1 analogues as such are potent in vivo, which may be determined as is known in the art in any suitable animal model, as well as in clinical trials.

The Sprague Dawley rat is one example of a suitable animal model, and the acute effect on food intake and/or body weight may be determined in such rats in vivo, e.g. as described in Example 36. In a particular embodiment an acute effect of the derivatives of the invention on food intake and body weight is observed at 48 hours after administration.

Additional particular embodiments are disclosed in the sections headed PARTICULAR EMBODIMENTS, ADDITIONAL PARTICULAR EMBODIMENTS, and STILL FURTHER PARTICULAR EMBODIMENTS.

Biological Activity—In Vitro Receptor Binding

According to the second functional aspect, the derivatives of the invention, as well as the constituent GLP-1 analogues as such bind very well to the GLP-1 receptor, e.g. at a high concentration of albumin. This may be determined as described in Example 34.

Generally, the binding to the GLP-1 receptor at low albumin concentration should be as good as possible, corresponding to a low $IC_{50}$ value.

The $IC_{50}$ value at high albumin concentration reflects the influence of serum albumin on the binding of the derivative to the GLP-1 receptor. As is known, the GLP-1 derivatives can bind to serum albumin and if this is the case then the $IC_{50}$ value at high serum albumin will be higher than the $IC_{50}$ value at low albumin. An increased $IC_{50}$ value at high serum albumin represents a reduced binding to the GLP-1 receptor caused by serum albumin binding competing with the binding to the GLP-1 receptor.

In a particular embodiment, the derivatives of the invention bind very well to the GLP-1 receptor at a low albumin concentration, but they also bind very well at a high albumin concentration.

As an example, in a particular embodiment, the GLP-1 receptor binding affinity ($IC_{50}$) of the derivatives of the invention in the presence of 2.0% HSA (high albumin) is at 300 nM or below.

Additional particular embodiments are disclosed in the sections headed PARTICULAR EMBODIMENTS, ADDITIONAL PARTICULAR EMBODIMENTS, and STILL FURTHER PARTICULAR EMBODIMENTS.

Pharmacokinetics Profile

According to the third functional aspect, the derivatives of the invention have improved pharmacokinetic properties such as increased terminal half-life, and/or decreased clearance.

Increasing terminal half-life and/or decreasing of the clearance means that the compound in question is eliminated slower from the body. For the derivatives of the invention this entails an extended duration of pharmacological effect.

The pharmacokinetic properties of the derivatives of the invention may suitably be determined in-vivo in pharmacokinetic (PK) studies. Such studies are conducted to evaluate how pharmaceutical compounds are absorbed, distributed, and eliminated in the body, and how these processes affect the concentration of the compound in the body, over the course of time.

In the discovery and preclinical phase of pharmaceutical drug development, animal models such as the mouse, rat, monkey, dog, or pig, may be used to perform this characterisation. Any of these models can be used to test the pharmacokinetic properties of the derivatives of the invention.

In such studies, animals are typically administered with a single dose of the drug, either intravenously (i.v.), subcutaneously (s.c.), or orally (p.o.) in a relevant formulation. Blood samples are drawn at predefined time points after dosing, and samples are analysed for concentration of drug with a relevant quantitative assay. Based on these measurements, time-plasma concentration profiles for the compound of study are plotted and a so-called non-compartmental pharmacokinetic analysis of the data is performed.

For most compounds, the terminal part of the plasma-concentration profiles will be linear when drawn in a semi-logarithmic plot, reflecting that after the initial absorption and distribution, drug is removed from the body at a constant fractional rate. The rate (lambda Z or $\lambda_z$) is equal to minus the slope of the terminal part of the plot. From this rate, also a terminal half-life may be calculated, as $t\frac{1}{2}=\ln(2)/\lambda_z$ (see, e.g., Johan Gabrielsson and Daniel Weiner: Pharmacokinetics and Pharmacodynamic Data Analysis, Concepts & Applications, 3rd Ed., Swedish Pharmaceutical Press, Stockholm (2000)).

Clearance can be determined after i.v. administration and is defined as the dose (D) divided by area under the curve (AUC) on the plasma concentration versus time profile (Rowland, M and Tozer T N: Clinical Pharmacokinetics: Concepts and Applications, $3^{rd}$ edition, 1995 Williams Wilkins).

The estimate of terminal half-life and/or clearance is relevant for evaluation of dosing regimens and an important parameter in drug development, in the evaluation of new drug compounds.

Pharmacokinetics Profile—Half Life In Vivo in Minipigs

According to the third functional aspect, the derivatives of the invention have improved pharmacokinetic properties.

In a particular embodiment, the pharmacokinetic properties may be determined as terminal half-life ($T_{1/2}$) in vivo in minipigs after i.v. administration, e.g. as described in Example 35 herein.

In a particular embodiment the derivatives of the invention have an excellent terminal half-life in minipigs which makes them suitable for once-monthly administration. In a particular embodiment, the terminal half-life of the derivatives of the invention in minipigs after i.v. administration is at least 100 hours.

Additional particular embodiments are disclosed in the sections headed PARTICULAR EMBODIMENTS, ADDITIONAL PARTICULAR EMBODIMENTS, and STILL FURTHER PARTICULAR EMBODIMENTS.

Production Processes

The production of peptides like GLP-1(7-37) and GLP-1 analogues is well known in the art.

The GLP-1 moiety of the derivatives of the invention (or fragments thereof) as well as the GLP-1 analogues of the invention may for instance be produced by classical peptide synthesis, e.g., solid phase peptide synthesis using t-Boc or Fmoc chemistry or other well established techniques, see, e.g., Greene and Wuts, "Protective Groups in Organic Synthesis", John Wiley & Sons, 1999, Florencio Zaragoza Dörwald, "Organic Synthesis on solid Phase", Wiley-VCH Verlag GmbH, 2000, and "Fmoc Solid Phase Peptide Synthesis", Edited by W. C. Chan and P. D. White, Oxford University Press, 2000.

Also, or alternatively, they may be produced by recombinant methods, viz. by culturing a host cell containing a DNA sequence encoding the analogue and capable of expressing the peptide in a suitable nutrient medium under conditions permitting the expression of the peptide. Non-limiting examples of host cells suitable for expression of these peptides are: *Escherichia coli, Saccharomyces cerevisiae*, as well as mammalian BHK or CHO cell lines.

Those derivatives of the invention which include non-natural amino acids and/or a covalently attached N-terminal mono- or dipeptide mimetic may e.g. be produced as described in the experimental part. Or see e.g., Hodgson et al: "The synthesis of peptides and proteins containing non-natural amino acids", Chemical Society Reviews, vol. 33, no. 7 (2004), p. 422-430; and WO 2009/083549 A1 entitled "Semi-recombinant preparation of GLP-1 analogues".

Specific examples of methods of preparing a number of the derivatives of the invention are included in the experimental part.

Pharmaceutical Compositions

The invention also relates to pharmaceutical compositions comprising a derivative of the invention or a pharmaceutically acceptable salt, amide, or ester thereof, and a pharmaceutically acceptable excipient. Such compositions may be prepared as is known in the art.

The term "excipient" broadly refers to any component other than the active therapeutic ingredient(s). The excipient may be an inert substance, an inactive substance, and/or a not medicinally active substance.

The excipient may serve various purposes, e.g. as a carrier, vehicle, diluent, tablet aid, and/or to improve administration, and/or absorption of the active substance.

The formulation of pharmaceutically active ingredients with various excipients is known in the art, see e.g. Remington: The Science and Practice of Pharmacy (e.g. $19^{th}$ edition (1995), and any later editions).

Non-limiting examples of excipients are: Solvents, diluents, buffers, preservatives, tonicity regulating agents, chelating agents, and stabilisers.

Examples of formulations include liquid formulations, i.e. aqueous formulations comprising water. A liquid formulation may be a solution, or a suspension. An aqueous formulation typically comprises at least 50% w/w water, or at least 60%, 70%, 80%, or even at least 90% w/w of water.

Alternatively, a pharmaceutical composition may be a solid formulation, e.g. a freeze-dried or spray-dried composition, which may be used as is, or whereto the physician or the patient adds solvents, and/or diluents prior to use.

The pH in an aqueous formulation may be anything between pH 3 and pH 10, for example from about 7.0 to about 9.5; or from about 3.0 to about 7.0, such as from 7.0 to 9.5, or from 3.0 to 7.0.

A pharmaceutical composition may comprise a buffer. The buffer may e.g. be selected from sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid, and mixtures thereof.

A pharmaceutical composition may comprise a preservative. The preservative may e.g. be selected from phenol, o-cresol, m-cresol, p-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, bronopol, benzoic acid, imidurea, chlorohexidine, sodium dehydroacetate, chlorocresol, ethyl p-hydroxybenzoate, benzethonium chloride, chlorphenesine (3p-chlorphenoxypropane-1,2-diol), and mixtures thereof. The preservative may be present in a concentration from 0.1 mg/ml to 20 mg/ml. A pharmaceutical composition may comprise an isotonic agent. The isotonic agent may e.g. be selected from a salt (e.g. sodium chloride), a sugar or sugar alcohol, an amino acid (e.g. glycine, histidine, arginine, lysine, isoleucine, aspartic acid, tryptophan, threonine), an alditol (e.g. glycerol (glycerine), 1,2-propanediol (propyleneglycol), 1,3-propanediol, 1,3-butanediol) polyethyleneglycol (e.g. PEG400), and mixtures thereof. Any sugar such as mono-, di-, or polysaccharides, or water-soluble glucans, including for example fructose, glucose, mannose, sorbose, xylose, maltose, lactose, sucrose, trehalose, dextran, pullulan, dextrin, cyclodextrin, alfa and beta HPCD, soluble starch, hydroxyethyl starch and carboxymethylcellulose-Na may be used. Sugar alcohol is defined as a C4-C8 hydrocarbon having at least one —OH group and includes, for example, mannitol, sorbitol, inositol, galactitol, dulcitol, xylitol, and arabitol. In one embodiment, the sugar alcohol additive is mannitol.

A pharmaceutical composition may comprise a chelating agent. The chelating agent may e.g. be selected from salts of ethylenediaminetetraacetic acid (EDTA), citric acid, and aspartic acid, and mixtures thereof.

A pharmaceutical composition may comprise a stabiliser. The stabiliser may e.g. be one or more oxidation inhibitors, aggregation inhibitors, surfactants, and/or one or more protease inhibitors. Non-limiting examples of these various kinds of stabilisers are disclosed in the following.

The term "aggregate formation" refers to a physical interaction between the polypeptide molecules resulting in formation of oligomers, which may remain soluble, or large visible aggregates that precipitate from the solution. Aggregate formation by a polypeptide during storage of a liquid pharmaceutical composition can adversely affect biological activity of that polypeptide, resulting in loss of therapeutic efficacy of the pharmaceutical composition. Furthermore, aggregate formation may cause other problems such as blockage of tubing, membranes, or pumps when the polypeptide-containing pharmaceutical composition is administered using an infusion system.

A pharmaceutical composition may comprise an amount of an amino acid base sufficient to decrease aggregate formation of the polypeptide during storage of the composition. The term "amino acid base" refers to one or more amino acids (such as methionine, histidine, imidazole, arginine, lysine, isoleucine, aspartic acid, tryptophan, threonine), or analogues thereof. Any amino acid may be present either in its free base form or in its salt form. Any stereoisomer (i.e., L, D, or a mixture thereof) of the amino acid base may be present.

Methionine (or other sulphuric amino acids or amino acid analogous) may be added to inhibit oxidation of methionine residues to methionine sulfoxide when the polypeptide acting as the therapeutic agent is a polypeptide comprising at least one methionine residue susceptible to such oxidation. Any stereoisomer of methionine (L or D) or combinations thereof can be used.

A pharmaceutical composition may comprise a stabiliser selected from high molecular weight polymers or low molecular compounds. The stabiliser may e.g. be selected from polyethylene glycol (e.g. PEG 3350), polyvinyl alcohol (PVA), polyvinylpyrrolidone, carboxy-/hydroxycellulose or derivates thereof (e.g. HPC, HPC-SL, HPC-L and HPMC), cyclodextrins, sulphur-containing substances as monothioglycerol, thioglycolic acid and 2-methylthioethanol, and different salts (e.g. sodium chloride). A pharmaceutical composition may comprise additional stabilising agents such as, but not limited to, methionine and EDTA, which protect the polypeptide against methionine oxidation, and a nonionic surfactant, which protects the polypeptide against aggregation associated with freeze-thawing or mechanical shearing.

A pharmaceutical composition may comprise one or more surfactants. The term "surfactant" refers to any molecules or ions that are comprised of a water-soluble (hydrophilic) part, and a fat-soluble (lipophilic) part. The surfactant may e.g. be selected from anionic surfactants, cationic surfactants, nonionic surfactants, and/or zwitterionic surfactants.

A pharmaceutical composition may comprise one or more protease inhibitors, such as, e.g., EDTA (ethylenediamine tetraacetic acid), and/or benzamidineHCl.

Additional, optional, ingredients of a pharmaceutical composition include, e.g., wetting agents, emulsifiers, antioxidants, bulking agents, metal ions, oily vehicles, proteins (e.g., human serum albumin, gelatine), and/or a zwitterion (e.g., an amino acid such as betaine, taurine, arginine, glycine, lysine and histidine).

Still further, a pharmaceutical composition may be formulated as is known in the art of oral formulations of insulinotropic compounds, e.g. using any one or more of the formulations described in WO 2008/145728.

An administered dose may contain from 0.1 mg-100 mg of the derivative, from 1-100 mg of the derivative, or from 1-50 mg of the derivative.

The derivative may be administered in the form of a pharmaceutical composition. It may be administered to a patient in need thereof at several sites, for example, at topical sites such as skin or mucosal sites; at sites which bypass absorption such as in an artery, in a vein, or in the heart; and at sites which involve absorption, such as in the skin, under the skin, in a muscle, or in the abdomen.

The route of administration may be, for example, lingual; sublingual; buccal; in the mouth; oral; in the stomach; in the intestine; nasal; pulmonary, such as through the bronchioles, the alveoli, or a combination thereof; parenteral, epidermal; dermal; transdermal; conjunctival; uretal; vaginal; rectal; and/or ocular. A composition may be an oral composition, and the route of administration is per oral.

A composition may be administered in several dosage forms, for example as a solution; a suspension; an emulsion; a microemulsion; multiple emulsions; a foam; a salve; a paste; a plaster; an ointment; a tablet; a coated tablet; a chewing gum; a rinse; a capsule such as hard or soft gelatine capsules; a suppositorium; a rectal capsule; drops; a gel; a spray; a powder; an aerosol; an inhalant; eye drops; an ophthalmic ointment; an ophthalmic rinse; a vaginal pessary; a vaginal ring; a vaginal ointment; an injection solution; an in situ transforming solution such as in situ gelling, setting, precipitating, and in situ crystallisation; an infusion solution; or as an implant.

A composition may be a tablet, optionally coated, a capsule, or a chewing gum.

A composition may further be compounded in a drug carrier or drug delivery system, e.g. in order to improve stability, bioavailability, and/or solubility. In a particular embodiment a composition may be attached to such system through covalent, hydrophobic, and/or electrostatic interactions. The purpose of such compounding may be, e.g., to decrease adverse effects, achieve chronotherapy, and/or increase patient compliance.

A composition may also be used in the formulation of controlled, sustained, protracting, retarded, and/or slow release drug delivery systems.

Parenteral administration may be performed by subcutaneous, intramuscular, intraperitoneal, or intravenous injection by means of a syringe, optionally a pen-like syringe, or by means of an infusion pump.

A composition may be administered nasally in the form of a solution, a suspension, or a powder; or it may be administered pulmonally in the form of a liquid or powder spray.

Transdermal administration is a still further option, e.g. by needle-free injection, from a patch such as an iontophoretic patch, or via a transmucosal route, e.g. buccally.

A composition may be a stabilised formulation. The term "stabilised formulation" refers to a formulation with increased physical and/or chemical stability, preferably both. In general, a formulation must be stable during use and storage (in compliance with recommended use and storage conditions) until the expiration date is reached.

The term "physical stability" refers to the tendency of the polypeptide to form biologically inactive and/or insoluble aggregates as a result of exposure to thermo-mechanical stress, and/or interaction with destabilising interfaces and surfaces (such as hydrophobic surfaces). The physical stability of an aqueous polypeptide formulation may be evaluated by means of visual inspection, and/or by turbidity measurements after exposure to mechanical/physical stress (e.g. agitation) at different temperatures for various time periods. Alternatively, the physical stability may be evaluated using a spectroscopic agent or probe of the conformational status of the polypeptide such as e.g. Thioflavin T or "hydrophobic patch" probes.

The term "chemical stability" refers to chemical (in particular covalent) changes in the polypeptide structure leading to formation of chemical degradation products potentially having a reduced biological potency, and/or increased immunogenic effect as compared to the intact polypeptide. The chemical stability can be evaluated by measuring the amount of chemical degradation products at various time-points after exposure to different environmental conditions, e.g. by SEC-HPLC, and/or RP-HPLC.

The treatment with a derivative according to the present invention may also be combined with one or more additional pharmacologically active substances, e.g. selected from antidiabetic agents, antiobesity agents, appetite regulating agents, antihypertensive agents, agents for the treatment and/or prevention of complications resulting from or associated with diabetes and agents for the treatment and/or prevention of complications and disorders resulting from or associated with obesity. Examples of these pharmacologically active substances are: Insulin, sulphonylureas, biguanides, meglitinides, glucosidase inhibitors, glucagon agonists, glucagon antagonists, DPP-IV (dipeptidyl peptidase-IV) inhibitors, inhibitors of hepatic enzymes involved in stimulation of gluconeogenesis and/or glycogenolysis, glucose uptake modulators, compounds modifying the lipid metabolism such as antihyperlipidemic agents as HMG CoA inhibitors (statins), Gastric Inhibitory Polypeptides (GIP analogs), compounds lowering food intake, RXR agonists and agents acting on the ATP-dependent potassium channel of the 3-cells; Cholestyramine, colestipol, clofibrate, gemfibrozil, lovastatin, pravastatin, simvastatin, probucol, dextrothyroxine, neteglinide, repaglinide; 3-blockers such as alprenolol, atenolol, timolol, pindolol, propranolol and metoprolol, ACE (angiotensin converting enzyme) inhibitors such as benazepril, captopril, enalapril, fosinopril, lisinopril, alatriopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin; CART (cocaine amphetamine regulated transcript) agonists, NPY (neuropeptide Y) antagonists, PYY agonists, Y2 receptor agonists, Y4 receptor agonits, mixed Y2/Y4 receptor agonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, β3 agonists, oxyntomodulin and analogues, MSH (melanocyte-stimulating hormone) agonists, MCH (melanocyte-concentrating hormone) antagonists, CCK (cholecystokinin) agonists, serotonin re-uptake inhibitors, serotonin and noradrenaline re-uptake inhibitors, mixed serotonin and noradrenergic compounds, 5HT (serotonin) agonists, bombesin agonists, fibroblast growth factor 21 (FGF-21), galanin antagonists, growth hormone, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, RXR (retinoid X receptor) modulators, TR β agonists; histamine H3 antagonists, Gastric Inhibitory Polypeptide agonists or antagonists (GIP analogs), gastrin and gastrin analogs.

The treatment with a derivative according to this invention may also be combined with a surgery that influences the glucose levels, and/or lipid homeostasis such as gastric banding or gastric bypass.

Pharmaceutical Indications

The present invention also relates to a derivative of the invention, for use as a medicament.

In particular embodiments, the derivative of the invention may be used for the following medical treatments:

(i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C;

(ii) delaying or preventing diabetic disease progression, such as progression in type 2 diabetes, delaying the progression of impaired glucose tolerance (IGT) to insulin requiring type 2 diabetes, delaying or preventing insulin resistance, and/or delaying the progression of non-insulin requiring type 2 diabetes to insulin requiring type 2 diabetes;

(iii) improving β-cell function, such as decreasing β-cell apoptosis, increasing β-cell function and/or β-cell mass, and/or for restoring glucose sensitivity to β-cells;

(iv) prevention and/or treatment of cognitive disorders and/or neurodegenerative disorders, such as Alzheimer's disease, Parkinson's disease, and/or multiple sclerosis;

(v) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, such as osteoarthritis and/or urine incontinence;

(vi) prevention and/or treatment of diabetic complications, such as angiopathy; neuropathy, including peripheral neuropathy; nephropathy; and/or retinopathy;

(vii) improving lipid parameters, such as prevention and/or treatment of dyslipidemia, lowering total serum lipids; increasing HDL; lowering small, dense LDL; lowering VLDL; lowering triglycerides; lowering cholesterol; lowering plasma levels of lipoprotein a (Lp(a)) in a human; inhibiting generation of apolipoprotein a (apo(a)) in vitro and/or in vivo;

(viii) prevention and/or treatment of cardiovascular diseases, such as syndrome X, atherosclerosis, myocardial infarction, coronary heart disease, reperfusion injury, stroke, cerebral ischemia, an early cardiac or early cardiovascular disease, left ventricular hypertrophy, coronary artery disease, hypertension, essential hypertension, acute hypertensive emergency, cardiomyopathy, heart insufficiency, exercise intolerance, acute and/or chronic heart failure, arrhythmia, cardiac dysrhythmia, syncopy, angina pectoris, cardiac bypass and/or stent reocclusion, intermittent claudication (atheroschlerosis oblitterens), diastolic dysfunction, and/or systolic dysfunction; and/or reduction of blood pressure, such as reduction of systolic blood pressure;

(ix) prevention and/or treatment of gastrointestinal diseases, such as inflammatory bowel disease, short bowel syndrome, or Crohn's disease or colitis; dyspepsia, and/or gastric ulcers; and/or inflammation, such as psoriasis, psoriactic arthritis, rheumatoid arthritis, and/or systemic lupus erythematosus;

(x) prevention and/or treatment of critical illness, such as treatment of a critically ill patient, a critical illness polynephropathy (CIPNP) patient, and/or a potential CIPNP patient; prevention of development of critical illness or CIPNP; prevention, treatment and/or cure of systemic inflammatory response syndrome (SIRS) in a patient; prevention or reduction of the likelihood of a patient suffering from bacteraemia, septicaemia, and/or septic shock during hospitalisation; and/or stabilising blood glucose, insulin balance and optionally metabolism in intensive care unit patients with acute illness;

(xi) prevention and/or treatment of polycystic ovary syndrome (PCOS);

(xii) prevention and/or treatment of cerebral disease, such as cerebral ischemia, cerebral haemorrhage, and/or traumatic brain injury;

(xiii) prevention and/or treatment of sleep apnoea; and/or (xiv) prevention and/or treatment of abuse, such as alcohol abuse and/or drug abuse.

In a particular embodiment the indication is selected from the group consisting of (i)-(xiv), such as indications (i)-(viii), (x)-(xiii), and/or (xiv), and relates in one way or the other to diabetes.

In another particular embodiment, the indication is selected from the group consisting of (i)-(iii) and (v)-(viii), such as indications (i), (ii), and/or (iii); or indication (v), indication (vi), indication (vii), and/or indication (viii).

In a still further particular embodiment, the indication is (i). In a further particular embodiment the indication is (v). In a still further particular embodiment the indication is (viii).

The following indications are particularly preferred: Type 2 diabetes, and/or obesity.

In some embodiments the invention relates to a method for weight management. In some embodiments the invention relates to a method for reduction of appetite. In some embodiments the invention relates to a method for reduction of food intake.

Generally, all subjects suffering from obesity are also considered to be suffering from overweight. In some embodiments the invention relates to a method for treatment or prevention of obesity. In some embodiments the invention relates to use of the derivative or analogue of the invention for treatment or prevention of obesity. In some embodiments the subject suffering from obesity is human, such as an adult human or a paediatric human (including infants, children, and adolescents). Body mass index (BMI) is a measure of body fat based on height and weight. The formula for calculation is BMI=weight in kilograms/height in meters$^2$. A human subject suffering from obesity may have a BMI of ≥30; this subject may also be referred to as obese. In some embodiments the human subject suffering from obesity may have a BMI of ≥35 or a BMI in the range of ≥30 to <40. In some embodiments the obesity is severe obesity or morbid obesity, wherein the human subject may have a BMI of ≥40.

In some embodiments the invention relates to a method for treatment or prevention of overweight, optionally in the presence of at least one weight-related comorbidity. In some embodiments the invention relates to use of the derivative or analogue of the invention for treatment or prevention of overweight, optionally in the presence of at least one weight-related comorbidity. In some embodiments the subject suffering from overweight is human, such as an adult human or a paediatric human (including infants, children, and adolescents). In some embodiments a human subject suffering from overweight may have a BMI of ≥25, such as a BMI of ≥27. In some embodiments a human subject suffering from overweight has a BMI in the range of 25 to <30 or in the range of 27 to <30. In some embodiments the weight-related comorbidity is selected from the group consisting of hypertension, diabetes (such as type 2 diabetes), dyslipidaemia, high cholesterol, and obstructive sleep apnoea.

In some embodiments the invention relates to a method for reduction of body weight. In some embodiments the invention relates to use of the derivative or analogue of the invention for reduction of body weight. A human to be subjected to reduction of body weight according to the present invention may have a BMI of ≥25, such as a BMI of ≥27 or a BMI of ≥30. In some embodiments the human to be subjected to reduction of body weight according to the present invention may have a BMI of 35 or a BMI of ≥40. The term "reduction of body weight" may include treatment or prevention of obesity and/or overweight.

Particular Embodiments

The following are particular embodiments of the invention:
1. A derivative of a GLP-1 analogue of the general Formula I:

Xaa$_7$-Xaa$_8$-Glu-Gly-Thr-Xaa$_{12}$-Thr-Ser-Asp-Xaa$_{16}$-Ser-Xaa$_{18}$-Xaa$_{19}$-Xaa$_{20}$-Glu-Xaa$_{22}$-Xaa$_{23}$-Ala-Xaa$_{25}$-Xaa$_{26}$-Xaa$_{27}$-Phe-Ile-Xaa$_{30}$-Xaa$_{31}$-Leu-Xaa$_{33}$-Xaa$_{34}$-Xaa$_{35}$-Xaa$_{36}$-Xaa$_{37}$-Xaa$_{38}$ (SEQ ID NO:9), wherein Xaa$_7$ is L-histidine, (S)-2-Hydroxy-3-(1H-imidazol-4-yl)-propionic acid, D-histidine, deamino-histidine, homohistidine, N$^\alpha$-acetyl-histidine, N$^\alpha$-formyl-histidine, N$^\alpha$-methyl-histidine, 3-pyridylalanine, 2-pyridylalanine, or 4-pyridylalanine;

Xaa$_8$ is Ala, Gly, Ser, Aib, (1-aminocyclopropyl) carboxylic acid, or (1-aminocyclobutyl) carboxylic acid;

Xaa$_{12}$ is Phe or Leu;
Xaa$_{16}$ is Val or Leu;
Xaa$_{18}$ is Ser, Val, Arg, or Leu;
Xaa$_{19}$ is Tyr or Gln;
Xaa$_{20}$ is Leu or Met;
Xaa$_{22}$ is Gly or Glu;
Xaa$_{23}$ is Gln, Glu, or Arg;
Xaa$_{25}$ is Ala or Val;
Xaa$_{26}$ is Arg;
Xaa$_{27}$ is Glu or Leu;
Xaa$_{30}$ is Ala, Glu, or Arg;
Xaa$_{31}$ is Trp or His;
Xaa$_{33}$ is Val;
Xaa$_{34}$ is Arg, His, Asn, Gln, or Lys;
Xaa$_{35}$ is Gly, Ala, or Lys;
Xaa$_{36}$ is Arg, Gly, or Lys;
Xaa$_{37}$ is Gly, Pro, or Lys;
Xaa$_{38}$ is Lys, or absent;

wherein at least one of Xaa$_{34}$, Xaa$_{35}$, Xaa$_{36}$, Xaa$_{37}$, and Xaa$_{35}$ is Lys;

which derivative comprises a side chain that is attached to the Lys residue of Xaa$_{34}$, Xaa$_{35}$, Xaa$_{36}$, Xaa$_{37}$, or Xaa$_{38}$, which side chain comprises:

(i) a Branched linker of Chem. 11

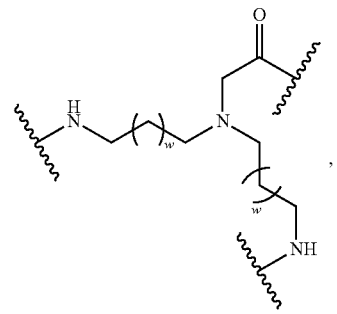

Chem. 11 wherein w is an integer in the range of 0-2;

(ii) a 1$^{st}$ and a 2$^{nd}$ Protractor selected from Chem. 12, Chem. 12a, and Chem. 13:

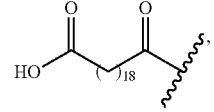

Chem. 12

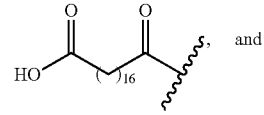

and

Chem. 12a

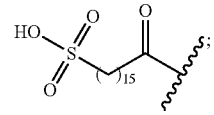

Chem. 13 and
(iii) at least one Linker element-1 of Chem. 1

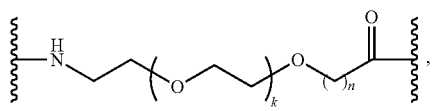

Chem. 1 wherein k is an integer in the range of 1-23, and n is an integer in the range of 1-5;
wherein the Branched linker is connected
a) at its —CO end to the epsilon amino group of the Lys residue of $Xaa_{34}$, $Xaa_{35}$, $Xaa_{36}$, $Xaa_{37}$, or $Xaa_{38}$, via an optional Pre-linker, and
b) at each of its two —NH ends to the —CO end of each of the $1^{st}$ and $2^{nd}$ Protractor, respectively, via a $1^{st}$ and a $2^{nd}$ Post-linker, respectively, each of the $1^{st}$ and the $2^{nd}$ Post-linker preferably comprising an —NH group and a —CO group; and wherein
if the Pre-linker is present it comprises the Linker element-1, or
if the Pre-linker is absent, each of the $1^{st}$ Post-linker and the $2^{nd}$ Post-linker comprises the Linker element-1;
or a pharmaceutically acceptable salt, amide, or ester thereof.

2. The derivative of claim 1 wherein the analogue has the general Formula I':
$Xaa_7$-$Xaa_8$-Glu-Gly-Thr-$Xaa_{12}$-Thr-Ser-Asp-$Xaa_{16}$-Ser-$Xaa_{18}$-$Xaa_{19}$-$Xaa_{20}$-Glu-$Xaa_{22}$-$Xaa_{23}$-Ala-$Xaa_{25}$-$Xaa_{26}$-$Xaa_{27}$-Phe-Ile-$Xaa_{30}$-$Xaa_{31}$-Leu-$Xaa_{33}$-$Xaa_{34}$-$Xaa_{35}$-$Xaa_{36}$-$Xaa_{37}$-$Xaa_{38}$, wherein
$Xaa_7$ is L-histidine or deamino-histidine;
$Xaa_8$ is Aib;
$Xaa_{12}$ is Phe;
$Xaa_{16}$ is Val;
$Xaa_{18}$ is Ser;
$Xaa_{19}$ is Tyr;
$Xaa_{20}$ is Leu;
$Xaa_{22}$ is Glu;
$Xaa_{23}$ is Gln;
$Xaa_{25}$ is Ala;
$Xaa_{26}$ is Arg;
$Xaa_{27}$ is Glu;
$Xaa_{30}$ is Ala or Glu;
$Xaa_{31}$ is Trp;
$Xaa_{33}$ is Val;
$Xaa_{34}$ is Arg or Lys;
$Xaa_{35}$ is Gly or Lys;
$Xaa_{36}$ is Arg or Lys;
$Xaa_{37}$ is Pro or Lys;
$Xaa_{38}$ is Lys or absent;
wherein at least one of $Xaa_{34}$, $Xaa_{35}$, $Xaa_{36}$, $Xaa_{37}$, and $Xaa_{35}$ is Lys.

3. The derivative of any of embodiments 1-2, wherein in Formula I $Xaa_7$ is L-histidine or deamino-histidine; $Xaa_8$ is Aib; $Xaa_{12}$ is Phe; $Xaa_{16}$ is Val; $Xaa_{18}$ is Ser; $Xaa_{19}$ is Tyr; $Xaa_{20}$ is Leu; $Xaa_{22}$ is Glu; $Xaa_{23}$ is Gln; $Xaa_{25}$ is Ala; $Xaa_{26}$ is Arg; $Xaa_{27}$ is Glu; $Xaa_{30}$ is Ala or Glu; $Xaa_{31}$ is Trp; $Xaa_{33}$ is Val; $Xaa_{34}$ is Arg or Lys; $Xaa_{35}$ is Gly or Lys; $Xaa_{36}$ is Arg or Lys; $Xaa_{37}$ is Pro or Lys; and/or $Xaa_{38}$ is Lys or absent; and wherein at least one of $Xaa_{34}$, $Xaa_{35}$, $Xaa_{36}$, $Xaa_{37}$, and $Xaa_{38}$ is Lys.

4. The derivative of any of embodiments 1-3, wherein the GLP-1 analogue has a maximum of 10 amino acid changes as compared to the sequence of GLP-1(7-37) (SEQ ID NO: 1).

5. The derivative of any of embodiments 1-4, wherein the GLP-1 analogue has a maximum of 9 amino acid changes as compared to the sequence of GLP-1(7-37) (SEQ ID NO: 1).

6. The derivative of any of embodiments 1-5, wherein the GLP-1 analogue has a maximum of 8 amino acid changes as compared to the sequence of GLP-1(7-37) (SEQ ID NO: 1).

7. The derivative of any of embodiments 1-6, wherein the GLP-1 analogue has a maximum of 7 amino acid changes as compared to the sequence of GLP-1(7-37) (SEQ ID NO: 1).

8. The derivative of any of embodiments 1-7, wherein the GLP-1 analogue has a maximum of 6 amino acid changes as compared to the sequence of GLP-1(7-37) (SEQ ID NO: 1).

9. The derivative of any of embodiments 1-8, wherein the GLP-1 analogue has a maximum of 5 amino acid changes as compared to the sequence of GLP-1(7-37) (SEQ ID NO: 1).

10. The derivative of any of embodiments 1-9, wherein the GLP-1 analogue has a maximum of 4 amino acid changes as compared to the sequence of GLP-1(7-37) (SEQ ID NO: 1).

11. The derivative of any of embodiments 1-10, wherein the GLP-1 analogue has a maximum of 3 amino acid changes as compared to the sequence of GLP-1(7-37) (SEQ ID NO: 1).

12. The derivative of any of embodiments 1-11, wherein the GLP-1 analogue has a maximum of 2 amino acid changes as compared to the sequence of GLP-1(7-37) (SEQ ID NO: 1).

13. The derivative of any of embodiments 1-12, wherein the GLP-1 analogue has a maximum of 1 change as compared to the sequence of GLP-1(7-37) (SEQ ID NO: 1).

14. The derivative of any of embodiments 1-13, wherein the GLP-1 analogue has at least 1 amino acid change as compared to the sequence of GLP-1(7-37) (SEQ ID NO: 1).

15. The derivative of any of embodiments 1-14, wherein the GLP-1 analogue has at least 2 amino acid changes as compared to the sequence of GLP-1(7-37) (SEQ ID NO: 1).

16. The derivative of any of embodiments 1-15, wherein the GLP-1 analogue has at least 3 amino acid changes as compared to the sequence of GLP-1(7-37) (SEQ ID NO: 1).

17. The derivative of any of embodiments 1-16, wherein the GLP-1 analogue has at least 4 amino acid changes as compared to the sequence of GLP-1(7-37) (SEQ ID NO: 1).

18. The derivative of any of embodiments 1-17, wherein the GLP-1 analogue has at least 5 amino acid changes as compared to the sequence of GLP-1(7-37) (SEQ ID NO: 1).

19. The derivative of any of embodiments 1-18, wherein the GLP-1 analogue has at least 6 amino acid changes as compared to the sequence of GLP-1(7-37) (SEQ ID NO: 1).

20. The derivative of any of embodiments 1-19 wherein the number of amino acid changes as compared to GLP-1(7-37) (SEQ ID NO: 1) is identified by handwriting and visual inspection.

21. The derivative of any of embodiments 1-20 wherein the number of amino acid changes as compared to GLP-1(7-37) (SEQ ID NO: 1) is identified by by use of a standard protein or peptide alignment program.

22. The derivative of embodiment 21, wherein the alignment program is a Needleman-Wunsch alignment.

23. The derivative of any of embodiments 21-22, wherein the default scoring matrix and the default identity matrix is used.

24. The derivative of any of embodiments 21-23, wherein the scoring matrix is BLOSUM62.

25. The derivative of any of embodiments 21-24, wherein the penalty for the first residue in a gap is –10 (minus ten).

26. The derivative of any of embodiments 21-25, wherein the penalties for additional residues in a gap is –0.5 (minus point five).

27. The derivative of any of embodiments 1-26, wherein one of $Xaa_{34}$, $Xaa_{35}$, $Xaa_{36}$, $Xaa_{37}$, and $Xaa_{38}$ is Lys.

28. The derivative of any of embodiments 1-27, wherein the GLP-1 analogue is selected from the peptides of SEQ ID NO: 2, SEQ ID NO: 3, SEQ ID NO: 4, SEQ ID NO: 6, SEQ ID NO: 7, and SEQ ID NO: 8.
29. The derivative of any of embodiments 1-28, wherein each of the $1^{st}$ and $2^{nd}$ protractor is Chem. 12.
30. The derivative of any of embodiments 1-28, wherein each of the $1^{st}$ and $2^{nd}$ protractor is Chem. 12a.
31. The derivative of any of embodiments 1-28, wherein each of the $1^{st}$ and $2^{nd}$ protractor is Chem. 13.
32. The derivative of any of embodiments 1-31, wherein the side chain is attached to the Lys residue of $Xaa_{34}$.
33. The derivative of any of embodiments 1-31, wherein the side chain is attached to the Lys residue of $Xaa_{35}$.
34. The derivative of any of embodiments 1-31, wherein the side chain is attached to the Lys residue of $Xaa_{36}$.
35. The derivative of any of embodiments 1-31, wherein the side chain is attached to the Lys residue of $Xaa_{37}$.
36. The derivative of any of embodiments 1-31, wherein the side chain is attached to the Lys residue of $Xaa_{38}$.
37. The derivative of any of embodiments 1-36, wherein in Chem. 11 w is 1.
38. The derivative of any of embodiments 1-37, wherein the Pre-linker is present.
39. The derivative of any of embodiments 1-38, wherein the Pre-linker comprises the Linker element-1 (Chem. 1).
40. The derivative of any of embodiments 1-39, wherein each of the $1^{st}$ Post-linker and the $2^{nd}$ Post-linker comprises the Linker element-1.
41. The derivative of any of embodiments 1-39, wherein only the Pre-linker comprises the Linker element-1.
42. The derivative of any of embodiments 1-39, wherein each of the $1^{st}$ Post-linker and the $2^{nd}$ Post-linker does not comprise the Linker element-1.
43. The derivative of any of embodiments 1-39, wherein none of the $1^{st}$ Post-linker and the $2^{nd}$ Post-linker comprises the Linker element-1.
44. The derivative of any of embodiments 1-40, wherein the Pre-linker and each of the $1^{st}$ Post-linker and the $2^{nd}$ Post-linker comprises the Linker element-1.
45. The derivative of any of embodiments 1-44, wherein the Pre-linker is absent.
46. The derivative of any of embodiments 1-45, wherein the Pre-linker is not present.
47. The derivative of any of embodiments 1-46, which has no Pre-linker.
48. The derivative of any of embodiments 1-47, wherein each of the $1^{st}$ Post-linker and the $2^{nd}$ Post-linker comprises the Linker element-1 (Chem. 1).
49. The derivative of any of embodiments 1-48, which comprises at least two times Linker element-1.
50. The derivative of any of embodiments 1-49, which includes exactly m times Linker element-1, where m is an integer in the range of 2-12.
51. The derivative of embodiment 50, wherein m is 2.
52. The derivative of embodiment 50, wherein m is 4.
53. The derivative of embodiment 50, wherein m is 6.
54. The derivative of embodiment 50, wherein m is 8.
55. The derivative of embodiment 50, wherein m is 10.
56. The derivative of embodiment 50, wherein m is 12.
57. The derivative of any of embodiments 1-56, which comprises at least one block consisting of q juxtaposed Linker element-1, where q is an integer in the range of 1-6, and where juxtaposed means mutually connected, via amide bonds.
58. The derivative of any of embodiments 1-57, which comprises at least one block consisting of q Linker element-1 in a row, connected via amide bonds, where q is an integer in the range of 1-6.
59. The derivative of any of embodiments 1-58, where q is an integer in the range of 2-6.
60. The derivative of any of embodiments 57-59, wherein q is 1.
61. The derivative of any of embodiments 57-59, wherein q is 2.
62. The derivative of any of embodiments 57-59, wherein q is 3.
63. The derivative of any of embodiments 57-59, wherein q is 4.
64. The derivative of any of embodiments 57-59, wherein q is 5.
65. The derivative of any of embodiments 57-59, wherein q is 6.
66. The derivative of any of embodiments 57-65, which includes exactly one block of q juxtaposed Linker element-1.
67. The derivative of embodiment 66, wherein q is 2, 4, or 6.
68. The derivative of any of embodiments 66-67, wherein q is 2
69. The derivative of any of embodiments 66-67, wherein q is 4
70. The derivative of any of embodiments 66-67, wherein q is 6
71. The derivative of any of embodiments 66-70, wherein the block is in the Pre-linker.
72. The derivative of any of embodiments 57-65, which includes exactly two blocks of q juxtaposed Linker element-1.
73. The derivative of embodiment 72, wherein q is 1, 2, 3, 4, 5, or 6.
74. The derivative of any of embodiments 72-73, wherein q is 1.
75. The derivative of any of embodiments 72-73, wherein q is 2.
76. The derivative of any of embodiments 72-73, wherein q is 3.
77. The derivative of any of embodiments 72-73, wherein q is 4.
78. The derivative of any of embodiments 72-73, wherein q is 5.
79. The derivative of any of embodiments 72-73, wherein q is 6.
80. The derivative of any of embodiments 72-79, wherein the two blocks are in the $1^{st}$ and $2^{nd}$ Post-linker, one block in each.
81. The derivative of any of embodiments 57-65, which includes exactly three blocks of q juxtaposed Linker element-1.
82. The derivative of embodiment 81, wherein q is 2 or 4.
83. The derivative of any of embodiments 80-82, wherein q is 2.
84. The derivative of any of embodiments 80-82, wherein q is 4.
85. The derivative of any of embodiments 81-84, wherein the three blocks are in the Pre-linker, the $1^{st}$ Post-linker, and the $2^{nd}$ Post-linker, one block in each.
86. The derivative of any of embodiments 1-85, wherein k is 1, 3, 11, 15, or 23.
87. The derivative of any of embodiments 1-86, wherein k is 1.

88. The derivative of any of embodiments 1-86, wherein k is 3.
89. The derivative of any of embodiments 1-86, wherein k is 11.
90. The derivative of any of embodiments 1-86, wherein k is 15.
91. The derivative of any of embodiments 1-86, wherein k is 23.
92. The derivative of any of embodiments 1-91, wherein n is 1 or 2.
93. The derivative of any of embodiments 1-92, wherein n is 1.
94. The derivative of any of embodiments 1-93, wherein n is 2.
95. The derivative of any of embodiments 1-94, wherein k is 1 and n is 1.
96. The derivative of any of embodiments 1-94, wherein k is 3 and n is 2.
97. The derivative of any of embodiments 1-94, wherein k is 11 and n is 2.
98. The derivative of any of embodiments 1-94, wherein k is 15 and n is 2.
99. The derivative of any of embodiments 1-94, wherein k is 23 and n is 2.
100. The derivative of any of embodiments 1-99, which comprises a Linker element-2 of Chem. 2:

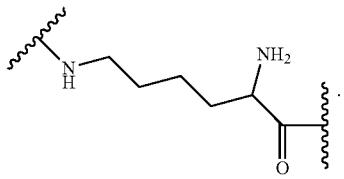 [SMILES: *NCCCCC(N)C(*)=O]

101. The derivative of embodiment 100, wherein Chem. 2 is a di-radical of Lys.
102. The derivative of any of embodiments 100-101, wherein Chem. 2 is a di-radical of eps-Lys.
103. The derivative of any of embodiments 100-102, wherein Chem. 2 is a di-radical of L-eps-Lys.
104. The derivative of any of embodiments 100-103, which comprises p times the Linker element-2, where p is an integer in the range of 0-2.
105. The derivative of embodiment 104, wherein p is 2.
106. The derivative of any of embodiments 1-105, which comprises a Linker element-3 of Chem. 3:

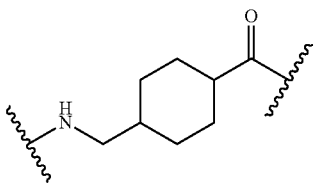

107. The derivative of embodiment 106, wherein Chem. 3 is a di-radical of tranexamic acid.
108. The derivative of any of embodiments 106-107, wherein Chem. 3 is a di-radical of trans-4-(aminomethyl) cyclohexanecarboxylic acid.

109. The derivative of any of embodiments 1-108, which comprises a Linker element-4 of Chem. 4:

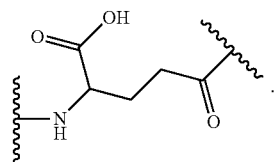 [SMILES: *NC(CCC(*)=O)C(=O)O]

110. The derivative of embodiment 109, wherein Chem. 4 is a di-radical of Glu.
111. The derivative of any of embodiments 109-110, wherein Chem. 4 is a di-radical of gGlu.
112. The derivative of any of embodiments 109-111, wherein Chem. 4 is a di-radical of L-gGlu.
113. The derivative of any of embodiments 1-112, which comprises a Linker element-5 of Chem. 5:

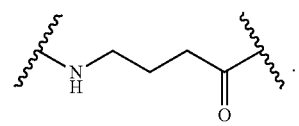 [SMILES: *NCCCC(*)=O]

114. The derivative of embodiment 113, wherein Chem. 5 is a di-radical of 4-amino butanoic acid.
115. The derivative of any of embodiments 1-114, which comprises a Linker element-6 of Chem. 6:

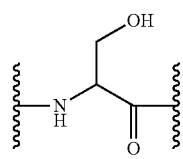

116. The derivative of embodiment 115, wherein Chem. 6 is a di-radical of Ser.
117. The derivative of any of embodiments 115-116, wherein Chem. 6 is a di-radical of L-Ser.
118. The derivative of any of embodiments 1-117, which comprises the Pre-linker.
119. The derivative of embodiment 118, wherein the Branched linker is connected, at its —CO end, to the epsilon amino group of the Lys residue of $Xaa_{34}$, $Xaa_{35}$, $Xaa_{36}$, $Xaa_{37}$, or $Xaa_{38}$, via the Pre-linker.
120. The derivative of any of embodiments 118-119, wherein the Pre-linker includes exactly q times the Linker element-1, where q is 2, 4, or 6.
121. The derivative of embodiment 120, wherein q is 2.
122. The derivative of embodiment 120, wherein q is 4.
123. The derivative of embodiment 120, wherein q is 6.
124. The derivative of any of embodiments 120-123, wherein k is 1.
125. The derivative of any of embodiments 120-124, wherein n is 1.
126. The derivative of any of embodiments 1-117, which does not comprise the Pre-linker.
127. The derivative of any of embodiments 1-117 and 126, wherein the Branched linker is directly connected, at its —CO end, to the epsilon amino group of the Lys residue of $Xaa_{34}$, $Xaa_{35}$, $Xaa_{36}$, $Xaa_{37}$, or $Xaa_{38}$.

128. The derivative of any of embodiments 1-127, wherein the $1^{st}$ and the $2^{nd}$ Post-linker each includes exactly s times the Linker element-1, where s is 0 or an integer in the range of 1-6, and at least one further linker element selected from Linker element-2, Linker element-3, Linker element-4, Linker element-5, and Linker element-6; wherein the derivative preferably comprises no more than four, more preferably no more than three further linker elements, of the same or different kind.

129. The derivative of any of embodiments 1-128, wherein the $1^{st}$ and the $2^{nd}$ Post-linker each includes exactly s times the Linker element-1, where s is 0 or an integer in the range of 1-6, and at least two further linker elements of the same or different kind and selected from Linker element-2, Linker element-3, Linker element-4, Linker element-5, and Linker element-6; wherein the derivative preferably comprises no more than four, more preferably no more than three further linker elements, of the same or different kind.

130. The derivative of any of embodiments 1-129, wherein each of the $1^{st}$ and $2^{nd}$ Post-linker consists of two times Linker element-2, and five times Linker element-1 of Chem. 1 where k is 1 and n is 1, interconnected via amide bonds and in the sequence indicated, and wherein each of the $1^{st}$ and the $2^{nd}$ Post-linker is connected at its —NH end to the —CO end of the $1^{st}$ and the $2^{nd}$ Protractor, respectively, and at its —CO end to each of the —NH ends of the Branched linker.

131. The derivative of any of embodiments 1-129, wherein each of the $1^{st}$ and $2^{nd}$ Post-linker consists of two times Linker element-2, and four times Linker element-1 of Chem. 1 where k is 1 and n is 1, interconnected via amide bonds and in the sequence indicated, and wherein each of the $1^{st}$ and the $2^{nd}$ Post-linker is connected at its —NH end to the —CO end of the $1^{st}$ and the $2^{nd}$ Protractor, respectively, and at its —CO end to each of the —NH ends of the Branched linker.

132. The derivative of any of embodiments 1-129, wherein each of the $1^{st}$ and $2^{nd}$ Post-linker consists of Linker element-3, Linker element-4, and six times Linker element-1 of Chem. 1 where k is 1 and n is 1, interconnected via amide bonds and in the sequence indicated, and wherein each of the $1^{st}$ and the $2^{nd}$ Post-linker is connected at its —NH end to the —CO end of the $1^{st}$ and the $2^{nd}$ Protractor, respectively, and at its —CO end to each of the —NH ends of the Branched linker.

133. The derivative of any of embodiments 1-129, wherein each of the $1^{st}$ and $2^{nd}$ Post-linker consists of two times Linker element-2, and three times Linker element-1 of Chem. 1 where k is 3 and n is 2, interconnected via amide bonds and in the sequence indicated, and wherein each of the $1^{st}$ and the $2^{nd}$ Post-linker is connected at its —NH end to the —CO end of the $1^{st}$ and the $2^{nd}$ Protractor, respectively, and at its —CO end to each of the —NH ends of the Branched linker.

134. The derivative of any of embodiments 1-129, wherein each of the $1^{st}$ and $2^{nd}$ Post-linker consists of two times Linker element-2, and Linker element-1 of Chem. 1 where k is 23 and n is 2, interconnected via amide bonds and in the sequence indicated, and wherein each of the $1^{st}$ and the $2^{nd}$ Post-linker is connected at its —NH end to the —CO end of the $1^{st}$ and the $2^{nd}$ Protractor, respectively, and at its —CO end to each of the —NH ends of the Branched linker.

135. The derivative of any of embodiments 1-129, wherein each of the $1^{st}$ and $2^{nd}$ Post-linker consists of two times Linker element-2, and Linker element-1 of Chem. 1 where k is 15 and n is 2, interconnected via amide bonds and in the sequence indicated, and wherein each of the $1^{st}$ and the $2^{nd}$ Post-linker is connected at its —NH end to the —CO end of the $1^{st}$ and the $2^{nd}$ Protractor, respectively, and at its —CO end to each of the —NH ends of the Branched linker.

136. The derivative of any of embodiments 1-129, wherein each of the $1^{st}$ and $2^{nd}$ Post-linker consists of two times Linker element-2, and Linker element-1 of Chem. 1 where k is 11 and n is 2, interconnected via amide bonds and in the sequence indicated, and wherein each of the $1^{st}$ and the $2^{nd}$ Post-linker is connected at its —NH end to the —CO end of the $1^{st}$ and the $2^{nd}$ Protractor, respectively, and at its —CO end to each of the —NH ends of the Branched linker.

137. The derivative of any of embodiments 1-129, wherein each of the $1^{st}$ and $2^{nd}$ Post-linker consists of Linker element-5, two times Linker element-2, and five times Linker element-1 of Chem. 1 where k is 1 and n is 1, interconnected via amide bonds and in the sequence indicated, and wherein each of the $1^{st}$ and the $2^{nd}$ Post-linker is connected at its —NH end to the —CO end of the $1^{st}$ and the $2^{nd}$ Protractor, respectively, and at its —CO end to each of the —NH ends of the Branched linker.

138. The derivative of any of embodiments 1-129, wherein each of the $1^{st}$ and $2^{nd}$ Post-linker consists of Linker element-3, Linker element-4, and five times Linker element-1 of Chem. 1 where k is 1 and n is 1, interconnected via amide bonds and in the sequence indicated, and wherein each of the $1^{st}$ and the $2^{nd}$ Post-linker is connected at its —NH end to the —CO end of the $1^{st}$ and the $2^{nd}$ Protractor, respectively, and at its —CO end to each of the —NH ends of the Branched linker.

139. The derivative of any of embodiments 1-129, wherein each of the $1^{st}$ and $2^{nd}$ Post-linker consists of Linker element-3, Linker element-4, and four times Linker element-1 of Chem. 1 where k is 1 and n is 1, interconnected via amide bonds and in the sequence indicated, and wherein each of the $1^{st}$ and the $2^{nd}$ Post-linker is connected at its —NH end to the —CO end of the $1^{st}$ and the $2^{nd}$ Protractor, respectively, and at its —CO end to each of the —NH ends of the Branched linker.

140. The derivative of any of embodiments 1-129, wherein each of the $1^{st}$ and $2^{nd}$ Post-linker consists of Linker element-3, Linker element-4, and two times Linker element-1 of Chem. 1 where k is 1 and n is 1, interconnected via amide bonds and in the sequence indicated, and wherein each of the $1^{st}$ and the $2^{nd}$ Post-linker is connected at its —NH end to the —CO end of the $1^{st}$ and the $2^{nd}$ Protractor, respectively, and at its —CO end to each of the —NH ends of the Branched linker.

141. The derivative of any of embodiments 1-129, wherein each of the $1^{st}$ and $2^{nd}$ Post-linker consists of Linker element-3, and Linker element-4, interconnected via amide bonds and in the sequence indicated, and wherein each of the $1^{st}$ and the $2^{nd}$ Post-linker is connected at its —NH end to the —CO end of the $1^{st}$ and the $2^{nd}$ Protractor, respectively, and at its —CO end to each of the —NH ends of the Branched linker.

142. The derivative of any of embodiments 1-129, wherein each of the $1^{st}$ and $2^{nd}$ Post-linker consists of Linker element-5, two times Linker element-2, and four times Linker element-1 of Chem. 1 where k is 1 and n is 1, interconnected via amide bonds and in the sequence indicated, and wherein each of the $1^{st}$ and the $2^{nd}$ Post-linker is connected at its —NH end to the —CO end of the $1^{st}$ and the $2^{nd}$ Protractor, respectively, and at its —CO end to each of the —NH ends of the Branched linker.

143. The derivative of any of embodiments 1-129, wherein each of the $1^{st}$ and $2^{nd}$ Post-linker consists of Linker element-5, two times Linker element-2, and six times Linker element-1 of Chem. 1 where k is 1 and n is 1, interconnected via amide bonds and in the sequence indicated, and wherein each of the $1^{st}$ and the $2^{nd}$ Post-linker is connected at its —NH end to the —CO end of the $1^{st}$ and the $2^{nd}$ Protractor, respectively, and at its —CO end to each of the —NH ends of the Branched linker.

144. The derivative of any of embodiments 1-129, wherein each of the $1^{st}$ and $2^{nd}$ Post-linker consists of Linker element-5, Linker element-4, and four times Linker element-1 of Chem. 1 where k is 1 and n is 1, interconnected via amide bonds and in the sequence indicated, and wherein each of the $1^{st}$ and the $2^{nd}$ Post-linker is connected at its —NH end to the —CO end of the $1^{st}$ and the $2^{nd}$ Protractor, respectively, and at its —CO end to each of the —NH ends of the Branched linker.

145. The derivative of any of embodiments 1-129, wherein each of the $1^{st}$ and $2^{nd}$ Post-linker consists of Linker element-5, Linker element-4, and five times Linker element-1 of Chem. 1 where k is 1 and n is 1, interconnected via amide bonds and in the sequence indicated, and wherein each of the $1^{st}$ and the $2^{nd}$ Post-linker is connected at its —NH end to the —CO end of the $1^{st}$ and the $2^{nd}$ Protractor, respectively, and at its —CO end to each of the —NH ends of the Branched linker.

146. The derivative of any of embodiments 1-129, wherein each of the $1^{st}$ and $2^{nd}$ Post-linker consists of Linker element-5, Linker element-4, and six times Linker element-1 of Chem. 1 where k is 1 and n is 1, interconnected via amide bonds and in the sequence indicated, and wherein each of the $1^{st}$ and the $2^{nd}$ Post-linker is connected at its —NH end to the —CO end of the $1^{st}$ and the $2^{nd}$ Protractor, respectively, and at its —CO end to each of the —NH ends of the Branched linker.

147. The derivative of any of embodiments 1-129, wherein each of the $1^{st}$ and $2^{nd}$ Post-linker consists of Linker element-5, Linker element-3, Linker element-4, and four times Linker element-1 of Chem. 1 where k is 1 and n is 1, interconnected via amide bonds and in the sequence indicated, and wherein each of the $1^{st}$ and the $2^{nd}$ Post-linker is connected at its —NH end to the —CO end of the $1^{st}$ and the $2^{nd}$ Protractor, respectively, and at its —CO end to each of the —NH ends of the Branched linker.

148. The derivative of any of embodiments 1-129, wherein each of the $1^{st}$ and $2^{nd}$ Post-linker consists of Linker element-5, Linker element-3, Linker element-4, and five times Linker element-1 of Chem. 1 where k is 1 and n is 1, interconnected via amide bonds and in the sequence indicated, and wherein each of the $1^{st}$ and the $2^{nd}$ Post-linker is connected at its —NH end to the —CO end of the $1^{st}$ and the $2^{nd}$ Protractor, respectively, and at its —CO end to each of the —NH ends of the Branched linker.

149. The derivative of any of embodiments 1-129, wherein each of the $1^{st}$ and $2^{nd}$ Post-linker consists of Linker element-5, Linker element-3, Linker element-4, and six times Linker element-1 of Chem. 1 where k is 1 and n is 1, interconnected via amide bonds and in the sequence indicated, and wherein each of the $1^{st}$ and the $2^{nd}$ Post-linker is connected at its —NH end to the —CO end of the $1^{st}$ and the $2^{nd}$ Protractor, respectively, and at its —CO end to each of the —NH ends of the Branched linker.

150. The derivative of any of embodiments 1-129, wherein each of the $1^{st}$ and $2^{nd}$ Post-linker consists of Linker element-4, and four times Linker element-1 of Chem. 1 where k is 1 and n is 1, interconnected via amide bonds and in the sequence indicated, and wherein each of the $1^{st}$ and the $2^{nd}$ Post-linker is connected at its —NH end to the —CO end of the $1^{st}$ and the $2^{nd}$ Protractor, respectively, and at its —CO end to each of the —NH ends of the Branched linker.

151. The derivative of any of embodiments 1-129, wherein each of the $1^{st}$ and $2^{nd}$ Post-linker consists of Linker element-4, wherein each of the $1^{st}$ and the $2^{nd}$ Post-linker is connected at its —NH end to the —CO end of the $1^{st}$ and the $2^{nd}$ Protractor, respectively, and at its —CO end to each of the —NH ends of the Branched linker.

152. The derivative of any of embodiments 1-129, wherein each of the $1^{st}$ and $2^{nd}$ Post-linker consists of Linker element-3, Linker element-4, and Linker element-6, interconnected via amide bonds and in the sequence indicated, and wherein each of the $1^{st}$ and the $2^{nd}$ Post-linker is connected at its —NH end to the —CO end of the $1^{st}$ and the $2^{nd}$ Protractor, respectively, and at its —CO end to each of the —NH ends of the Branched linker.

153. The derivative of any of embodiments 1-152, wherein the Pre-linker consists of two times Linker element-1 of Chem. 1 where k is 1 and n is 1, interconnected via amide bonds, and wherein the Pre-linker is connected at its —NH end to the —CO end of the Branched linker, and at its —CO end to the epsilon amino group of the Lys residue of $Xaa_{34}$, $Xaa_{35}$, $Xaa_{36}$, $Xaa_{37}$, or $Xaa_{38}$.

154. The derivative of embodiment 153, wherein each of the $1^{st}$ and $2^{nd}$ Post-linker is as defined in embodiment 139.

155. The derivative of any of embodiments 1-152, wherein the Pre-linker consists of four times Linker element-1 of Chem. 1 where k is 1 and n is 1, interconnected via amide bonds, and wherein the Pre-linker is connected at its —NH end to the —CO end of the Branched linker, and at its —CO end to the epsilon amino group of the Lys residue of $Xaa_{34}$, $Xaa_{35}$, $Xaa_{36}$, $Xaa_{37}$, or $Xaa_{38}$.

156. The derivative of embodiment 155, wherein each of the $1^{st}$ and $2^{nd}$ Post-linker is as defined in embodiment 140.

157. The derivative of embodiment 155, wherein each of the $1^{st}$ and $2^{nd}$ Post-linker is as defined in embodiment 141.

158. The derivative of embodiment 154, wherein each of the $1^{st}$ and $2^{nd}$ Post-linker is as defined in embodiment 151.

159. The derivative of any of embodiments 1-152, wherein the Pre-linker consists of six times Linker element-1 of Chem. 1 where k is 1 and n is 1, interconnected via amide bonds, and wherein the Pre-linker is connected at its —NH end to the —CO end of the Branched linker, and at its —CO end to the epsilon amino group of the Lys residue of $Xaa_{34}$, $Xaa_{35}$, $Xaa_{36}$, $Xaa_{37}$, or $Xaa_{38}$.

160. The derivative of embodiment 158, wherein each of the $1^{st}$ and $2^{nd}$ Post-linker is as defined in embodiment 141.

161. The derivative of embodiment 158, wherein each of the $1^{st}$ and $2^{nd}$ Post-linker is as defined in embodiment 152.

162. The derivative of embodiment 158, wherein each of the $1^{st}$ and $2^{nd}$ Post-linker is as defined in embodiment 151.

163. The derivative of any of embodiments 1-162, wherein the Branched linker is connected, via amide bonds, a) at its —CO end to the epsilon amino group of the Lys residue of $Xaa_{34}$, $Xaa_{35}$, $Xaa_{36}$, $Xaa_{37}$, or $Xaa_{38}$, via the optional Pre-linker, and b) at each of its two —N ends to the —CO end of each of the $1^{st}$ and $2^{nd}$ Protractor, respectively, via a $1^{st}$ and a $2^{nd}$ Post-linker, respectively.

164. The derivative of any of embodiments 1-163, wherein one of $Xaa_{36}$, $Xaa_{37}$, and $Xaa_{38}$ is Lys;

which derivative comprises a side chain that is attached to the Lys residue of $Xaa_{36}$, $Xaa_{37}$, or $Xaa_{38}$, which side chain comprises:
(i) a Branched linker of formula Chem. 11

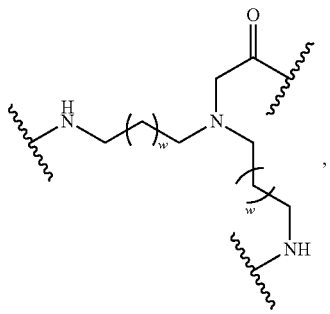

Chem. 11 wherein w is 1;
(ii) a 1$^{st}$ and a 2$^{nd}$ Protractor selected from Chem. 12 and Chem. 12a:

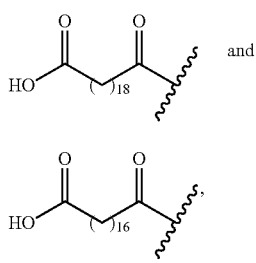

Chem. 12 and

Chem. 12a (iii) at least eight times a Linker element-1 of Chem. 1:

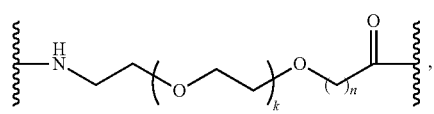

Chem. 1 wherein k is 1 and n is 1;
wherein the Branched linker is connected a) at its —CO end to the epsilon amino group of the Lys residue of Xaa$_{36}$, Xaa$_{37}$, or Xaa$_{38}$, via an optional Pre-linker, and b) at each of its two —NH ends to the —CO end of each of the 1$^{st}$ and 2$^{nd}$ Protractor, respectively, via a 1$^{st}$ and a 2$^{nd}$ Post-linker, respectively; and wherein if the Pre-linker is present it comprises at least two times the Linker element-1, or if the Pre-linker is absent, each of the 1$^{st}$ Post-linker and the 2$^{nd}$ Post-linker comprises at least four times the Linker element-1;

or a pharmaceutically acceptable salt, amide, or ester thereof.

165. The derivative of any of embodiments 1-164, wherein one of Xaa$_{36}$, Xaa$_{37}$, and Xaa$_{38}$ is Lys, and which derivative comprises a side chain that is attached to the Lys residue of Xaa$_{36}$, Xaa$_{37}$, or Xaa$_{38}$, which side chain consists of:
(i) a Branched linker of Chem. 11

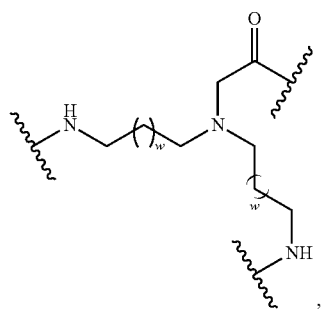

Chem. 11 wherein w is 1;
(ii) a 1$^{st}$ and a 2$^{nd}$ Protractor selected from Chem. 12 and Chem. 12a:

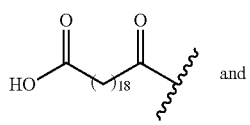

Chem. 12 and

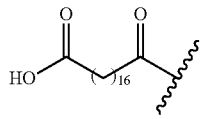

Chem. 12a (iii) at least eight times a Linker element-1 of Chem. 1

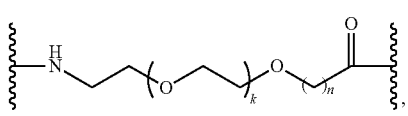

Chem. 1 wherein k is 1 and n is 1;
wherein the Branched linker is connected a) at its —CO end to the epsilon amino group of the Lys residue of Xaa$_{36}$, Xaa$_{37}$, or Xaa$_{38}$, via an optional Pre-linker, and b) at each of its two —NH ends to the —CO end of each of the 1$^{st}$ and 2$^{nd}$ Protractor, respectively, via a 1$^{st}$ and a 2$^{nd}$ Post-linker, respectively; and
wherein if the Pre-linker is present it consists of two to four times the Linker element-1, or if the Pre-linker is absent, each of the 1$^{st}$ Post-linker and the 2$^{nd}$ Post-linker consists of four to six times the Linker element-1;

or a pharmaceutically acceptable salt, amide, or ester thereof.

166. The derivative of any of embodiments 1-165 wherein the GLP-1 analogue has the following changes as compared to SEQ ID NO: 1: (8Aib, 22E, 26R, 34R), and in addition either (i) 36K, (ii) 37K, or (iii) (37P and 38K).

167. The derivative of any of embodiments 1-166, wherein the GLP-1 analogue has the sequence of any one of SEQ ID NOs: 2, 4, or 6.

168. The derivative of any of embodiments 1-167, wherein the total number ("m") of Linker element-1 in the entire molecule is between 8 and 12, such as 8, 10, or 12.
169. The derivative of any of embodiments 1-168, wherein the number ("s") of juxtaposed Linker element-1 in each of the $1^{st}$ Post-linker and the $2^{nd}$ Post-linker is between 2 and 6, such as 2, 4, or 6.
170. The derivative of any of embodiments 1-169, wherein each of the $1^{st}$ and $2^{nd}$ Post-linker comprises one Linker element-4 of Chem. 4, which is a di-radical of gGlu, preferably in the L-form.
171. The derivative of any of embodiments 1-170, wherein each of the $1^{st}$ and $2^{nd}$ Post-linker comprises one Linker element-3 of Chem. 3, which is a di-radical of tranexamic acid, preferably trans-4-(aminomethyl)cyclohexanecarboxylic acid.
172. The derivative of any of embodiments 1-171, wherein the number of juxtaposed Linker element-1 in the Pre-linker, if present, is between 2 and 4, such as 2, or 4.
173. The derivative of any of embodiments 1-172, which is selected from Chem. 23, Chem. 30, Chem. 31, Chem. 32, and Chem. 48; or a pharmaceutically acceptable salt, amide, or ester thereof.
174. A GLP-1 derivative, preferably the derivative of any of embodiments 1-173, which is selected from Chem. 21, Chem. 22, Chem. 23, Chem. 24, Chem. 25, Chem. 26, Chem. 27, Chem. 28, Chem. 29, Chem. 30, Chem. 31, Chem. 32, Chem. 33, Chem. 34, Chem. 35, Chem. 36, Chem. 37, Chem. 38, Chem. 39, Chem. 40, Chem. 41, Chem. 42, Chem. 43, Chem. 44, Chem. 45, Chem. 46, Chem. 47, Chem. 48, Chem. 49, Chem. 50, Chem. 51, and Chem. 52; or a pharmaceutically acceptable salt, amide, or ester thereof.
175. A GLP-1 derivative, preferably the derivative of any of embodiments 1-174, which is selected from the compounds of Examples 1-32, or a pharmaceutically acceptable salt, amide, or ester thereof.
176. A GLP-1 analogue which comprises the following changes when compared to GLP-1(7-37) (SEQ ID NO: 1): (7Imp, 8Aib, 22E, 26R, 34R, 37K), (8Aib, 22E, 26R, 34R, 37P), or (8Aib, 22E, 26R, 34R, 37P, 38K).
177. A GLP-1 analogue such as the GLP-1 analogue of embodiment 176 which is selected from SEQ ID NO: 3, SEQ ID NO: 4, SEQ ID NO: 6, SEQ ID NO: 7, and SEQ ID NO: 8; or a pharmaceutically acceptable salt, amide, or ester thereof.
178. The GLP-1 analogue of any of embodiments 176-177 which is an intermediate of the GLP-1 derivative of any of embodiments 1-175.
179. A compound of formula II:

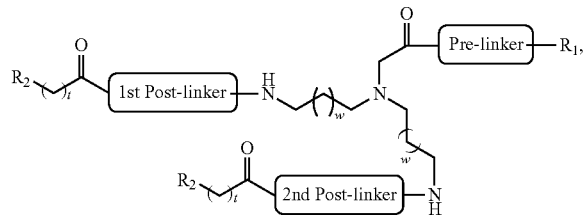

wherein
w is an integer in the range of 0-2,
t is 15, 16, or 18,
$R_1$ is —OH or a suitable activation group, $R_2$ is —COOH, —SO$_3$H, a suitable protective group for —COOH, or a suitable protective group for —SO$_3$H,
the Pre-linker is optional, and each of the $1^{st}$ and the $2^{nd}$ Post-linker preferably comprises an —NH group and a —CO group;
which side chain moiety comprises at least one Linker element-1 of Chem. 1:

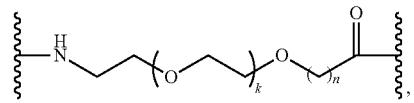

wherein k is an integer in the range of 1-23, and n is an integer in the range of 1-5;
with the proviso that
if the Pre-linker is present it comprises a Linker element-1 and $R_1$ is attached to the —CO group thereof, or
if the Pre-linker is absent, each of the $1^{st}$ Post-linker and the $2^{nd}$ Post-linker comprises a Linker element-1, and $R_1$ is attached to the —CO group shown on the left-hand side of the Pre-linker in formula II;

or a pharmaceutically acceptable salt, amide, or ester thereof.
180. The compound of embodiment 179, wherein w is 1.
181. The compound of any of embodiments 179-180, wherein t is 15, and $R_2$ is —SO$_3$H or a suitable protective group for —SO$_3$H.
182. The compound of any of embodiments 179-180, wherein t is 16 and $R_1$ is —OH or a suitable activation group.
183. The compound of any of embodiments 179-180, wherein t is 18 and $R_1$ is —OH or a suitable activation group.
184. The compound of any of embodiments 179-183, wherein $R_1$ is —OH or a suitable leaving group.
185. The compound of any of embodiments 179-184, wherein $R_1$ is —OH.
186. The compound of any of embodiments 179-184, wherein $R_1$ is a suitable leaving group forming an active ester together with a carbonyl group.
187. The compound of any of embodiments 179-184 and 186, wherein $R_1$ is selected from Chem. 120 (—OPfp), Chem. 121 (OPnp), and Chem. 122 (OSuc).
188. The compound of any of embodiments 179-187, wherein $R_2$ is —COOH.
189. The compound of any of embodiments 179-187, wherein $R_2$ is —SO$_3$H.
190. The compound of any of embodiments 179-187, wherein $R_2$ is a suitable protective group for —COOH.
191. The compound of any of embodiments 179-187, wherein the protective group for —COOH is a suitable non-reactive ester.
192. The compound of embodiment 191, wherein the non-reactive ester is selected from Chem. 123 (—COOtBu), Chem. 124 (—COOBz), Chem. 125 (—COOMe), and Chem. 127 (—COCH$_2$CCl$_3$).
193. The compound of any of embodiments 179-187, wherein $R_2$ is a suitable protective group for —SO$_3$H.
194. The compound of embodiment 193, wherein the protective group for —SO$_3$H is a suitable sulfonic ester.
195. The compound of embodiment 194, wherein the sulfonic ester is selected from Chem. 126 (—COSC(CH$_3$)$_3$) and Chem. 128 (—SO$_3$CH(CH$_3$)C$_7$H$_7$).

196. The compound of any of embodiments 179-195, wherein k is 1, 3, 11, 15, or 23.
197. The compound of any of embodiments 179-196, wherein k is 1.
198. The compound of any of embodiments 179-196, wherein k is 3.
199. The compound of any of embodiments 179-196, wherein k is 11.
200. The compound of any of embodiments 179-196, wherein k is 15.
201. The compound of any of embodiments 179-196, wherein k is 23.
202. The compound of any of embodiments 179-201, wherein n is 1 or 2.
203. The compound of any of embodiments 179-202, wherein n is 1.
204. The compound of any of embodiments 179-202, wherein n is 2.
205. The compound of any of embodiments 179-204, wherein k is 1 and n is 1.
206. The compound of any of embodiments 179-204, wherein k is 3 and n is 2.
207. The compound of any of embodiments 179-204, wherein k is 11 and n is 2.
208. The compound of any of embodiments 179-204, wherein k is 15 and n is 2.
209. The compound of any of embodiments 179-204, wherein k is 23 and n is 2.
210. The compound of any of embodiments 179-209, wherein the Pre-linker is present.
211. The compound of any of embodiments 179-209, wherein the Pre-linker is absent.
212. The compound of any of embodiments 179-211, which comprises at least two times Linker element-1.
213. The compound of any of embodiments 179-212, which includes exactly m times Linker element-1, where m is an integer in the range of 2-12.
214. The compound of embodiment 213, wherein m is 2.
215. The compound of embodiment 213, wherein m is 4.
216. The compound of embodiment 213, wherein m is 6.
217. The compound of embodiment 213, wherein m is 8.
218. The compound of embodiment 213, wherein m is 10.
219. The compound of embodiment 213, wherein m is 12.
220. The compound of any of embodiments 179-219, wherein the $1^{st}$ and the $2^{nd}$ Post-linker each includes exactly s times the Linker element-1 of Chem. 1, where s is 0 or an integer in the range of 1-6, and at least one further linker element selected from Linker element-2 of Chem. 2, Linker element-3 of Chem. 3, Linker element-4 of Chem. 4, Linker element-5 of Chem. 5, and Linker element-6 of Chem. 6; wherein in Chem. 4 the free acid group (—COOH) is substituted with $R_3$,
in Chem. 2 the free amino group (—$NH_2$) is substituted with $R_5$, and
in Chem. 6 the free hydroxyl group (—OH) is substituted with $R_4$,
wherein
$R_3$ is selected from —COOH and suitable protective groups for carboxylic acid groups;
$R_4$ is selected from —OH and suitable protective groups for hydroxy groups; and
$R_5$ is selected from —$NH_2$ and suitable protective groups for amino groups.

221. The compound of embodiment 220, wherein $R_3$ is —COOH.
222. The compound of embodiment 220, wherein $R_3$ is a suitable protective group for a carboxylic acid group.
223. The compound of embodiment 220, wherein the suitable protective group for a carboxylic acid group is a suitable ester group.
224. The compound of embodiment 223, wherein the suitable ester group is selected from Chem. 123 (—COOtBu), Chem. 124 (—COOBz), Chem. 125 (—COOMe), Chem. 126 (—COSC($CH_3$)$_3$), and Chem. 127 (—COC$H_2$C$Cl_3$).
225. The compound of any of embodiments 220-224, wherein $R_4$ is —OH.
226. The compound of any of embodiments 220-224, wherein $R_4$ is a suitable protective group for a hydroxy group.
227. The compound of embodiment 226, wherein the suitable protective group for a hydroxy group is a suitable ether group or a suitable ester group.
228. The compound of embodiment 227, wherein the suitable ether group, and the suitable ester group, respectively, is selected from the following ether and ester groups, respectively: Chem. 129 (—OtBu), Chem. 130 (—OC$H_2$OC$H_3$), Chem. 131 (tetrahydropyran-2-yloxy), Chem. 132 (—OC$H_2$CHC$H_2$), Chem. 133 (—OBz), Chem. 134 (—OSi($CH_3$)$_2$C($CH_3$)$_3$), Chem. 135 (—OSi($C_6H_5$)C($CH_3$)$_3$), Chem. 136 (—OCOC$H_3$), and Chem. 137 (—OCOC$_6H_5$).
229. The compound of any of embodiments 220-228, wherein $R_5$ is selected from —$NH_2$ and suitable protective groups for amino groups.
230. The compound of any of embodiments 220-229, wherein $R_5$ is —$NH_2$.
231. The compound of any of embodiments 220-229, wherein $R_5$ is a suitable protective group for an amino group.
232. The compound of embodiment 231, wherein the suitable protective group for an amino group is a suitable carbamate.
233. The compound of embodiment 232, wherein the suitable carbamate is selected from Chem. 138 (—NHFmoc), Chem. 139 (—NHBoc), and Chem. 140 (—NHCbz).
234. The compound of any of embodiments 220-233, wherein each of the $1^{st}$ Post-linker and the $2^{nd}$ Post-linker comprises at least two of said further linker elements, of the same or different kind.
235. The compound of any of embodiments 220-234, wherein each of the $1^{st}$ Post-linker and the $2^{nd}$ Post-linker comprises no more than four of said further linker elements, of the same or different kind.
236. The compound of any of embodiments 220-235, wherein each of the $1^{st}$ Post-linker and the $2^{nd}$ Post-linker comprises no more than three of said further linker elements, of the same or different kind.
237. The compound of any of embodiments 220-236, wherein the one or more further linker element(s) selected from Linker element-2 (eps-Lys), Linker element-4 (gGlu), and Linker element-6 (Ser) is/are in the L-form.
238. The compound of any of embodiments 220-237, wherein the one or more further linker element(s) selected from Linker element-3 (Trx) is a di-radical of trans-4-(aminomethyl)cyclohexanecarboxylic acid.
239. A compound selected from Chem. 90, Chem. 91, Chem. 92, Chem. 93, Chem. 94, Chem. 95, Chem. 96, Chem. 97, Chem. 98, Chem. 99, Chem. 100, Chem. 101, Chem. 102, Chem. 103, Chem. 104, Chem. 105, Chem. 106, Chem. 107, Chem. 108, Chem. 109, Chem. 110, Chem. 111, Chem. 112, Chem. 113, Chem. 114, Chem. 115, and Chem. 116; or a pharmaceutically acceptable salt, amide, or ester thereof.

240. The compound of embodiment 239, wherein the various Chem. nos. are defined in Tables A and B in the description.
241. The compound of any of embodiments 239-240, which is a compound of any of embodiments 179-238.
242. The compound of any of embodiments 179-241, which is an intermediate of the GLP-1 derivative of any of embodiments 1-175.
243. Use of the compound of any of embodiments 179-242 for attachment to a biologically active peptide or protein under the formation of a derivative thereof.
244. The use of embodiment 243 which has the effect of prolonging the duration of action and/or improving the pharmacokinetic properties in vivo of the derivative as compared to that of the biologically active peptide or protein, in any relevant animal model.
245. The use of any of embodiments 243-244, wherein the compound is attached to a Lys residue of the biologically active peptide or protein, under the formation of an amide bond between the epsilon amino group of the Lys residue and
  i) if a Pre-linker is present, the —CO group of the Pre-linker, or
  ii) if a Pre-linker is absent, the —CO group to which the Pre-linker is attached, by reference to Formula II.
246. The use of any of embodiments 243-245, wherein the biologically active peptide or protein is GLP-1(7-37) (SEQ ID NO: 1) or an analogue thereof, preferably an analogue as defined in any of embodiments 1-28.
247. A method of preparing a derivative of a biologically active peptide or protein which method comprises attaching a compound as defined in any of embodiments 179-242 to the biologically active peptide or protein.
248. The method of embodiment 247 which comprises the step of synthesising the compound, e.g. on solid support or by solution phase chemistry.
249. The method of any of embodiments 247-248, which comprises the step of attaching the compound to the biologically active peptide or protein, e.g. using appropriate activation and protective groups.
250. The method of any of embodiments 247-249, wherein the derivative has an improved duration of action and/or improved pharmacokinetic properties in vivo as compared to that of the pharmaceutical peptide, in any relevant animal model.
251. The method of any of embodiments 247-250, wherein the compound is attached to a Lys residue of the biologically active peptide or protein, under the formation of an amide bond between the epsilon amino group of the Lys residue and
  i) if a Pre-linker is present, the —CO group of the Pre-linker, or
  ii) if a Pre-linker is absent, the —CO group to which the Pre-linker is attached, by reference to Formula II.
252. The method of any of embodiments 247-251, wherein the biologically active peptide or protein is GLP-1(7-37) (SEQ ID NO: 1) or an analogue thereof, preferably an analogue as defined in any of embodiments 1-28.
253. A method of preparing a compound according to any of embodiments 179-242, which is conducted on solid support or by solution phase chemistry.
254. The method of embodiment 253 which is conducted on solid support.
255. The method of any of embodiments 253-254, wherein appropriate activation and protective groups are used.
256. The method of any of embodiments 253-255, wherein the compound is prepared on a suitable resin.
257. The method of any of embodiments 253-256, wherein an appropriately protected reagent dissolved in a suitable solvent is coupled to the resin.
258. The method of any of embodiments 253-257, wherein the protection is removed by appropriate treatment and one or more subsequent corresponding coupling and de-protecting steps are performed, with resin washing step(s) in between.
259. The method of any of embodiments 253-258, wherein a repetitive cycle of coupling, washing, protection removal, and washing is performed.
260. The method of any of embodiments 253-259, which results in the crude compound of any of embodiments 179-242.
261. The method of any of embodiments 253-260, wherein the compound is liberated from the resin using a suitable reagent.
262. The method of any of embodiments 253-261, wherein the compound is concentrated, e.g. concentrated to dryness in vacuo.
263. The method of any of embodiments 253-262, wherein the compound is purified, e.g. using flash chromatography.
264. The method of any of embodiments 253-265, wherein the compound is activated for coupling to a biologically active peptide or protein.
265. The method of any of embodiments 253-264, wherein the activated compound is dissolved in a suitable solvent.
266. The method of any of embodiments 253-265, wherein the biologically active peptide or protein is dissolved in a suitable solvent.
267. The method of any of embodiments 253-266, wherein the activated compound is added drop wise to the dissolved peptide or protein under stirring at a suitable pH for a suitable time and then left for a suitable time for the reaction to occur.
268. The method of any of embodiments 253-267, wherein after the attachment reaction the pH is changed to the isoelectric point of the resulting derivative (peptide-side-chain conjugate) and the precipitated derivative is isolated, e.g. by centrifugation.
269. The method of any of embodiments 253-268, wherein the precipitate is washed in one or more additional steps with a suitable washing medium and then isolated, e.g. by centrifugation.
270. A method of preparing a compound according to any of embodiments 179-242, wherein the compound is prepared by solution phase chemistry.
271. The method of embodiment 270, wherein the compound is attached to a biologically active peptide or protein using suitable activation and protective groups.
272. The method of any of embodiments 270-271, wherein for attachment of the thus prepared compound to the peptide or protein one or more steps of any of embodiments 264-269 are applied.
273. The derivative or analogue of any of embodiments 1-178, which is a GLP-1 receptor agonist.
274. The derivative or analogue of any of embodiments 1-178 or 273, which is a full GLP-1 receptor agonist.
275. The derivative or analogue of any of embodiments 1-178 or 273-274, which is biologically active in vitro.
276. The derivative or analogue of any of embodiments 1-178 or 273-275, which is potent in vitro.
277. The derivative or analogue of any of embodiments 1-178 or 273-276, which is capable of activating the human GLP-1 receptor.
278. The derivative or analogue of any of embodiments 1-178 or 273-277, which is capable of activating the human GLP-1 receptor in an assay with whole cells expressing the human GLP-1 receptor, wherein the assay is performed in the absence of HSA (0% HSA).

279. The derivative or analogue of any of embodiments 1-178 or 273-278, where the response of the human GLP-1 receptor is measured in a reporter gene assay, such as the assay of Example 33.

280. The derivative or analogue of any of embodiments 273-279, wherein the GLP-1 receptor agonism, the in vitro biological activity, the in vitro potency, or the capability of activating the human GLP-1 receptor, respectively, is determined essentially as described in Example 33.

281. The derivative or analogue of any of embodiments 1-178 or 273-280, which has an in vitro potency corresponding to an $EC_{50}$ of 300 pM or below.

282. The derivative or analogue of any of embodiments 1-178 or 273-281, which has an in vitro potency corresponding to an $EC_{50}$ of 200 pM or below.

283. The derivative or analogue of any of embodiments 1-178 or 273-282, which has an in vitro potency corresponding to an $EC_{50}$ of 100 pM or below.

284. The derivative or analogue of any of embodiments 1-178 or 273-283, which has an in vitro potency corresponding to an $EC_{50}$ of 75 pM or below.

285. The derivative or analogue of any of embodiments 1-178 or 273-284, which has an in vitro potency corresponding to an $EC_{50}$ of 50 pM or below.

286. The derivative or analogue of any of embodiments 1-178 or 273-285, which has an in vitro potency corresponding to an $EC_{50}$ of 25 pM or below.

287. The derivative or analogue of any of embodiments 1-178 or 273-286, which has an in vitro potency corresponding to an $EC_{50}$ of 15 pM or below.

288. The derivative or analogue of any of embodiments 1-178 or 273-287, which has an in vitro potency corresponding to an $EC_{50}$ of 10 pM or below.

289. The derivative or analogue of any of embodiments 1-178 or 273-288, which has an in vitro potency corresponding to an $EC_{50}$ of 7.0 pM or below.

290. The derivative or analogue of any of embodiments 1-178 or 273-289, which has an in vitro potency corresponding to an $EC_{50}$ of 5.0 pM or below.

291. The derivative or analogue of any of embodiments 1-178 or 273-290, which has an in vitro potency corresponding to an $EC_{50}$ of 3.0 pM or below.

292. The derivative or analogue of any of embodiments 1-178 or 273-291, wherein the $EC_{50}$ is determined essentially as described in Example 33.

293. The derivative or analogue of any of embodiments 1-178 or 273-292, which has an in vitro potency corresponding to an $EC_{50}$ of less than 30 times the $EC_{50}$ of semaglutide, wherein the $EC_{50}$ of semaglutide is determined in the same way as the $EC_{50}$ of the derivative.

294. The derivative or analogue of any of embodiments 1-178 or 273-293, which has an in vitro potency corresponding to an $EC_{50}$ of less than 20 times the $EC_{50}$ of semaglutide, wherein the $EC_{50}$ of semaglutide is determined in the same way as the $EC_{50}$ of the derivative.

295. The derivative or analogue of any of embodiments 1-178 or 273-294, which has an in vitro potency corresponding to an $EC_{50}$ of less than 10 times the $EC_{50}$ of semaglutide, wherein the $EC_{50}$ of semaglutide is determined in the same way as the $EC_{50}$ of the derivative.

296. The derivative or analogue of any of embodiments 1-178 or 273-295, which has an in vitro potency corresponding to an $EC_{50}$ of less than 7 times the $EC_{50}$ of semaglutide, wherein the $EC_{50}$ of semaglutide is determined in the same way as the $EC_{50}$ of the derivative.

297. The derivative or analogue of any of embodiments 1-178 or 273-296, which has an in vitro potency corresponding to an $EC_{50}$ of less than 5 times the $EC_{50}$ of semaglutide, wherein the $EC_{50}$ of semaglutide is determined in the same way as the $EC_{50}$ of the derivative.

298. The derivative or analogue of any of embodiments 1-178 or 273-297, which has an in vitro potency corresponding to an $EC_{50}$ of less than 2 times the $EC_{50}$ of semaglutide, wherein the $EC_{50}$ of semaglutide is determined in the same way as the $EC_{50}$ of the derivative.

299. The derivative or analogue of any of embodiments 1-178 or 273-298, which has an in vitro potency corresponding to an $EC_{50}$ of less than the $EC_{50}$ of semaglutide, wherein the $EC_{50}$ of semaglutide is determined in the same way as the $EC_{50}$ of the derivative.

300. The derivative or analogue of any of embodiments 1-178 or 273-299, which has an in vitro potency corresponding to an $EC_{50}$ of less than half the $EC_{50}$ of semaglutide, wherein the $EC_{50}$ of semaglutide is determined in the same way as the $EC_{50}$ of the derivative.

301. The derivative or analogue of any of embodiments 1-178 or 273-300, which has an in vitro potency corresponding to an $EC_{50}$ of less than 30% of the $EC_{50}$ of semaglutide, wherein the $EC_{50}$ of semaglutide is determined in the same way as the $EC_{50}$ of the derivative.

302. The derivative or analogue of any of embodiments 1-178 or 273-301, wherein the $EC_{50}$ is determined essentially as described in Example 33.

303. The derivative or analogue of any of embodiments 1-178 or 273-302, which is capable of binding to the GLP-1 receptor.

304. The derivative or analogue of any of embodiments 1-178 or 273-303, which is capable of binding to the GLP-1 receptor at a low concentration of HSA (max. 0.001% final assay concentration).

305. The derivative or analogue of any of embodiments 1-178 or 273-304, which is capable of binding to the GLP-1 receptor at a high concentration of HSA (2.0% final assay concentration).

306. The derivative or analogue of any of embodiments 303-305, wherein the binding to the human GLP-1 receptor is measured in a competitive binding assay, such as the assay of Example 34.

307. The derivative or analogue of any of embodiments 303-306, wherein the binding to the human GLP-1 receptor in vitro is determined essentially as described in Example 34.

308. The derivative or analogue of any of embodiments 1-178 or 273-307, which at a low concentration of HSA is capable of binding to the human GLP-1 receptor with an $IC_{50}$ of 5.0 nM or below.

309. The derivative or analogue of any of embodiments 1-178 or 273-308, which at a low concentration of HSA is capable of binding to the human GLP-1 receptor with an $IC_{50}$ of 3.0 nM or below.

310. The derivative or analogue of any of embodiments 1-178 or 273-309, which at a low concentration of HSA is capable of binding to the human GLP-1 receptor with an $IC_{50}$ of 2.0 nM or below.

311. The derivative or analogue of any of embodiments 1-178 or 273-310, which at a low concentration of HSA is capable of binding to the human GLP-1 receptor with an $IC_{50}$ of 1.0 nM or below.

312. The derivative or analogue of any of embodiments 1-178 or 273-311, which at a low concentration of HSA is capable of binding to the human GLP-1 receptor with an $IC_{50}$ of 0.50 nM or below.

313. The derivative or analogue of any of embodiments 1-178 or 273-312, which at a low concentration of HSA is capable of binding to the human GLP-1 receptor with an $IC_{50}$ of 0.30 nM or below.

314. The derivative or analogue of any of embodiments 1-178 or 273-313, which at a low concentration of HSA is capable of binding to the human GLP-1 receptor with an $IC_{50}$ of 0.15 nM or below.

315. The derivative or analogue of any of embodiments 1-178 or 273-314, which at a low concentration of HSA is capable of binding to the human GLP-1 receptor with an $IC_{50}$ of 0.10 nM or below.

316. The derivative or analogue of any of embodiments 308-315, wherein the $IC_{50}$ is determined essentially as described in Example 34, in a reaction with max. 0.001% HSA (final assay concentration).

317. The derivative or analogue of any of embodiments 1-178 or 273-316, which at a low concentration of HSA is capable of binding to the human GLP-1 receptor with an $IC_{50}$ of less than 10 times the $IC_{50}$ of semaglutide, wherein the $IC_{50}$ of semaglutide is determined in the same way as the $IC_{50}$ of the derivative.

318. The derivative or analogue of any of embodiments 1-178 or 273-317, which at a low concentration of HSA is capable of binding to the human GLP-1 receptor with an $IC_{50}$ of less than 8 times the $IC_{50}$ of semaglutide, wherein the $IC_{50}$ of semaglutide is determined in the same way as the $IC_{50}$ of the derivative.

319. The derivative or analogue of any of embodiments 1-178 or 273-318, which at a low concentration of HSA is capable of binding to the human GLP-1 receptor with an $IC_{50}$ of less than 6 times the $IC_{50}$ of semaglutide, wherein the $IC_{50}$ of semaglutide is determined in the same way as the $IC_{50}$ of the derivative.

320. The derivative or analogue of any of embodiments 1-178 or 273-319, which at a low concentration of HSA is capable of binding to the human GLP-1 receptor with an $IC_{50}$ of less than 4 times the $IC_{50}$ of semaglutide, wherein the $IC_{50}$ of semaglutide is determined in the same way as the $IC_{50}$ of the derivative.

321. The derivative or analogue of any of embodiments 1-178 or 273-320, which at a low concentration of HSA is capable of binding to the human GLP-1 receptor with an $IC_{50}$ of less than 2 times the $IC_{50}$ of semaglutide, wherein the $IC_{50}$ of semaglutide is determined in the same way as the $IC_{50}$ of the derivative.

322. The derivative or analogue of any of embodiments 1-178 or 273-321, which at a low concentration of HSA is capable of binding to the human GLP-1 receptor with an $IC_{50}$ of less than the $IC_{50}$ of semaglutide, wherein the $IC_{50}$ of semaglutide is determined in the same way as the $IC_{50}$ of the derivative.

323. The derivative or analogue of any of embodiments 1-178 or 273-322, which at a low concentration of HSA is capable of binding to the human GLP-1 receptor with an $IC_{50}$ of less than 0.50 times the $IC_{50}$ of semaglutide, wherein the $IC_{50}$ of semaglutide is determined in the same way as the $IC_{50}$ of the derivative.

324. The derivative or analogue of any of embodiments 1-178 or 273-323, which at a low concentration of HSA is capable of binding to the human GLP-1 receptor with an $IC_{50}$ of less than 0.25 times the $IC_{50}$ of semaglutide, wherein the $IC_{50}$ of semaglutide is determined in the same way as the $IC_{50}$ of the derivative.

325. The derivative or analogue of any of embodiments 1-178 or 273-324, which at a low concentration of HSA is capable of binding to the human GLP-1 receptor with an $IC_{50}$ of less than 0.15 times the $IC_{50}$ of semaglutide, wherein the $IC_{50}$ of semaglutide is determined in the same way as the $IC_{50}$ of the derivative.

326. The derivative or analogue of any of embodiments 317-325, wherein the $IC_{50}$ is determined essentially as described in Example 34, in a reaction with max. 0.001% HSA (final assay concentration).

327. The derivative or analogue of any of embodiments 1-178 or 273-326, which at 2.0% HSA (final assay concentration) is capable of binding to the human GLP-1 receptor with an $IC_{50}$ of 300 nM or below.

328. The derivative or analogue of any of embodiments 1-178 or 273-327, which at 2.0% HSA (final assay concentration) is capable of binding to the human GLP-1 receptor with an $IC_{50}$ of 125 nM or below.

329. The derivative or analogue of any of embodiments 1-178 or 273-328, which at 2.0% HSA (final assay concentration) is capable of binding to the human GLP-1 receptor with an $IC_{50}$ of 75 nM or below.

330. The derivative or analogue of any of embodiments 1-178 or 273-329, which at 2.0% HSA (final assay concentration) is capable of binding to the human GLP-1 receptor with an $IC_{50}$ of 50 nM or below.

331. The derivative or analogue of any of embodiments 1-178 or 273-330, which at 2.0% HSA (final assay concentration) is capable of binding to the human GLP-1 receptor with an $IC_{50}$ of 30 nM or below.

332. The derivative or analogue of any of embodiments 1-178 or 273-331, which at 2.0% HSA (final assay concentration) is capable of binding to the human GLP-1 receptor with an $IC_{50}$ of 15 nM or below.

333. The derivative or analogue of any of embodiments 1-178 or 273-332, which at 2.0% HSA (final assay concentration) is capable of binding to the human GLP-1 receptor with an $IC_{50}$ of 8 nM or below.

334. The derivative or analogue of any of embodiments 327-333, wherein the $IC_{50}$ is determined essentially as described in Example 34, in a reaction with 2.0% HSA (final assay concentration).

335. The derivative or analogue of any of embodiments 1-178 or 273-334, which at 2.0% HSA (final assay concentration) is capable of binding to the human GLP-1 receptor with an $IC_{50}$ of less than the $IC_{50}$ of semaglutide, wherein the $IC_{50}$ of semaglutide is determined in the same way as the $IC_{50}$ of the derivative.

336. The derivative or analogue of any of embodiments 1-178 or 273-335, which at 2.0% HSA (final assay concentration) is capable of binding to the human GLP-1 receptor with an $IC_{50}$ of less than 0.5 times the $IC_{50}$ of semaglutide, wherein the $IC_{50}$ of semaglutide is determined in the same way as the $IC_{50}$ of the derivative.

337. The derivative or analogue of any of embodiments 1-178 or 273-336, which at 2.0% HSA (final assay concentration) is capable of binding to the human GLP-1 receptor with an $IC_{50}$ of less than 0.25 times the $IC_{50}$ of semaglutide, wherein the $IC_{50}$ of semaglutide is determined in the same way as the $IC_{50}$ of the derivative.

338. The derivative or analogue of any of embodiments 1-178 or 273-337, which at 2.0% HSA (final assay concentration) is capable of binding to the human GLP-1 receptor with an $IC_{50}$ of less than 0.10 times the $IC_{50}$ of semaglutide, wherein the $IC_{50}$ of semaglutide is determined in the same way as the $IC_{50}$ of the derivative.

339. The derivative or analogue of any of embodiments 1-178 or 273-338, which at 2.0% HSA (final assay concentration) is capable of binding to the human GLP-1 receptor with an $IC_{50}$ of less than 0.050 times the $IC_{50}$ of semaglutide, wherein the $IC_{50}$ of semaglutide is determined in the same way as the $IC_{50}$ of the derivative.

340. The derivative or analogue of any of embodiments 1-178 or 273-339, which at 2.0% HSA (final assay concentration) is capable of binding to the human GLP-1 receptor with an $IC_{50}$ of less than 0.020 times the $IC_{50}$ of semaglutide, wherein the $IC_{50}$ of semaglutide is determined in the same way as the $IC_{50}$ of the derivative.

341. The derivative or analogue of any of embodiments 335-340, wherein the $IC_{50}$ is determined essentially as described in Example 34, in a reaction with 2.0% HSA (final assay concentration).

342. The derivative of any of embodiments 1-178 or 273-341, which has improved pharmacokinetic properties.

343. The derivative of any of embodiments 1-178 or 273-342, which has an increased half-life and/or a decreased clearance.

344. The derivative of any of embodiments 1-178 or 273-343, which is suitable for once-monthly administration.

345. The derivative of any of embodiments 1-178 or 273-344, for s.c. administration.

346. The derivative of any of embodiments 1-178 or 273-345, wherein the derivative is tested in vivo in pharmacokinetic (PK) studies.

347. The derivative of any of embodiments 1-178 or 273-346, wherein the derivative is tested in any suitable animal model, such as mouse, rat, monkey, dog, or pig.

348. The derivative of any of embodiments 1-178 or 273-347, which is compared with semaglutide.

349. The derivative of any of embodiments 1-178 or 273-348, which has an improved terminal half-life (T½) in vivo in minipigs after i.v. administration as compared to semaglutide.

350. The derivative of embodiment 349, wherein the terminal half-life is determined in vivo in minipigs after i.v. administration using any suitable study protocol, such as the one described in Example 35.

351. The derivative of any of embodiments 349-350, wherein the terminal half-life is determined in vivo in minipigs after i.v. administration, essentially as described in Example 35.

352. The derivative of any of embodiments 1-178 or 273-351, which has a terminal half-life (T½) in vivo in minipigs after i.v. administration of at least 100 hours.

353. The derivative of any of embodiments 1-178 or 273-352, which has a terminal half-life (T½) in vivo in minipigs after i.v. administration of at least 115 hours.

354. The derivative of any of embodiments 1-178 or 273-353, which has a terminal half-life (T½) in vivo in minipigs after i.v. administration of at least 130 hours.

355. The derivative of any of embodiments 1-178 or 273-354, which has a terminal half-life (T½) in vivo in minipigs after i.v. administration of at least 145 hours.

356. The derivative of any of embodiments 1-178 or 273-355, which has a terminal half-life (T½) in vivo in minipigs after i.v. administration of at least 155 hours.

357. The derivative of any of embodiments 1-178 or 273-356, which has a terminal half-life (T½) in vivo in minipigs after i.v. administration of at least 180 hours.

358. The derivative of any of embodiments 1-178 or 273-357, which has a terminal half-life (T½) in vivo in minipigs after i.v. administration of at least 200 hours.

359. The derivative of any of embodiments 1-178 or 273-358, which has a terminal half-life (T½) in vivo in minipigs after i.v. administration of at least 225 hours.

360. The derivative of any of embodiments 1-178 or 273-359, which has a terminal half-life (T½) in vivo in minipigs after i.v. administration of at least 2.0 times the terminal half-life of semaglutide, determined in the same way.

361. The derivative of any of embodiments 1-178 or 273-360, which has a terminal half-life (T½) in vivo in minipigs after i.v. administration of at least 2.5 times the terminal half-life of semaglutide, determined in the same way.

362. The derivative of any of embodiments 1-178 or 273-361, which has a terminal half-life (T½) in vivo in minipigs after i.v. administration of at least 2.8 times the terminal half-life of semaglutide, determined in the same way.

363. The derivative of any of embodiments 1-178 or 273-362, which has a terminal half-life (T½) in vivo in minipigs after i.v. administration of at least 3.0 times the terminal half-life of semaglutide, determined in the same way.

364. The derivative of any of embodiments 1-178 or 273-363, which has a terminal half-life (T½) in vivo in minipigs after i.v. administration of at least 3.5 times the terminal half-life of semaglutide, determined in the same way.

365. The derivative of any of embodiments 1-178 or 273-364, which has a terminal half-life (T½) in vivo in minipigs after i.v. administration of at least 4.0 times the terminal half-life of semaglutide, determined in the same way.

366. The derivative of any of embodiments 352-365, wherein the terminal half-life ($T_{1/2}$) is determined essentially as described in Example 35.

367. The derivative of any of embodiments 1-178 or 273-366, which is potent in vivo.

368. The derivative of any of embodiments 1-178 or 273-367, which is potent in vivo when determined in any suitable animal model, such as mouse, rat, or pig.

369. The derivative of embodiment 368, wherein the animal model is Sprague Dawley rats.

370. The derivative of any of embodiments 1-178 or 273-369, wherein an acute effect on food intake is determined, wherein acute preferably refers to a single s.c. injection of a suitable dose of the derivative in question.

371. The derivative of embodiment 370, wherein a suitable dose is 100 nmol/kg.

372. The derivative of embodiment 370, wherein a suitable dose is 50 nmol/kg.

373. The derivative of any of embodiments 1-178 or 273-372, wherein an acute effect on body weight is determined, and wherein acute preferably refers to a single s.c. injection of a suitable dose of the derivative in question.

374. The derivative of embodiment 373, wherein a suitable dose is 100 nmol/kg.

375. The derivative of embodiment 373, wherein a suitable dose is 50 nmol/kg.

376. The derivative of any of embodiments 1-178 or 273-375, wherein an acute effect on food intake and/or body weight is determined in vivo in Sprague Dawley rats using any suitable study protocol and methodology, e.g. as described in Example 36.

377. The derivative of any of embodiments 1-178 or 273-376, wherein an acute effect on food intake and/or body weight is determined in vivo in Sprague Dawley rats, essentially as described in Example 36.

378. The derivative of any of embodiments 367-377, wherein the acute effect is a change in food intake at 48 h of at least −20%, calculated as [[(food intake at 48 h)−(baseline food intake)]/(baseline food intake)]×100%], where baseline food intake refers to the level before the administration of any treatment.

379. The derivative of any of embodiments 367-378, wherein the acute effect is a change in food intake at 48 h of at least −25%, calculated as [[(food intake at 48 h)−(baseline food intake)]/(baseline food intake)]×100%], where baseline food intake refers to the level before the administration of any treatment.

380. The derivative of any of embodiments 367-379, wherein the acute effect is a change in food intake at 48 h of at least −50%, calculated as [[(food intake at 48 h)−(baseline food intake)]/(baseline food intake)]×100%], where baseline food intake refers to the level before the administration of any treatment.

381. The derivative of any of embodiments 367-380, wherein the acute effect is a change in food intake at 48 h of at least −75%, calculated as [[(food intake at 48 h)−(baseline food intake)]/(baseline food intake)]×100%], where baseline food intake refers to the level before the administration of any treatment.

382. The derivative of any of embodiments 367-381, wherein the acute effect is a change in body weight at 48 h of at least −1%, calculated as [[(body weight at 48 h)−(baseline body weight)]/(baseline body weight)]×100%], where baseline body weight refers to the level before the administration of any treatment.

383. The derivative of any of embodiments 367-382, wherein the acute effect is a change in body weight at 48 h of at least −4%, calculated as [[(body weight at 48 h)−(baseline body weight)]/(baseline body weight)]×100%], where baseline body weight refers to the level before the administration of any treatment.

384. The derivative of any of embodiments 367-383, wherein the acute effect is a change in body weight at 48 h of at least −5%, calculated as [[(body weight at 48 h)−(baseline body weight)]/(baseline body weight)]×100%], where baseline body weight refers to the level before the administration of any treatment.

385. The derivative of any of embodiments 367-384, wherein the acute effect is a change in body weight at 48 h of at least −8%, calculated as [[(body weight at 48 h)−(baseline body weight)]/(baseline body weight)]×100%], where baseline body weight refers to the level before the administration of any treatment.

386. The derivative of any of embodiments 367-385, wherein the acute effect is a change in body weight at 48 h of at least −12%, calculated as [[(body weight at 48 h)−(baseline body weight)]/(baseline body weight)]×100%], where baseline body weight refers to the level before the administration of any treatment.

387. A pharmaceutical composition comprising a derivative or an analogue according to any of embodiments 1-178 or 273-386, and a pharmaceutically acceptable excipient.

388. A derivative or an analogue according to any of embodiments 1-178 or 273-386, for use as a medicament.

389. A derivative or an analogue according to any of embodiments 1-178 or 273-386, for use in (i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C;

(ii) delaying or preventing diabetic disease progression, such as progression in type 2 diabetes, delaying the progression of impaired glucose tolerance (IGT) to insulin requiring type 2 diabetes, delaying or preventing insulin resistance, and/or delaying the progression of non-insulin requiring type 2 diabetes to insulin requiring type 2 diabetes;

(iii) improving β-cell function, such as decreasing β-cell apoptosis, increasing β-cell function and/or β-cell mass, and/or for restoring glucose sensitivity to β-cells;

(iv) prevention and/or treatment of cognitive disorders and/or neurodegenerative disorders, such as Alzheimer's disease, Parkinson's disease, and/or multiple sclerosis;

(v) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, such as osteoarthritis and/or urine incontinence;

(vi) prevention and/or treatment of diabetic complications, such as angiopathy; neuropathy, including peripheral neuropathy; nephropathy; and/or retinopathy;

(vii) improving lipid parameters, such as prevention and/or treatment of dyslipidemia, lowering total serum lipids; increasing HDL; lowering small, dense LDL; lowering VLDL; lowering triglycerides; lowering cholesterol; lowering plasma levels of lipoprotein a (Lp(a)) in a human; inhibiting generation of apolipoprotein a (apo(a)) in vitro and/or in vivo;

(viii) prevention and/or treatment of cardiovascular diseases, such as syndrome X, atherosclerosis, myocardial infarction, coronary heart disease, reperfusion injury, stroke, cerebral ischemia, an early cardiac or early cardiovascular disease, left ventricular hypertrophy, coronary artery disease, hypertension, essential hypertension, acute hypertensive emergency, cardiomyopathy, heart insufficiency, exercise intolerance, acute and/or chronic heart failure, arrhythmia, cardiac dysrhythmia, syncopy, angina pectoris, cardiac bypass and/or stent reocclusion, intermittent claudication (atheroschlerosis oblitterens), diastolic dysfunction, and/or systolic dysfunction; and/or reduction of blood pressure, such as reduction of systolic blood pressure;

(ix) prevention and/or treatment of gastrointestinal diseases, such as inflammatory bowel disease, short bowel syndrome, or Crohn's disease or colitis; dyspepsia, and/or gastric ulcers; and/or inflammation, such as psoriasis, psoriactic arthritis, rheumatoid arthritis, and/or systemic lupus erythematosus;

(x) prevention and/or treatment of critical illness, such as treatment of a critically ill patient, a critical illness polynephropathy (CIPNP) patient, and/or a potential CIPNP patient; prevention of development of critical illness or CIPNP; prevention, treatment and/or cure of systemic inflammatory response syndrome (SIRS) in a patient; prevention or reduction of the likelihood of a patient suffering from bacteraemia, septicaemia, and/or septic shock during hospitalisation; and/or stabilising blood glucose, insulin balance and optionally metabolism in intensive care unit patients with acute illness;

(xi) prevention and/or treatment of polycystic ovary syndrome (PCOS);

(xii) prevention and/or treatment of cerebral disease, such as cerebral ischemia, cerebral haemorrhage, and/or traumatic brain injury;

(xiii) prevention and/or treatment of sleep apnoea; and/or (xiv) prevention and/or treatment of abuse, such as alcohol abuse and/or drug abuse.

390. Use of a derivative or an analogue according to any of embodiments 1-178 or 273-386, in the manufacture of a medicament for (i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C;

(ii) delaying or preventing diabetic disease progression, such as progression in type 2 diabetes, delaying the progression of impaired glucose tolerance (IGT) to insulin requiring type 2 diabetes, delaying or preventing insulin resistance, and/or delaying the progression of non-insulin requiring type 2 diabetes to insulin requiring type 2 diabetes;

(iii) improving β-cell function, such as decreasing β-cell apoptosis, increasing β-cell function and/or β-cell mass, and/or for restoring glucose sensitivity to β-cells;

(iv) prevention and/or treatment of cognitive disorders and/or neurodegenerative disorders, such as Alzheimer's disease, Parkinson's disease, and/or multiple sclerosis;

(v) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, such as osteoarthritis and/or urine incontinence;

(vi) prevention and/or treatment of diabetic complications, such as angiopathy; neuropathy, including peripheral neuropathy; nephropathy; and/or retinopathy;

(vii) improving lipid parameters, such as prevention and/or treatment of dyslipidemia, lowering total serum lipids; increasing HDL; lowering small, dense LDL; lowering VLDL; lowering triglycerides; lowering cholesterol; lowering plasma levels of lipoprotein a (Lp(a)) in a human; inhibiting generation of apolipoprotein a (apo(a)) in vitro and/or in vivo;

(viii) prevention and/or treatment of cardiovascular diseases, such as syndrome X, atherosclerosis, myocardial infarction, coronary heart disease, reperfusion injury, stroke, cerebral ischemia, an early cardiac or early cardiovascular disease, left ventricular hypertrophy, coronary artery disease, hypertension, essential hypertension, acute hypertensive emergency, cardiomyopathy, heart insufficiency, exercise intolerance, acute and/or chronic heart failure, arrhythmia, cardiac dysrhythmia, syncopy, angina pectoris, cardiac bypass and/or stent reocclusion, intermittent claudication (atheroschlerosis oblitterens), diastolic dysfunction, and/or systolic dysfunction; and/or reduction of blood pressure, such as reduction of systolic blood pressure;

(ix) prevention and/or treatment of gastrointestinal diseases, such as inflammatory bowel disease, short bowel syndrome, or Crohn's disease or colitis; dyspepsia, and/or gastric ulcers; and/or inflammation, such as psoriasis, psoriactic arthritis, rheumatoid arthritis, and/or systemic lupus erythematosus;

(x) prevention and/or treatment of critical illness, such as treatment of a critically ill patient, a critical illness polynephropathy (CIPNP) patient, and/or a potential CIPNP patient; prevention of development of critical illness or CIPNP; prevention, treatment and/or cure of systemic inflammatory response syndrome (SIRS) in a patient; prevention or reduction of the likelihood of a patient suffering from bacteraemia, septicaemia, and/or septic shock during hospitalisation; and/or stabilising blood glucose, insulin balance and optionally metabolism in intensive care unit patients with acute illness;

(xi) prevention and/or treatment of polycystic ovary syndrome (PCOS);

(xii) prevention and/or treatment of cerebral disease, such as cerebral ischemia, cerebral haemorrhage, and/or traumatic brain injury;

(xiii) prevention and/or treatment of sleep apnoea; and/or (xiv) prevention and/or treatment of abuse, such as alcohol abuse and/or drug abuse.

391. A method for (i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C;

(ii) delaying or preventing diabetic disease progression, such as progression in type 2 diabetes, delaying the progression of impaired glucose tolerance (IGT) to insulin requiring type 2 diabetes, delaying or preventing insulin resistance, and/or delaying the progression of non-insulin requiring type 2 diabetes to insulin requiring type 2 diabetes;

(iii) improving β-cell function, such as decreasing β-cell apoptosis, increasing β-cell function and/or β-cell mass, and/or for restoring glucose sensitivity to β-cells;

(iv) prevention and/or treatment of cognitive disorders and/or neurodegenerative disorders, such as Alzheimer's disease, Parkinson's disease, and/or multiple sclerosis;

(v) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, such as osteoarthritis and/or urine incontinence;

(vi) prevention and/or treatment of diabetic complications, such as angiopathy; neuropathy, including peripheral neuropathy; nephropathy; and/or retinopathy;

(vii) improving lipid parameters, such as prevention and/or treatment of dyslipidemia, lowering total serum lipids; increasing HDL; lowering small, dense LDL; lowering VLDL; lowering triglycerides; lowering cholesterol; lowering plasma levels of lipoprotein a (Lp(a)) in a human; inhibiting generation of apolipoprotein a (apo(a)) in vitro and/or in vivo;

(viii) prevention and/or treatment of cardiovascular diseases, such as syndrome X, atherosclerosis, myocardial infarction, coronary heart disease, reperfusion injury, stroke, cerebral ischemia, an early cardiac or early cardiovascular disease, left ventricular hypertrophy, coronary artery disease, hypertension, essential hypertension, acute hypertensive emergency, cardiomyopathy, heart insufficiency, exercise intolerance, acute and/or chronic heart failure, arrhythmia, cardiac dysrhythmia, syncopy, angina pectoris, cardiac bypass and/or stent reocclusion, intermittent claudication (atheroschlerosis oblitterens), diastolic dysfunction, and/or systolic dysfunction; and/or reduction of blood pressure, such as reduction of systolic blood pressure;

(ix) prevention and/or treatment of gastrointestinal diseases, such as inflammatory bowel disease, short bowel syndrome, or Crohn's disease or colitis; dyspepsia, and/or gastric ulcers; and/or inflammation, such as psoriasis, psoriactic arthritis, rheumatoid arthritis, and/or systemic lupus erythematosus;

(x) prevention and/or treatment of critical illness, such as treatment of a critically ill patient, a critical illness polynephropathy (CIPNP) patient, and/or a potential CIPNP patient; prevention of development of critical illness or CIPNP; prevention, treatment and/or cure of systemic inflammatory response syndrome (SIRS) in a patient; prevention or reduction of the likelihood of a patient suffering from bacteraemia, septicaemia, and/or septic shock during hospitalisation; and/or stabilising blood glucose, insulin balance and optionally metabolism in intensive care unit patients with acute illness;

(xi) prevention and/or treatment of polycystic ovary syndrome (PCOS);

(xii) prevention and/or treatment of cerebral disease, such as cerebral ischemia, cerebral haemorrhage, and/or traumatic brain injury;

(xiii) prevention and/or treatment of sleep apnoea; and/or (xiv) prevention and/or treatment of abuse, such as alcohol abuse and/or drug abuse;

wherein a pharmaceutically active amount of a derivative or an analogue according to any of embodiments 1-178 or 273-386, is administered.

Additional Particular Embodiments

The following are additional particular embodiments of the invention:

1. A derivative of a GLP-1 analogue of the general Formula I:

Xaa$_7$-Xaa$_8$-Glu-Gly-Thr-Xaa$_{12}$-Thr-Ser-Asp-Xaa$_{16}$-Ser-Xaa$_{18}$-Xaa$_{19}$-Xaa$_{20}$-Glu-Xaa$_{22}$-Xaa$_{23}$-Ala-Xaa$_{25}$-Xaa$_{26}$-Xaa$_{27}$-Phe-Ile-Xaa$_{30}$-Xaa$_{31}$-Leu-Xaa$_{33}$-Xaa$_{34}$-Xaa$_{35}$-Xaa$_{36}$-Xaa$_{37}$-Xaa$_{38}$ (SEQ ID NO:9), wherein Xaa$_7$ is L-histidine, (S)-2-Hydroxy-3-(1H-imidazol-4-yl)-propionic acid, D-histidine, deamino-histidine, homohistidine, N$^\alpha$-acetyl-histidine, N$^\alpha$-formyl-histidine, N$^\alpha$-methyl-histidine, 3-pyridylalanine, 2-pyridylalanine, or 4-pyridylalanine;

Xaa$_8$ is Ala, Gly, Ser, Aib, (1-aminocyclopropyl) carboxylic acid, or (1-aminocyclobutyl) carboxylic acid;

Xaa$_{12}$ is Phe or Leu;

Xaa$_{16}$ is Val or Leu;

Xaa$_{18}$ is Ser, Val, Arg, or Leu;

Xaa$_{19}$ is Tyr or Gln;

Xaa$_{20}$ is Leu or Met;

Xaa$_{22}$ is Gly or Glu;

Xaa$_{23}$ is Gln, Glu, or Arg;

Xaa$_{25}$ is Ala or Val;

Xaa$_{26}$ is Arg;

Xaa$_{27}$ is Glu or Leu;

Xaa$_{30}$ is Ala, Glu, or Arg;

Xaa$_{31}$ is Trp or His;

Xaa$_{33}$ is Val;

Xaa$_{34}$ is Arg, His, Asn, or Gln;

Xaa$_{35}$ is Gly or Ala;

Xaa$_{36}$ is Arg or Gly;

Xaa$_{37}$ is Gly, Pro, or Lys;

Xaa$_{38}$ is Lys, or absent;

wherein at least one of Xaa$_{37}$ and Xaa$_{38}$ is Lys;

which derivative comprises a side chain that is attached to the Lys residue of Xaa$_{37}$ or Xaa$_{38}$, which side chain comprises:

(i) a Branched linker of formula Chem. 11

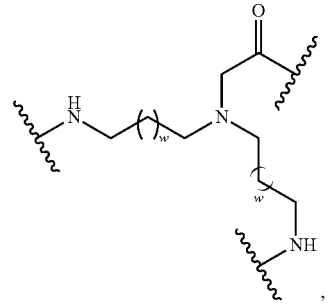

Chem. 11 wherein w is an integer in the range of 0-2;

(ii) a 1$^{st}$ and a 2$^{nd}$ Protractor selected from Chem. 12 and Chem. 13:

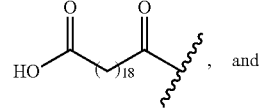

Chem. 12

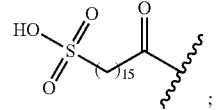

Chem. 13 and (iii) at least one Linker element-1 of Chem. 1:

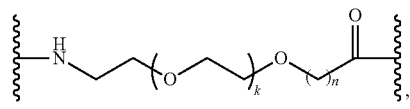

Chem. 1 wherein k is an integer in the range of 1-23, and n is an integer in the range of 1-5;

wherein the Branched linker is connected a) at its —CO end to the epsilon amino group of the Lys residue of Xaa$_{37}$ or Xaa$_{35}$, via an optional Pre-linker, and b) at each of its two —NH ends to the —CO end of each of the 1$^{st}$ and 2$^{nd}$ Protractor, respectively, via a 1$^{st}$ and a 2$^{nd}$ Post-linker, respectively; and wherein at least one of the Pre-linker, the 1$^{st}$ Post-linker, and the 2$^{nd}$ Post-linker comprises the Linker element-1;

or a pharmaceutically acceptable salt, amide, or ester thereof.

2. The derivative of embodiment 1, wherein Xaa$_7$ is L-histidine, or deamino-histidine; Xaa$_8$ is Aib; Xaa$_{12}$ is Phe; Xaa$_{16}$ is Val; Xaa$_{18}$ is Ser; Xaa$_{19}$ is Tyr; Xaa$_{20}$ is Leu; Xaa$_{22}$ is Glu; Xaa$_{23}$ is Gln; Xaa$_{25}$ is Ala; Xaa$_{26}$ is Arg; Xaa$_{27}$ is Glu; Xaa$_{30}$ is Ala; Xaa$_{31}$ is Trp; Xaa$_{33}$ is Val; Xaa$_{34}$ is Arg; Xaa$_{35}$ is Gly; Xaa$_{36}$ is Arg; Xaa$_{37}$ is Pro, or Lys; and Xaa$_{35}$ is Lys, or absent; and wherein at least one of Xaa$_{37}$ and Xaa$_{38}$ is Lys.

3. The derivative of any of embodiments 1-2, wherein one of Xaa$_{37}$ and Xaa$_{35}$ is Lys.

4. The derivative of any of embodiments 1-3, wherein the GLP-1 analogue is selected from the peptides of SEQ ID NO: 2, SEQ ID NO: 3, and SEQ ID NO: 4.
5. The derivative of any of embodiments 1-4, wherein each of the 1$^{st}$ and 2$^{nd}$ protractor is Chem. 12.
6. The derivative of any of embodiments 1-4, wherein each of the 1$^{st}$ and 2$^{nd}$ protractor is Chem. 13.
7. The derivative of any of embodiments 1-6, wherein the side chain is attached to the Lys residue of Xaa$_{37}$.
8. The derivative of any of embodiments 1-6, wherein the side chain is attached to the Lys residue of Xaa$_{38}$.
9. The derivative of any of embodiments 1-8, wherein in Chem. 11 w is 1.
10. The derivative of any of embodiments 1-9, which comprises at least two times Linker element-1.
11. The derivative of any of embodiments 1-10, which includes exactly m times Linker element-1, where m is an integer in the range of 2-12.
12. The derivative of embodiment 11, wherein m is 2.
13. The derivative of embodiment 11, wherein m is 6.
14. The derivative of embodiment 11, wherein m is 8.
15. The derivative of embodiment 11, wherein m is 10.
16. The derivative of embodiment 11, wherein m is 12.
17. The derivative of any of embodiments 1-16, which comprises at least one group consisting of q juxtaposed Linker element-1, where q is an integer in the range of 1-6, and where juxtaposed means mutually connected, via amide bonds.
18. The derivative of any of embodiments 1-16, which comprises at least one group consisting of q Linker element-1 in a row, connected via amide bonds, where q is an integer in the range of 1-6.
19. The derivative of any of embodiments 17-18, wherein q is 1.
20. The derivative of any of embodiments 17-18, wherein q is 2.
21. The derivative of any of embodiments 17-18, wherein q is 3.
22. The derivative of any of embodiments 17-18, wherein q is 4.
23. The derivative of any of embodiments 17-18, wherein q is 5.
24. The derivative of any of embodiments 17-18, wherein q is 6.
25. The derivative of any of embodiments 17-18, which includes exactly one of said groups.
26. The derivative of embodiment 25, wherein q is 2, 4, or 6.
27. The derivative of any of embodiments 17-18, which includes exactly two of said groups.
28. The derivative of embodiment 27, wherein q is 1, 2, 3, 4, 5, or 6.
29. The derivative of any of embodiments 17-18, which includes exactly three of said groups.
30. The derivative of embodiment 29, wherein q is 2 or 4.
31. The derivative of any of embodiments 1-30, wherein k is 1, 3, 11, 15, or 23.
32. The derivative of any of embodiments 1-31, wherein n is 1 or 2.
33. The derivative of any of embodiments 1-32, wherein k is 1 and n is 1.
34. The derivative of any of embodiments 1-32, wherein k is 3 and n is 2.
35. The derivative of any of embodiments 1-32, wherein k is 11 and n is 2.
36. The derivative of any of embodiments 1-32, wherein k is 15 and n is 2.
37. The derivative of any of embodiments 1-32, wherein k is 23 and n is 2.
38. The derivative of any of embodiments 1-37, which comprises a Linker element-2 of formula Chem. 2:
*—NH—(CH$_2$)$_4$—CH(NH$_2$)—CO—*.
39. The derivative of embodiment 38, wherein Chem. 2 is a di-radical of Lys.
40. The derivative of any of embodiments 38-39, wherein Chem. 2 is a di-radical of eps-Lys.
41. The derivative of any of embodiments 38-40, wherein Chem. 2 is a di-radical of L-eps-Lys.
42. The derivative of any of embodiments 38-41, which comprises p times the Linker element-2, where p is an integer in the range of 0-2.
43. The derivative of embodiment 42, wherein p is 2.
44. The derivative of any of embodiments 1-43, which comprises a Linker element-3 of formula Chem. 3:

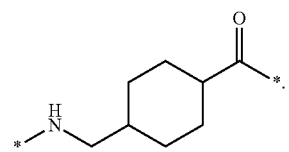

45. The derivative of embodiment 44, wherein Chem. 3 is a di-radical of tranexamic acid.
46. The derivative of any of embodiments 44-45, wherein Chem. 3 is a di-radical of trans-4-(aminomethyl)cyclohexanecarboxylic acid.
47. The derivative of any of embodiments 1-46, which comprises a Linker element-4 of formula Chem. 4:
*—NH—CH(COOH)—(CH$_2$)$_2$—CO—*.
48. The derivative of embodiment 47, wherein Chem. 4 is a di-radical of Glu.
49. The derivative of any of embodiments 47-48, wherein Chem. 4 is a di-radical of gGlu.
50. The derivative of any of embodiments 47-49, wherein Chem. 4 is a di-radical of L-gGlu.
51. The derivative of any of embodiments 1-50, which comprises a Linker element-5 of formula Chem. 5:
*—NH—(CH$_2$)$_3$—CO—*.
52. The derivative of embodiment 51, wherein Chem. 5 is a di-radical of 4-amino butanoic acid.
53. The derivative of any of embodiments 1-52, which comprises the Pre-linker.
54. The derivative of embodiment 53, wherein the Branched linker is connected, at its —CO end, to the epsilon amino group of the Lys residue of Xaa$_{37}$ or Xaa$_{35}$, via the Pre-linker.
55. The derivative of any of embodiments 53-54, wherein the Pre-linker includes exactly q times the Linker element-1, where q is 2, 4, or 6.
56. The derivative of embodiment 55, wherein q is 2.
57. The derivative of embodiment 55, wherein q is 4.
58. The derivative of embodiment 55, wherein q is 6.
59. The derivative of any of embodiments 53-58, wherein k is 1.
60. The derivative of any of embodiments 53-59, wherein n is 1.
61. The derivative of any of embodiments 1-52, which does not comprise the Pre-linker.
62. The derivative of any of embodiments 1-52, wherein the Branched linker is directly connected, at its —CO end, to the epsilon amino group of the Lys residue of Xaa$_{37}$ or Xaa$_{38}$.

63. The derivative of any of embodiments 1-62, wherein the $1^{st}$ and the $2^{nd}$ Post-linker each includes exactly s times the Linker element-1, where s is 0 or an integer in the range of 1-6, and at least one further linker element selected from Linker element-2, Linker element-3, Linker element-4, and Linker element-5.

64. The derivative of any of embodiments 1-63, wherein the $1^{st}$ and the $2^{nd}$ Post-linker each includes exactly s times the Linker element-1, where s is 0 or an integer in the range of 1-6, and at least two further linker elements selected from Linker element-2, Linker element-3, Linker element-4, and Linker element-5.

65. The derivative of any of embodiments 1-64, wherein each of the $1^{st}$ and $2^{nd}$ Post-linker consists of two times Linker element-2, and five times Linker element-1 of Chem. 1 where k is 1 and n is 1, interconnected via amide bonds and in the sequence indicated, and wherein each of the $1^{st}$ and the $2^{nd}$ Post-linker is connected at its —NH end to the —CO end of the $1^{st}$ and the $2^{nd}$ Protractor, respectively, and at its —CO end to each of the —NH ends of the Branched linker.

66. The derivative of any of embodiments 1-64, wherein each of the $1^{st}$ and $2^{nd}$ Post-linker consists of two times Linker element-2, and four times Linker element-1 of Chem. 1 where k is 1 and n is 1, interconnected via amide bonds and in the sequence indicated, and wherein each of the $1^{st}$ and the $2^{nd}$ Post-linker is connected at its —NH end to the —CO end of the $1^{st}$ and the $2^{nd}$ Protractor, respectively, and at its —CO end to each of the —NH ends of the Branched linker.

67. The derivative of any of embodiments 1-64, wherein each of the $1^{st}$ and $2^{nd}$ Post-linker consists of Linker element-3, and six times Linker element-1 of Chem. 1 where k is 1 and n is 1, interconnected via amide bonds and in the sequence indicated, and wherein each of the $1^{st}$ and the $2^{nd}$ Post-linker is connected at its —NH end to the —CO end of the $1^{st}$ and the $2^{nd}$ Protractor, respectively, and at its —CO end to each of the —NH ends of the Branched linker.

68. The derivative of any of embodiments 1-64, wherein each of the $1^{st}$ and $2^{nd}$ Post-linker consists of two times Linker element-2, and three times Linker element-1 of Chem. 1 where k is 3 and n is 2, interconnected via amide bonds and in the sequence indicated, and wherein each of the $1^{st}$ and the $2^{nd}$ Post-linker is connected at its —NH end to the —CO end of the $1^{st}$ and the $2^{nd}$ Protractor, respectively, and at its —CO end to each of the —NH ends of the Branched linker.

69. The derivative of any of embodiments 1-64, wherein each of the $1^{st}$ and $2^{nd}$ Post-linker consists of two times Linker element-2, and Linker element-1 of Chem. 1 where k is 23 and n is 2, interconnected via amide bonds and in the sequence indicated, and wherein each of the $1^{st}$ and the $2^{nd}$ Post-linker is connected at its —NH end to the —CO end of the $1^{st}$ and the $2^{nd}$ Protractor, respectively, and at its —CO end to each of the —NH ends of the Branched linker.

70. The derivative of any of embodiments 1-64, wherein each of the $1^{st}$ and $2^{nd}$ Post-linker consists of two times Linker element-2, and Linker element-1 of Chem. 1 where k is 15 and n is 2, interconnected via amide bonds and in the sequence indicated, and wherein each of the $1^{st}$ and the $2^{nd}$ Post-linker is connected at its —NH end to the —CO end of the $1^{st}$ and the $2^{nd}$ Protractor, respectively, and at its —CO end to each of the —NH ends of the Branched linker.

71. The derivative of any of embodiments 1-64, wherein each of the $1^{st}$ and $2^{nd}$ Post-linker consists of two times Linker element-2, and Linker element-1 of Chem. 1 where k is 11 and n is 2, interconnected via amide bonds and in the sequence indicated, and wherein each of the $1^{st}$ and the $2^{nd}$ Post-linker is connected at its —NH end to the —CO end of the $1^{st}$ and the $2^{nd}$ Protractor, respectively, and at its —CO end to each of the —NH ends of the Branched linker.

72. The derivative of any of embodiments 1-64, wherein each of the $1^{st}$ and $2^{nd}$ Post-linker consists of Linker element-5, two times Linker element-2, and five times Linker element-1 of Chem. 1 where k is 1 and n is 1, interconnected via amide bonds and in the sequence indicated, and wherein each of the $1^{st}$ and the $2^{nd}$ Post-linker is connected at its —NH end to the —CO end of the $1^{st}$ and the $2^{nd}$ Protractor, respectively, and at its —CO end to each of the —NH ends of the Branched linker.

73. The derivative of any of embodiments 1-64, wherein each of the $1^{st}$ and $2^{nd}$ Post-linker consists of Linker element-3, Linker element-4, and six times Linker element-1 of Chem. 1 where k is 1 and n is 1, interconnected via amide bonds and in the sequence indicated, and wherein each of the $1^{st}$ and the $2^{nd}$ Post-linker is connected at its —NH end to the —CO end of the $1^{st}$ and the $2^{nd}$ Protractor, respectively, and at its —CO end to each of the —NH ends of the Branched linker.

74. The derivative of any of embodiments 1-64, wherein each of the $1^{st}$ and $2^{nd}$ Post-linker consists of Linker element-3, Linker element-4, and four times Linker element-1 of Chem. 1 where k is 1 and n is 1, interconnected via amide bonds and in the sequence indicated, and wherein each of the $1^{st}$ and the $2^{nd}$ Post-linker is connected at its —NH end to the —CO end of the $1^{st}$ and the $2^{nd}$ Protractor, respectively, and at its —CO end to each of the —NH ends of the Branched linker.

75. The derivative of any of embodiments 1-64, wherein each of the $1^{st}$ and $2^{nd}$ Post-linker consists of Linker element-3, Linker element-4, and two times Linker element-1 of Chem. 1 where k is 1 and n is 1, interconnected via amide bonds and in the sequence indicated, and wherein each of the $1^{st}$ and the $2^{nd}$ Post-linker is connected at its —NH end to the —CO end of the $1^{st}$ and the $2^{nd}$ Protractor, respectively, and at its —CO end to each of the —NH ends of the Branched linker.

76. The derivative of any of embodiments 1-64, wherein each of the $1^{st}$ and $2^{nd}$ Post-linker consists of Linker element-3, and Linker element-4, interconnected via amide bonds and in the sequence indicated, and wherein each of the $1^{st}$ and the $2^{nd}$ Post-linker is connected at its —NH end to the —CO end of the $1^{st}$ and the $2^{nd}$ Protractor, respectively, and at its —CO end to each of the —NH ends of the Branched linker.

77. The derivative of any of embodiments 1-64, wherein each of the $1^{st}$ and $2^{nd}$ Post-linker consists of Linker element-5, two times Linker element-2, and four times Linker element-1 of Chem. 1 where k is 1 and n is 1, interconnected via amide bonds and in the sequence indicated, and wherein each of the $1^{st}$ and the $2^{nd}$ Post-linker is connected at its —NH end to the —CO end of the $1^{st}$ and the $2^{nd}$ Protractor, respectively, and at its —CO end to each of the —NH ends of the Branched linker.

78. The derivative of any of embodiments 1-64, wherein each of the $1^{st}$ and $2^{nd}$ Post-linker consists of Linker element-5, two times Linker element-2, and six times Linker element-1 of Chem. 1 where k is 1 and n is 1, interconnected via amide bonds and in the sequence indicated, and wherein each of the $1^{st}$ and the $2^{nd}$ Post-linker is connected at its —NH end to the —CO end of the $1^{st}$ and the $2^{nd}$ Protractor, respectively, and at its —CO end to each of the —NH ends of the Branched linker.

79. The derivative of any of embodiments 1-64, wherein each of the $1^{st}$ and $2^{nd}$ Post-linker consists of Linker element-5, Linker element-4, and four times Linker element-1 of Chem. 1 where k is 1 and n is 1, interconnected via amide bonds and in the sequence indicated, and wherein each of the $1^{st}$ and the $2^{nd}$ Post-linker is connected at its —NH end to the —CO end of the $1^{st}$ and the $2^{nd}$ Protractor, respectively, and at its —CO end to each of the —NH ends of the Branched linker.

80. The derivative of any of embodiments 1-79, wherein the Pre-linker consists of two times Linker element-1 of Chem. 1 where k is 1 and n is 1, interconnected via amide bonds, and wherein the Pre-linker is connected at its —NH end to the —CO end of the Branched linker, and at its —CO end to the epsilon amino group of the Lys residue of $Xaa_{37}$ or $Xaa_{38}$.

81. The derivative of embodiment 80, wherein the $1^{st}$ and $2^{nd}$ Post-linker is as defined in embodiment 74.

82. The derivative of any of embodiments 1-79, wherein the Pre-linker consists of four times Linker element-1 of Chem. 1 where k is 1 and n is 1, interconnected via amide bonds, and wherein the Pre-linker is connected at its —NH end to the —CO end of the Branched linker, and at its —CO end to the epsilon amino group of the Lys residue of $Xaa_{37}$ or $Xaa_{38}$.

83. The derivative of embodiment 82, wherein the $1^{st}$ and $2^{nd}$ Post-linker is as defined in embodiment 75.

84. The derivative of any of embodiments 1-79, wherein the Pre-linker consists of six times Linker element-1 of Chem. 1 where k is 1 and n is 1, interconnected via amide bonds, and wherein the Pre-linker is connected at its —NH end to the —CO end of the Branched linker, and at its —CO end to the epsilon amino group of the Lys residue of $Xaa_{37}$ or $Xaa_{38}$.

85. The derivative of embodiment 84, wherein the $1^{st}$ and $2^{nd}$ Post-linker is as defined in embodiment 76.

86. The derivative of any of embodiments 1-85, wherein the Branched linker is connected, via amide bonds,
   a) at its —CO end to the epsilon amino group of the Lys residue of $Xaa_{37}$ or $Xaa_{35}$, via the optional Pre-linker, and
   b) at each of its two —N ends to the —CO end of each of the $1^{st}$ and $2^{nd}$ Protractor, respectively, via a $1^{st}$ and a $2^{nd}$ Post-linker, respectively.

87. A GLP-1 derivative, preferably the derivative of any of embodiments 1-86, which is selected from Chem. 21, Chem. 22, Chem. 23, Chem. 24, Chem. 25, Chem. 26, Chem. 27, Chem. 28, Chem. 29, Chem. 30, Chem. 31, Chem. 32, Chem. 33, Chem. 34, Chem. 35, and Chem. 36; or a pharmaceutically acceptable salt, amide, or ester thereof.

88. A GLP-1 derivative, preferably the derivative of any of embodiments 1-87, which is selected from the compounds of Examples 1-16, or a pharmaceutically acceptable salt, amide, or ester thereof.

89. A GLP-1 analogue which comprises the following changes when compared to GLP-1(7-37) (SEQ ID NO: 1): (7Imp, 8Aib, 22E, 26R, 34R, 37K), (8Aib, 22E, 26R, 34R, 37P), or (8Aib, 22E, 26R, 34R, 37P, 38K).

90. The GLP-1 analogue of embodiment 89, which is selected from the following analogues of GLP-1(7-37) (SEQ ID NO: 1): (7Imp, 8Aib, 22E, 26R, 34R, 37K), and (8Aib, 22E, 26R, 34R, 37P, 38K); or a pharmaceutically acceptable salt, amide, or ester thereof.

91. The GLP-1 analogue of any of embodiments 89-90, which is a peptide selected from SEQ ID NO: 3, and SEQ ID NO: 4; or a pharmaceutically acceptable salt, amide, or ester thereof.

92. The derivative or analogue of any of embodiments 1-91, which is a GLP-1 receptor agonist.

93. The derivative or analogue of any of embodiments 1-92, which is a full GLP-1 receptor agonist.

94. The derivative or analogue of any of embodiments 1-93, which is biologically active in vitro.

95. The derivative or analogue of any of embodiments 1-94, which is potent in vitro.

96. The derivative or analogue of any of embodiments 1-95, which is capable of activating the human GLP-1 receptor.

97. The derivative or analogue of any of embodiments 1-96, which is capable of activating the human GLP-1 receptor in an assay with whole cells expressing the human GLP-1 receptor, wherein the assay is performed in the absence of HSA (0% HSA).

98. The derivative or analogue of any of embodiments 1-98, where the response of the human GLP-1 receptor is measured in a reporter gene assay, such as the assay of Example 33.

99. The derivative or analogue of any of embodiments 92-98, wherein the GLP-1 receptor agonism, the in vitro biological activity, the in vitro potency, or the capability of activating the human GLP-1 receptor, respectively, is determined essentially as described in Example 33.

100. The derivative or analogue of any of embodiments 1-99, which has an in vitro potency corresponding to an $EC_{50}$ of 300 pM or below.

101. The derivative or analogue of any of embodiments 1-100, which has an in vitro potency corresponding to an $EC_{50}$ of 200 pM or below.

102. The derivative or analogue of any of embodiments 1-101, which has an in vitro potency corresponding to an $EC_{50}$ of 100 pM or below.

103. The derivative or analogue of any of embodiments 1-102, which has an in vitro potency corresponding to an $EC_{50}$ of 75 pM or below.

104. The derivative or analogue of any of embodiments 1-103, which has an in vitro potency corresponding to an $EC_{50}$ of 50 pM or below.

105. The derivative or analogue of any of embodiments 1-104, which has an in vitro potency corresponding to an $EC_{50}$ of 25 pM or below.

106. The derivative or analogue of any of embodiments 1-105, which has an in vitro potency corresponding to an $EC_{50}$ of 15 pM or below.

107. The derivative or analogue of any of embodiments 1-106, which has an in vitro potency corresponding to an $EC_{50}$ of 10 pM or below.

108. The derivative or analogue of any of embodiments 1-107, which has an in vitro potency corresponding to an $EC_{50}$ of 7 pM or below.

109. The derivative or analogue of any of embodiments 100-108, wherein the $EC_{50}$ is determined essentially as described in Example 33.

110. The derivative or analogue of any of embodiments 1-109, which has an in vitro potency corresponding to an $EC_{50}$ of less than 30 times the $EC_{50}$ of semaglutide, wherein the $EC_{50}$ of semaglutide is determined in the same way as the $EC_{50}$ of the derivative.

111. The derivative or analogue of any of embodiments 1-110, which has an in vitro potency corresponding to an $EC_{50}$ of less than 20 times the $EC_{50}$ of semaglutide, wherein the $EC_{50}$ of semaglutide is determined in the same way as the $EC_{50}$ of the derivative.

112. The derivative or analogue of any of embodiments 1-111, which has an in vitro potency corresponding to an $EC_{50}$ of less than 10 times the $EC_{50}$ of semaglutide, wherein the $EC_{50}$ of semaglutide is determined in the same way as the $EC_{50}$ of the derivative.

113. The derivative or analogue of any of embodiments 1-112, which has an in vitro potency corresponding to an $EC_{50}$ of less than 7 times the $EC_{50}$ of semaglutide, wherein the $EC_{50}$ of semaglutide is determined in the same way as the $EC_{50}$ of the derivative.

114. The derivative or analogue of any of embodiments 1-113, which has an in vitro potency corresponding to an $EC_{50}$ of less than 5 times the $EC_{50}$ of semaglutide, wherein the $EC_{50}$ of semaglutide is determined in the same way as the $EC_{50}$ of the derivative.

115. The derivative or analogue of any of embodiments 1-114, which has an in vitro potency corresponding to an $EC_{50}$ of less than 2 times the $EC_{50}$ of semaglutide, wherein the $EC_{50}$ of semaglutide is determined in the same way as the $EC_{50}$ of the derivative.

116. The derivative or analogue of any of embodiments 1-115, which has an in vitro potency corresponding to an $EC_{50}$ of less than the $EC_{50}$ of semaglutide, wherein the $EC_{50}$ of semaglutide is determined in the same way as the $EC_{50}$ of the derivative.

117. The derivative or analogue of any of embodiments 110-116, wherein the $EC_{50}$ is determined essentially as described in Example 33.

118. The derivative or analogue of any of embodiments 1-117, which is capable of binding to the GLP-1 receptor.

119. The derivative or analogue of any of embodiments 1-118, which is capable of binding to the GLP-1 receptor at a low concentration of HSA (max. 0.001% final assay concentration).

120. The derivative or analogue of any of embodiments 1-119, which is capable of binding to the GLP-1 receptor at a high concentration of HSA (2.0% final assay concentration).

121. The derivative or analogue of any of embodiments 118-120, wherein the binding to the human GLP-1 receptor is measured in a competitive binding assay, such as the assay of Example 34.

122. The derivative or analogue of any of embodiments 118-121, wherein the binding to the human GLP-1 receptor in vitro is determined essentially as described in Example 34.

123. The derivative or analogue of any of embodiments 1-122, which at a low concentration of HSA is capable of binding to the human GLP-1 receptor with an $IC_{50}$ of 5.0 nM or below.

124. The derivative or analogue of any of embodiments 1-123, which at a low concentration of HSA is capable of binding to the human GLP-1 receptor with an $IC_{50}$ of 3.0 nM or below.

125. The derivative or analogue of any of embodiments 1-124, which at a low concentration of HSA is capable of binding to the human GLP-1 receptor with an $IC_{50}$ of 2.0 nM or below.

126. The derivative or analogue of any of embodiments 1-125, which at a low concentration of HSA is capable of binding to the human GLP-1 receptor with an $IC_{50}$ of 1.0 nM or below.

127. The derivative or analogue of any of embodiments 1-126, which at a low concentration of HSA is capable of binding to the human GLP-1 receptor with an $IC_{50}$ of 0.50 nM or below.

128. The derivative or analogue of any of embodiments 1-127, which at a low concentration of HSA is capable of binding to the human GLP-1 receptor with an $IC_{50}$ of 0.30 nM or below.

129. The derivative or analogue of any of embodiments 1-128, which at a low concentration of HSA is capable of binding to the human GLP-1 receptor with an $IC_{50}$ of 0.15 nM or below.

130. The derivative or analogue of any of embodiments 123-129, wherein the $IC_{50}$ is determined essentially as described in Example 34, in a reaction with max. 0.001% HSA (final assay concentration).

131. The derivative or analogue of any of embodiments 1-130, which at a low concentration of HSA is capable of binding to the human GLP-1 receptor with an $IC_{50}$ of less than 10 times the $IC_{50}$ of semaglutide, wherein the $IC_{50}$ of semaglutide is determined in the same way as the $IC_{50}$ of the derivative.

132. The derivative or analogue of any of embodiments 1-131, which at a low concentration of HSA is capable of binding to the human GLP-1 receptor with an $IC_{50}$ of less than 8 times the $IC_{50}$ of semaglutide, wherein the $IC_{50}$ of semaglutide is determined in the same way as the $IC_{50}$ of the derivative.

133. The derivative or analogue of any of embodiments 1-132, which at a low concentration of HSA is capable of binding to the human GLP-1 receptor with an $IC_{50}$ of less than 6 times the $IC_{50}$ of semaglutide, wherein the $IC_{50}$ of semaglutide is determined in the same way as the $IC_{50}$ of the derivative.

134. The derivative or analogue of any of embodiments 1-133, which at a low concentration of HSA is capable of binding to the human GLP-1 receptor with an $IC_{50}$ of less than 4 times the $IC_{50}$ of semaglutide, wherein the $IC_{50}$ of semaglutide is determined in the same way as the $IC_{50}$ of the derivative.

135. The derivative or analogue of any of embodiments 1-134, which at a low concentration of HSA is capable of binding to the human GLP-1 receptor with an $IC_{50}$ of less than 2 times the $IC_{50}$ of semaglutide, wherein the $IC_{50}$ of semaglutide is determined in the same way as the $IC_{50}$ of the derivative.

136. The derivative or analogue of any of embodiments 1-135, which at a low concentration of HSA is capable of binding to the human GLP-1 receptor with an $IC_{50}$ of less than the $IC_{50}$ of semaglutide, wherein the $IC_{50}$ of semaglutide is determined in the same way as the $IC_{50}$ of the derivative.

137. The derivative or analogue of any of embodiments 1-136, which at a low concentration of HSA is capable of binding to the human GLP-1 receptor with an $IC_{50}$ of less than 0.50 times the $IC_{50}$ of semaglutide, wherein the $IC_{50}$ of semaglutide is determined in the same way as the $IC_{50}$ of the derivative.

138. The derivative or analogue of any of embodiments 131-137, wherein the $IC_{50}$ is determined essentially as described in Example 34, in a reaction with max. 0.001% HSA (final assay concentration).

139. The derivative or analogue of any of embodiments 1-138, which at 2.0% HSA (final assay concentration) is capable of binding to the human GLP-1 receptor with an $IC_{50}$ of 300 nM or below.

140. The derivative or analogue of any of embodiments 1-139, which at 2.0% HSA (final assay concentration) is capable of binding to the human GLP-1 receptor with an $IC_{50}$ of 125 nM or below.

141. The derivative or analogue of any of embodiments 1-140, which at 2.0% HSA (final assay concentration) is capable of binding to the human GLP-1 receptor with an $IC_{50}$ of 75 nM or below.

142. The derivative or analogue of any of embodiments 1-141, which at 2.0% HSA (final assay concentration) is capable of binding to the human GLP-1 receptor with an $IC_{50}$ of 50 nM or below.

143. The derivative or analogue of any of embodiments 1-142, which at 2.0% HSA (final assay concentration) is capable of binding to the human GLP-1 receptor with an $IC_{50}$ of 30 nM or below.

144. The derivative or analogue of any of embodiments 1-143, which at 2.0% HSA (final assay concentration) is capable of binding to the human GLP-1 receptor with an $IC_{50}$ of 15 nM or below.

145. The derivative or analogue of any of embodiments 139-144, wherein the $IC_{50}$ is determined essentially as described in Example 34, in a reaction with 2.0% HSA (final assay concentration).

146. The derivative or analogue of any of embodiments 1-145, which at 2.0% HSA (final assay concentration) is capable of binding to the human GLP-1 receptor with an $IC_{50}$ of less than the $IC_{50}$ of semaglutide, wherein the $IC_{50}$ of semaglutide is determined in the same way as the $IC_{50}$ of the derivative.

147. The derivative or analogue of any of embodiments 1-146, which at 2.0% HSA (final assay concentration) is capable of binding to the human GLP-1 receptor with an $IC_{50}$ of less than 0.5 times the $IC_{50}$ of semaglutide, wherein the $IC_{50}$ of semaglutide is determined in the same way as the $IC_{50}$ of the derivative.

148. The derivative or analogue of any of embodiments 1-147, which at 2.0% HSA (final assay concentration) is capable of binding to the human GLP-1 receptor with an $IC_{50}$ of less than 0.25 times the $IC_{50}$ of semaglutide, wherein the $IC_{50}$ of semaglutide is determined in the same way as the $IC_{50}$ of the derivative.

149. The derivative or analogue of any of embodiments 1-148, which at 2.0% HSA (final assay concentration) is capable of binding to the human GLP-1 receptor with an $IC_{50}$ of less than 0.10 times the $IC_{50}$ of semaglutide, wherein the $IC_{50}$ of semaglutide is determined in the same way as the $IC_{50}$ of the derivative.

150. The derivative or analogue of any of embodiments 1-149, which at 2.0% HSA (final assay concentration) is capable of binding to the human GLP-1 receptor with an $IC_{50}$ of less than 0.050 times the $IC_{50}$ of semaglutide, wherein the $IC_{50}$ of semaglutide is determined in the same way as the $IC_{50}$ of the derivative.

151. The derivative or analogue of any of embodiments 146-150, wherein the $IC_{50}$ is determined essentially as described in Example 34, in a reaction with 2.0% HSA (final assay concentration).

152. The derivative of any of embodiments 1-151, which has improved pharmacokinetic properties.

153. The derivative of any of embodiments 1-152, which has an increased half-life and/or a decreased clearance.

154. The derivative of any of embodiments 1-153, which is suitable for once-monthly administration.

155. The derivative of any of embodiments 1-154, for s.c. administration.

156. The derivative of any of embodiments 1-155, wherein the derivative is tested in vivo in pharmacokinetic (PK) studies.

157. The derivative of any of embodiments 1-156, wherein the derivative is tested in any suitable animal model, such as mouse, rat, monkey, dog, or pig.

158. The derivative of any of embodiments 1-157, which is compared with semaglutide.

159. The derivative of any of embodiments 1-158, which has an improved terminal half-life (T½) in vivo in minipigs after i.v. administration as compared to semaglutide.

160. The derivative of embodiment 159, wherein the terminal half-life is determined in vivo in minipigs after i.v. administration using any suitable study protocol, such as the one described in Example 35.

161. The derivative of any of embodiments 159-160, wherein the terminal half-life is determined in vivo in minipigs after i.v. administration, essentially as described in Example 35.

162. The derivative of any of embodiments 1-161, which has a terminal half-life (T½) in vivo in minipigs after i.v. administration of at least 100 hours.

163. The derivative of any of embodiments 1-162, which has a terminal half-life (T½) in vivo in minipigs after i.v. administration of at least 115 hours.

164. The derivative of any of embodiments 1-163, which has a terminal half-life (T½) in vivo in minipigs after i.v. administration of at least 130 hours.

165. The derivative of any of embodiments 1-164, which has a terminal half-life (T½) in vivo in minipigs after i.v. administration of at least 145 hours.

166. The derivative of any of embodiments 1-165, which has a terminal half-life (T½) in vivo in minipigs after i.v. administration of at least 155 hours.

167. The derivative of any of embodiments 1-166, which has a terminal half-life (T½) in vivo in minipigs after i.v. administration of at least 2.0 times the terminal half-life of semaglutide, determined in the same way.

168. The derivative of any of embodiments 1-167, which has a terminal half-life (T½) in vivo in minipigs after i.v. administration of at least 2.5 times the terminal half-life of semaglutide, determined in the same way.

169. The derivative of any of embodiments 1-168, which has a terminal half-life (T½) in vivo in minipigs after i.v. administration of at least 2.8 times the terminal half-life of semaglutide, determined in the same way.

170. The derivative of any of embodiments 162-169, wherein the terminal half-life ($T_{1/2}$) is determined essentially as described in Example 35.

171. The derivative of any of embodiments 1-170, which is potent in vivo.

172. The derivative of any of embodiments 1-171, which is potent in vivo when determined in any suitable animal model, such as mouse, rat, or pig.

173. The derivative of embodiment 172, wherein the animal model is Sprague Dawley rats.

174. The derivative of any of embodiments 1-173, wherein an acute effect on food intake is determined, wherein acute preferably refers to a single s.c. injection of 100 nmol/kg of the derivative in question.

175. The derivative of any of embodiments 1-174, wherein an acute effect on body weight is determined, and wherein acute preferably refers to a single s.c. injection of 100 nmol/kg of the derivative in question.

176. The derivative of any of embodiments 1-175, wherein an acute effect on food intake and/or body weight is determined in vivo in Sprague Dawley rats using any suitable study protocol and methodology, e.g. as described in Example 36.

177. The derivative of any of embodiments 1-176, wherein an acute effect on food intake and/or body weight is determined in vivo in Sprague Dawley rats, essentially as described in Example 36.

178. The derivative of any of embodiments 174-177, wherein the acute effect is a change in food intake at 48 h of at least −25%, calculated as [[(food intake at 48 h)−(baseline food intake)]/(baseline food intake)]×100%], where baseline food intake refers to the level before the administration of any treatment.

179. The derivative of any of embodiments 174-178, wherein the acute effect is a change in food intake at 48 h of at least −50%, calculated as [[(food intake at 48 h)−(baseline food intake)]/(baseline food intake)]×100%], where baseline food intake refers to the level before the administration of any treatment.

180. The derivative of any of embodiments 174-179, wherein the acute effect is a change in food intake at 48 h of at least −75%, calculated as [[(food intake at 48 h)−(baseline food intake)]/(baseline food intake)]×100%], where baseline food intake refers to the level before the administration of any treatment.

181. The derivative of any of embodiments 174-180, wherein the acute effect is a change in body weight at 48 h of at least −5%, calculated as [[(body weight at 48 h)−(baseline body weight)]/(baseline body weight)]×100%], where baseline body weight refers to the level before the administration of any treatment.

182. The derivative of any of embodiments 174-181, wherein the acute effect is a change in body weight at 48 h of at least −8%, calculated as [[(body weight at 48 h)−(baseline body weight)]/(baseline body weight)]×100%], where baseline body weight refers to the level before the administration of any treatment.

183. The derivative of any of embodiments 174-182, wherein the acute effect is a change in body weight at 48 h of at least −12%, calculated as [[(body weight at 48 h)−(baseline body weight)]/(baseline body weight)]×100%], where baseline body weight refers to the level before the administration of any treatment.

184. A pharmaceutical composition comprising a derivative or an analogue according to any of embodiments 1-183, and a pharmaceutically acceptable excipient.

185. A derivative or an analogue according to any of embodiments 1-183, for use as a medicament.

186. A derivative or an analogue according to any of embodiments 1-183, for use in (i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C;

(ii) delaying or preventing diabetic disease progression, such as progression in type 2 diabetes, delaying the progression of impaired glucose tolerance (IGT) to insulin requiring type 2 diabetes, delaying or preventing insulin resistance, and/or delaying the progression of non-insulin requiring type 2 diabetes to insulin requiring type 2 diabetes;

(iii) improving β-cell function, such as decreasing β-cell apoptosis, increasing β-cell function and/or β-cell mass, and/or for restoring glucose sensitivity to β-cells;

(iv) prevention and/or treatment of cognitive disorders and/or neurodegenerative disorders, such as Alzheimer's disease, Parkinson's disease, and/or multiple sclerosis;

(v) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, such as osteoarthritis and/or urine incontinence;

(vi) prevention and/or treatment of diabetic complications, such as angiopathy; neuropathy, including peripheral neuropathy; nephropathy; and/or retinopathy;

(vii) improving lipid parameters, such as prevention and/or treatment of dyslipidemia, lowering total serum lipids; increasing HDL; lowering small, dense LDL; lowering VLDL; lowering triglycerides; lowering cholesterol; lowering plasma levels of lipoprotein a (Lp(a)) in a human; inhibiting generation of apolipoprotein a (apo(a)) in vitro and/or in vivo;

(viii) prevention and/or treatment of cardiovascular diseases, such as syndrome X, atherosclerosis, myocardial infarction, coronary heart disease, reperfusion injury, stroke, cerebral ischemia, an early cardiac or early cardiovascular disease, left ventricular hypertrophy, coronary artery disease, hypertension, essential hypertension, acute hypertensive emergency, cardiomyopathy, heart insufficiency, exercise intolerance, acute and/or chronic heart failure, arrhythmia, cardiac dysrhythmia, syncopy, angina pectoris, cardiac bypass and/or stent reocclusion, intermittent claudication (atheroschlerosis oblitterens), diastolic dysfunction, and/or systolic dysfunction; and/or reduction of blood pressure, such as reduction of systolic blood pressure;

(ix) prevention and/or treatment of gastrointestinal diseases, such as inflammatory bowel disease, short bowel syndrome, or Crohn's disease or colitis; dyspepsia, and/or gastric ulcers; and/or inflammation, such as psoriasis, psoriactic arthritis, rheumatoid arthritis, and/or systemic lupus erythematosus;

(x) prevention and/or treatment of critical illness, such as treatment of a critically ill patient, a critical illness polynephropathy (CIPNP) patient, and/or a potential CIPNP patient; prevention of development of critical illness or CIPNP; prevention, treatment and/or cure of systemic inflammatory response syndrome (SIRS) in a patient; prevention or reduction of the likelihood of a patient suffering from bacteraemia, septicaemia, and/or septic shock during hospitalisation; and/or stabilising blood glucose, insulin balance and optionally metabolism in intensive care unit patients with acute illness;

(xi) prevention and/or treatment of polycystic ovary syndrome (PCOS);

(xii) prevention and/or treatment of cerebral disease, such as cerebral ischemia, cerebral haemorrhage, and/or traumatic brain injury;

(xiii) prevention and/or treatment of sleep apnoea; and/or (xiv) prevention and/or treatment of abuse, such as alcohol abuse and/or drug abuse.

187. Use of a derivative or an analogue according to any of embodiments 1-183, in the manufacture of a medicament for (i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C;

(ii) delaying or preventing diabetic disease progression, such as progression in type 2 diabetes, delaying the progression of impaired glucose tolerance (IGT) to insulin requiring type 2 diabetes, delaying or preventing insulin resistance, and/or delaying the progression of non-insulin requiring type 2 diabetes to insulin requiring type 2 diabetes;

(iii) improving β-cell function, such as decreasing β-cell apoptosis, increasing β-cell function and/or β-cell mass, and/or for restoring glucose sensitivity to β-cells;

(iv) prevention and/or treatment of cognitive disorders and/or neurodegenerative disorders, such as Alzheimer's disease, Parkinson's disease, and/or multiple sclerosis;

(v) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, such as osteoarthritis and/or urine incontinence;

(vi) prevention and/or treatment of diabetic complications, such as angiopathy; neuropathy, including peripheral neuropathy; nephropathy; and/or retinopathy;

(vii) improving lipid parameters, such as prevention and/or treatment of dyslipidemia, lowering total serum lipids; increasing HDL; lowering small, dense LDL; lowering VLDL; lowering triglycerides; lowering cholesterol; lowering plasma levels of lipoprotein a (Lp(a)) in a human; inhibiting generation of apolipoprotein a (apo(a)) in vitro and/or in vivo;

(viii) prevention and/or treatment of cardiovascular diseases, such as syndrome X, atherosclerosis, myocardial infarction, coronary heart disease, reperfusion injury, stroke, cerebral ischemia, an early cardiac or early cardiovascular disease, left ventricular hypertrophy, coronary artery disease, hypertension, essential hypertension, acute hypertensive emergency, cardiomyopathy, heart insufficiency, exercise intolerance, acute and/or chronic heart failure, arrhythmia, cardiac dysrhythmia, syncopy, angina pectoris, cardiac bypass and/or stent reocclusion, intermittent claudication (atheroschlerosis oblitterens), diastolic dysfunction, and/or systolic dysfunction; and/or reduction of blood pressure, such as reduction of systolic blood pressure;

(ix) prevention and/or treatment of gastrointestinal diseases, such as inflammatory bowel disease, short bowel syndrome, or Crohn's disease or colitis; dyspepsia, and/or gastric ulcers; and/or inflammation, such as psoriasis, psoriactic arthritis, rheumatoid arthritis, and/or systemic lupus erythematosus;

(x) prevention and/or treatment of critical illness, such as treatment of a critically ill patient, a critical illness polynephropathy (CIPNP) patient, and/or a potential CIPNP patient; prevention of development of critical illness or CIPNP; prevention, treatment and/or cure of systemic inflammatory response syndrome (SIRS) in a patient; prevention or reduction of the likelihood of a patient suffering from bacteraemia, septicaemia, and/or septic shock during hospitalisation; and/or stabilising blood glucose, insulin balance and optionally metabolism in intensive care unit patients with acute illness;

(xi) prevention and/or treatment of polycystic ovary syndrome (PCOS);

(xii) prevention and/or treatment of cerebral disease, such as cerebral ischemia, cerebral haemorrhage, and/or traumatic brain injury;

(xiii) prevention and/or treatment of sleep apnoea; and/or (xiv) prevention and/or treatment of abuse, such as alcohol abuse and/or drug abuse.

188. A method for (i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C;

(ii) delaying or preventing diabetic disease progression, such as progression in type 2 diabetes, delaying the progression of impaired glucose tolerance (IGT) to insulin requiring type 2 diabetes, delaying or preventing insulin resistance, and/or delaying the progression of non-insulin requiring type 2 diabetes to insulin requiring type 2 diabetes;

(iii) improving β-cell function, such as decreasing β-cell apoptosis, increasing β-cell function and/or β-cell mass, and/or for restoring glucose sensitivity to β-cells;

(iv) prevention and/or treatment of cognitive disorders and/or neurodegenerative disorders, such as Alzheimer's disease, Parkinson's disease, and/or multiple sclerosis;

(v) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, such as osteoarthritis and/or urine incontinence;

(vi) prevention and/or treatment of diabetic complications, such as angiopathy; neuropathy, including peripheral neuropathy; nephropathy; and/or retinopathy;

(vii) improving lipid parameters, such as prevention and/or treatment of dyslipidemia, lowering total serum lipids; increasing HDL; lowering small, dense LDL; lowering VLDL; lowering triglycerides; lowering cholesterol; lowering plasma levels of lipoprotein a (Lp(a)) in a human; inhibiting generation of apolipoprotein a (apo(a)) in vitro and/or in vivo;

(viii) prevention and/or treatment of cardiovascular diseases, such as syndrome X, atherosclerosis, myocardial infarction, coronary heart disease, reperfusion injury, stroke, cerebral ischemia, an early cardiac or early cardiovascular disease, left ventricular hypertrophy, coronary artery disease, hypertension, essential hypertension, acute hypertensive emergency, cardiomyopathy, heart insufficiency, exercise intolerance, acute and/or chronic heart failure, arrhythmia, cardiac dysrhythmia, syncopy, angina pectoris, cardiac bypass and/or stent reocclusion, intermittent claudication (atheroschlerosis oblitterens), diastolic dysfunction, and/or systolic dysfunction; and/or reduction of blood pressure, such as reduction of systolic blood pressure;

(ix) prevention and/or treatment of gastrointestinal diseases, such as inflammatory bowel disease, short bowel syndrome, or Crohn's disease or colitis; dyspepsia, and/or gastric ulcers; and/or inflammation, such as psoriasis, psoriactic arthritis, rheumatoid arthritis, and/or systemic lupus erythematosus;

(x) prevention and/or treatment of critical illness, such as treatment of a critically ill patient, a critical illness polynephropathy (CIPNP) patient, and/or a potential CIPNP patient; prevention of development of critical illness or CIPNP; prevention, treatment and/or cure of systemic inflammatory response syndrome (SIRS) in a patient; prevention or reduction of the likelihood of a patient suffering from bacteraemia, septicaemia, and/or septic shock during hospitalisation; and/or stabilising blood glucose, insulin balance and optionally metabolism in intensive care unit patients with acute illness;

(xi) prevention and/or treatment of polycystic ovary syndrome (PCOS);

(xii) prevention and/or treatment of cerebral disease, such as cerebral ischemia, cerebral haemorrhage, and/or traumatic brain injury;

(xiii) prevention and/or treatment of sleep apnoea; and/or (xiv) prevention and/or treatment of abuse, such as alcohol abuse and/or drug abuse;

wherein a pharmaceutically active amount of a derivative or an analogue according to any of embodiments 1-183, is administered.

Still Further Particular Embodiments

The following are still further particular embodiments of the invention:

1. A derivative of a GLP-1 analogue of the general Formula I:

Xaa$_7$-Xaa$_8$-Glu-Gly-Thr-Xaa$_{12}$-Thr-Ser-Asp-Xaa$_{16}$-Ser-Xaa$_{18}$-Xaa$_{19}$-Xaa$_{20}$-Glu-Xaa$_{22}$-Xaa$_{23}$-Ala-Xaa$_{25}$-Xaa$_{26}$-Xaa$_{27}$-Phe-Ile-Xaa$_{30}$-Xaa$_{31}$-Leu-Xaa$_{33}$-Xaa$_{34}$-Xaa$_{35}$-Xaa$_{36}$-Xaa$_{37}$-Xaa$_{38}$ (SEQ ID NO:9), wherein Xaa$_7$ is L-histidine, (S)-2-Hydroxy-3-(1H-imidazol-4-yl)-propionic acid, D-histidine, deamino-histidine, homohistidine, N$^\alpha$-acetyl-histidine, N$^\alpha$-formyl-histidine, N$^\alpha$-methyl-histidine, 3-pyridylalanine, 2-pyridylalanine, or 4-pyridylalanine; Xaa$_8$ is Ala, Gly, Ser, Aib, (1-aminocyclopropyl) carboxylic acid, or (1-aminocyclobutyl) carboxylic acid; Xaa$_{12}$ is Phe or Leu; Xaa$_{16}$ is Val or Leu; Xaa$_{18}$ is Ser, Val, Arg, or Leu; Xaa$_{19}$ is Tyr or Gln; Xaa$_{20}$ is Leu or Met; Xaa$_{22}$ is Gly or Glu; Xaa$_{23}$ is Gln, Glu, or Arg; Xaa$_{25}$ is Ala or Val; Xaa$_{26}$ is Arg; Xaa$_{27}$ is Glu or Leu; Xaa$_{30}$ is Ala, Glu, or Arg; Xaa$_{31}$ is Trp or His; Xaa$_{33}$ is Val; Xaa$_{34}$ is Arg, His, Asn, or Gln; Xaa$_{35}$ is Gly or Ala; Xaa$_{36}$ is Arg or Gly; Xaa$_{37}$ is Gly, Pro, or Lys; Xaa$_{38}$ is Lys, or absent; wherein at least one of Xaa$_{37}$ and Xaa$_{35}$ is Lys; which derivative comprises a side chain that is attached to the Lys residue of Xaa$_{37}$ or Xaa$_{35}$, which side chain comprises:

(i) a Branched linker of formula Chem. 11

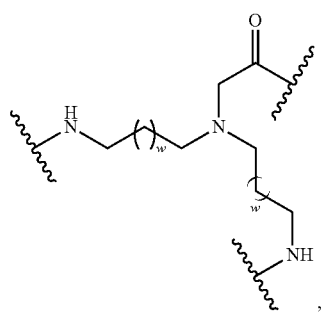

Chem. 11 wherein w is an integer in the range of 0-2;

(ii) a 1$^{st}$ and a 2$^{nd}$ Protractor selected from Chem. 12 and Chem. 13

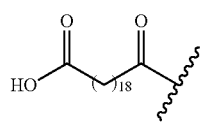

Chem. 12

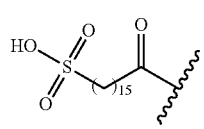

Chem. 13 and (iii) at least one Linker element-1 of Chem. 1:

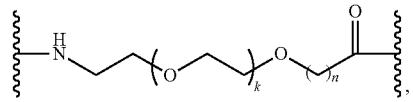

Chem. 1 wherein k is an integer in the range of 1-23, and n is an integer in the range of 1-5;

wherein the Branched linker is connected
a) at its —CO end to the epsilon amino group of the Lys residue of Xaa$_{37}$ or Xaa$_{35}$, via an optional Pre-linker, and
b) at each of its two —NH ends to the —CO end of each of the 1$^{st}$ and 2$^{nd}$ Protractor, respectively, via a 1$^{st}$ and a 2$^{nd}$ Post-linker, respectively; and wherein at least one of the Pre-linker, the 1$^{st}$ Post-linker, and the 2$^{nd}$ Post-linker comprises the Linker element-1;

or a pharmaceutically acceptable salt, amide, or ester thereof.

2. The derivative of embodiment 1, wherein w is 1.

3. The derivative of any of embodiments 1-2, which includes exactly m times Linker element-1, where m is an integer in the range of 2-12.

4. The derivative of any of embodiments 1-3, wherein k is 1, 3, 11, 15, or 23.

5. The derivative of any of embodiments 1-4, wherein n is 1 or 2.

6. The derivative of any of embodiments 1-5, which comprises a Linker element-2 of formula

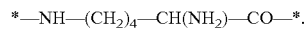

Chem. 2:

7. The derivative of any of embodiments 1-6, which comprises a Linker element-3 of formula

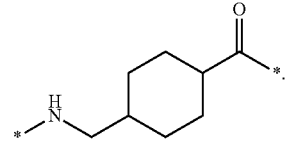

Chem. 3

8. The derivative of any of embodiments 1-7, which comprises a Linker element-4 of formula

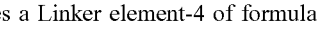

Chem. 4:

9. The derivative of any of embodiments 1-8, which comprises a Linker element-5 of formula

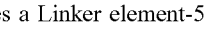

Chem. 5:

10. The derivative of any of embodiments 1-9, which comprises the Pre-linker.

11. The derivative of any of embodiments 1-9, which does not comprise the Pre-linker.

12. A GLP-1 derivative selected from Chem. 21, Chem. 22, Chem. 23, Chem. 24, Chem. 25, Chem. 26, Chem. 27, Chem. 28, Chem. 29, Chem. 30, Chem. 31, Chem. 32, Chem. 33, Chem. 34, Chem. 35, and Chem. 36; or a pharmaceutically acceptable salt, amide, or ester thereof.

13. A pharmaceutical composition comprising a derivative according to any of embodiments 1-12, and a pharmaceutically acceptable excipient.

14. A derivative according to any of embodiments 1-12, for use as a medicament.

15. A derivative according to any of embodiments 1-12, for use in (i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C;

(ii) delaying or preventing diabetic disease progression, such as progression in type 2 diabetes, delaying the progression of impaired glucose tolerance (IGT) to insulin requiring type 2 diabetes, delaying or preventing insulin resistance, and/or delaying the progression of non-insulin requiring type 2 diabetes to insulin requiring type 2 diabetes;

(iii) improving β-cell function, such as decreasing β-cell apoptosis, increasing β-cell function and/or β-cell mass, and/or for restoring glucose sensitivity to β-cells;

(iv) prevention and/or treatment of cognitive disorders and/or neurodegenerative disorders, such as Alzheimer's disease, Parkinson's disease, and/or multiple sclerosis;

(v) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, such as osteoarthritis and/or urine incontinence;

(vi) prevention and/or treatment of diabetic complications, such as angiopathy; neuropathy, including peripheral neuropathy; nephropathy; and/or retinopathy;

(vii) improving lipid parameters, such as prevention and/or treatment of dyslipidemia, lowering total serum lipids; increasing HDL; lowering small, dense LDL; lowering VLDL; lowering triglycerides; lowering cholesterol; lowering plasma levels of lipoprotein a (Lp(a)) in a human; inhibiting generation of apolipoprotein a (apo(a)) in vitro and/or in vivo;

(viii) prevention and/or treatment of cardiovascular diseases, such as syndrome X, atherosclerosis, myocardial infarction, coronary heart disease, reperfusion injury, stroke, cerebral ischemia, an early cardiac or early cardiovascular disease, left ventricular hypertrophy, coronary artery disease, hypertension, essential hypertension, acute hypertensive emergency, cardiomyopathy, heart insufficiency, exercise intolerance, acute and/or chronic heart failure, arrhythmia, cardiac dysrhythmia, syncopy, angina pectoris, cardiac bypass and/or stent reocclusion, intermittent claudication (atherosclerosis obliterens), diastolic dysfunction, and/or systolic dysfunction; and/or reduction of blood pressure, such as reduction of systolic blood pressure;

(ix) prevention and/or treatment of gastrointestinal diseases, such as inflammatory bowel disease, short bowel syndrome, or Crohn's disease or colitis; dyspepsia, and/or gastric ulcers; and/or inflammation, such as psoriasis, psoriactic arthritis, rheumatoid arthritis, and/or systemic lupus erythematosus;

(x) prevention and/or treatment of critical illness, such as treatment of a critically ill patient, a critical illness polynephropathy (CIPNP) patient, and/or a potential CIPNP patient; prevention of development of critical illness or CIPNP; prevention, treatment and/or cure of systemic inflammatory response syndrome (SIRS) in a patient; prevention or reduction of the likelihood of a patient suffering from bacteraemia, septicaemia, and/or septic shock during hospitalisation; and/or stabilising blood glucose, insulin balance and optionally metabolism in intensive care unit patients with acute illness;

(xi) prevention and/or treatment of polycystic ovary syndrome (PCOS);

(xii) prevention and/or treatment of cerebral disease, such as cerebral ischemia, cerebral haemorrhage, and/or traumatic brain injury;

(xiii) prevention and/or treatment of sleep apnoea; and/or (xiv) prevention and/or treatment of abuse, such as alcohol abuse and/or drug abuse.

In some embodiments the GLP-1 derivative of the invention is not selected from Chem. 21, Chem. 22, Chem. 23, Chem. 24, Chem. 25, Chem. 26, Chem. 27, Chem. 28, Chem. 29, Chem. 30, Chem. 31, Chem. 32, Chem. 33, Chem. 34, Chem. 35, Chem. 36, Chem. 37, Chem. 38, Chem. 39, Chem. 40, Chem. 41, Chem. 42, Chem. 43, Chem. 44, Chem. 45, Chem. 46, Chem. 47, Chem. 48, Chem. 49, Chem. 50, Chem. 51, and Chem. 52; and is also not a pharmaceutically acceptable salt, amide, or ester thereof.

In some embodiments the GLP-1 analogue of the invention is not selected from SEQ ID NO: 3, SEQ ID NO: 4, SEQ ID NO: 6, SEQ ID NO: 7, and SEQ ID NO: 8; and is also not a pharmaceutically acceptable salt, amide, or ester thereof.

In some embodiments the intermediate product of the invention is not selected from Chem. 90, Chem. 91, Chem. 92, Chem. 93, Chem. 94, Chem. 95, Chem. 96, Chem. 97, Chem. 98, Chem. 99, Chem. 100, Chem. 101, Chem. 102, Chem. 103, Chem. 104, Chem. 105, Chem. 106, Chem. 107, Chem. 108, Chem. 109, Chem. 110, Chem. 111, Chem. 112, Chem. 113, Chem. 114, Chem. 115, and Chem. 116; and is also not a pharmaceutically acceptable salt, amide, or ester thereof.

EXAMPLES

This experimental part starts with a list of abbreviations, and is followed by a section including general methods for synthesising and characterising analogues and derivatives of the invention. Then follows a number of examples which relate to the preparation of specific GLP-1 derivatives, and at the end a number of examples have been included relating to the activity and properties of these analogues and derivatives (section headed pharmacological methods).

The examples serve to illustrate the invention.

List of Abbreviations

Aib: α-aminoisobutyric acid (2-Aminoisobutyric acid)
Abu: 4-aminobutanoic acid
AcOH: acetic acid
Ado: 8-amino-3,6-dioxaoctanoic acid
API: Active Pharmaceutical Ingredient
AUC: Area Under the Curve
BG: Blood Glucose
BHK Baby Hamster Kidney
BW: Body Weight
Boc: t-butyloxycarbonyl
Bom: benzyloxymethyl
BSA: Bovine serum albumin
Bz: benzyl
BW: body weight
C20 diacid: icosanedioic acid
CAS: Chemical Abstracts Service
Clt: 2-chlorotrityl collidine: 2,4,6-trimethylpyridine
COOBz: benzyloxycarbonyl
COOMe: methoxycarbonyl
COOtBu: tert-butoxycarbonyl
DCM: dichloromethane
Dde: 1-(4,4-dimethyl-2,6-dioxocyclohexylidene)ethyl
DIC: diisopropylcarbodiimide
DIPEA: diisopropylethylamine
DMEM: Dulbecco's Modified Eagle's Medium (DMEM)
dPEG: discrete polyethylene glycol
EDTA: ethylenediaminetetraacetic acid
EGTA: ethylene glycol tetraacetic acid
FCS: Fetal Calf Serum
Fmoc: 9-fluorenylmethyloxycarbonyl
FI: food intake
HATU: (O-(7-azabenzotriazol-1-yl)-1,1,3,3-tetramethyluronium hexa fluorophosphate)
HBTU: (2-(1H-benzotriazol-1-yl-)-1,1,3,3 tetramethyluronium hexafluorophosphate)
HEPES: 4-(2-hydroxyethyl)-1-piperazineethanesulfonic acid
HFIP 1,1,1,3,3,3-hexafluoro-2-propanol or hexafluoroisopropanol
HOAt: 1-hydroxy-7-azabenzotriazole
HOBt: 1-hydroxybenzotriazole
HPLC: High Performance Liquid Chromatography
HSA: Human Serum Albumin
IBMX: 3-isobutyl-1-methylxanthine
Imp: imidazopropionic acid (3-(Imidazol-5-yl)propanoic acid), alternative name is deamino histidine
Inp: isonipecotic acid
i.v. intravenously
ivDde: 1-(4,4-dimethyl-2,6-dioxocyclohexylidene)-3-methylbutyl
IVGTT: Intravenous Glucose Tolerance Test
LCMS: Liquid Chromatography Mass Spectroscopy
LYD: Landrace Yorkshire Duroc
MALDI-MS: See MALDI-TOF MS
MALDI-TOF MS: Matrix-Assisted Laser Desorption/Ionisation Time of Flight Mass Spectroscopy
MeOH: methanol
Mmt: 4-methoxytrityl
Mtt: 4-methyltrityl
NHBoc: tert-butoxycarbonylamino
NHCbz: benzyloxycarbonylamino
NHFmoc: 9H-fluoren-9-ylmethoxycarbonylamino
NMP: N-methyl pyrrolidone
OBz: benzyloxy
OPfp: 2,3,4,5,6-pentafluorophenoxy
OPnp: 4-nitrophenoxy
OSuc: (2,5-dioxopyrrolidin-1-yl)oxy
OtBu: tert butyl ester
Oxyma Pure®: Cyano-hydroxyimino-acetic acid ethyl ester
Pbf: 2,2,4,6,7-pentamethyldihydrobenzofuran-5-sulfonyl
PBS: Phosphate Buffered Saline
PD: Pharmacodynamic
PEG: polyethylene glycol
Pen/Strep: Pencillin/Streptomycin
PK: Pharmacokinetic
PyBOP: benzotriazol-1-yl-oxytripyrrolidinophosphonium hexafluorophosphate
RP: Reverse Phase
RP-HPLC: Reverse Phase High Performance Liquid Chromatography
RT: Room Temperature
Rt: Retention time
s.c.: Subcutaneously
SD: Standard Deviation
SEC-HPLC: Size Exclusion High Performance Liquic Chromatography
SEM: Standard Error of Mean
SPA: Scintillation Proximity Assay
SPPS: Solid Phase Peptide Synthesis
Sulfonic acid-C16:
  16-sulfohexadecanoic acid
tBu: tert. butyl
TFA: trifluoroacetic acid
TIS: triisopropylsilane
TLC: Thin Layer Chromatography
Tos: tosylate (or pare-toluenesulfonyl)
Tris: tris(hydroxymethyl)aminomethane or 2-amino-2-hydroxymethyl-propane-1,3-diol
Trt: triphenylmethyl (trityl)
Trx: tranexamic acid (trans-4-(aminomethyl)cyclohexanecarboxylic acid)
UPLC: Ultra Performance Liquid Chromatography
Special Materials and Methods
Icosanedioic acid mono-tert-butyl ester
Fmoc-8-amino-3,6-dioxaoctanoic acid
Fmoc-15-amino-4,7,10,13-tetraoxapentadecanoic acid
1-(9-Fluorenylmethyloxycarbonyl)amino-3,6,9,12,15,18,21,24,27,30,33,36-dodecaoxanonatriacontan-39-oic acid
alpha-(9-Fluorenylmethyloxycarbonyl)amino-omega-carboxy hexadeca(ethylene glycol)
Fmoc-tranexamic acid
Fmoc-isonipecotic acid
Boc-Lys(Fmoc)-OH
4-(Fmoc-amino)butyric acid
Fmoc-Glu-OtBu
N,N-bis(N'-Fmoc-3-aminopropyl)-glycine potassium hemisulfate
16-Sulfo-hexadecanoic acid
Fmoc-Lys(Mtt)-Wang resin
Chemical Methods
This section is divided in two: Section A relating to general methods (of preparation (A1); and of detection and characterisation (A2)), and section B, in which the preparation and characterisation of a number of specific example compounds is described.
A. General Methods
A1. Methods of Preparation
This section relates to methods for solid phase peptide synthesis (SPPS methods, including methods for de-protection of amino acids, methods for cleaving the peptide from the resin, and for its purification), as well as methods for detecting and characterising the resulting peptide (LCMS, MALDI, and UPLC methods). The solid phase synthesis of peptides may in some cases be improved by the use of di-peptides protected on the di-peptide amide bond with a group that can be cleaved under acidic conditions such as, but not limited to, 2-Fmoc-oxy-4-methoxybenzyl, or 2,4,6-trimethoxybenzyl. In cases where a serine or a threonine is present in the peptide, pseudoproline di-peptides may be used (available from, e.g., Novabiochem, see also W. R. Sampson (1999), J. Pep. Sci. 5, 403). The Fmoc-protected amino acid derivatives used were the standard recommended: Fmoc-Ala-OH, Fmoc-Arg(Pbf)-OH, Fmoc-Asn(Trt)-OH, Fmoc-Asp(OtBu)-OH, Fmoc-Cys(Trt)-OH, Fmoc-Gln(Trt)-OH, Fmoc-Glu(OtBu)-OH, Fmoc-Gly-OH, Fmoc-His(Trt)-OH, Fmoc-Ile-OH, Fmoc-Leu-OH, Fmoc-Lys(Boc)-OH, Fmoc-Met-OH, Fmoc-Phe-OH, Fmoc-Pro-OH, Fmoc-Ser(tBu)-OH, Fmoc-Thr(tBu)-OH, Fmoc-Trp(Boc)-OH, Fmoc-Tyr(tBu)-OH, or, Fmoc-Val-OH etc. supplied from e.g. Anaspec, Bachem, Iris Biotech, or Novabiochem. Where nothing else is specified the natural L-form of the amino acids are used. The N-terminal amino acid was Boc protected at the alpha amino group (e.g. Boc-His(Boc)-OH, or Boc-His(Trt)-OH for peptides with His at the N-terminus). In case of modular side chain or albumin binding moiety attachment using SPPS the following suitably protected building blocks such as but not limited to Fmoc-8-amino-3,6-dioxaoctanoic acid, Fmoc-tranexamic acid, Fmoc-Glu-OtBu, and icosanedioic acid mono-tert-butyl ester were used. All operations stated below were performed at 250-µmol synthesis scale.

1. Synthesis of Resin Bound Protected Peptide Backbone

Method: SPPS_P

SPPS_P was performed on a Prelude Solid Phase Peptide Synthesizer from Protein Technologies (Tucson, Ariz. 85714 U.S.A.) at 250-pmol scale using six fold excess of Fmoc-amino acids (300 mM in NMP with 300 mM HOAt or Oxyma Pure®) relative to resin loading, e.g. low load Fmoc-Lys(Mtt)-Wang resin (0.35 mmol/g). Fmoc-deprotection was performed using 20% piperidine in NMP. Coupling was performed using 3:3:3:4 amino acid/(HOAt or Oxyma Pure®)/DIC/collidine in NMP. NMP and DCM top washes (7 ml, 0.5 min, 2×2 each) were performed between deprotection and coupling steps. Coupling times were generally 60 minutes. Some amino acids including, but not limited to Fmoc-Arg(Pbf)-OH, Fmoc-Aib-OH or Boc-His(Trt)-OH were "double coupled", meaning that after the first coupling (e.g. 60 min), the resin is drained and more reagents are added (amino acid, (HOAt or Oxyma Pure®), DIC, and collidine), and the mixture allowed to react again (e.g. 60 min).

Method: SPPS_L

SPPS_L was performed on a microwave-based Liberty peptide synthesiser from CEM Corp. (Matthews, N.C. 28106, U.S.A.) at 250-µmol or 100-µmol scale using six fold excess of Fmoc-amino acids (300 mM in NMP with 300 mM HOAt or Oxyma Pure®) relative to resin loading, e.g. low load Fmoc-Lys(Mtt)-Wang resin (0.35 mmol/g). Fmoc-deprotection was performed using 5% piperidine in NMP at up to 75° C. for 30 seconds where after the resin was drained and washed with NMP and the Fmoc-deprotection was repeated this time for 2 minutes at 75° C. Coupling was performed using 1:1:1 amino acid/(HOAt or Oxyma Pure®)/DIC in NMP. Coupling times and temperatures were generally 5 minutes at up to 75° C. Longer coupling times were used for larger scale reactions, for example 10 min. Histidine amino acids were double coupled at 50° C., or quadruple coupled if the previous amino acid was sterically hindered (e.g. Aib). Arginine amino acids were coupled at RT for 25 minutes and then heated to 75° C. for 5 min. Some amino acids such as but not limited to Aib, were "double coupled", meaning that after the first coupling (e.g. 5 min at 75° C.), the resin is drained and more reagents are added (amino acid, (HOAt or Oxyma Pure®) and DIC), and the mixture is heated again (e.g. 5 min at 75° C.). NMP washes (5×10 ml) were performed between deprotection and coupling steps.

2. Synthesis of Albumin Binder (Side Chain)

Icosanedioic acid mono-tert-butyl ester can be prepared as known in the art. For a method please refer to WO 2010102886 A1.

16-Sulfo-hexadecanoic acid can be prepared as follows:
16-Hexadecanolide (150 g, 589 mmol) was dissolved in MeOH (2500 mL) and toluene-4-sulfonic acid (13.5 g, 71.0 mmol) was added. Reaction mixture was heated to reflux for 16 hrs. After cooling down sodium hydrogencarbonate was added (8.40 g, 112 mmol) and the reaction mixture was stirred 15 minutes. Solvents were evaporated, ethyl-acetate was added (2000 mL) and the mixture was extracted with water (400 mL), 10% solution of sodium hydrogencarbonate (2×400 mL) and brine (200 mL). After drying with anhydrous $MgSO_4$, filtration and evaporation of solvents crude product was obtained. It has been recrystallised from hexane (1500 mL). After filtration 16-hydroxyhexadecanoic acid methyl ester was obtained as a white solid.

Yield: 161.0 g (96%).

Above prepared ester was dissolved in DCM (1200 mL). Triethylamine was added (118 mL, 847.8 mmol), reaction mixture was cooled to 0° C. and mesylchloride (55 mL) was added slowly during 10 minutes. After one hour the reaction mixture was allowed to warm to room temperature and has been stirred overnight. After 16 hrs water was added (20 mL) and the mixture was stirred 30 minutes. Solvents were evaporated, ethyl-acetate was added (1600 mL) and the mixture was extracted with 1M HCl (2×600 mL), 5% solution of sodium carbonate (2×400 mL) and water (400 mL). After drying with anhydrous $MgSO_4$, filtration and evaporation of solvents 16-mesylhexadecanoic acid methyl ester was obtained as white solid.

Yield: 205.1 g (100%).

Above prepared mesylate was dissolved in ethanole (2000 mL), thiourea (81.0 g, 1.068 mol) and NaI (92.2 g, 0.616 mmol) were added and the reaction mixture was refluxed two days. After cooling down solvents were evaporated and solution of NaOH (184 g) in water (1600 mL) was added. Resulting suspension was heated 2 hrs to reflux and poured into 10% HCl (2000 mL). After 15 minutes another portion of conc. HCl was added (120 mL). White precipitate was filtered and washed with water, dried and evaporated several times with toluene. 16-Mercaptohexadecanoic acid was obtained as a white solid.

Yield: 165.1 g (100%).

16-Mercaptohexadecanoic acid (165.1 g, 0.572 mmol) was dissolved in DCM (1600 mL) and 2N HCl was added (800 mL). Bromine (200 mL) was slowly added, forming first white precipitate which has been dissolved after adding the whole bromine volume. The mixture was stirred 3 hrs at room temperature. Both DCM and bromine were evaporated, three more portions of DCM (3×500 mL) were added and evaporated to get rid of the rest of bromine. 2M NaOH was added until brown colour disappeared and the reaction mixture was heated to reflux for 1 hr. Conc. HCl was added to acidic pH, precipitate was filtered off and centrifuged and decanted six times with water. The title product was obtained as a white solid.

Yield: 151.6 g (74%).

1H NMR spectrum (300 MHz, DMSO, 5H): 11.97 (bs, 1H); 2.39 (m, 2H); 2.18 (t, J=7.3 Hz, 2H); 1.49 (m, 4H); 1.23 (m, 22H).

3. Attachment of Side Chains to Resin Bound Protected Peptide Backbone

When an acylation is present on a lysine side chain, the epsilon amino group of lysine to be acylated was protected with either Mtt, Mmt, Dde, ivDde, or Boc, depending on the route for attachment of the protracting moiety and linker. Dde- or ivDde-deprotection was performed with 2% hydrazine in NMP (2×20 ml, each 10 min) followed by NMP washings (4×20 ml). Mtt- or Mmt-deprotection was performed with 2% TFA and 2-3% TIS in DCM (5×20 ml, each 10 min) followed by DCM (2×20 ml), 10% MeOH and 5% DIPEA in DCM (2×20 ml) and NMP (4×20 ml) washings, or by treatment with hexafluoroisopropanol/DCM (75:25, 5×20 ml, each 10 min) followed by washings as above. In some cases the Mtt group was removed by automated steps on the Liberty peptide synthesiser. Mtt deprotection was performed with hexafluoroisopropanol or hexafluoroisopropanol/DCM (75:25) at room temperature for 30 min followed by washing with DCM (7 ml×5), followed by washing with 5% piperidine (7 ml×5) and NMP washings. The protracting moiety and/or linker can be attached to the peptide either by acylation of the resin bound peptide or by acylation in solution of the unprotected peptide. In case of attachment of the protracting moiety and/or linker to the protected peptidyl resin the attachment can be modular using SPPS and suitably protected building blocks.

Method: SC_P

The N-E-lysine protection group was removed as described above and the chemical modification of the lysine was performed by one or more automated steps on the Prelude peptide synthesiser using suitably protected building blocks as described above. Double couplings were performed as described in SPPS_P with 3 hours per coupling.

Method: SC_L

The N-E-lysine protection group was removed as described above and the chemical modification of the lysine was performed by one or more automated steps on the Liberty peptide synthesiser using suitably protected building blocks as described above. Double couplings were performed as described in SPPS_L.

Method: SC_M_1

The N-E-lysine protection group was removed as described above and the chemical modification of the lysine was performed by one or more manual steps using suitably protected building blocks as described above. The SC_M_1 was performed at 500-µmol scale using four or six fold excess of Fmoc-amino acids (300 mM in NMP with 300 mM HOAt, Oxyma Pure®) relative to resin loading. Fmoc-deprotection was performed using 20% piperidine in NMP for 5 minutes at room temperature where after the resin was drained and washed with NMP and the Fmoc-deprotection was repeated this time for 15 minutes at room temperature. Coupling was performed using 1:1:1 amino acid/Oxyma Pure®)/DIC in NMP. Coupling times were generally 60 minutes at room temperature. Some building blocks were double coupled meaning that after the first coupling (e.g. 60 min), the resin is drained and more reagents are added (amino acid, (HOAt or Oxyma Pure®), DIC, and collidine), and the mixture allowed to react again (e.g. 60 min).

Method: SC_M_2

Coupling of Fmoc-L-cysteic acid at 250 µmol or 500-µmol scale using two to four fold excess of the above acid dissolved DMF and the solution was mixed with PyBoP dissolved in NMP for 5 min. (300 mM in DMF with 300 mM PyBOP in NMP). The solution was added to the resin followed by addition of DIPEA (Acid/PyBOP/DIPEA (1:1:4). The resin was shaken for 2 hours. Double coupled.

Method: SC_M_3

Coupling of 16-Sulfo-hexadecanoic acid was performed at 250-µmol or 500-µmol scale using tree to four fold excess of the acid dissolved in boiling DMF followed by slowly cooling until 50° C. and addition of PyBoP dissolved in DMF (40 mM in DMF with 300 mM PyBOP) before adding the solution to the resin. Slowly addition of DIPEA (Acid/PyBOP/DIPEA (1:1:4). The resin was shaken for 2 hours. Double or triple coupled.

4. Cleavage of Resin Bound Peptide with or without Attached Side Chains and Purification Method: CP_M1

After synthesis the resin was washed with DCM, and the peptide was cleaved from the resin by a 2-3 hour treatment with TFA/TIS/water (95/2.5/2.5 or 92.5/5/2.5) followed by precipitation with diethylether. The peptide was dissolved in a suitable solvent (such as, e.g., 30% acetic acid) and purified by standard RP-HPLC on a C18, 5 µm column, using acetonitrile/water/TFA. The fractions were analysed by a combination of UPLC, MALDI and LCMS methods, and the appropriate fractions were pooled and lyophilised.

If desired the peptide counter ion can be exchanged to sodium using the methods known in the art. As an example approx. 2 g peptide was dissolved in 250 ml acetonitrile/water (50/50) and loaded onto a Waters X-Bridge C8, 5 µM, 50×250 mm column on a preparative RP-HPLC system. Following loading, the column was washed with water for 8 min at a flow rate of 60 ml/min and 0.01 N NaOH pH 11 at a flow rate of 60 ml/min for 2×8 min. The sodium salt of the peptide was eluted using an isocratic flow of water at 60 ml/min for 10 min followed by a linear gradient of 5% to 85% acetonitrile over 30 min.

A2. General Methods for Detection and Characterisation

1. LC-MS methods

Method: LCMS01

LCMS01 was performed on a setup consisting of Waters Acquity UPLC system and LCT Premier XE mass spectrometer from Micromass. Eluents: A: 0.1% Formic acid in water; B: 0.1% Formic acid in acetonitrile. The analysis was performed at RT by injecting an appropriate volume of the sample (preferably 2-10 µl) onto the column which was eluted with a gradient of A and B. The UPLC conditions, detector settings and mass spectrometer settings were: Column: Waters Acquity UPLC BEH, C-18, 1.7 µm, 2.1 mm×50 mm. Gradient: Linear 5%-95% acetonitrile during 4.0 min (alternatively 8.0 min) at 0.4 ml/min. Detection: 214 nm (analogue output from TUV (Tunable UV detector)) MS ionisation mode: API-ES. Scan: 100-2000 amu (alternatively 500-2000 amu), step 0.1 amu.

Method: LCMS27

LCMS27 was performed on a setup consisting of Agilent 1290 infinity series UPLC system and Agilent Technologies LC/MSD TOF 6230 (G6230A). Eluents: A: 99.90% $H_2O$, 0.02% TFA; B: 99.90% $CH_3CN$, 0.02% TFA. The analysis was performed at RT by injecting an appropriate volume of the sample onto an Eclipse C18+2.1×50 mm 1.8 u column which was eluted with a linear gradient of 5% to 95% B with a run-time of 6 min: 0-4.5 min 5-95% B, 4.5-5.0 min 95% B, 5.0-5.5 min 95-5% B, 5.5-6.0 min 5% B, a flow rate of 0.40 ml/min, and a column temperature of 40° C. The ionisation method was Agilent Jet Stream source. The scanning range was as follows: m/z min. 100, m/z max. 3200. Linear reflector mode was used. Positive mode was used. Mass found is m/z of the compounds.

Method: LCMS29

LCMS29 was performed on a setup consisting of Agilent 1290 infinity series UPLC system and Agilent Technologies LC/MSD TOF 6230 (G6230A). Eluents: A: 99.90% $H_2O$, 0.02% TFA; B: 99.90% $CH_3CN$, 0.02% TFA. The analysis was performed at RT by injecting an appropriate volume of the sample onto a Phenomenex Aeris widepore 3.6µ C4 50×2.1 mm column which was eluted with a step gradient: 5% to 90% B, gradient run-time: 10 min: 0.0-1.0 min 5-20% B, 1.0-7.0 min 20-90% B, 7.0-8.0 min 90% B, 8.0-8.5 min 90-5% B, 8.5-10 min 5% B. The flow rate was 0.40 ml/min and the column temperature 40° C. Mass found is m/z of the compounds. The ionisation method was Agilent Jet Stream source. The scanning range was as follows: m/z min. 100, m/z max. 3200. Linear reflector mode was used. Positive mode was used. Mass found is m/z of the compounds.

2. UPLC Method
Method: UPLC02

The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C. The UPLC system was connected to two eluent reservoirs containing: A: 99.95% $H_2O$, 0.05% TFA; B: 99.95% $CH_3CN$, 0.05% TFA. The following linear gradient was used: 95% A, 5% B to 95% A, 5% B over 16 minutes at a flow-rate of 0.40 ml/min.

B. Synthesis of Compounds of the Invention

Example 1

N{Epsilon-37}-[2-[bis[3-[[2-[2-[2-[[2-[2-[2-[[2-[2-[2-[[2-[2-[2-[[2-[2-[2-[[(2S)-2-amino-6-[[(2S)-2-amino-6-(19-carboxynonadecanoylamino)hexanoyl]amino]hexanoyl]amino]ethoxy]ethoxy]acetyl]amino]ethoxy]ethoxy]acetyl]amino]ethoxy]ethoxy]acetyl]amino]ethoxy]ethoxy]acetyl]amino]ethoxy]ethoxy]acetyl]amino]propyl]amino]acetyl]-[Ab8,Glu22,Arg26,Arg34,Lys37]-GLP-1-(7-37)-peptide Chem. 21
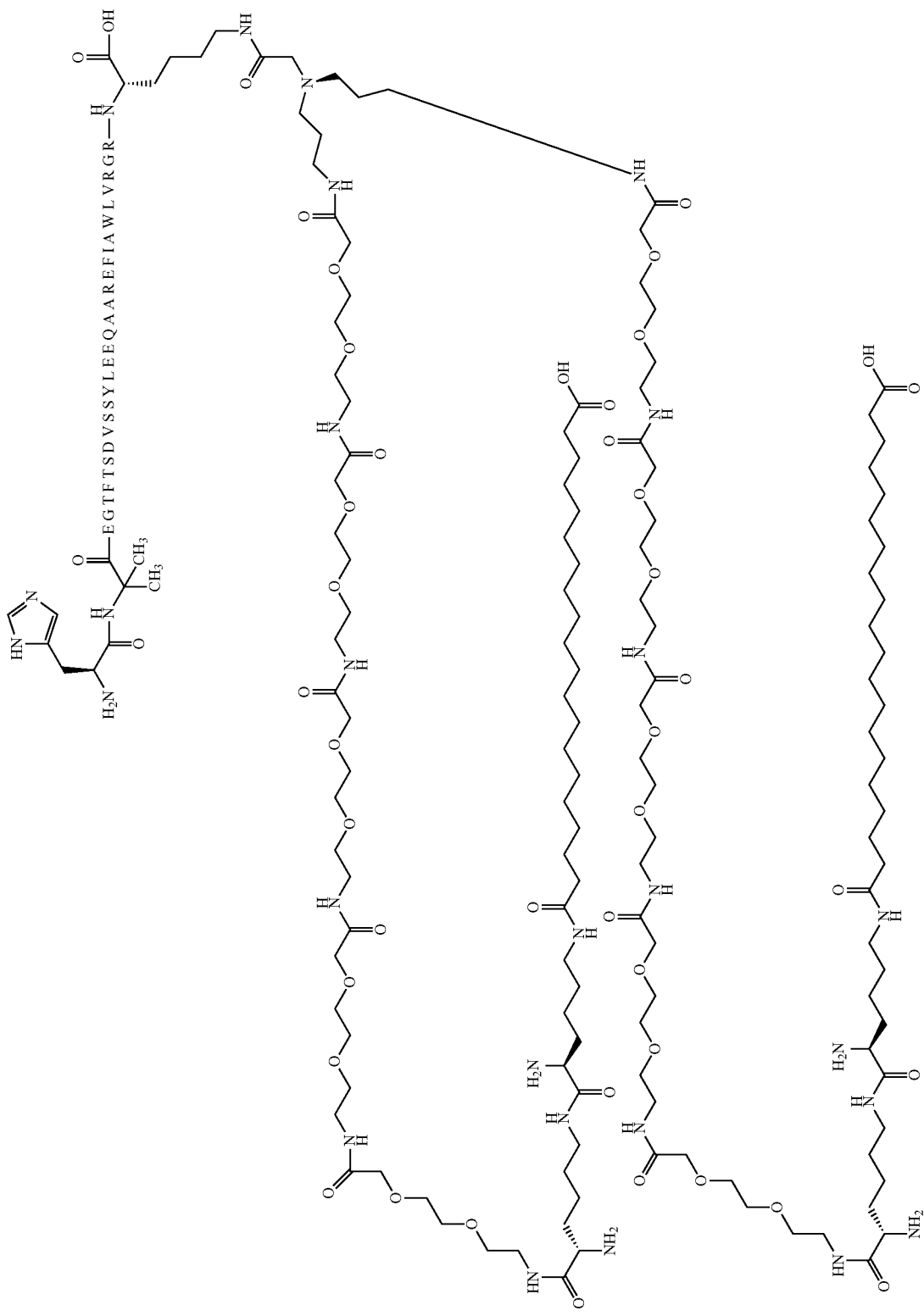

The peptide has SEQ ID NO: 2
Synthesis method: SPPS_L; SC_L; SC_M_3; CP_M1
UPLC02: RT=8.69 min
LCMS01: RT=2.07 min, m/z: 1587 $[M+4H]^{4+}$, 1270 $[M+5H]^{5+}$

Example 2

N{Epsilon-37}-[2-[bis[3-[[2-[2-[2-[[2-[2-[2-[[2-[2-[2-[[2-[2-[[(2S)-2- amino-6-[[(2S)-2-amino-6-(19-carboxynonadecanoylamino)hexanoyl]amino]hexanoyl]amino]ethoxy]ethoxy]acetyl]amino]ethoxy]ethoxy]acetyl]amino]ethoxy]ethoxy]acetyl]amino]ethoxy]ethoxy]acetyl]amino]propyl]amino]acetyl]-[Aib8,Glu22,Arg26,Arg34,Lys37]-GLP-1-(7-37)-peptide

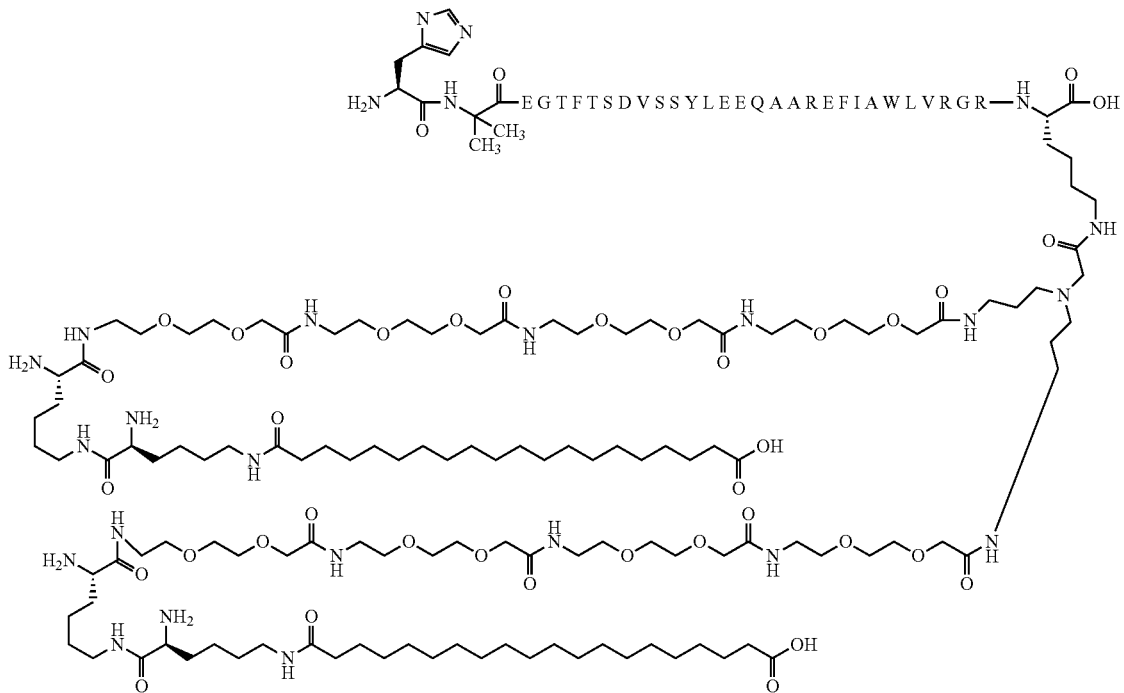

Chem. 22

The peptide has SEQ ID NO: 2
Synthesis method: SPPS_L; SC_L; SC_M_3; CP_M1
UPLC02: RT=8.80 min
LCMS01: RT=2.11 min, m/z: 1517 $[M+4H]^{4+}$, 1213 $[M+5H]^{5+}$ Example 3

N{Epsilon-37}-[2-[bis[3-[[2-[2-[2-[[2-[2-[2-[[2-[2-[2-[[2-[2-[2-[[2-[2-[2-[[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl]amino]ethoxy]ethoxy]acetyl]amino]ethoxy]ethoxy]acetyl]amino]ethoxy]ethoxy]acetyl]amino]propyl]amino]acetyl]-[Aib8,Glu22,Arg26,Arg34,Lys37]-GLP-1-(7-37)-peptide Chem. 23

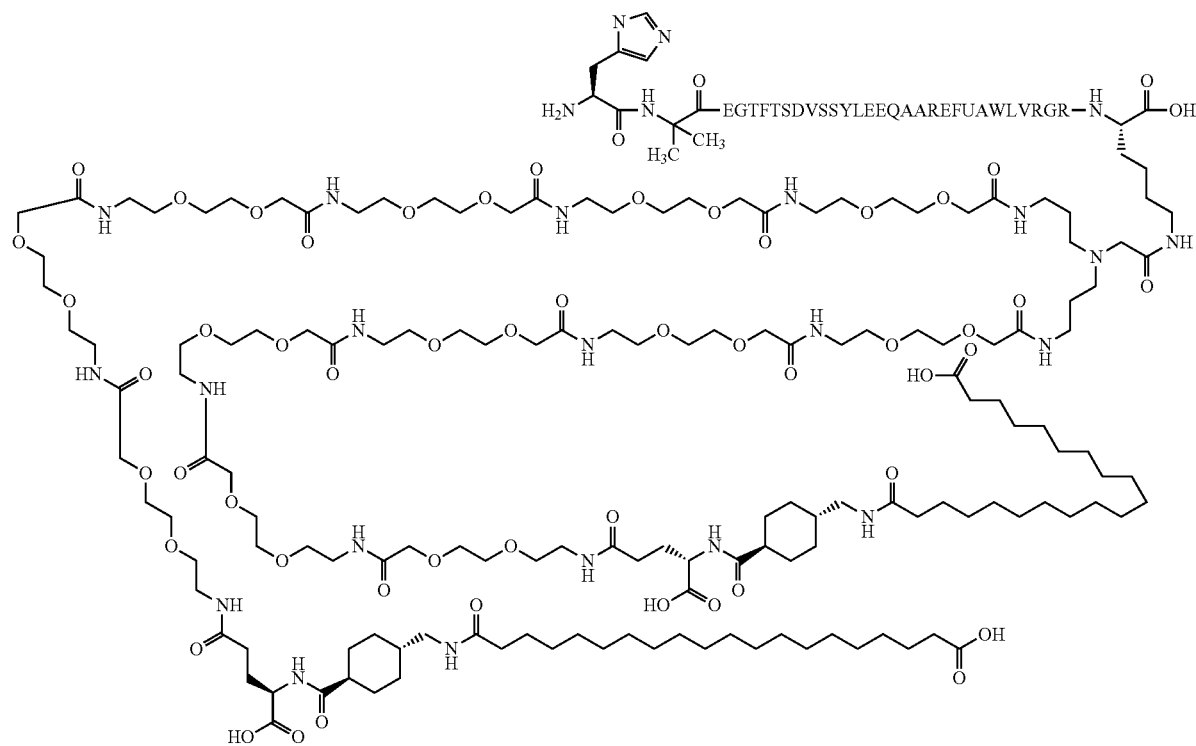

The peptide has SEQ ID NO: 2
Synthesis method: SPPS_P; SC_P; CP_M1
UPLC02: RT=10.5 min
LCMS01: RT=2.6 min, m/z: 1668 [M+4]$^{4+}$, 1335 [M+5H]$^{5+}$, 1112 [M+6H]$^{6+}$ Example 4

N{Epsilon-37}-[2-[3-[[2-[2-[2-[[2-[2-[2-[[2-[2-[2-[[2-[2-[2-[[(2S)-2-amino-6-[[(2S)-2-amino-6-(19-carboxynonadecanoylamino)hexanoyl]amino]hexanoyl]amino]ethoxy]ethoxy]acetyl]amino]ethoxy]ethoxy]acetyl]amino]ethoxy]ethoxy]acetyl]amino]propyl-[3-[[2-[2-[2-[[2-[2-[2-[[2-[2-[2-[[2-[2-[2-[[(2S)-2-amino-6-[[(2S)-2- amino-6-(19-carboxynonadecanoylamino)hexanoyl]amino]hexanoyl]amino]ethoxy]ethoxy]acetyl]amino]ethoxy]ethoxy]acetyl]amino]ethoxy]ethoxy]acetyl]amino]ethoxy]ethoxy]acetyl]amino]propyl]amino]acetyl]-[Imp7,Aib8,Glu22,Arg26,Arg34,Lys37]-GLP-1-(7-37)-peptide Chem. 24

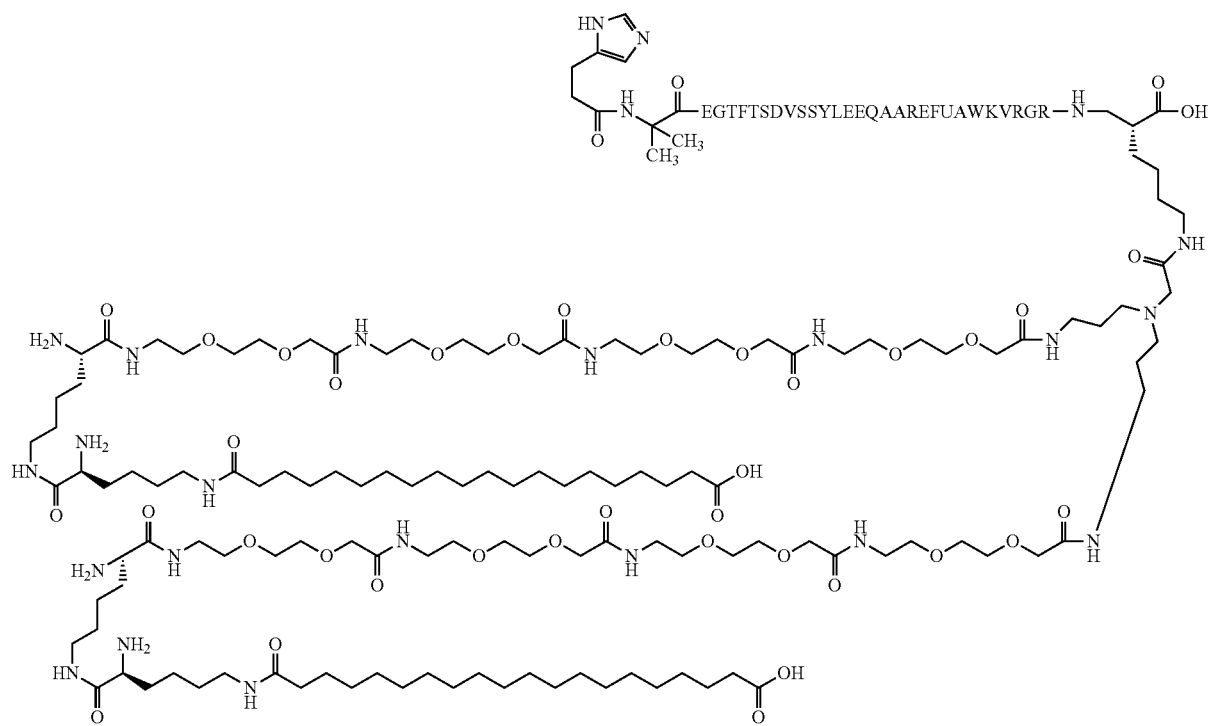

The peptide has SEQ ID NO: 3
Synthesis method: SPPS_L; SC_L; SC_M_3; CP_M1
UPLC02: RT=9.20 min
LCMS01: RT=2.13 min, m/z: 1512 [M+4H]$^{4+}$, 1210 [M+5H]$^{5+}$ Example 5

N{Epsilon-37}-[2-[bis[3-[3-[2-[2-[2-[2-[3-[2-[2-[2-[2-[3-[2-[2-[2-[2-[[(2S)-2-amino-6-[[(2S)-2-amino-6-(19-carboxynonadecanoylamino)hexanoyl]amino]hexanoyl]amino]ethoxy]ethoxy]ethoxy]ethoxy]propanoylamino]ethoxy]ethoxy]ethoxy]ethoxy]propanoylamino]ethoxy]ethoxy]ethoxy]ethoxy]propanoylamino]propyl]amino]acetyl]-[Aib8,Glu22,Arg26,Arg34,Lys37]-GLP-1-(7-37)-peptide Chem. 25

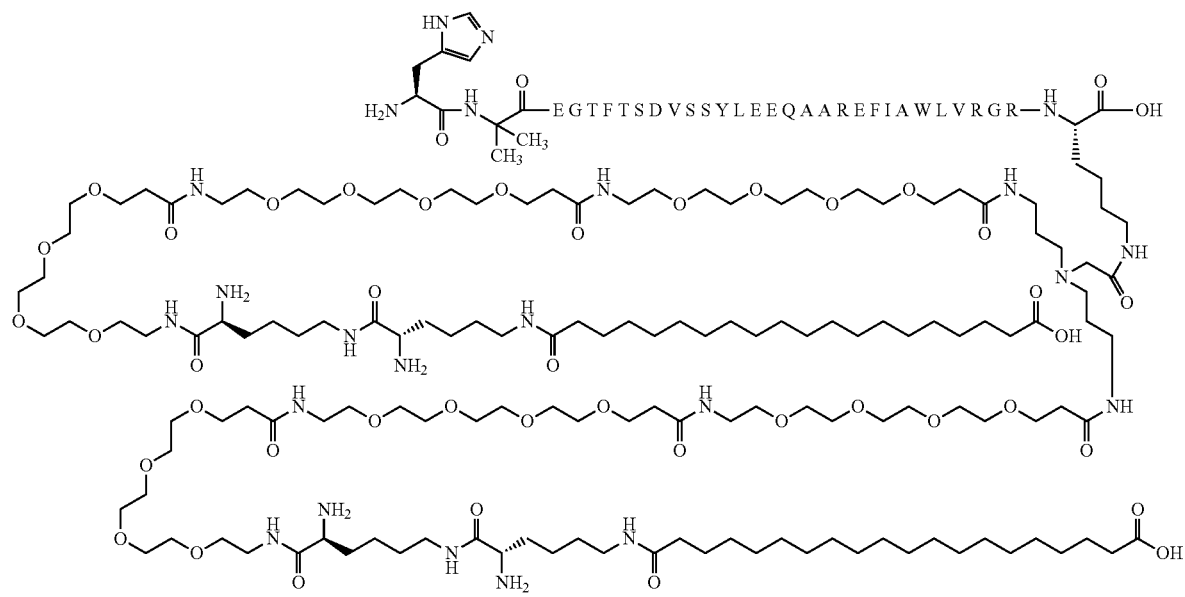

Synthesis method: SPPS_L; SC_L; SC_M_3; CP_M1
UPLC02: RT=8.91 min
LCMS01: RT=3.1 min, m/z: 2129 [M+3]$^{3+}$, 1597 [M+4H]$^{4+}$, 1278 [M+5H]$^{5+}$ Example 6

N{Epsilon-37}-[2-[bis[3-[3-[2-[2-[2-[2-[2-[2-[2-[2-[2-[2-[2-[2-[2-[2-[2-[2-[2-[2-[2-[2-[2-[[(2S)-2-amino-6-[[(2S)-2-amino-6-(19-carboxynonadecanoylamino)hexanoyl]amino]hexanoyl]amino]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]propanoylamino]propyl]amino]acetyl]-[Aib8,Glu22,Arg26,Arg34,Lys37]-GLP-1-(7-37)-peptide Chem. 26

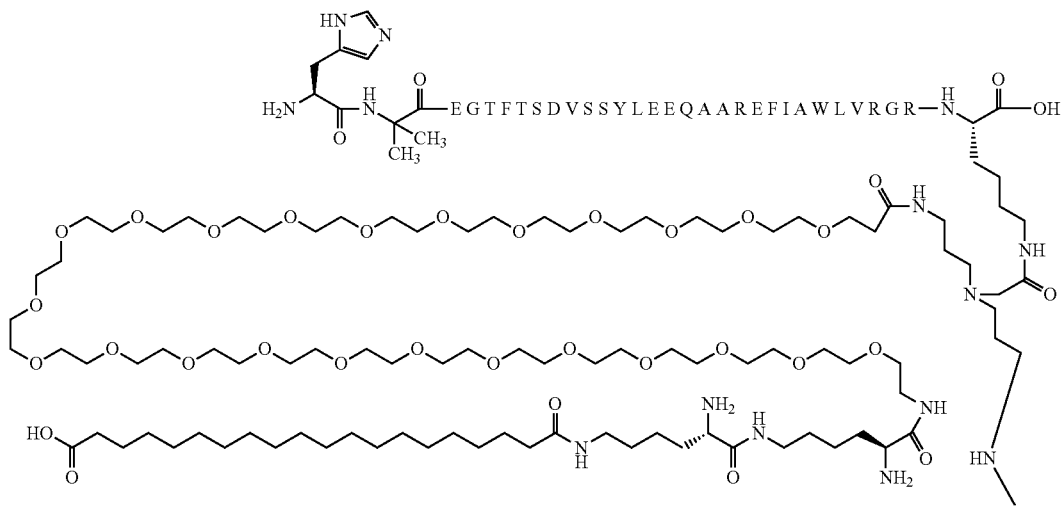

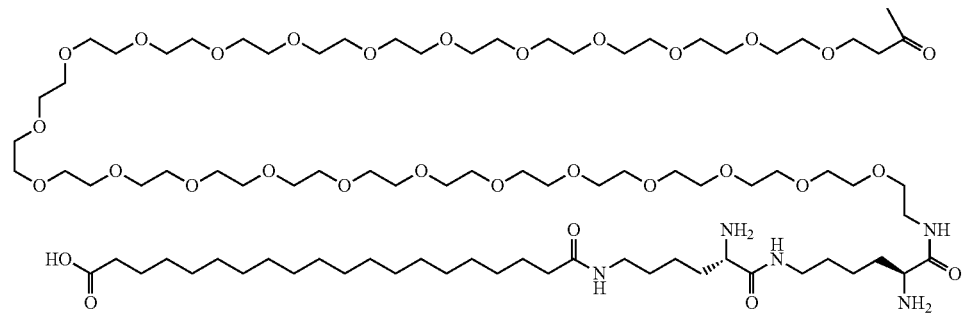

The peptide has SEQ ID NO: 2
Synthesis method: SPPS_L; SC_L; SC_M_3; CP M1
UPLC02: RT=9.69 min
LCMS01: RT=2.32 min, m/z: 1740 $[M+4H]^{4+}$, 1432 $[M+5H]^{5+}$ Example 7

N{Epsilon-37}-[2-[bis[3-[3-[2-[2-[2-[2-[2-[2-[2-[2-[2-[2-[2-[2-[2-[2-[[(2S)-2-amino-6-[[(2S)-2-amino-6-(19-carboxynonadecanoylamino)hexanoyl]amino]hexanoyl]amino]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]propanoylamino]propyl]amino]acetyl]-[Aib8,Glu22,Arg26,Arg34,Lys37]-GLP-1-(7-37)-peptide Chem. 27

The peptide has SEQ ID NO: 2
Synthesis method: SPPS_L; SC_L; SC_M_3; CP_M1
UPLC02: RT=9.00 min
LCMS01: RT=2.18 min, m/z: 1614 [M+4H]$^{4+}$, 1292 [M+5H]$^{5+}$, 1076 [M+5H]$^{6+}$ Example 8

N{Epsilon-37}-[2-[bis[3-[3-[2-[2-[2-[2-[2-[2-[2-[2-[2-[2-[2-[[(2S)-2- amino-6-[[(2S)-2-amino-6-(19-carboxynonadecanoylamino)hexanoyl]amino] hexanoyl]amino]ethoxy]ethoxy]ethoxy]ethoxy] ethoxy]ethoxy]ethoxy]ethoxy]ethoxy] ethoxy]ethoxy]propanoylamino]propyl]amino] acetyl]-[Aib8,Glu22,Arg26,Arg34,Lys37]-GLP-1-(7-37)-peptide

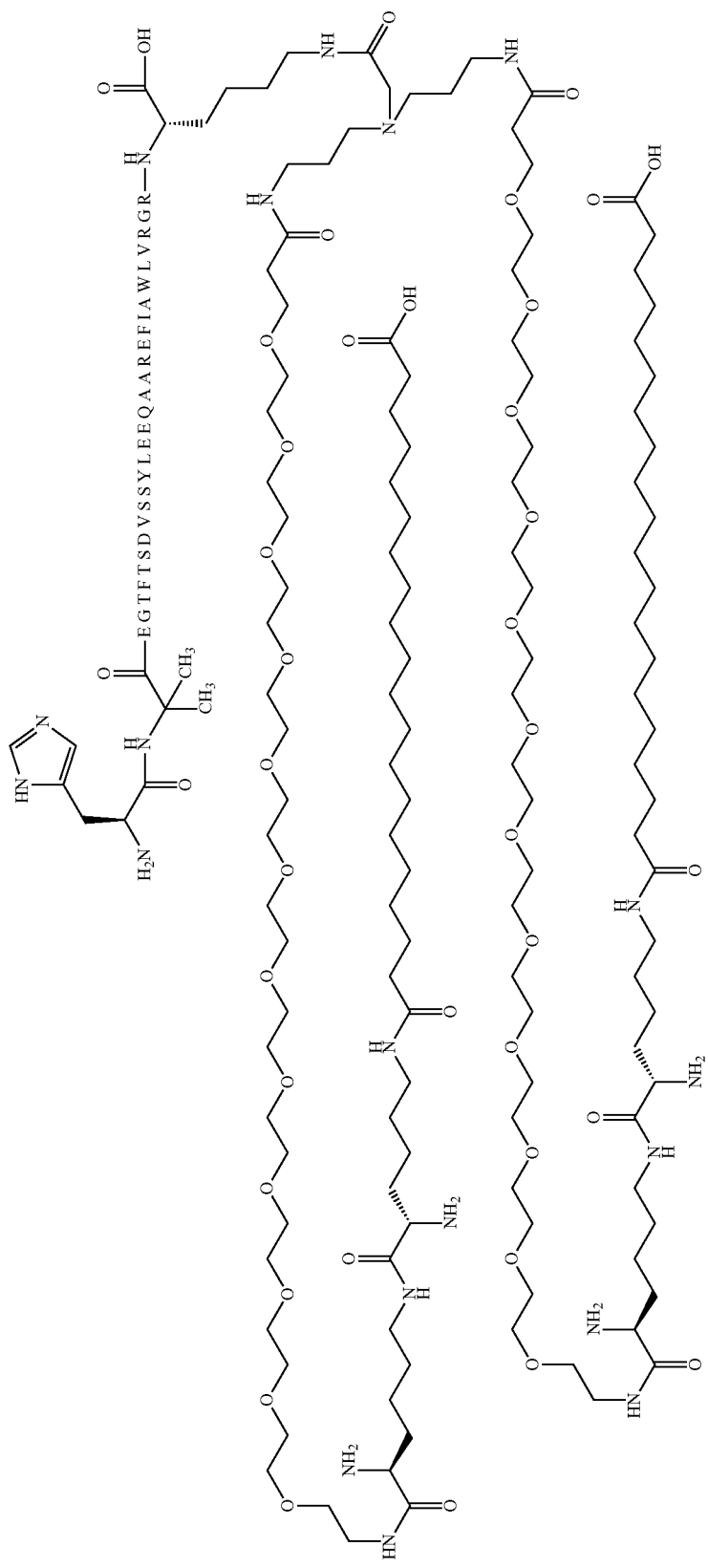

The peptide has SEQ ID NO: 2
Synthesis method: SPPS_L; SC_L; SC_M_3; CP_M1
UPLC02: RT=9.00 min
LCMS01: RT=2.19 min, m/z: 1526 [M+4H]$^{4+}$, 1221 [M+5H]$^{5+}$ Example 9

N{Epsilon-37}-[2-[bis[3-[[2-[2-[2-[[2-[2-[2-[[2-[2-[2-[[2-[2-[2-[[2-[2-[[(2S)-2-amino-6-[[(2S)-2-amino-6-[4-(16-sulfohexadecanoylamino)butanoylamino]hexanoyl]amino]hexanoyl]amino]ethoxy]ethoxy]acetyl]amino]ethoxy]ethoxy]acetyl]amino]ethoxy]ethoxy]acetyl]amino]ethoxy]ethoxy]acetyl]amino]ethoxy]ethoxy]acetyl]amino]propyl]amino]acetyl]-[Aib8,Glu22,Arg26,Arg34,Lys37]-GLP-1-(7-37)-peptide

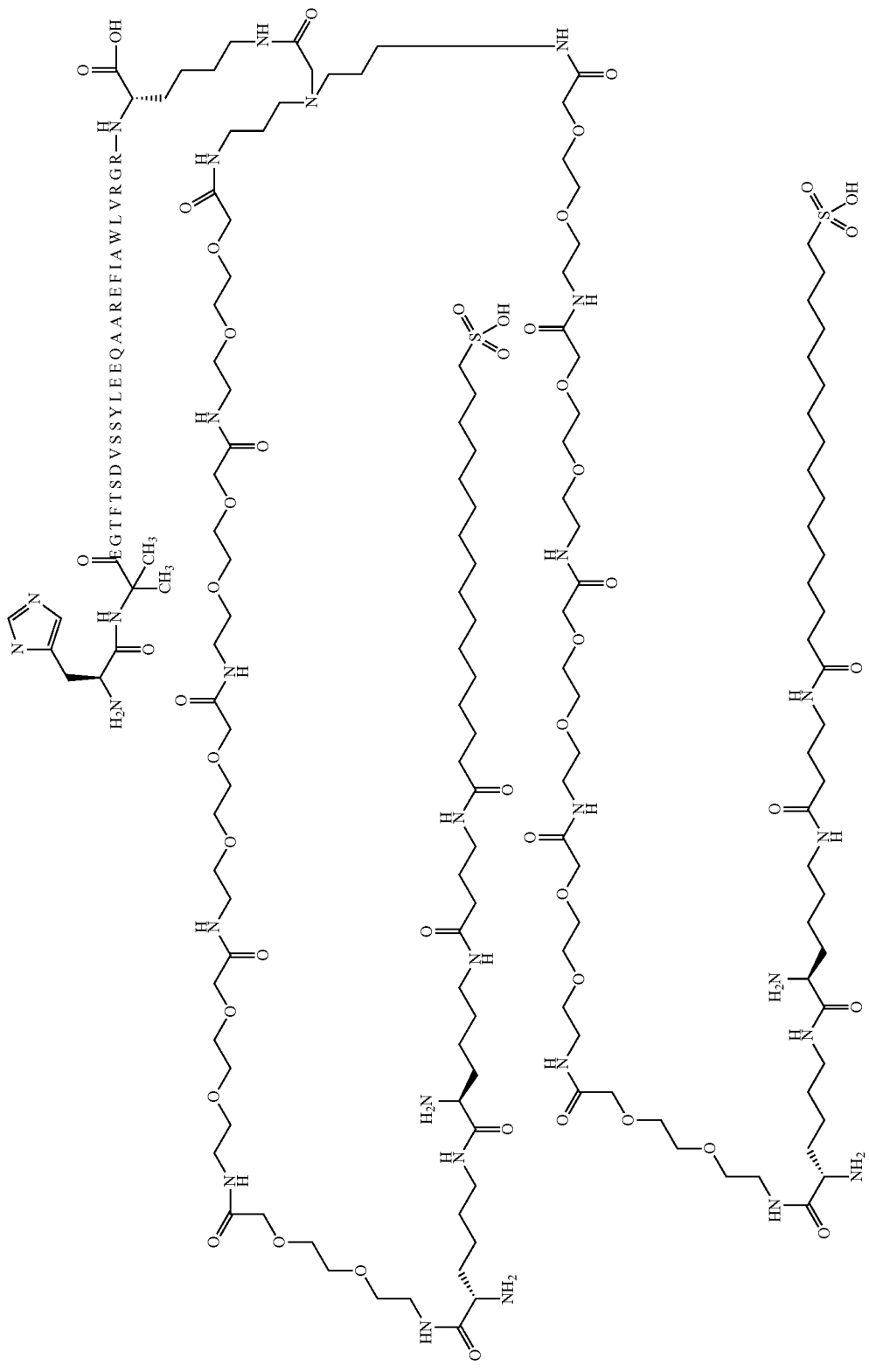
Chem. 29

The peptide has SEQ ID NO: 2
Synthesis method: SPPS_L; SC_L; SC_M_3; CP_M1
UPLC02: RT=7.18 min
LCMS01: RT=2.05 min, m/z: 1629 [M+4H]$^{4+}$, 1303 [M+5H]$^{5+}$ Example 10

N{Alpha}([Aib8,Glu22,Arg26,Arg34,Pro37]-GLP-1-(7-37)-peptidyl)-N{Epsilon}[2-[bis[3-[[2-[2-[2-[[2-[2-[2-[[2-[2-[2-[[2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl]amino]ethoxy]ethoxy]acetyl]amino]ethoxy]ethoxy]acetyl]amino]ethoxy]ethoxy]acetyl]amino]propyl]amino]acetyl]Lys

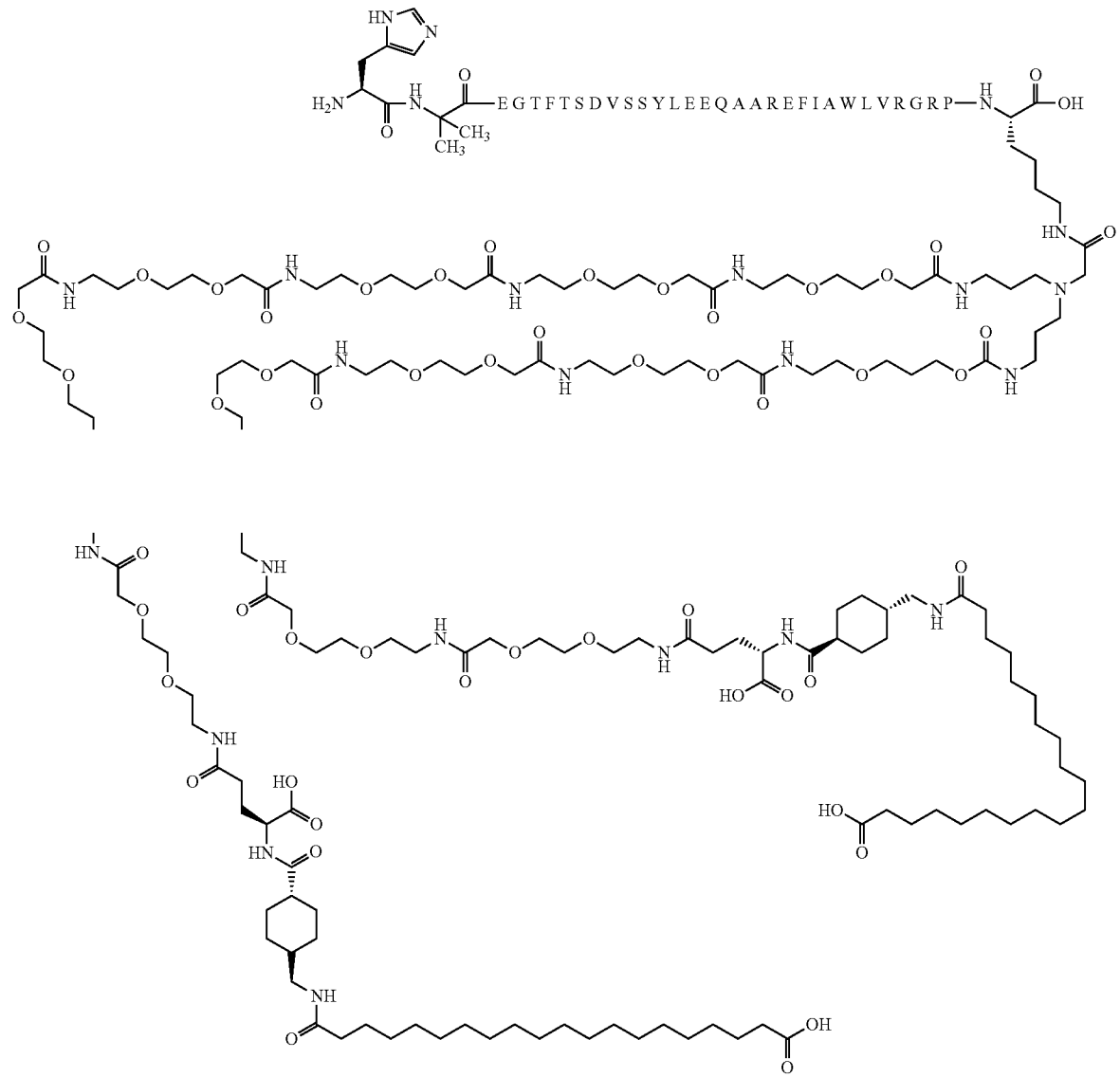

Chem. 30

The peptide has SEQ ID NO: 4
Synthesis method: SPPS_P; SC_P; CP_M1
UPLC02: RT=11.1 min
LCMS01: RT=2.8 min, m/z: 1692 [M+4H]$^{4+}$, 1354 [M+5H]$^{5+}$ Example 11

N{Epsilon-37}-[2-[2-[2-[[2-[2-[2-[[2-[bis[3-[[2-[2-[2-[[2-[2-[2-[[2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl]amino]ethoxy]ethoxy]acetyl]amino]ethoxy]ethoxy]acetyl]amino]ethoxy]ethoxy]acetyl]amino]propyl]amino]acetyl]amino]ethoxy]ethoxy]acetyl]amino]ethoxy]ethoxy]acetyl]-[Aib8,Glu22,Arg26,Arg34,Lys37]-GLP-1-(7-37)-peptide Chem. 31

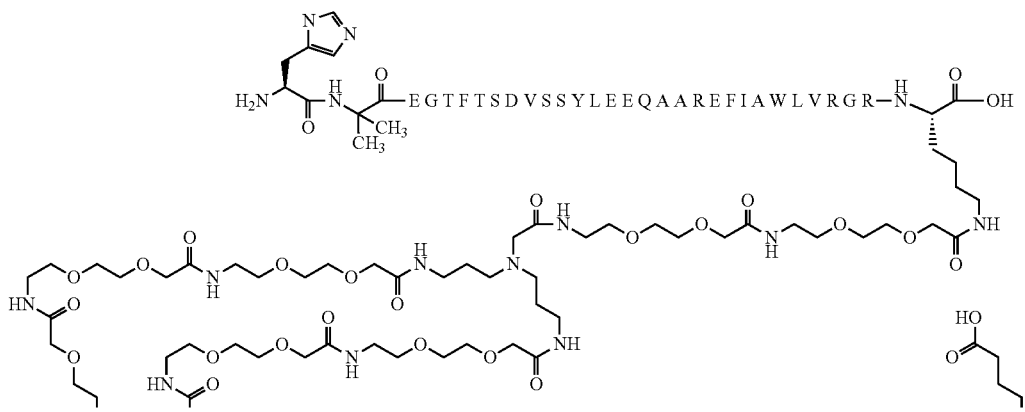

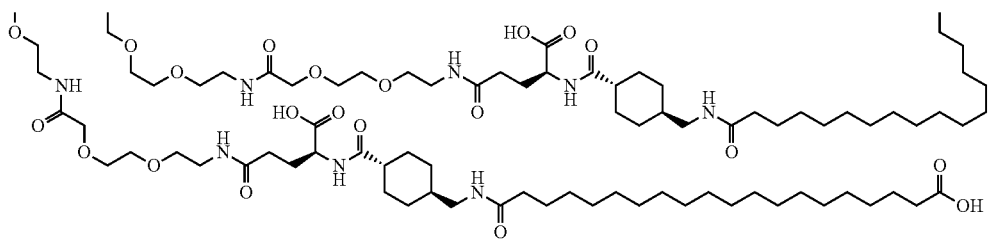

The peptide has SEQ ID NO: 2
Synthesis method: SPPS_P; SC_P; CP_M1
UPLC02: RT=10.7 min
LCMS01: RT=2.9 min, m/z: 1277 [M+5H]$^{5+}$, 1064 [M+6H]$^{6+}$, 912 [M+7H]$^{7+}$ Example 12

N{Epsilon-37}-[2-[2-[2-[[2-[2-[2-[[2-[2-[2-[[2-[2-[2-[[2-[bis[3-[[2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl]amino]propyl]amino]acetyl]amino]ethoxy]ethoxy]acetyl]amino]ethoxy]ethoxy]acetyl]amino]ethoxy]ethoxy]acetyl]-[Aib8,Glu22,Arg26,Arg34,Lys37]-GLP-1-(7-37)-peptide Chem. 32

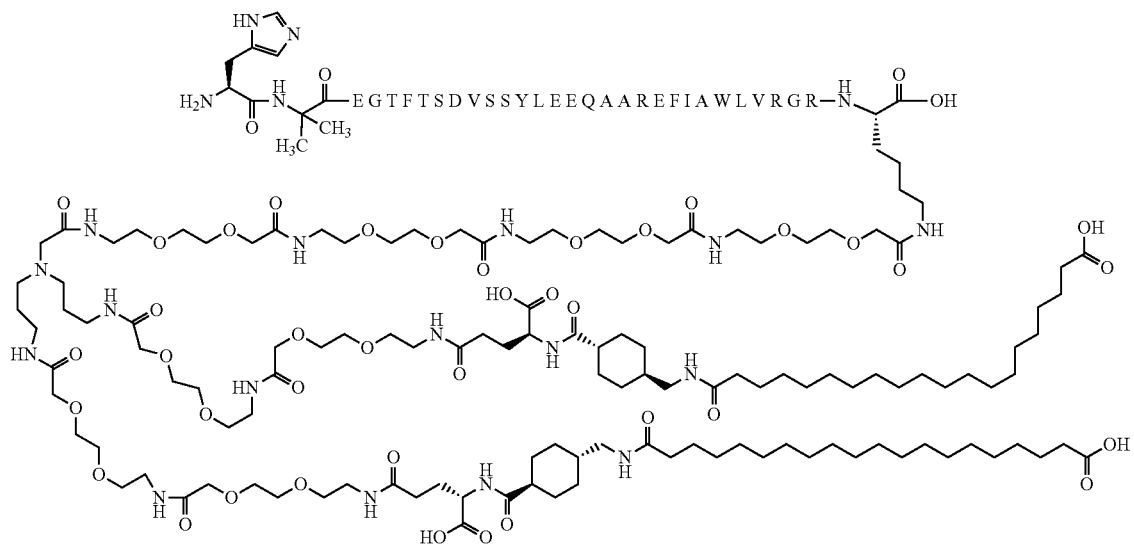

Synthesis method: SPPS_P; SC_P; CP_M1
UPLC02: RT=10.9 min
LCMS01: RT=3.0 min, m/z: 1218 [M+5H]$^{5+}$, 1016 [M+6H]$^{6+}$, 871 [M+7H]$^{7+}$ Example 13

N{Epsilon-37}-[2-[2-[2-[[2-[2-[2-[[2-[2-[2-[[2-[2-[2-[[2-[2-[2-[[2-[2-[2-[[2-[bis[3-[[(4S)-4-carboxy-4-[[4-[(19-carboxynonadecanoylamino)methyl]cyclohexanecarbonyl]amino]butanoyl]amino]propyl]amino]acetyl]amino]ethoxy]ethoxy]acetyl]amino]ethoxy]ethoxy]acetyl]amino]ethoxy]ethoxy]acetyl]amino]ethoxy]ethoxy]acetyl]amino]ethoxy]ethoxy]acetyl]amino]ethoxy]ethoxy]acetyl]-[Aib8,Glu22,Arg26,Arg34,Lys37]-GLP-1-(7-37)-peptide Chem. 33

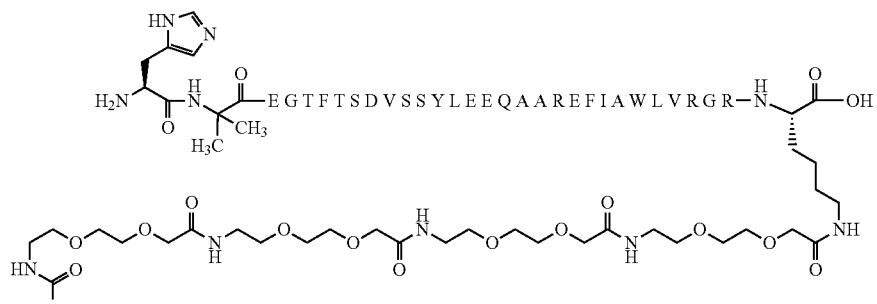

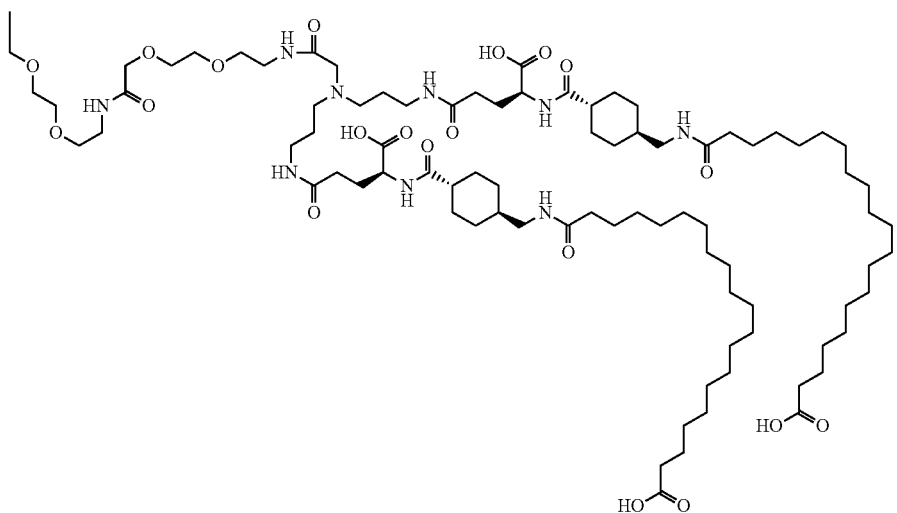

Synthesis method: SPPS_P; SC_P; CP_M1
UPLC02: RT=11.3 min
LCMS01: RT=3.0 min, m/z: 1160 [M+5H]$^{5+}$, 976 [M+6H]$^{6+}$, 829 [M+7H]$^{7+}$
Example 14
N{Epsilon-37}-[2-[bis[3-[[2-[2-[2-[[2-[2-[2-[[2-[2-[2-[[2-[2-[2-[[(2S)-2- amino-6-[[(2S)-2-amino-6-[4-(16-sulfohexadecanoylamino)butanoylamino]hexanoyl]amino]hexanoyl]amino]ethoxy]ethoxy]acetyl]amino]ethoxy]ethoxy]acetyl]amino]ethoxy]ethoxy]acetyl]amino]ethoxy]ethoxy]acetyl]amino]propyl]amino]acetyl]-[Aib8,Glu22,Arg26,Arg34,Lys37]-GLP-1-(7-37)-peptide
Chem. 34
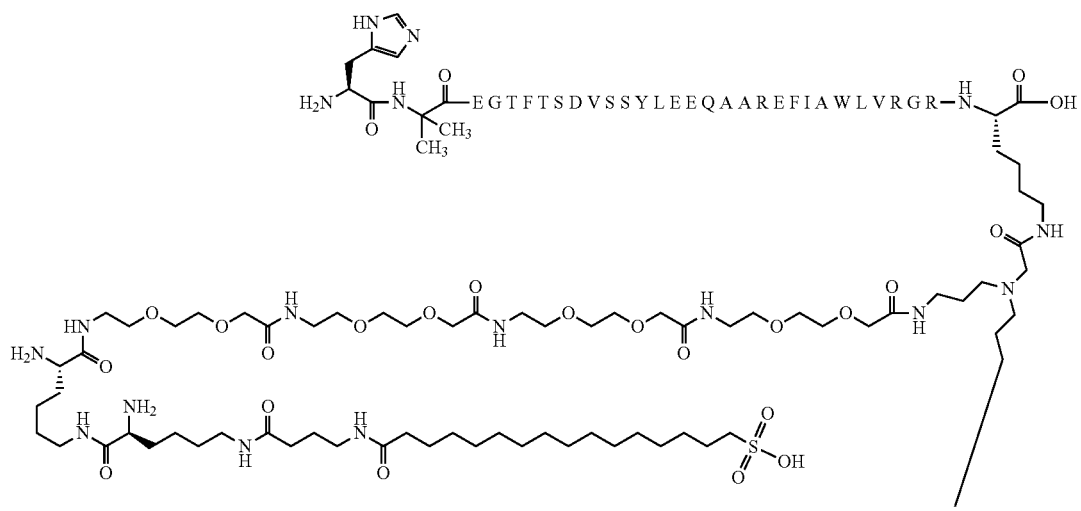
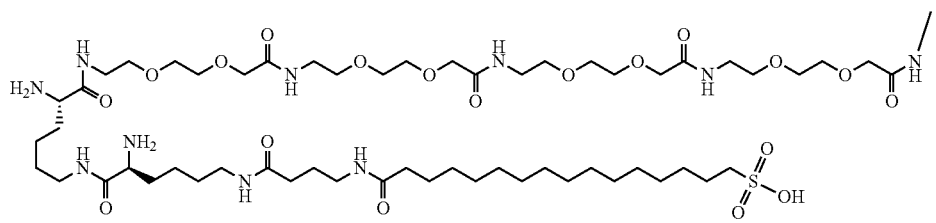

Synthesis method: SPPS_L; SC_P; SC_M_3; CP_M1
UPLC02: RT=7.24 minutes
LCMS01: RT=1.79 min, m/z: 1245 [M+5H]$^{5+}$, 1038 [M+6H]$^{6+}$, 889 [M+7H]$^{7+}$ Example 15

N{Epsilon-37}-[2-[bis[3-[[2-[2-[2-[[2-[2-[2-[[2-[2-[2-[[2-[2-[[2-[2-[2-[[(2S)-2-amino-6-[[(2S)-2-amino-6-[4-(16-sulfohexadecanoylamino)butanoylamino]hexanoyl]amino]hexanoyl]amino]ethoxy]ethoxy]acetyl]amino]ethoxy]ethoxy]acetyl]amino]ethoxy]ethoxy]acetyl]amino]ethoxy]ethoxy]acetyl]amino]ethoxy]ethoxy]acetyl]amino]ethoxy]ethoxy]acetyl]amino]propyl]amino]acetyl]-[Aib8,Glu22,Arg26,Arg34,Lys37]-GLP-1-(7-37)-peptide Chem. 35

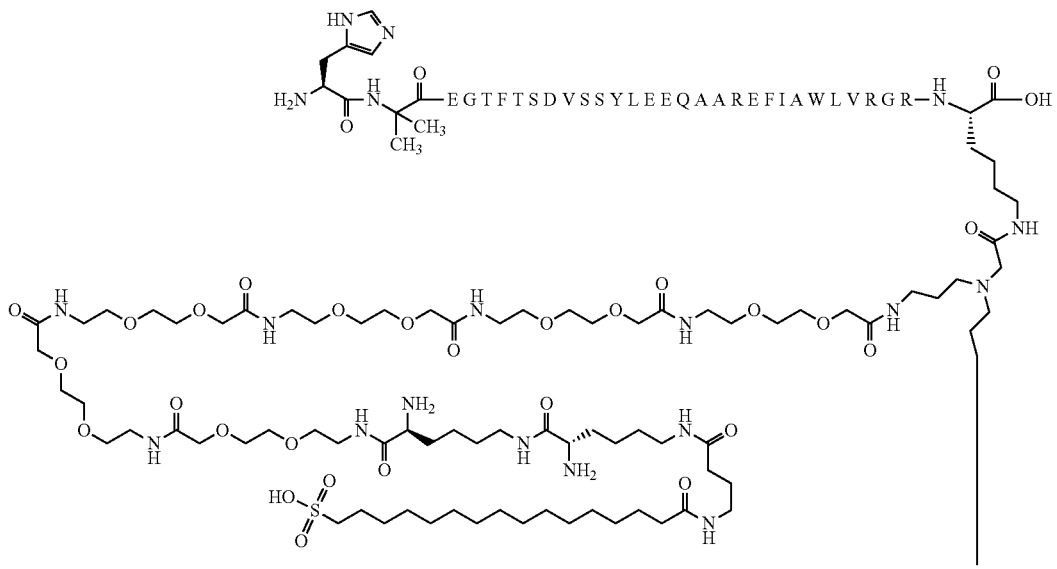

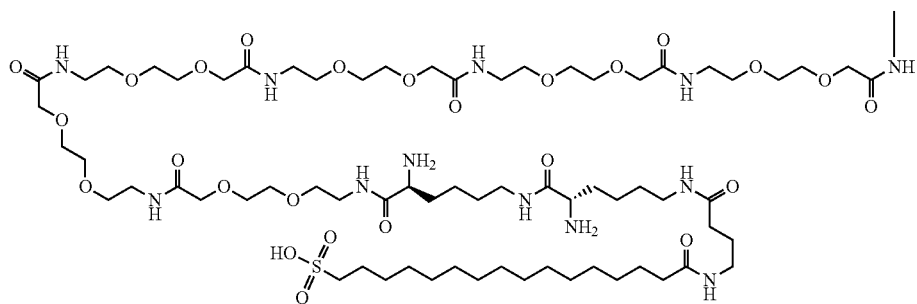

The peptide has SEQ ID NO: 2
Synthesis method: SPPS_L; SC_P; SC_M_3; CP_M1
UPLC02: RT=7.11 min
LCMS01: RT=1.77 min, m/z: 1361 [M+5H]$^{5+}$, 1134 [M+6H]$^{6+}$, 973 [M+7H]$^{7+}$ Example 16

N{Epsilon-37}-[2-[bis[3-[[2-[2-[2-[[2-[2-[2-[[2-[2-[2-[[2-[2-[2-[[(4S)-4- carboxy-4-[4-(16-sulfohexadecanoylamino)butanoylamino]butanoyl]amino]ethoxy]ethoxy]acetyl]amino]ethoxy]ethoxy]acetyl]amino]ethoxy]ethoxy]acetyl]amino]ethoxy]ethoxy]acetyl]amino]propyl]amino]acetyl]-[Aib8,Glu22,Arg26,Arg34,Lys37]-GLP-1-(7-37)-peptide

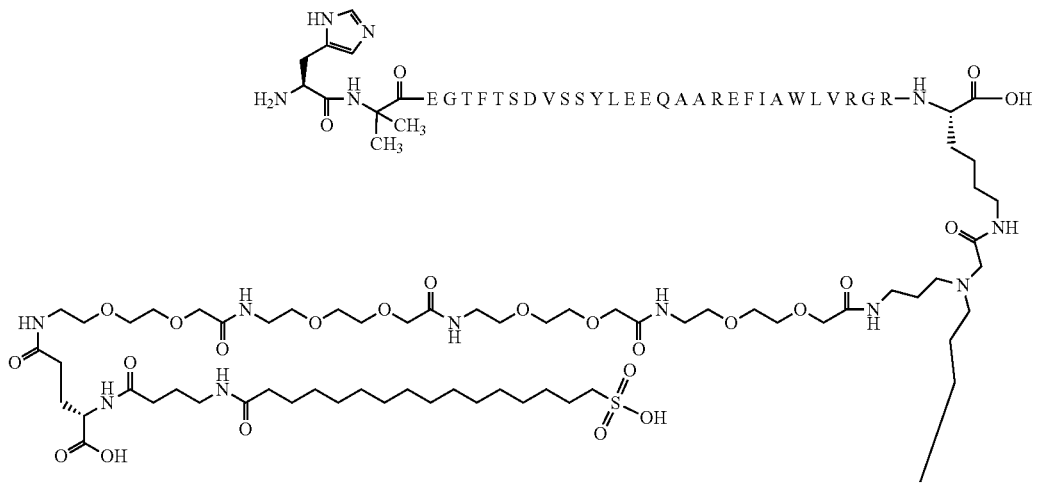

Chem. 36

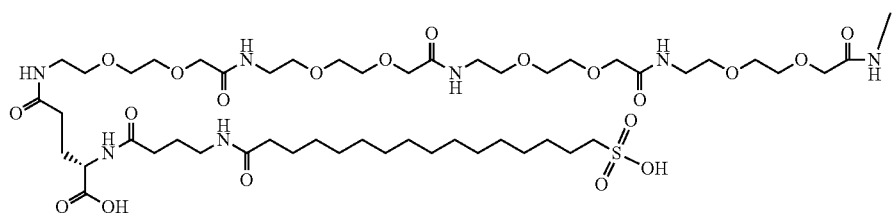

The peptide has SEQ ID NO: 2
Synthesis method: SPPS_L; SC_L; SC_M_3; CP M1
UPLC02: RT=8.24 min
LCMS01: RT=2.01 min, m/z: 1493 [M+4H]$^{4+}$, 1194 [M+5H]$^{5+}$ Example 17

N{Epsilon-37}-[2-[bis[3-[[2-[2-[2-[[2-[2-[2-[[2-[2-[2-[[2-[2-[2-[[2-[2-[2-[[(4S)-4-carboxy-4-[4-(16-sulfohexadecanoylamino)butanoylamino]butanoyl]amino]ethoxy]ethoxy]acetyl]amino]ethoxy]ethoxy]acetyl]amino]ethoxy]ethoxy]acetyl]amino]ethoxy]ethoxy]acetyl]amino]ethoxy]ethoxy]acetyl]amino]propyl]amino]acetyl]-[Aib8,Glu22,Arg26,Arg34,Lys37]-GLP-1-(7-37)-peptide Chem. 37

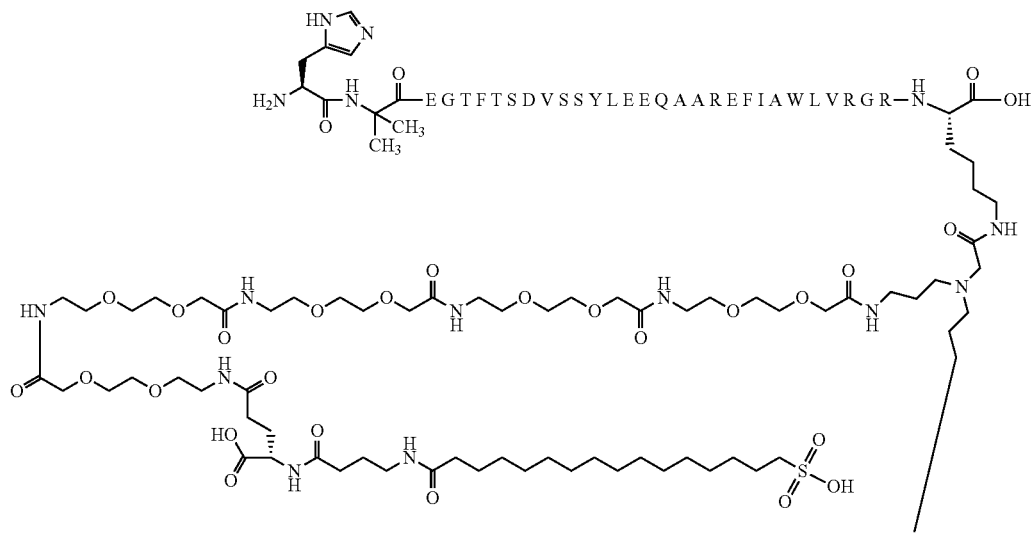

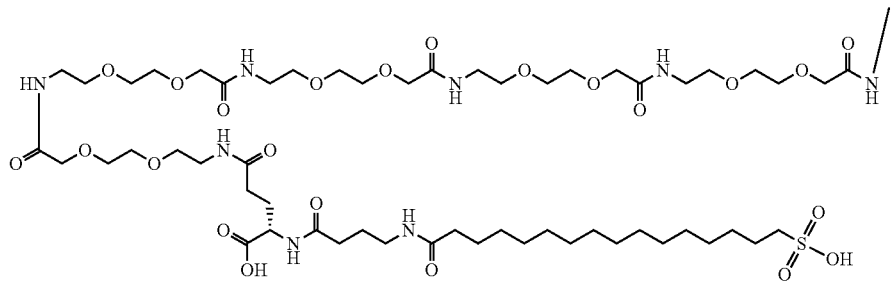

The peptide has SEQ ID NO: 2
Synthesis method: SPPS_L; SC_P; SC_M_3; CP_M1
UPLC02: RT=7.8 min
LCMS01: RT=2.27 min, m/z: 1565 [M+4H]$^{4+}$, 1252 [M+5H]$^{5+}$

Example 18

N{Epsilon-37}-[2-[bis[3-[[2-[2-[2-[[2-[2-[2-[[2-[2-[2-[[2-[2-[2-[[2-[2-[2-[[(4S)-4-carboxy-4-[4-(16-sulfohexadecanoylamino)butanoylamino]butanoyl]amino]ethoxy]ethoxy]acetyl]amino]ethoxy]ethoxy]acetyl]amino]ethoxy]ethoxy]acetyl]amino]ethoxy]ethoxy]acetyl]amino]ethoxy]ethoxy]acetyl]amino]propyl]amino]acetyl]-[Aib8,Glu22,Arg26,Arg34,Lys37]-GLP-1-(7-37)-peptide Chem. 38

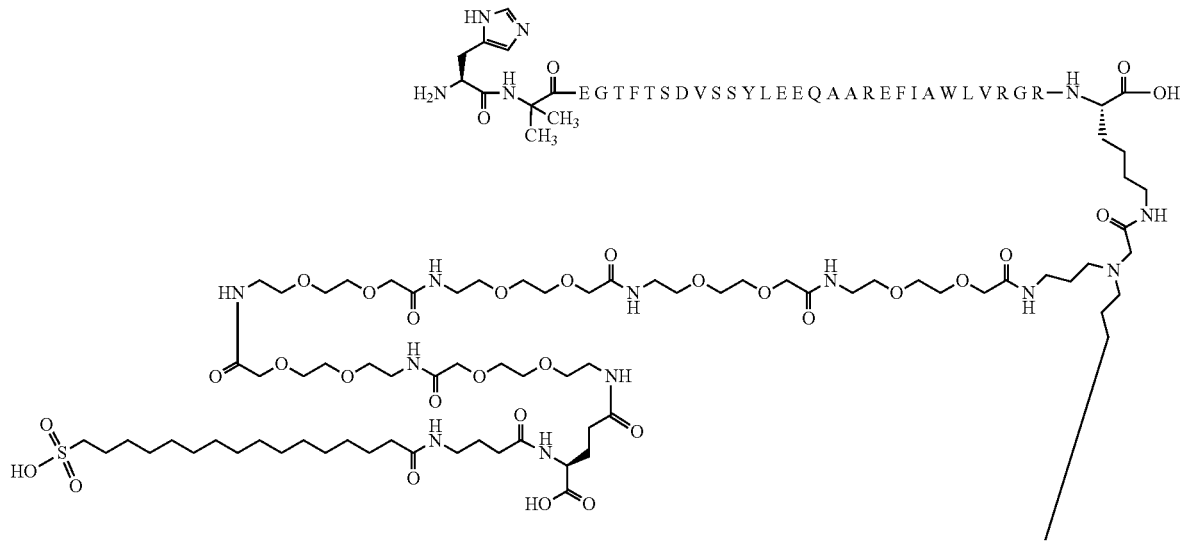

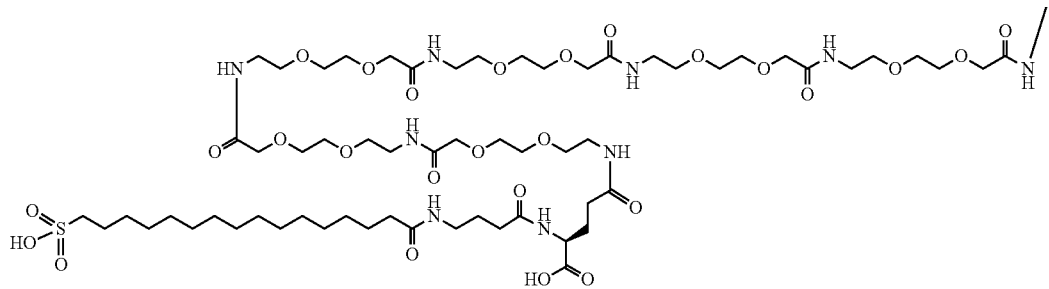

The peptide has SEQ ID NO: 2
Synthesis method: SPPS_L; SC_P; SC_M_3; CP_M1
UPLC02: RT=7.74 min
LCMS01: RT=2.24 min, m/z: 1638 $[M+4H]^{4+}$, 1310 $[M+5H]^{5+}$ Example 19

N{Epsilon-37}-[2-[bis[3-[[2-[2-[2-[[2-[2-[2-[[2-[2-[2-[[2-[2-[[(4S)-4- carboxy-4-[[4-[[4-(16-sulfo-hexadecanoylamino)butanoylamino]methyl]cyclo-hexanecarbonyl]amino]butanoyl]amino]ethoxy]ethoxy]acetyl]amino]ethoxy]ethoxy]acetyl]amino]ethoxy]ethoxy]acetyl]amino]ethoxy]ethoxy]acetyl]amino]propyl]amino]acetyl]-[Aib8,Glu22,Arg26,Arg34,Lys37]-GLP-1-(7-37)-peptide Chem. 39

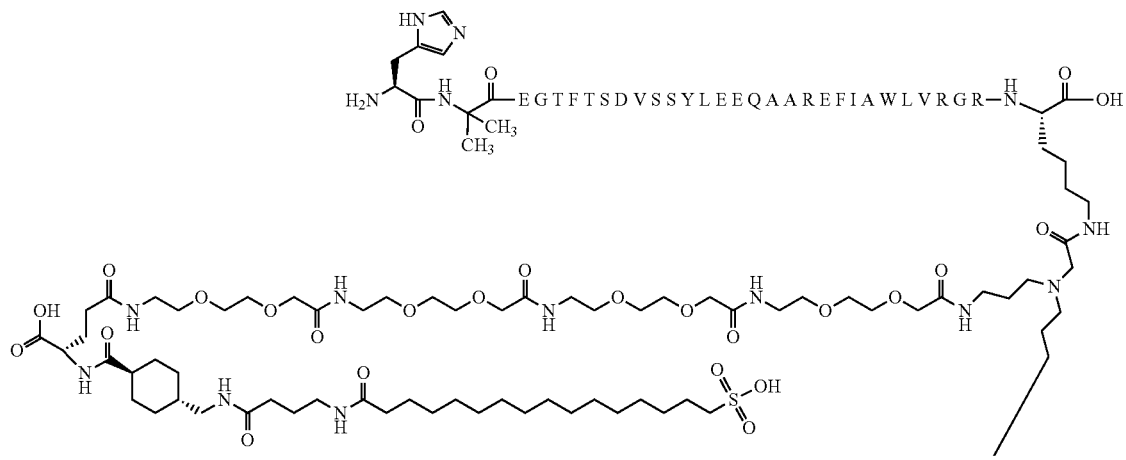

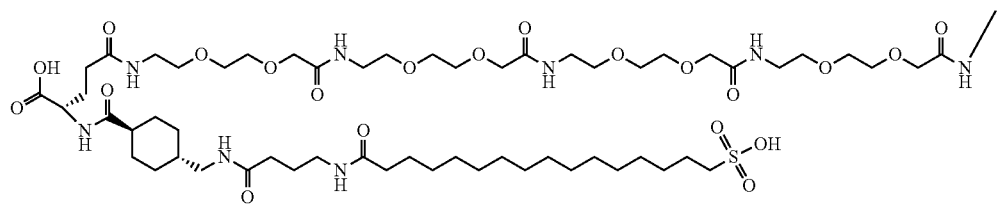

The peptide has SEQ ID NO: 2
Synthesis method: SPPS_L; SC_P; SC_M_3; CP_M1
UPLC02: RT=8.59 min
LCMS29: RT=3.5 min, m/z: 2082 [M+3H]$^{3+}$, 1562 [M+4H]$^{4+}$, 1250 [M+5H]$^{5+}$ Example 20

N{Epsilon-37}-[2-[bis[3-[[2-[2-[2-[[2-[2-[2-[[2-[2-[2-[[2-[2-[2-[[2-[2-[2-[[(4S)-4-carboxy-4-[[4-[[4-(16-sulfohexadecanoylamino)butanoylamino]methyl]cyclohexanecarbonyl]amino]butanoyl]amino]ethoxy]ethoxy]acetyl]amino]ethoxy]ethoxy]acetyl]amino]ethoxy]ethoxy]acetyl]amino]ethoxy]ethoxy]acetyl]amino]propyl]amino]acetyl]-[Aib8,Glu22,Arg26,Arg34,Lys37]-GLP-1-(7-37)-peptide Chem. 40

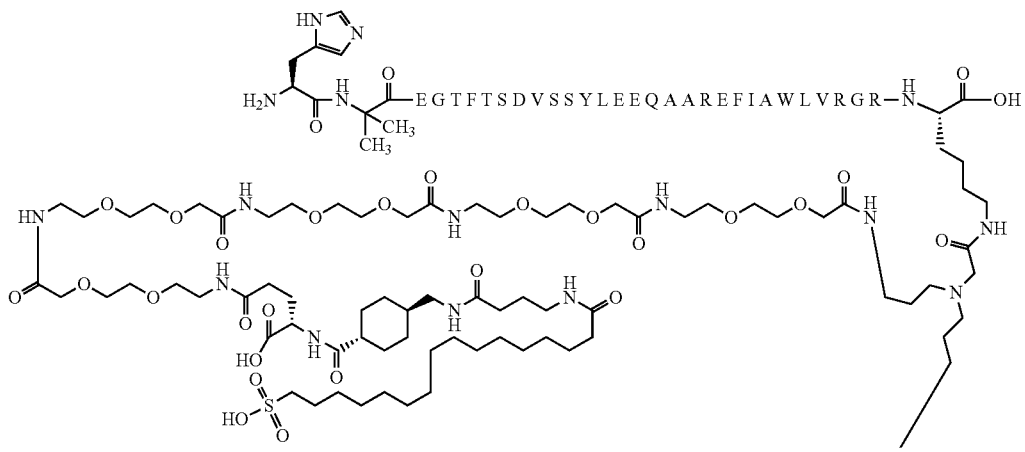

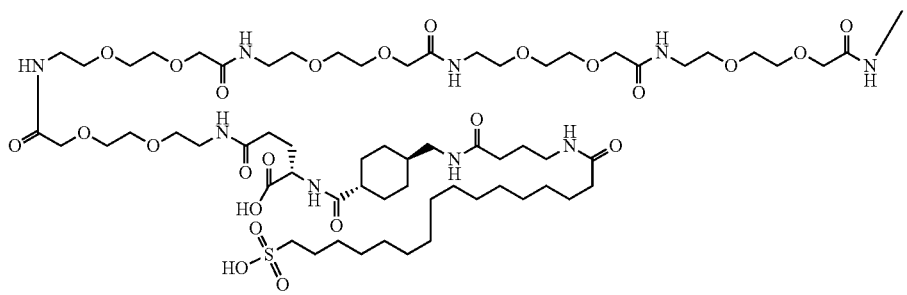

The peptide has SEQ ID NO: 2
Synthesis method: SPPS_L; SC_P; SC_M_3; CP_M1
UPLC02: RT=7.89 min
LCMS27: RT=3.4 min, m/z: 2179 [M+3H]$^{3+}$, 1634 [M+4H]$^{4+}$, 1307 [M+5H]$^{5+}$ Example 21

N{Epsilon-37}-[2-[bis[3-[[2-[2-[2-[[2-[2-[2-[[2-[2-[2-[[2-[2-[2-[[2-[2-[2-[[2-[2-[[(4S)-4-carboxy-4-[[4-[[4-(16-sulfohexadecanoylamino)butanoylamino]methyl]cyclohexanecarbonyl]amino]butanoyl]amino]ethoxy]ethoxy]acetyl]amino]ethoxy]ethoxy]acetyl]amino]ethoxy]ethoxy]acetyl]amino]ethoxy]ethoxy]acetyl]amino]ethoxy]ethoxy]acetyl]amino]ethoxy]ethoxy]acetyl]amino]propyl]amino]acetyl]-[Aib8,Glu22,Arg26,Arg34,Lys37]-GLP-1-(7-37)-peptide Chem. 41

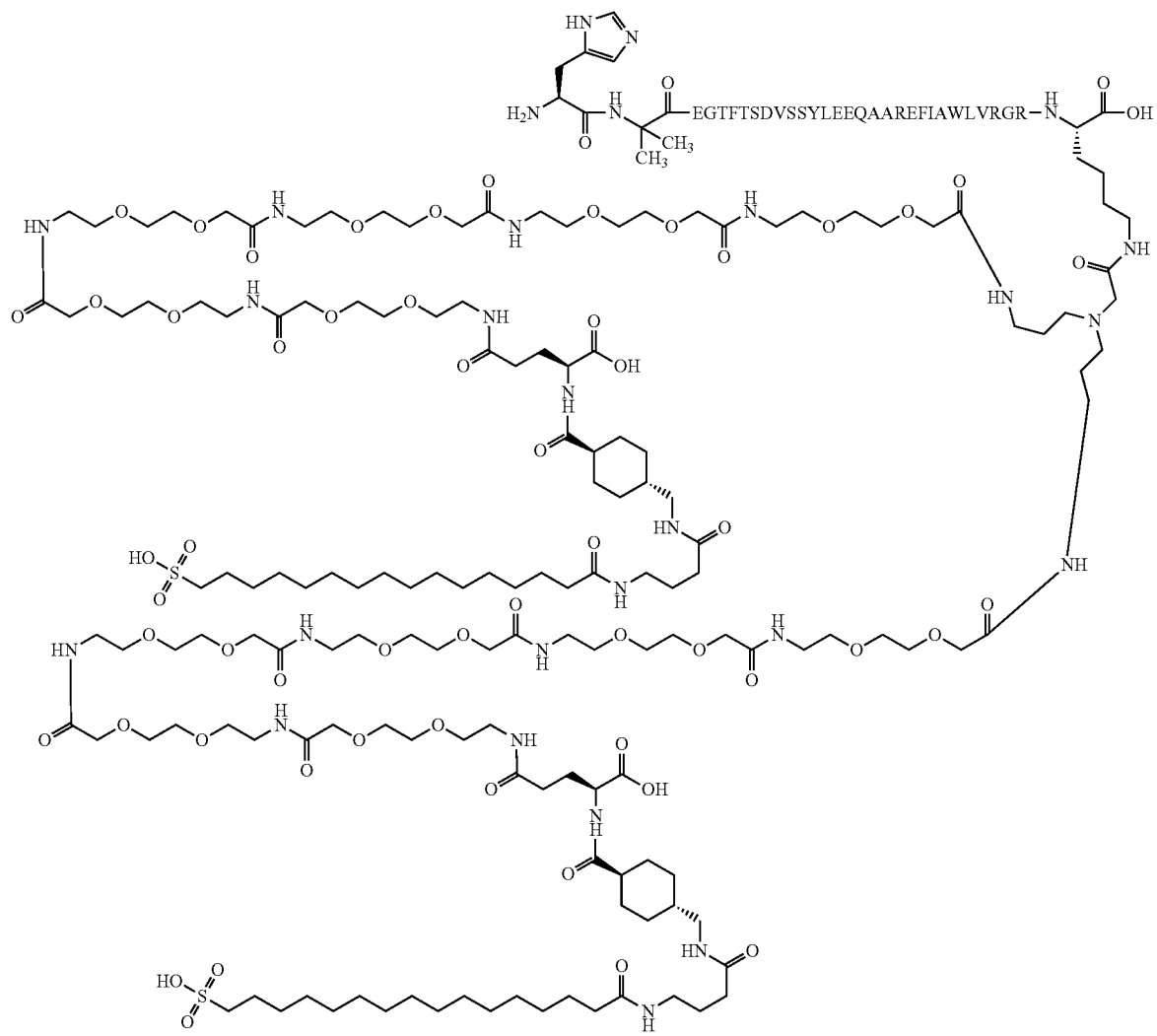

The peptide has SEQ ID NO: 2
Synthesis method: SPPS_L; SC_P; SC_M_3; CP_M1
UPLC02: RT=7.76 min
LCMS27: RT=3.4 min, m/z: 2276 $[M+3H]^{3+}$, 1707 $[M+4H]^{4+}$, 1366 $[M+5H]^{5+}$

Example 22

N{Epsilon-37}-[2-[bis[3-[[2-[2-[2-[[2-[2-[2-[[2-[2-[2-[[2-[2-[[(4S)-4- carboxy-4-[[4-[(16-sulfohexa-decanoylamino)methyl]cyclohexanecarbonyl]amino]butanoyl]amino]ethoxy]ethoxy]acetyl]amino]ethoxy]ethoxy]acetyl]amino]ethoxy]ethoxy]acetyl]amino]ethoxy]ethoxy]acetyl]amino]propyl]amino]acetyl]-[Aib8,Glu22,Arg26,Arg34,Lys37]-GLP-1-(7-37)-peptide Chem. 42

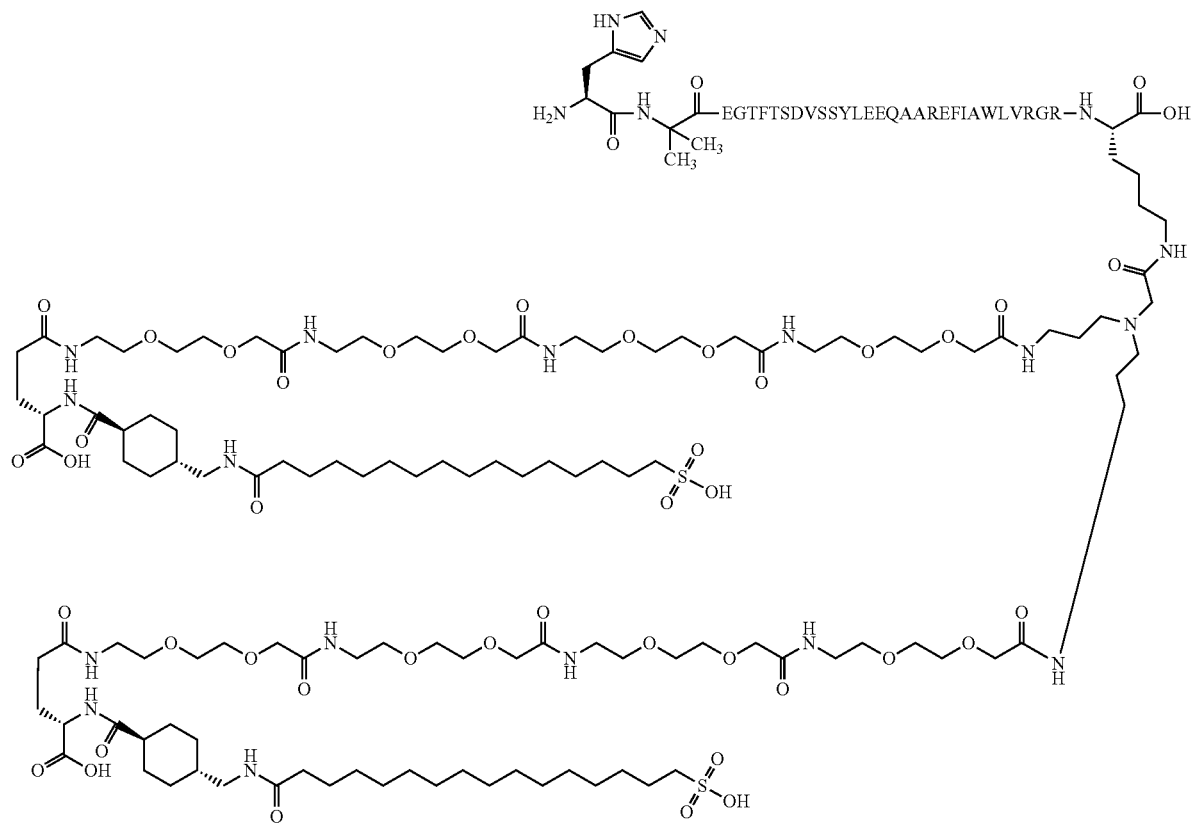

The peptide has SEQ ID NO: 2
Synthesis method: SPPS_L; SC_P; SC_M_3; CP_M1
UPLC02: RT=8.77 min
LCMS29: RT=3.55 min, m/z: 2025 [M+3H]$^{3+}$, 1519 [M+4H]$^{4+}$, 1215 [M+5H]$^{5+}$ Example 23

N{Epsilon-37}-[2-[bis[3-[[2-[2-[2-[[2-[2-[2-[[2-[2-[2-[[2-[2-[2-[[2-[2-[[(4S)-4-carboxy-4-[[4-[(16-sulfohexadecanoylamino)methyl]cyclohexanecarbonyl]amino]butanoyl]amino]ethoxy]ethoxy]acetyl]amino]ethoxy]ethoxy]acetyl]amino]ethoxy]ethoxy]acetyl]amino]ethoxy]ethoxy]acetyl]amino]ethoxy]ethoxy]acetyl]amino]propyl]amino]acetyl]-[Aib8,Glu22,Arg26,Arg34,Lys37]-GLP-1-(7-37)-peptide Chem. 43

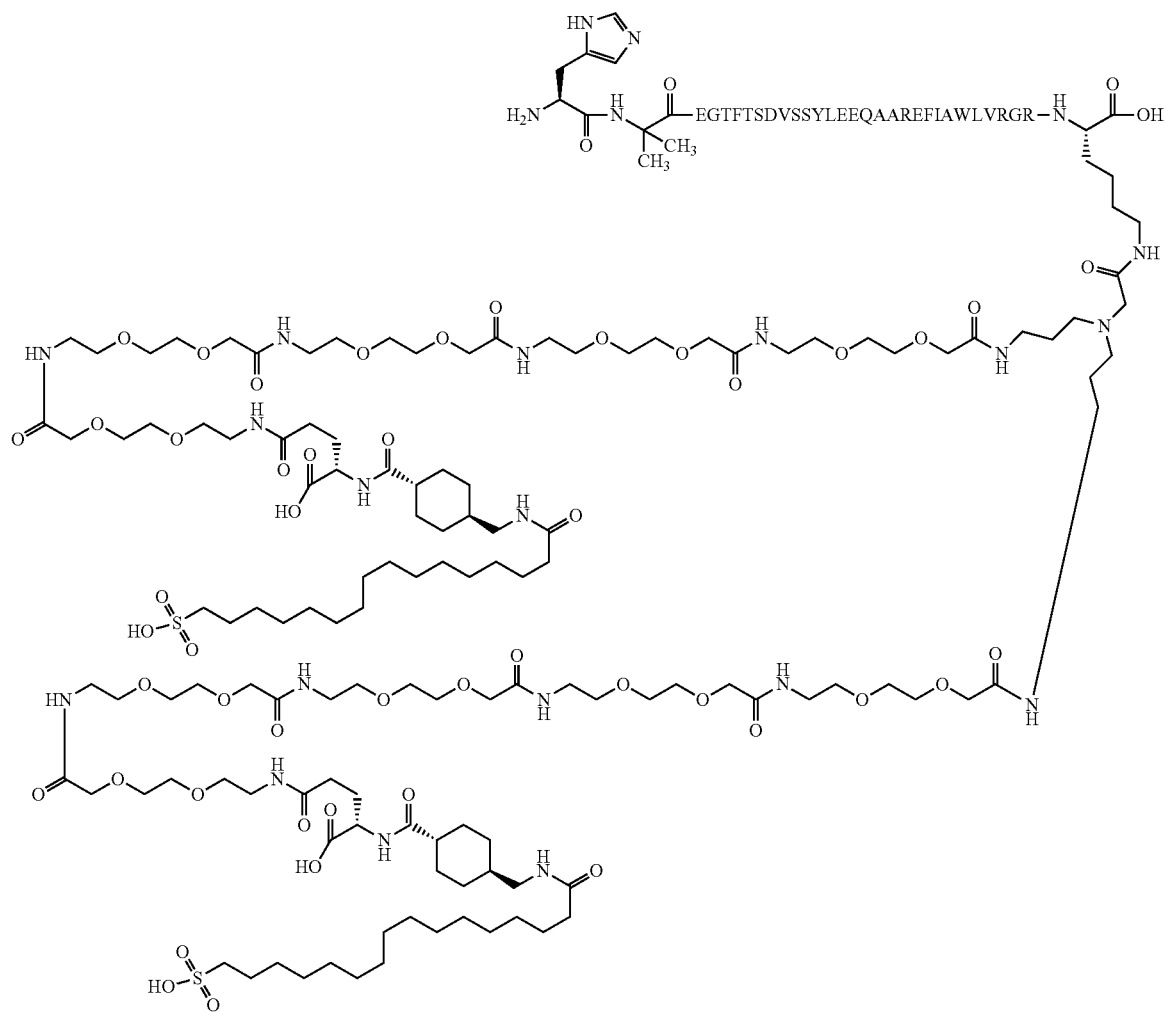

The peptide has SEQ ID NO: 2
Synthesis method: SPPS_L; SC_P; SC_M_3; CP_M1
UPLC02: RT=8.0 min
LCMS29: RT=3.5, m/z: 2122 $[M+3H]^{3+}$, 1592 $[M+4H]^{4+}$, 1274 $[M+5H]^{5+}$

Example 24

N{Epsilon-37}-[2-[bis[3-[[2-[2-[2-[[2-[2-[2-[[2-[2-[2-[[2-[2-[2-[[2-[2-[2-[[2-[2-[[(4S)-4-carboxy-4-[[4-[(16-sulfohexadecanoylamino)methyl]cyclohexanecarbonyl]amino]butanoyl]amino]ethoxy]ethoxy]acetyl]amino]ethoxy]ethoxy]acetyl]amino]ethoxy]ethoxy]acetyl]amino]ethoxy]ethoxy]acetyl]amino]ethoxy]ethoxy]acetyl]amino]propyl]amino]acetyl]-[Aib8,Glu22,Arg26,Arg34,Lys37]-GLP-1-(7-37)-peptide

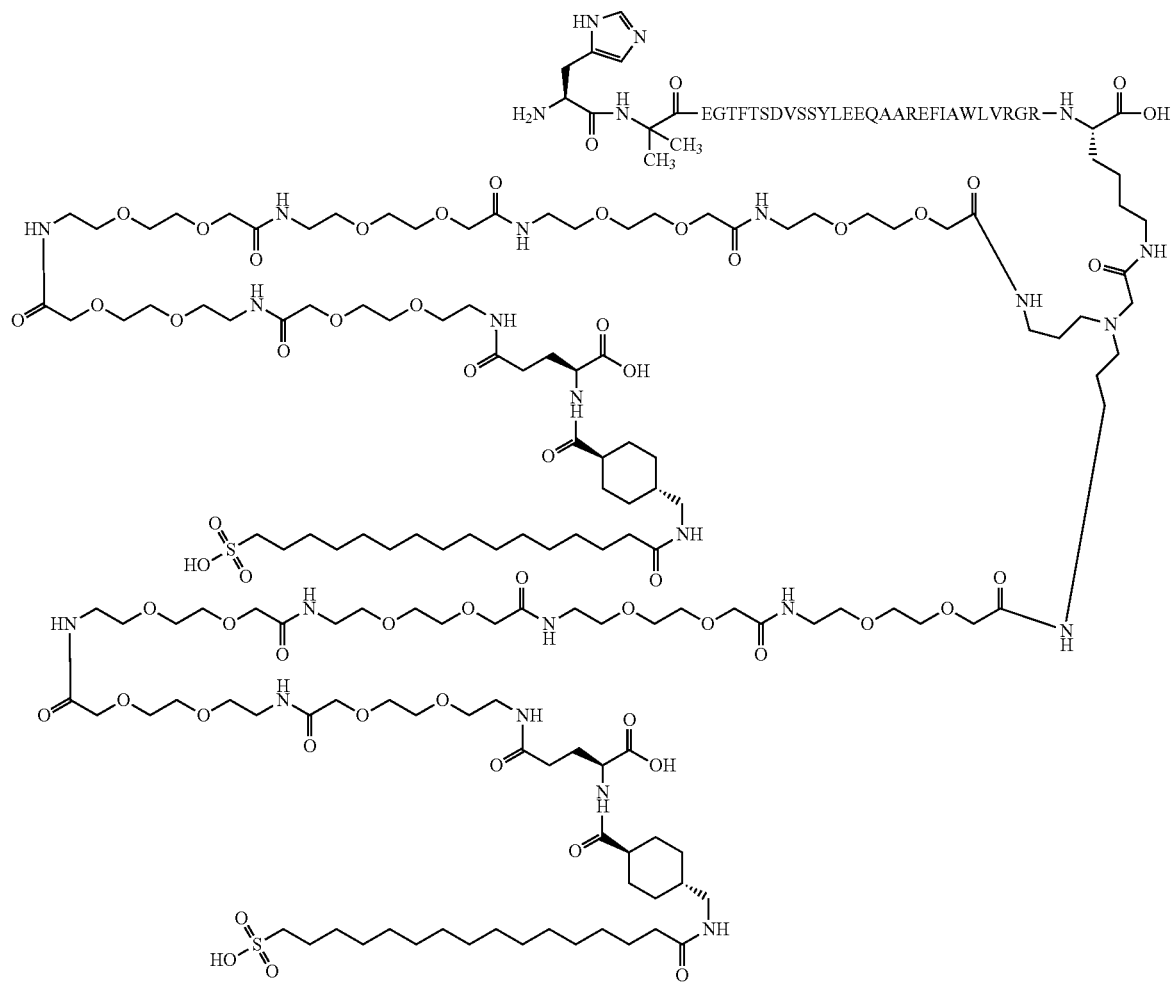

Chem. 44

The peptide has SEQ ID NO: 2
Synthesis method: SPPS_L; SC_P; SC_M_3; CP_M1
UPLC02: RT=8.62 min
LCMS27: RT=3.4 min, m/z: 2219 $[M+3H]^{3+}$, 1664 $[M+4H]^{4+}$, 1332 $[M+5H]^{5+}$ Example 25

N{Epsilon-37}-[2-[2-[2-[[2-[2-[2-[[2-[2-[2-[[2-[2-[2-[2-[2-[[2-[2-[2-[[2-[2-[2-[[2-[bis[3-[[(2S)-2-[[(4S)-4-carboxy-4-[[4-[(19-carboxynonadecanoylamino) methyl]cyclohexanecarbonyl]amino]butanoyl] amino]-3-hydroxypropanoyl]amino]propyl]amino] acetyl]amino]ethoxy]ethoxy]acetyl]amino]ethoxy] ethoxy]acetyl]amino]ethoxy]ethoxy]acetyl]amino] ethoxy]ethoxy]acetyl]amino]ethoxy]ethoxy]acetyl] amino]ethoxy]ethoxy]acetyl]-[Aib8,Glu22,Arg26, Arg34,Lys37]-GLP-1-(7-37)-peptide Chem. 45

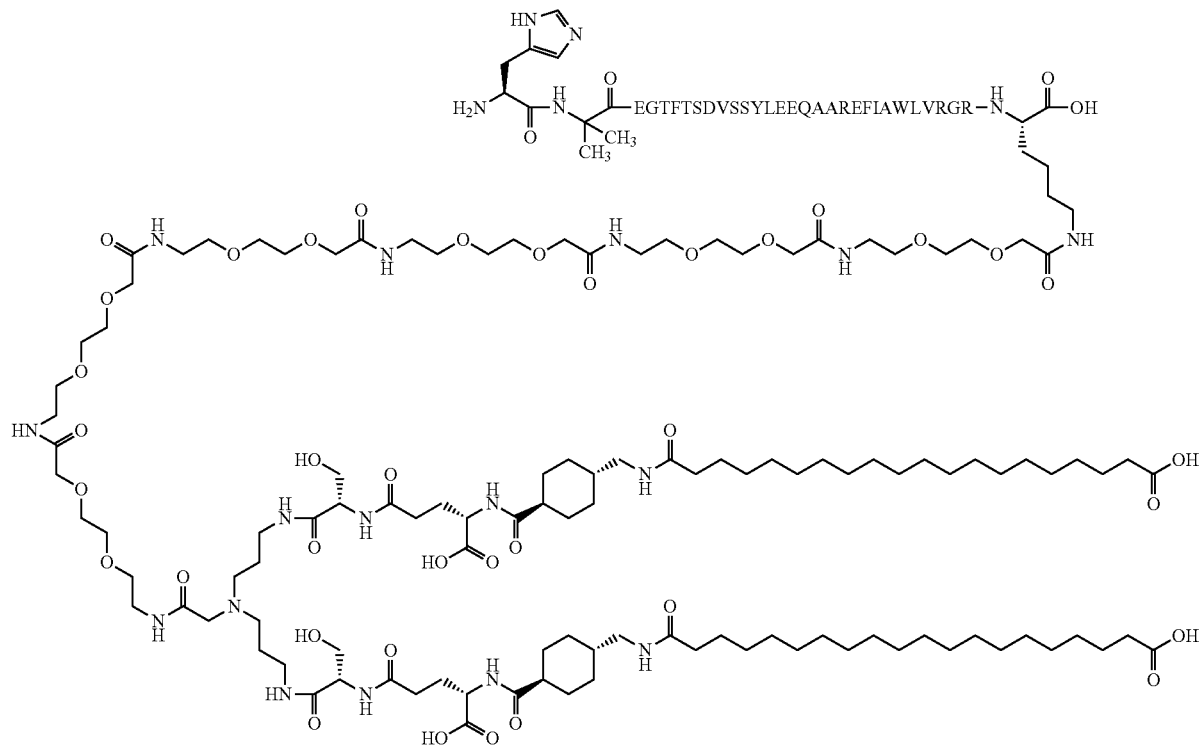

The peptide has SEQ ID NO: 2
Synthesis method: SPPS_P; SC_P; CP_M1
UPLC02: RT=10.6 min
LCMS01: RT=2.48 min, m/z: 1494 [M+4H]$^{4+}$, 1195 [M+5H]$^{5+}$ Example 26

N{Epsilon-37}-[2-[2-[2-[[2-[2-[2-[[2-[2-[2-[[2-[2-[2-[2-[2-[[2-[2-[2-[[2-[bis[3-[[(4S)-4-carboxy-4-(19-carboxynonadecanoylamino)butanoyl]amino]propyl]amino]acetyl]amino]ethoxy]ethoxy]acetyl]amino]ethoxy]ethoxy]acetyl]amino]ethoxy]ethoxy]acetyl]amino]ethoxy]ethoxy]acetyl]amino]ethoxy]ethoxy]acetyl]amino]ethoxy]ethoxy]acetyl]-[Aib8,Glu22,Arg26,Arg34,Lys37]-GLP-1-(7-37)-peptide Chem. 46

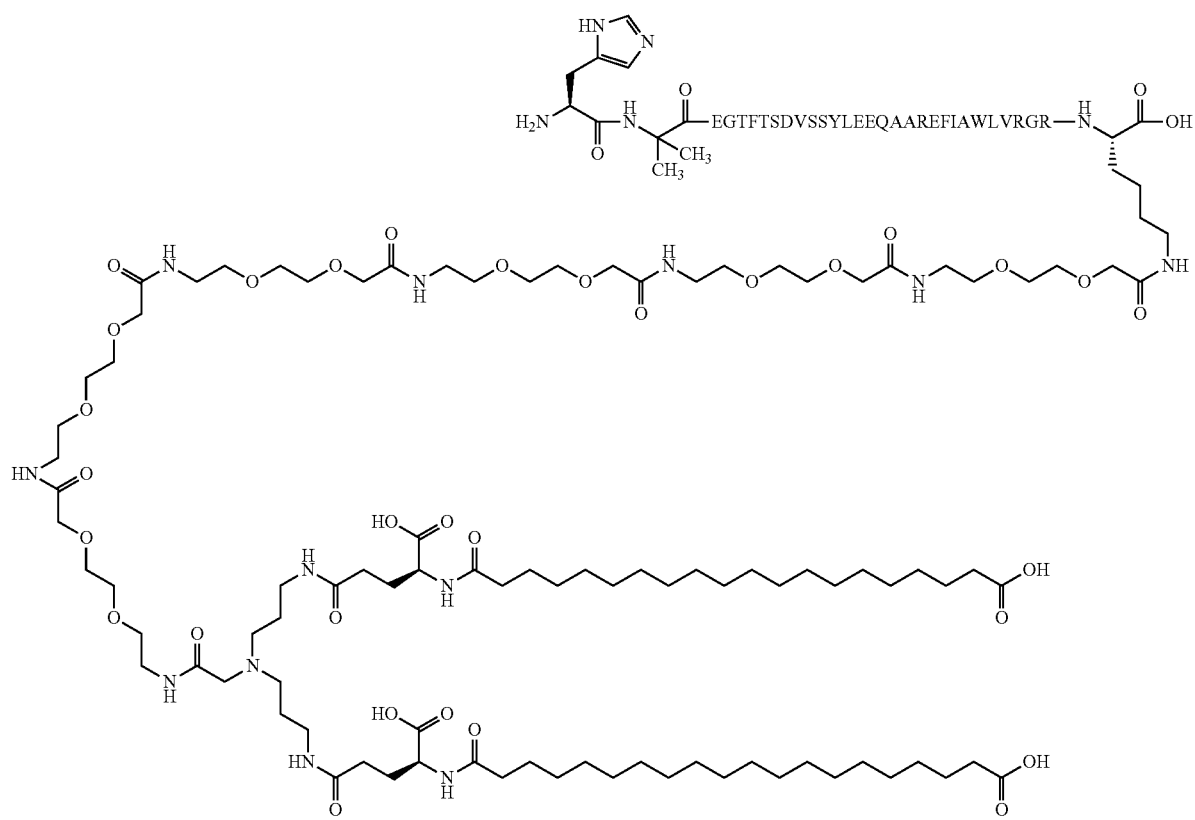

The peptide has SEQ ID NO: 2
Synthesis method: SPPS_P; SC_P; CP_M1
UPLC02: RT=11.41 min
LCMS01: RT=2.34 min, m/z: 1381 [M+4H]$^{4+}$, 1105 [M+5H]$^{5+}$ Example 27

N{Epsilon-37}-[2-[2-[2-[[2-[2-[2-[[2-[2-[2-[[2-[2-[2-[[2-[bis[3-[[(4S)-4- carboxy-4-[[4-[(19-carboxynonadecanoylamino)methyl]cyclohexanecarbonyl]amino]butanoyl]amino]propyl]amino]acetyl]amino]ethoxy]ethoxy]acetyl]amino]ethoxy]ethoxy]acetyl]amino]ethoxy]ethoxy]acetyl]amino]ethoxy]ethoxy]acetyl]-[Aib8,Glu22,Arg26,Arg34,Lys37]-GLP-1-(7-37)-peptide Chem. 47

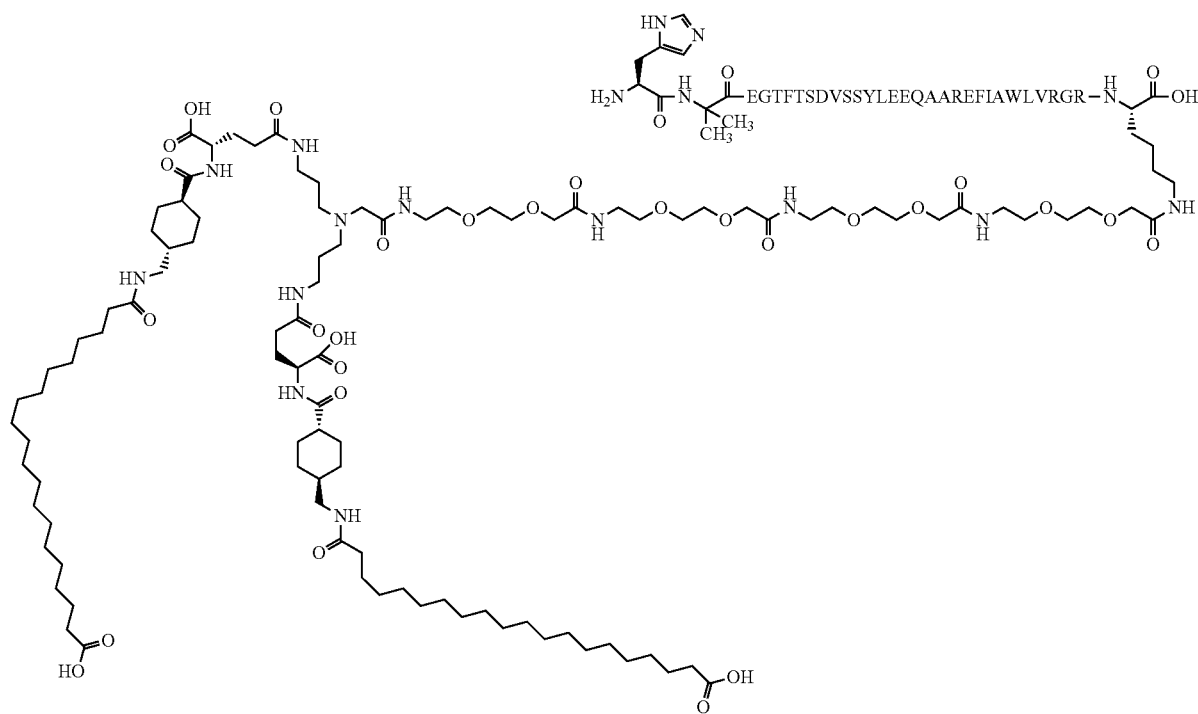

The peptide has SEQ ID NO: 2
Synthesis method: SPPS_P; SC_P; CP_M1
UPLC02: RT=12.1 min
LCMS01: RT=2.57 min, m/z: 1836 [M+3H]$^{3+}$, 1378 [M+4H]$^{4+}$, 1102 [M+5H]$^{5+}$
Example 28
N{Epsilon-36}-[2-[bis[3-[[2-[2-[2-[[2-[2-[2-[[2-[2-[2-[[2-[2-[2-[[(4S)-4- carboxy-4-(17-carboxyhepta-decanoylamino)butanoyl]amino]ethoxy]ethoxy] acetyl]amino]ethoxy]ethoxy]acetyl]amino]ethoxy] ethoxy]acetyl]amino]ethoxy]ethoxy]acetyl]amino] propyl]amino]acetyl]-[Aib8,Glu22,Arg26,Arg34, Lys36]-GLP-1-(7-37)-peptide
Chem. 48
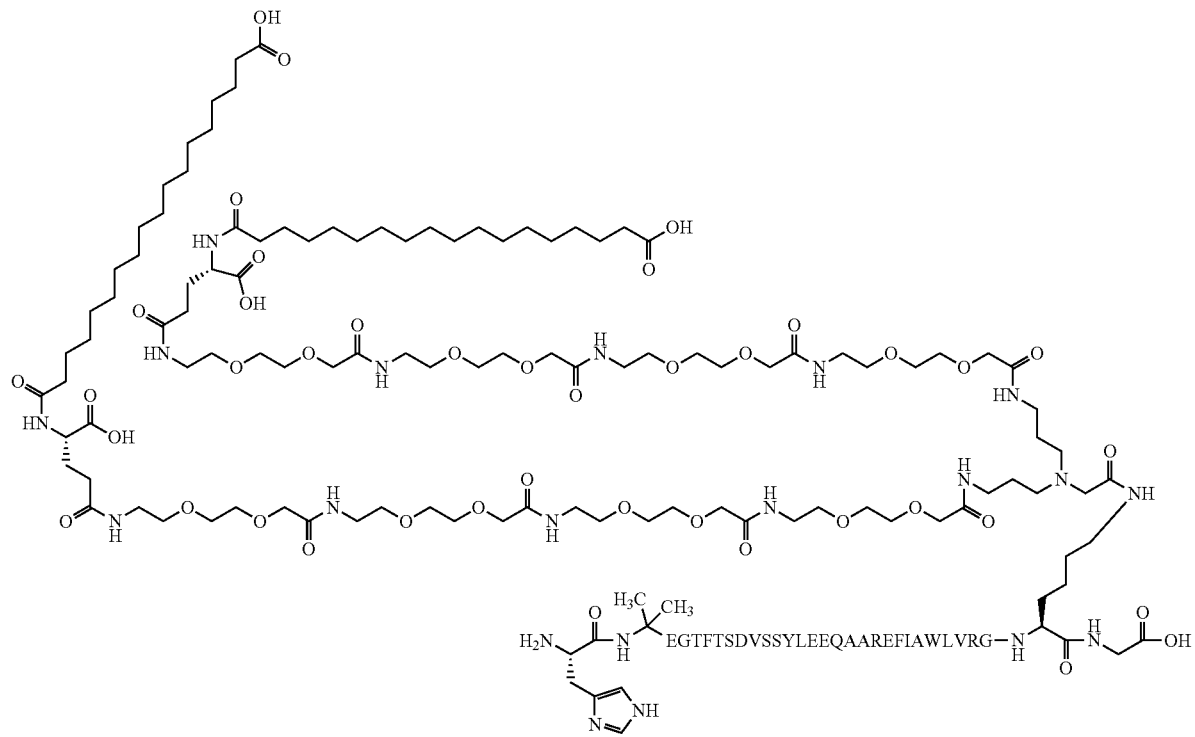

The peptide has SEQ ID NO: 6
Synthesis method: SPPS_P; SC_P; CP_M1
UPLC02: RT=9.55 min
LCMS01: RT=2.21 min, m/z: 1413 $[M+4H]^{4+}$, 1131 $[M+5H]^{5+}$
Example 29
N{Epsilon-36}-[2-[2-[2-[[2-[2-[2-[[2-[2-[2-[[2-[2-[2-[[2-[bis[3-[[(4S)-4- carboxy-4-(17-carboxyhepta-decanoylamino)butanoyl]amino]propyl]amino]acetyl]amino]ethoxy]ethoxy]acetyl]amino]ethoxy]ethoxy]acetyl]amino]ethoxy]ethoxy]acetyl]amino]ethoxy]ethoxy]acetyl]-[Aib8,Glu22,Arg26,Glu30,Arg34, Lys36]-GLP-1-(7-37)-peptide
Chem. 49
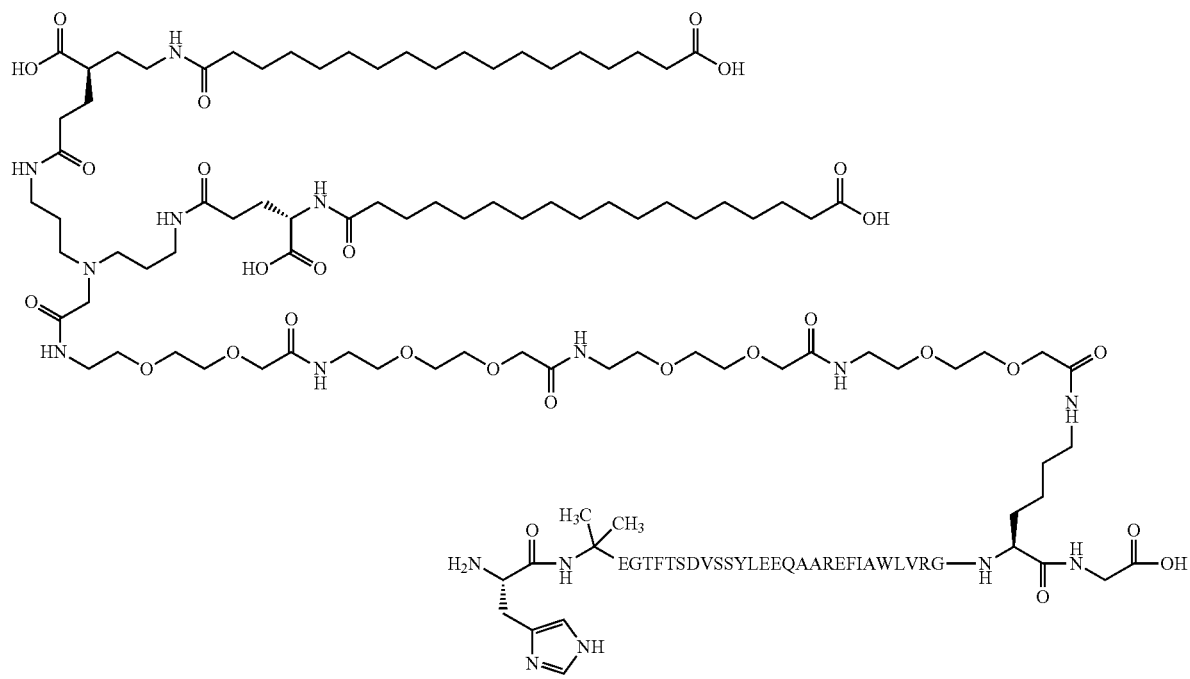

The peptide has SEQ ID NO: 7
Synthesis method: SPPS_P; SC_P; CP_M1
UPLC02: RT=10.07 min
LCMS01: RT=2.3 min, m/z: 1710 $[M+3H]^{3+}$, 1283 $[M+4H]^{4+}$, 1027 $[M+5H]^{5+}$ Example 30

N{Epsilon-36}-[2-[2-[2-[[2-[2-[2-[[2-[2-[2-[[2-[2-[2-[[2-[2-[2-[[2-[2-[2-[[2-[bis[3-[[(4S)-4-carboxy-4-[[4-[(19-carboxynonadecanoylamino)methyl]cyclohexanecarbonyl]amino]butanoyl]amino]propyl]amino]acetyl]amino]ethoxy]ethoxy]acetyl]amino]ethoxy]ethoxy]acetyl]amino]ethoxy]ethoxy]acetyl]amino]ethoxy]ethoxy]acetyl]amino]ethoxy]ethoxy]acetyl]amino]ethoxy]ethoxy]acetyl]-[Aib8,Glu22,Arg26,Arg34,Lys36]-GLP-1-(7-37)-peptide Chem. 50

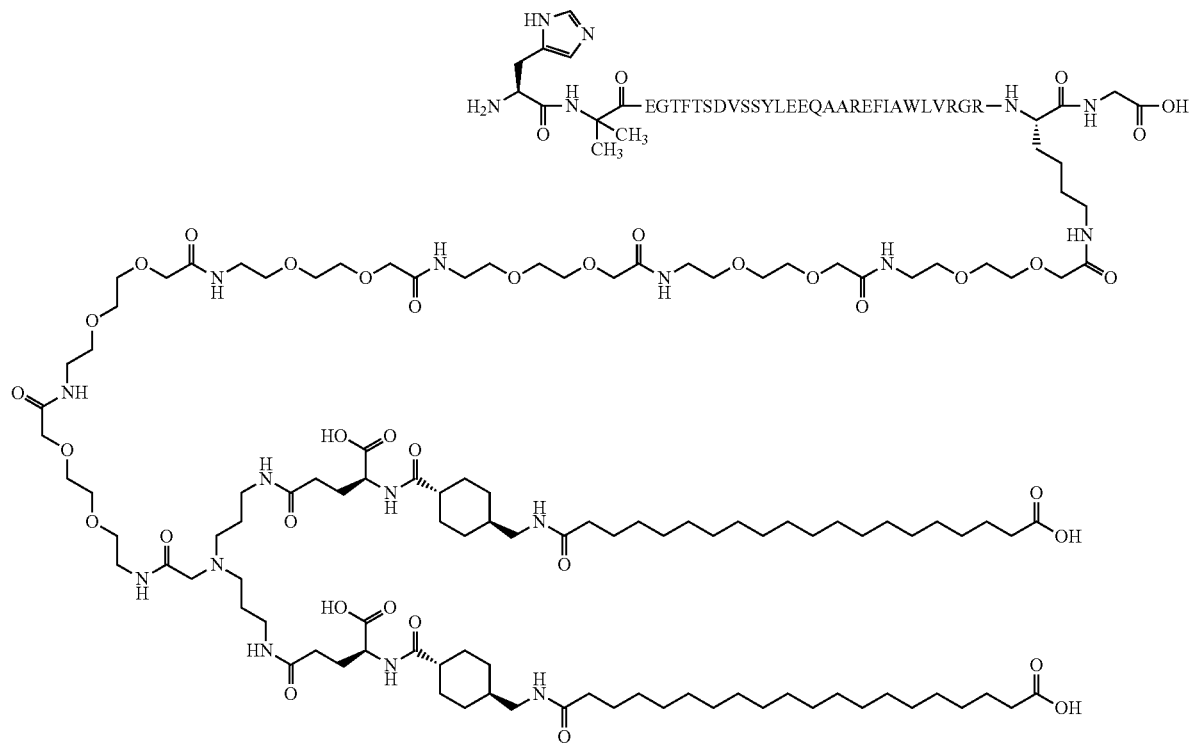

The peptide has SEQ ID NO: 6
Synthesis method: SPPS_P; SC_P; CP_M1
UPLC02: RT=10.97 min
LCMS01: RT=2.63 min, m/z: 1425 [M+4H]$^{4+}$, 1140 [M+5H]$^{5+}$

Example 31

N{Epsilon-35}-[2-[2-[2-[[2-[2-[2-[[2-[2-[2-[[2-[2-[2-[[2-[2-[2-[[2-[2-[2-[[2-[bis[3-[[(4S)-4-carboxy-4-[[4-[(19-carboxynonadecanoylamino)methyl]cyclohexanecarbonyl]amino]butanoyl]amino]propyl]amino]acetyl]amino]ethoxy]ethoxy]acetyl]amino]ethoxy]ethoxy]acetyl]amino]ethoxy]ethoxy]acetyl]amino]ethoxy]ethoxy]acetyl]amino]ethoxy]ethoxy]acetyl]-[Aib8,Glu22,Arg26,Arg34,Lys35]-GLP-1-(7-37)-peptide Chem. 51

The peptide has SEQ ID NO: 6
Synthesis method: SPPS_P; SC_P; CP_M1
UPLC02: RT=10.57 min
LCMS01: RT=2.47 min, m/z: 1450 [M+4H]$^{4+}$, 1160 [M+5H]$^{5+}$

Example 32

N{Epsilon-34}-[2-[2-[2-[[2-[2-[2-[[2-[2-[2-[[2-[2-[2-[2-[2-[[2-[2-[2-[[2-[bis[3-[[(4S)-4-carboxy-4-[[4-[(19-carboxynonadecanoylamino)methyl]cyclohexanecarbonyl]amino]butanoyl]amino]propyl]amino]acetyl]amino]ethoxy]ethoxy]acetyl]amino]ethoxy]ethoxy]acetyl]amino]ethoxy]ethoxy]acetyl]amino]ethoxy]ethoxy]acetyl]amino]ethoxy]ethoxy]acetyl]-[Aib8,Glu22,Arg26]-GLP-1-(7-37)-peptide

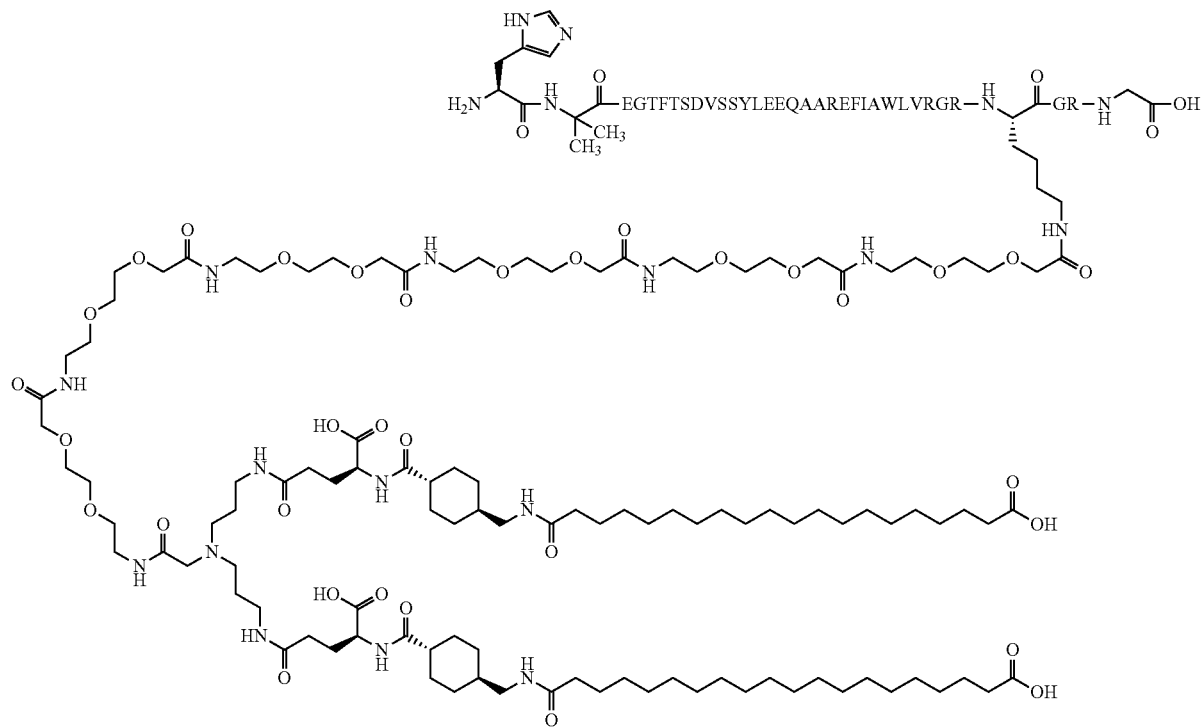

Chem. 52

The peptide has SEQ ID NO: 8
Synthesis method: SPPS_P; SC_P; CP_M1
UPLC02: RT=10.94 min
LCMS01: RT=2.62 min, m/z: 1425 [M+4H]$^{4+}$, 1140 [M+5H]$^{5+}$
Comparative Example 1
N{Epsilon-37}-[2-[2-[2-[[(2S)-2,6-bis[[2-[2-[2-(dodecanoylamino)ethoxy]ethoxy]acetyl]amino]hexanoyl]amino]ethoxy]ethoxy]acetyl]-[Aib8,Aib22,Aib35,Lys37]-GLP-1-(7-37)-peptide amide
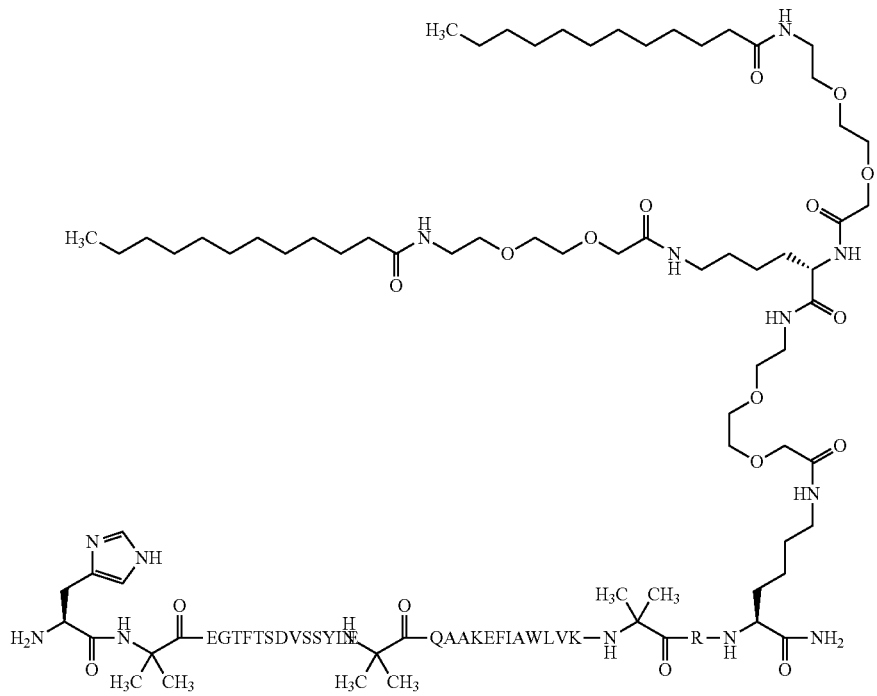
Chem. 53

The peptide has SEQ ID NO: 5
This is the compound of Example 8 of WO2005/027978 A2.
Synthesis method: SPPS_P; SC_P; CP_M1
UPLC02v01: Rt=11.4 min
LCMS01v01: Rt=2.7; m/4=1107; m/5=886

Comparative Example 2

N{Epsilon-37}-[2-[2-[2-[[(2S)-2,6-bis[[2-[2-[2-(tet-radecanoylamino)ethoxy]ethoxy]acetyl]amino]hexanoyl]amino]ethoxy]ethoxy]acetyl]-[Aib8,Aib22,Aib35,Lys37]-GLP-1-(7-37)-peptide amide

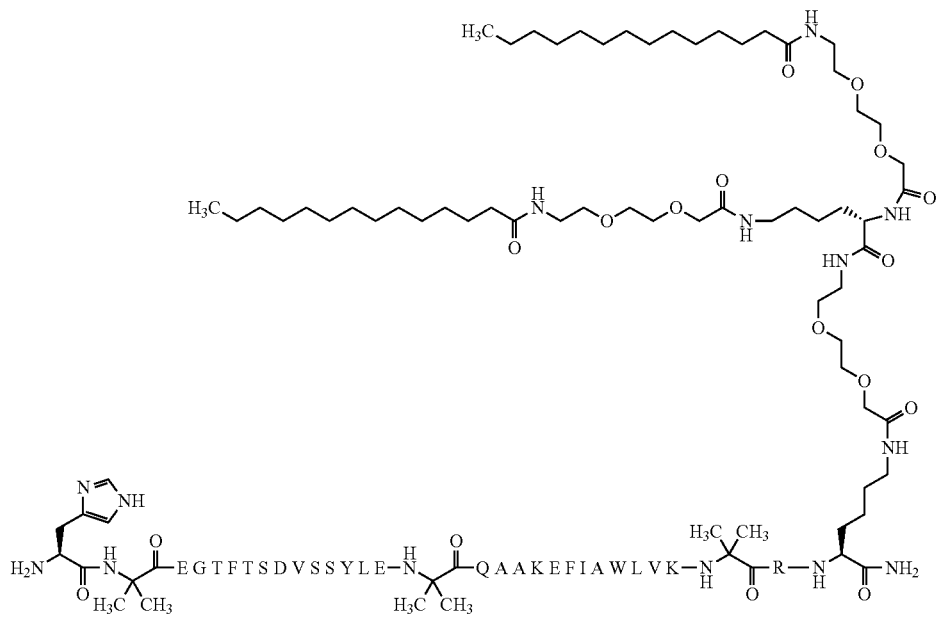

Chem. 54

The peptide has SEQ ID NO: 5
This is the compound of Example 9 of WO2005/027978 A2.
Synthesis method: SPPS_P; SC_P; CP_M1
UPLC02v01: Rt=12.9 min
LCMS01v01: Rt=2.9; m/3=1494; m/4=1121
Pharmacological Methods Example 33: In Vitro Potency The purpose of this example is to test the activity, or potency, of the GLP-1 derivatives in vitro. The in vitro potency is the measure of human GLP-1 receptor activation in a whole cell assay.

The potencies of the GLP-1 derivatives of Examples 1-32 and Comparative Examples 1-2 were determined as described below. Semaglutide was also included for comparison.
Principle In vitro potency was determined by measuring the response of the human GLP-1 receptor in a reporter gene assay. The assay was performed in a stably transfected BHK cell line that expresses the human GLP-1 receptor and contains the DNA for the cAMP response element (CRE) coupled to a promoter and the gene for firefly luciferase (CRE luciferase). When the human GLP-1 receptor is activated it results in the production of cAMP, which in turn results in the luciferase protein being expressed. When assay incubation is completed the luciferase substrate (luciferin) is added and the enzyme converts luciferin to oxyluciferin to produce bioluminescence. The luminescence is measured as the readout for the assay.
Cell Culture and Preparation The cells used in this assay (clone FCW467-12A/KZ10-1) were BHK cells with BHKTS13 as a parent cell line. The cells were derived from a clone (FCW467-12A) that expresses the human GLP-1 receptor and were established by further transfection with CRE luciferase to obtain the current clone.

The cells were cultured at 5% $CO_2$ in cell culture medium. They were aliquoted and stored in liquid nitrogen. Before each assay an aliquot was taken up and washed twice in PBS before being suspended at the desired concentration in the assay specific buffer. For 96-well plates the suspension was made to give a final concentration of $5 \times 10^3$ cells/well.
Materials The following chemicals were used in the assay: Pluronic F-68 (10%) (Gibco 2404), human serum albumin (HSA) (Sigma A9511), ovalbumin (Sigma A5503), DMEM w/o phenol red (Gibco 11880-028), 1 M Hepes (Gibco 15630), Glutamax 100× (Gibco 35050) and steadylite plus (PerkinElmer 6016757).
Buffers Cell culture medium consisted of DMEM medium with 10% FBS (Fetal Bovine Serum; Invitrogen 16140-071), 1 mg/ml G418 (Invitrogen 15140-122), 240 nM MTX (methotrexate; Sigma M9929) and 1% pen/strep (penicillin/streptomycin; Invitrogen 15140-122).

Assay medium consisted of DMEM w/o phenol red, 10 mM Hepes and 1× Glutamax. The assay buffer consisted of 2% ovalbumin and 0.2% Pluronic F-68 in assay medium.

Procedure

1) Cell stocks were thawed in a 37° C. water bath.
2) Cells were washed three times in PBS.
3) Cells were counted and adjusted to $5 \times 10^3$ cells/50 µl ($1 \times 10^5$ cells/ml) in assay medium. A 50 µl aliquot of cells was transferred to each well in the assay plate.
4) Stocks of the test compounds and reference compounds were diluted to a concentration of 0.2 µM in assay buffer. Compounds were diluted 10-fold to give the following concentrations: $2 \times 10^{-7}$ M, $2 \times 10^{-8}$ M; $2 \times 10^{-9}$ M, $2 \times 10^{-10}$ M, $2 \times 10^{-11}$ M, $2 \times 10^{-12}$ M, $2 \times 10^{-13}$ M, and $2 \times 10^{-14}$ M.
5) A 50 µl aliquot of compound or blank was transferred from the dilution plate to the assay plate. Compounds were tested at the following final concentrations: $1 \times 10^{-7}$ M, $1 \times 10^{-8}$ M; $1 \times 10^{-9}$ M, $1 \times 10^{-10}$ M, $1 \times 10^{-11}$ M, $1 \times 10^{-12}$ M, $1 \times 10^{-13}$ M, and $1 \times 10^{-14}$ M.
6) The assay plate was incubated for 3 h in a 5% $CO_2$ incubator at 37° C.
7) The assay plate was removed from the incubator and allowed to stand at room temperature for 15 min.
8) A 100 µl aliquot of steadylite plus reagent was added to each well of the assay plate.
9) Each assay plate was covered with aluminum foil to protect it from light and shaken for 30 min at room temperature.
10) Each assay plate was read in a BioTek Synergy 2 Multi-Mode Reader.

Calculations and Results

The data from the BioTek Synergy 2 Multi-Mode Reader were transferred to GraphPad Prism software. The software performs a non-linear regression (log(agonist) vs response (three parameters)). $EC_{50}$ values which were calculated by the software and reported in pM are shown in Table 1 below.

A minimum of two replicates were measured for each sample. The reported $EC_{50}$ values are averages of all of the measured values for each compound.

TABLE 1

| In vitro potency | |
|---|---|
| Example no. | $EC_{50}$ (pM) |
| 1 | 10 |
| 2 | 14 |
| 3 | 20 |
| 4 | 12 |
| 5 | 10 |
| 6 | 7.2 |
| 7 | 6.6 |
| 8 | 10 |
| 9 | 1.6 |
| 10 | 15 |
| 11 | 17 |
| 12 | 20 |
| 13 | 36 |
| 14 | 6.3 |
| 15 | 5.6 |
| 16 | 1.7 |
| 17 | 1.2 |
| 18 | 1.3 |
| 19 | 1.4 |
| 20 | 1.6 |
| 21 | 1.5 |
| 22 | 1.6 |

TABLE 1-continued

| In vitro potency | |
|---|---|
| Example no. | $EC_{50}$ (pM) |
| 23 | 1.4 |
| 24 | 1.8 |
| 25 | 30 |
| 26 | 13 |
| 27 | 41 |
| 28 | 4.3 |
| 29 | 7.1 |
| 30 | 16 |
| 31 | 9.5 |
| 32 | 13 |
| Comparative Example 1 | 14 |
| Comparative Example 2 | 16 |
| semaglutide | 8.3 |

All compounds reveal potency data that confirms that they are GLP-1 receptor agonists.

Example 34: GLP-1 Receptor Binding

The purpose of this example is to test the receptor binding of the GLP-1 derivatives in vitro. The receptor binding is a measure of affinity of a derivative for the human GLP-1 receptor.

Principle

The receptor binding of the GLP-1 derivatives of Examples 1-32 and Comparative Examples 1-2 to the human GLP-1 receptor was measured in a competitive binding assay. In this type of assay a labelled ligand (in this case $^{125}$I-GLP-1) is bound to the receptor. Each derivative is added in a series of concentrations to isolated membranes containing the human GLP-1 receptor and displacement of the labelled ligand is monitored. The receptor binding is reported as the concentration at which half of the labelled ligand is displaced from the receptor, the $IC_{50}$ value. Semaglutide was included as comparative compound. In order to test the binding of the derivatives to albumin, the assay is performed in a low concentration of serum albumin (HSA) (max. 0.001% final assay concentration as well as in the presence of a considerably higher concentration of serum albumin (HSA) (2.0% final assay concentration). An increase of the $IC_{50}$ value in the presence of serum albumin indicates an affinity to serum albumin and represents a method to predict a protracted pharmacokinetic profile of the test substance in animal models. Semaglutide was included for comparison.

Materials

The following chemicals were used in the assay: Human serum albumin (HSA) (Sigma A1653), DMEM w/o phenol red (Gibco 11880-028), Pen/strep (Invitrogen 15140-122), G418 (Invitrogen 10131-027), 1 M Hepes (Gibco 15630), EDTA (Invitrogen 15575-038), PBS (Invitrogen 14190-094), fetal calf serum (Invitrogen 16140-071), EGTA, $MgCl_2$ (Merck 1.05832.1000), Tween 20 (Amresco 0850C335), SPA particles (wheat germ agglutinin (WGA) SPA beads, Perkin Elmer RPNQ0001), [$^{125}$I]-GLP-1]-(7-36) $NH_2$ (produced in-house), OptiPlate™-96 (Packard 6005290).

Buffer 1 consisted of 20 mM Na-HEPES plus 10 mM EDTA and pH was adjusted to 7.4. Buffer 2 consisted of 20 mM Na-HEPES plus 0.1 mM EDTA and pH was adjusted to 7.4. Assay buffer consisted of 50 mM HEPES supplemented with 5 mM EGTA, 5 mM $MgCl_2$, 0.005% Tween 20 and pH was adjusted to 7.4. An 8% albumin stock consisted of HSA dissolved at 8% (w/v) in assay buffer. An 0.02% albumin stock consisted of HSA dissolved at 0.02% (w/v) in assay buffer.

Cell Culture and Membrane Preparation

The cells used in this assay (clone FCW467-12A) were BHK cells with BHKTS13 as a parent cell line. The cells express the human GLP-1 receptor.

The cells were grown at 5% $CO_2$ in DMEM, 10% fetal calf serum, 1% Pen/Strep (Penicillin/Streptomycin) and 1.0 mg/ml of the selection marker G418. To make a membrane preparation the cells were grown to approximately 80% confluence. The cells were washed twice in phosphate-buffered saline and harvested. The cells were pelleted using a brief centrifugation and the cell pellet was kept on ice. The cell pellet was homogenised with ULTRA-THURRAX™ dispersing instrument for 20-30 seconds in a suitable amount of buffer 1 (e.g., 10 ml). The homogenate was centrifuged for 15 minutes. The pellet was re-suspended (homogenised) in 10 ml buffer 2 and centrifuged. This step was repeated once more. The resulting pellet was re-suspended in buffer 2 and the protein concentration was determined. The membranes were aliquoted and stored at minus 80° C.

Procedure

1. For the receptor binding assay in the presence of low HSA (0.005%) 50 µl of the assay buffer was added to each well of an assay plate. Assay continued with step 3.
2. For the receptor binding assay in the presence of high HSA (2%) 50 µl of the 8% albumin stock was added to each well of an assay plate. Assay continued with step 3.
3. Test compounds were serially diluted to give the following concentrations: $8\times10^{-7}$ M, $8\times10^{-8}$ M, $8\times10^{-9}$ M, $8\times10^{-10}$ M, $8\times10^{-11}$ M, $8\times10^{-12}$ M and $8\times10^{-3}$ M. Twenty-five µl were added to appropriate wells in the assay plate.
4. Cell membrane aliquots were thawed and diluted to their working concentration. Fifty µl were added to each well in the assay plate.
5. WGA SPA beads were suspended in assay buffer at 20 mg/ml. The suspension was diluted to 10 mg/ml in assay buffer just prior to addition to the assay plate. Fifty µl were added to each well in the assay plate.
6. The incubation was started by adding 25 µl of 480 µM solution of [$^{125}$I]-GLP-1]-(7-36)$NH_2$ to each well of the assay plate. A 25 µl aliquot was reserved for measuring total counts/well.
7. The assay plate was incubated for 2 h at 30° C.
8. The assay plate was centrifuged for 10 min.
9. The assay plate was read in a Packard TopCount NXT instrument.

Calculations

The data from the TopCount instrument were transferred to GraphPad Prism software. Individual replicates were analysed using non-linear regression. IC50 values were calculated by the software and reported in nM. The reported values are averages of all of the measured values for each compound.

Results

The following results were obtained:

TABLE 2

| | GLP-1 receptor binding | |
|---|---|---|
| Example no | Low HSA $IC_{50}$ (nM) | High HSA $IC_{50}$ (nM) |
| 1 | 0.12 | 10 |
| 2 | 0.19 | 11 |
| 3 | 0.41 | 22 |
| 4 | 0.13 | 45 |
| 5 | 0.16 | 14 |
| 6 | 0.05 | 9.0 |
| 7 | 0.07 | 19 |
| 8 | 0.19 | 27 |
| 9 | 0.16 | 29 |
| 10 | 0.31 | 30 |
| 11 | 0.35 | 33 |
| 12 | 0.51 | 25 |
| 13 | 0.74 | 18 |
| 14 | 0.04 | 14 |
| 15 | 0.05 | 3.4 |
| 16 | 0.10 | 3.3 |
| 17 | 0.16 | 3.2 |
| 18 | 0.18 | 5.7 |
| 19 | 0.15 | 42 |
| 20 | 0.14 | 3.7 |
| 21 | 0.13 | 16 |
| 22 | 0.12 | 47 |
| 23 | 0.14 | 16 |
| 24 | 0.16 | 32 |
| 25 | 0.91 | 41 |
| 26 | 0.36 | 29 |
| 27 | 0.66 | 21 |
| 28 | 0.68 | 140 |
| 29 | 1.1 | 110 |
| 30 | 1.2 | 4.1 |
| 31 | 0.33 | 7.2 |
| 32 | 0.72 | 7.4 |
| Comparative Example 1 | 0.27 | 0.13 |
| Comparative Example 2 | 1.42 | 0.52 |
| semaglutide | 0.60 | 420 |

All compounds show a very good binding to the GLP-1 receptor in the absence of albumin.

Example 35: Pharmacokinetic Study in Minipigs

The purpose of this study is to determine the protraction in vivo of the GLP-1 derivatives after i.v. administration to minipigs, i.e. the prolongation of their time in the body and thereby their time of action. This is done in a pharmacokinetic (PK) study, where the terminal half-life of the derivative in question is determined. By terminal half-life is meant the time it takes to halve a certain plasma concentration in the terminal elimination phase.

The derivatives of Examples 3, 6, 9, and Comparative Examples 1 and 2 were dosed 5 nmol/kg. The derivatives of Examples 1, 2, 4, 5, 10, 11, 12, 26, and 27 were dosed 2 nmol/kg. Semaglutide was included for comparison (dosed 1.5 nmol/kg).

Male Göttingen minipigs were obtained from Ellegaard Göttingen Minipigs (Dalmose, Denmark) approximately 7-14 months of age and weighing approximately 16-35 kg were used in the studies. The minipigs were housed either individually (pigs with permanent catheters) or in a group and fed restrictedly once or twice daily with SDS minipig diet (Special Diets Services, Essex, UK).

After at least 2 weeks of acclimatisation two permanent central venous catheters were implanted in vena cava caudalis or cranialis in each animal. The animals were allowed 1 week recovery after the surgery, and were then used for repeated pharmacokinetic studies with a suitable wash-out period between successive GLP-1 derivative dosings.

The GLP-1 derivatives of Examples 3, 10, 11, 12, and 27 were dissolved in 50 mM sodium phosphate, 70 mM sodium chloride, 0.05% polysorbate 20, pH 7.4, to a concentration of 20-40 nmol/ml; the derivatives of Examples 1, 2, 4, 5, 6, 9, and Comparative Examples 1 and 2 were dissolved in 2 mM sodium acetate, 250 mM glycerol and 0.025% polysorbate 20, pH 4.0—all to a concentration of usually from 20-60 nmol/ml. The derivative of Example 26 was dissolved in 8 mM phosphate, 184 M propyleneglycol, pH 7.8, to a concentration of 40 nmol/ml. Semaglutide was dissolved to 15 nmol/ml in 50 mM sodium phosphate, 145 mM sodium chloride, 0.05% polysorbate 20, pH 7.4.

Intravenous injections (the volume corresponding to for example 0.050-0.125 ml/kg) of the compounds were given through one catheter or through the venflon, and blood was sampled at predefined time points for up till 25 days post dosing (preferably through the other catheter or by venipuncture). Blood samples (for example 0.8 ml) were collected in EDTA buffer (8 mM) and then centrifuged at 4° C. and 1942G for 10 minutes.

Plasma was pipetted into Micronic tubes on dry ice, and kept at −20° C. until analysed for plasma concentration of the respective GLP-1 compound using LOCI. Individual plasma concentration-time profiles were analyzed by a non-compartmental pharmacokinetic method in Phoenix v. 6.2 (Pharsight Inc., Mountain View, Calif., USA), or other relevant software for PK analysis, and the resulting terminal half-lives (harmonic mean) determined.

Results

TABLE 3

Pharmacokinetic study in minipigs (i.v.)

| Example no. | Terminal half-live (h) |
| --- | --- |
| 1 | 130 |
| 2 | 113 |
| 3 | 159 |
| 4 | 243 |
| 5 | 122 |
| 6 | 143 |
| 9 | 104 |
| 10 | 151 |
| 11 | 160 |
| 12 | 137 |
| 26 | 131 |
| 27 | 138 |
| Comparative Example 1 | 3 |
| Comparative Example 2 | 3 |
| semaglutide | 55 |

The tested derivatives of the invention have very long terminal half-lives (at least twice that of semaglutide, and at least thirty-five times that of the comparative example compounds).

Example 36: Pharmacodynamic Study in Rats

The purpose of the study is to verify the acute effect of the GLP-1 derivatives on food intake (FI) and body weight (BW) in lean rodents.

The GLP-1 derivatives of Examples 1-6, 9-13, and 25-27 were tested in a single-dose study in lean Sprague Dawley male rats as described in the following. The derivatives were tested at a dose of 50 nmol/kg (Examples 4, 10-13, and 25-27) or 100 nmol/kg (Examples 1-3, 5, 6, and 9).

Six lean male Sprague Dawley rats (~300 g) per compound to be tested (from Taconic, Denmark), fed from birth with the diet NIH31 (NIH 31M Rodent Diet, commercially available from Taconic Farms, Inc., US, see www.taconic.com), were enrolled for the study at the age of approximately 10 weeks. Upon arrival the rats had a chip inserted in the dorsal neck region to be used for registration in the HM2 automatic food intake system (Ellegaard systems A/S, Faaborg, Denmark). The rats were given free access to standard chow (e.g. Altromin 1324, Brogaarden, Gentofte, Denmark) and tap water and kept at a constant temperature, approximately 22° C. Rats were housed three per cage and after 1-2 weeks of acclimatisation, they were dosed according to BW. After dosing FI and BW were daily recorded for a duration of 144 hours. After the experiment the rats were euthanized.

The animals were grouped to receive treatment as follows: Vehicle, s.c. or GLP-1 derivative (Examples 1-6, 9-13, and 25-27), s.c., where vehicle was either 50 mM sodium phosphate, 70 mM sodium chloride, 0.05% polysorbate 80, pH 7.4 (Examples 3, 10-13, and 25-27), or 2 mM acetate, sodium, 250 mM glycerol, 0.025% (vol/vol) polysorbate 20, pH 4 (Examples 1, 2, 4-6, and 9).

The GLP-1 derivatives were dissolved in the vehicle to a dosing concentration of 50 or 100 nmol/ml. Animals were dosed once, at the start of the experiment, s.c. with a dose-volume of 1 ml/kg (i.e. 300 μl per 300 g rat).

The day before dosing FI and BW was recorded in all groups and used as baseline. On the day of dosing the GLP-1 derivative was dosed at approximately 10 am (time 0). On the following days, FI was continuously recorded using an automatic food and water recording system (HM2, see above) and BW was determined once daily. Rats were weighed individually on a digital weighing scale (accuracy 0.1 g).

The data are presented as percent change in FI or BW measured at the 48 h time point. For example, the percent change in FI at 48 h for each individual is calculated as follows: [[(food intake at 48 h)−(baseline food intake)]/(baseline food intake)]×100%], where baseline FI refers to the level before the administration of any treatment—and vice versa for the BW change. A negative value refers to a % reduction.

The following results were obtained (averages of all individual determinations corresponding to the respective treatment):

TABLE 4

Pharmacodynamic study in rats

| Example no. | % change in food intake 48 h | % change in body weight 48 h |
| --- | --- | --- |
| 1 | −75 | −12 |
| 2 | −83 | −12 |
| 3 | −52 | −8 |
| 4 | −56 | −11 |
| 5 | −78 | −13 |
| 6 | −77 | −13 |
| 9 | −80 | −14 |
| 10 | −31 | −4 |
| 11 | −57 | −7 |
| 12 | −53 | −7 |
| 13 | −27 | −3 |
| 25 | −29 | −7 |
| 26 | −32 | −3 |
| 27 | −21 | −1 |

The tested derivatives are biologically active in vivo and reduce food intake and body weight at 48 h after a single s.c. injection of either 50 nmol/kg or 100 nmol/kg. On an added note, food intake is a much more direct measure of bioactivity than is body weight as this is a single dose experiment.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:
1. A GLP-1 derivative selected from the group consisting of:
(SEQ ID NO: 2)
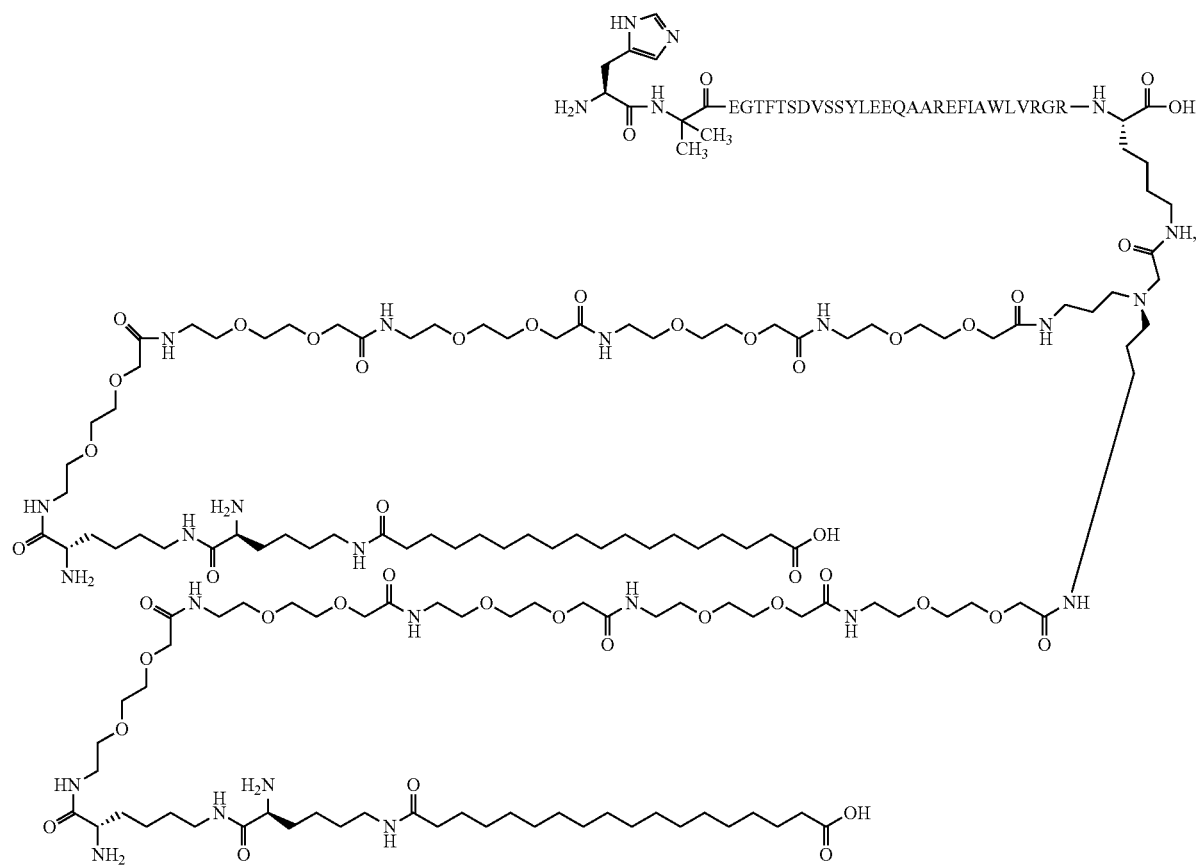
Chem. 21

(SEQ ID NO: 2)
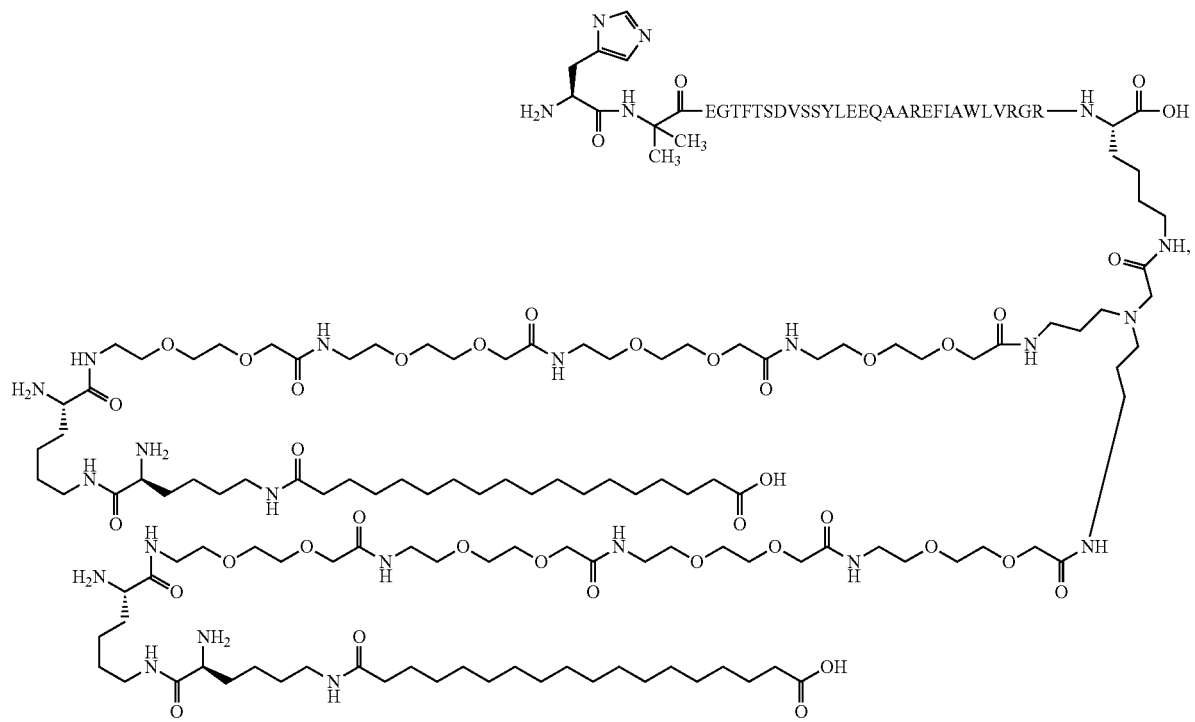
Chem. 22
(SEQ ID NO: 2)
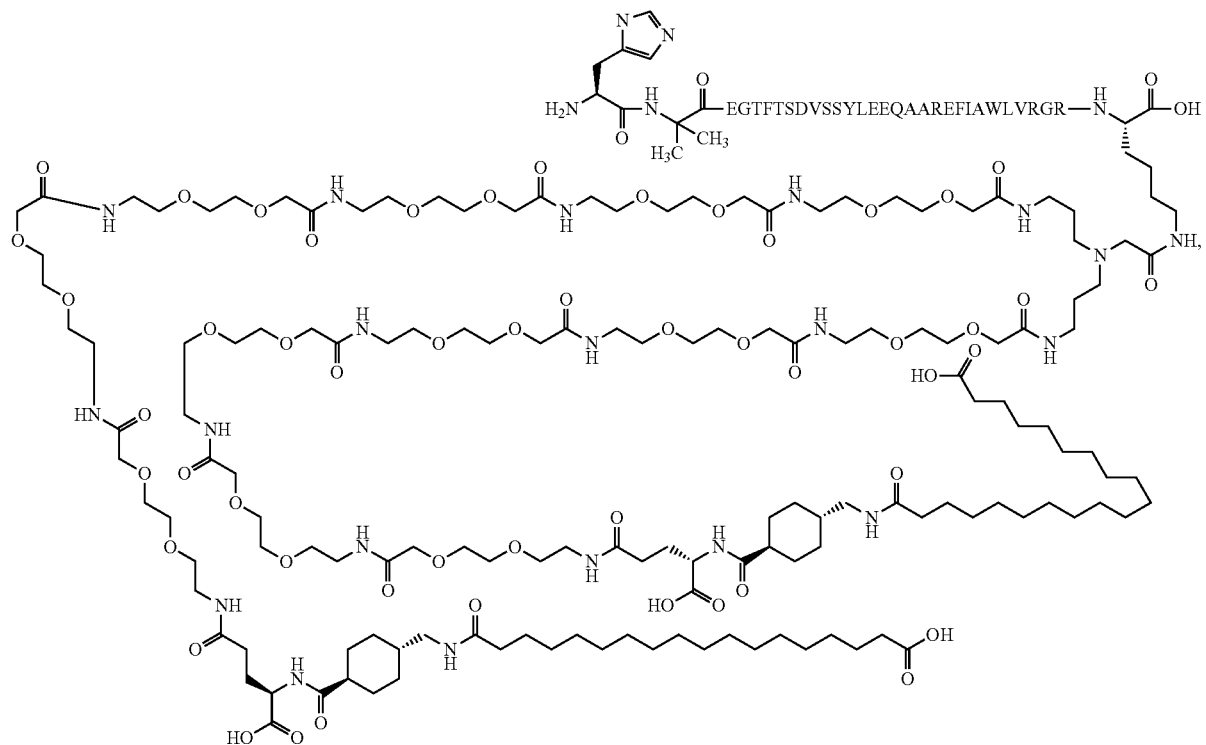
Chem. 23

(SEQ ID NO: 3)
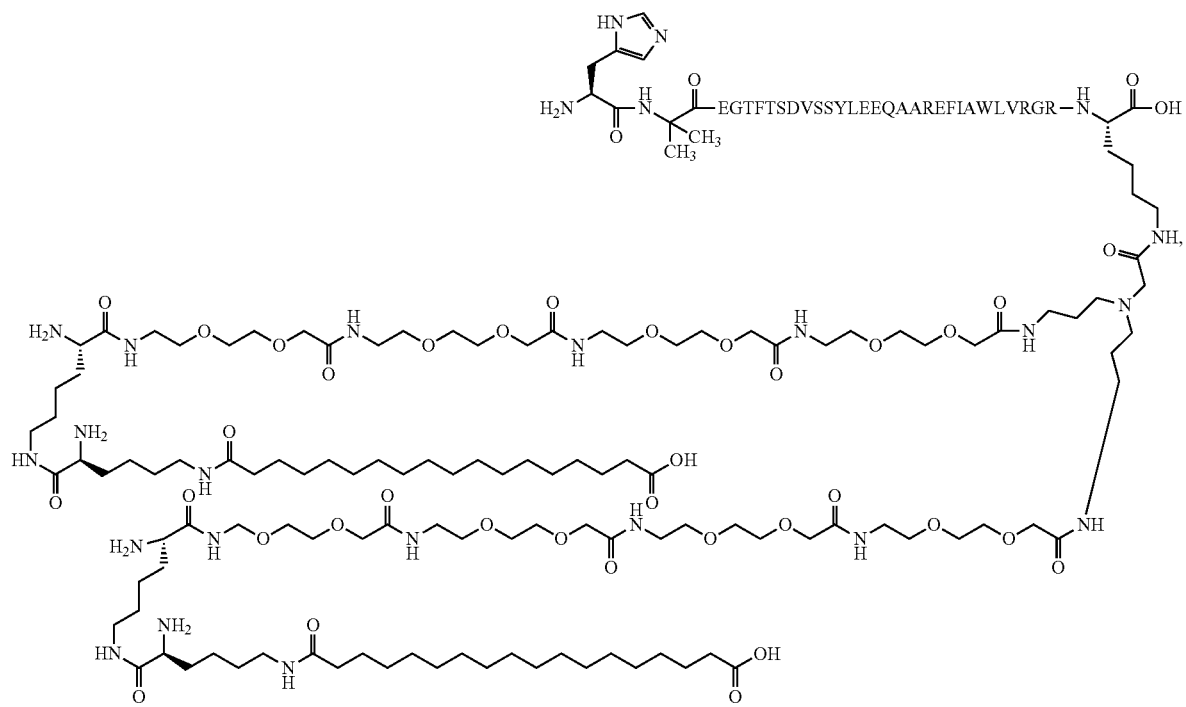
Chem. 24
(SEQ ID NO: 2)
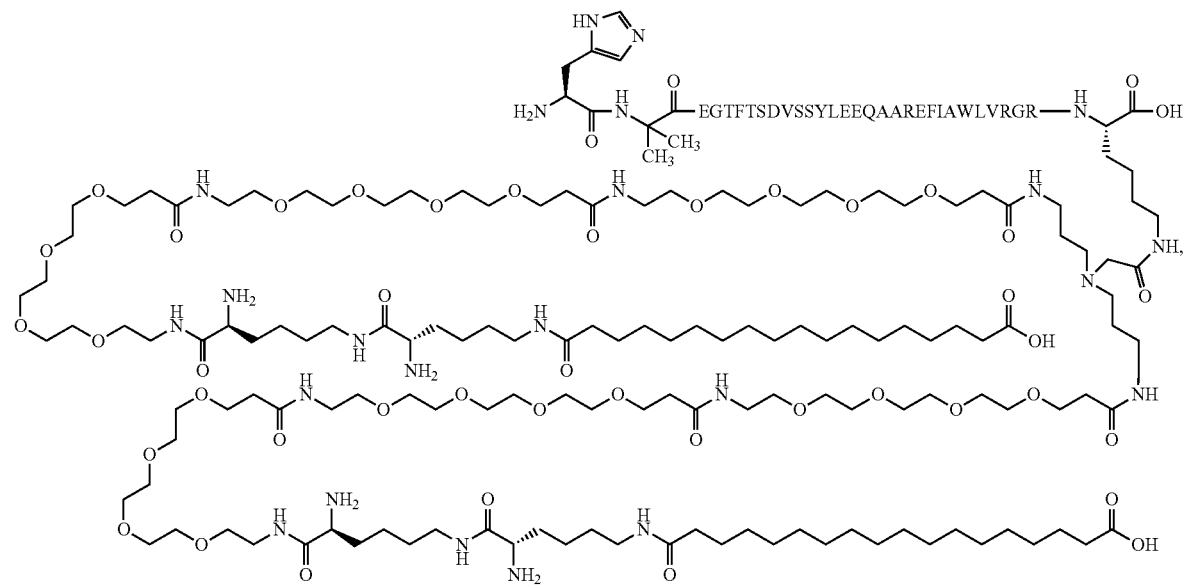
Chem. 25

(SEQ ID NO: 2)
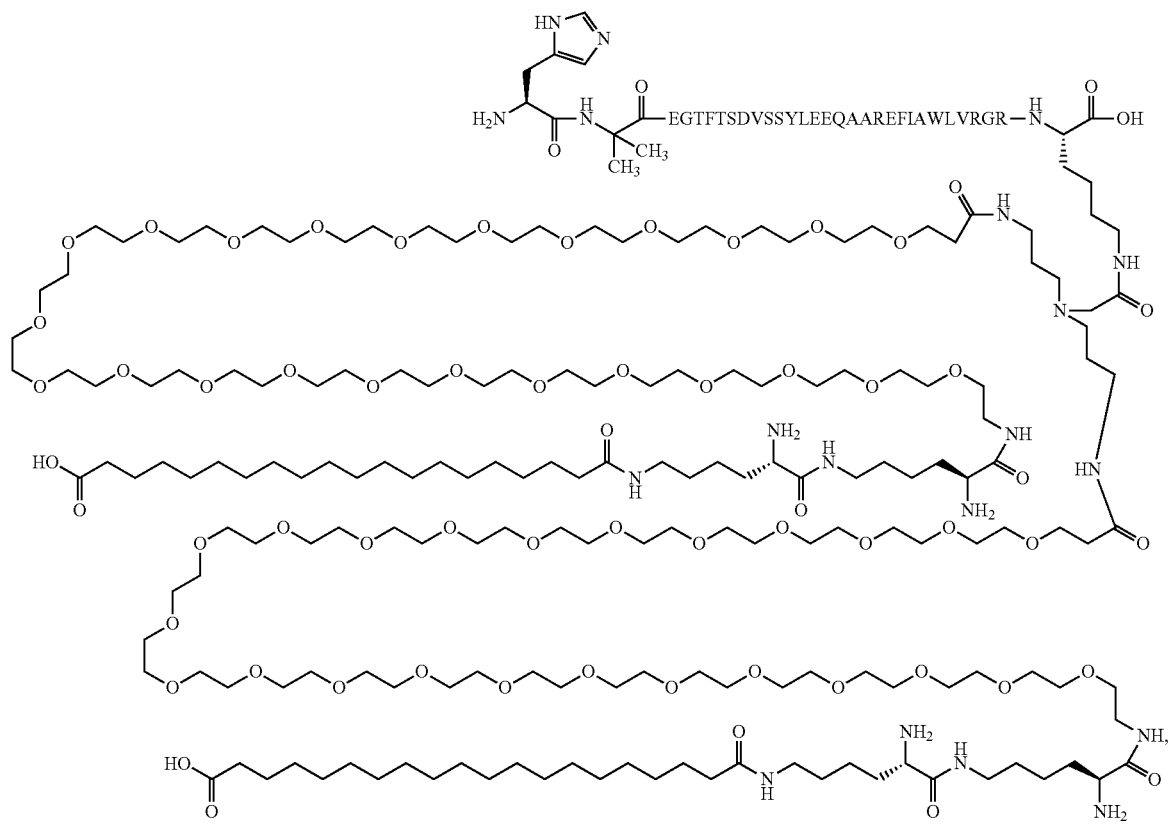
Chem. 26
(SEQ ID NO: 2)
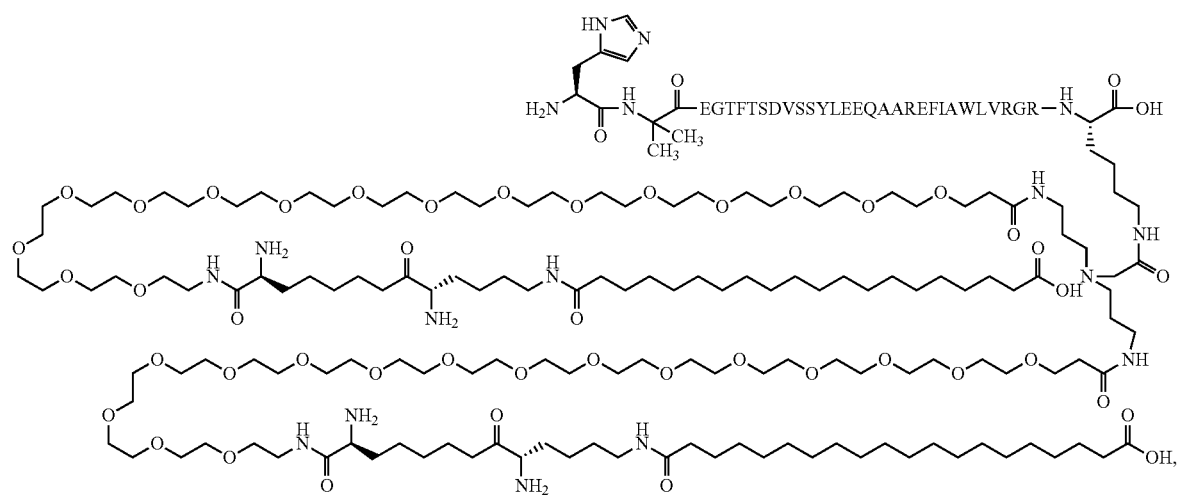
Chem. 27

(SEQ ID NO: 2)
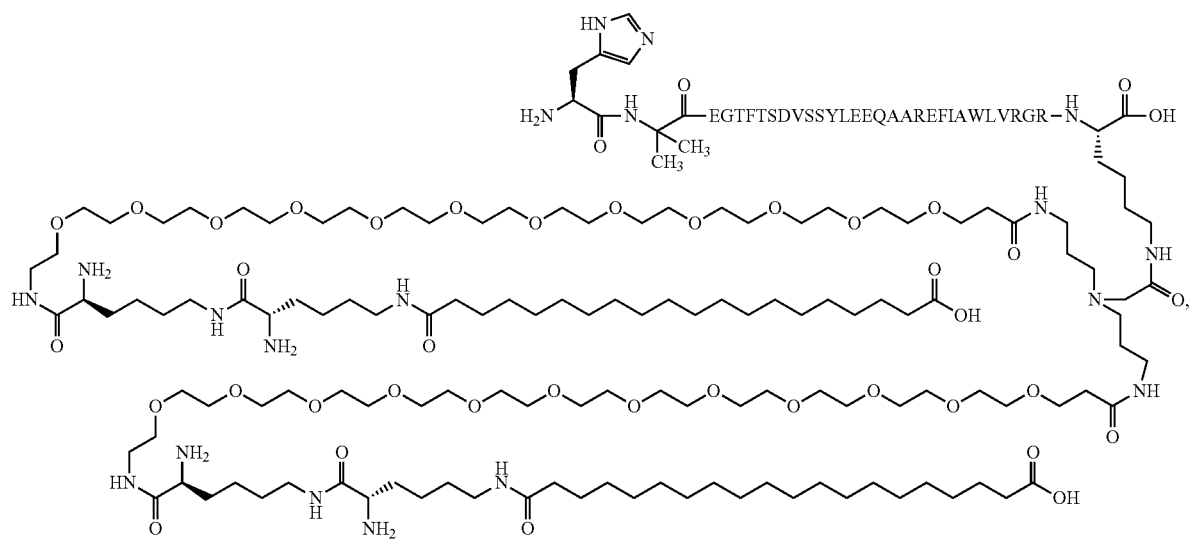
Chem. 28
(SEQ ID NO: 2)
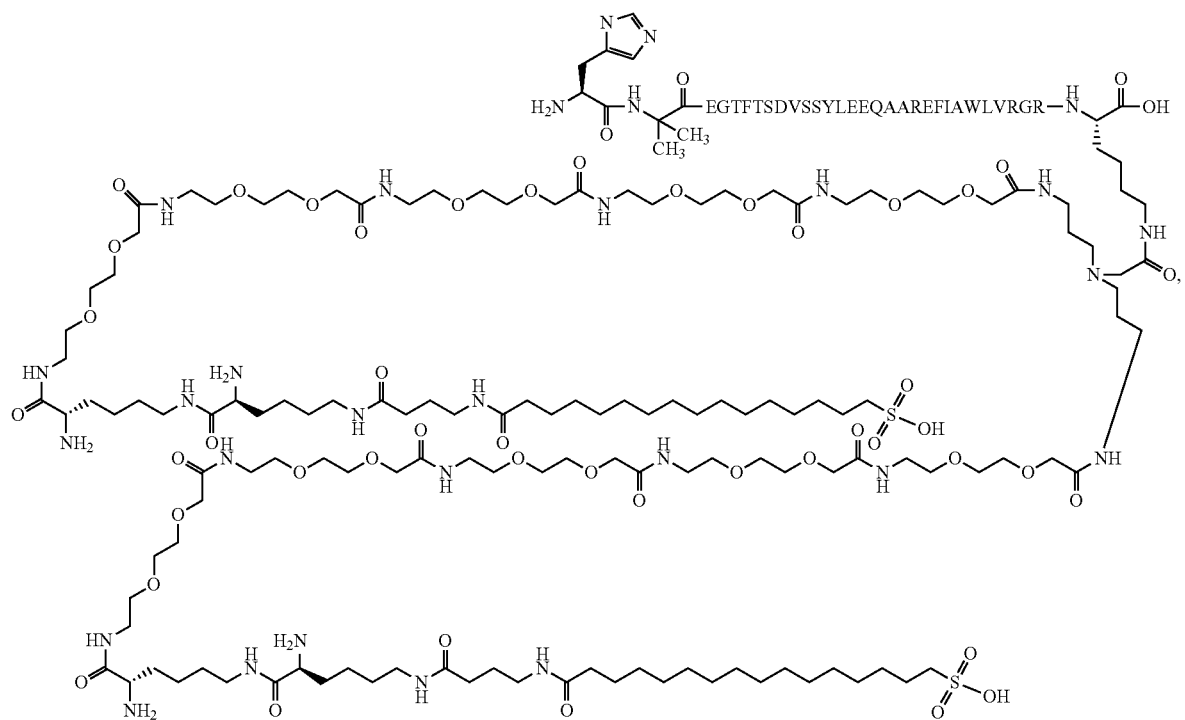
Chem. 29

(SEQ ID NO: 4)
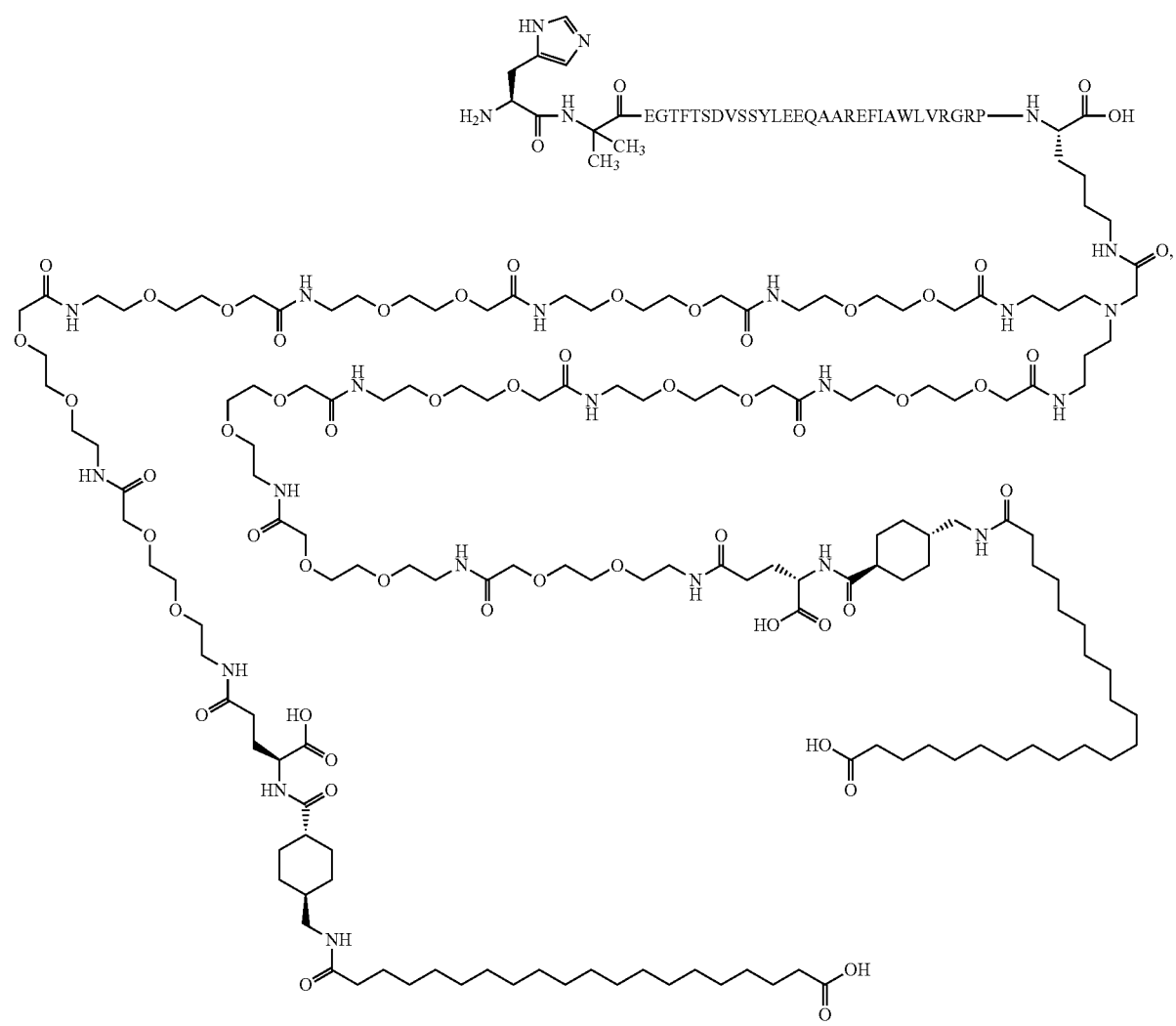
Chem. 30

(SEQ ID NO: 2)
Chem. 34
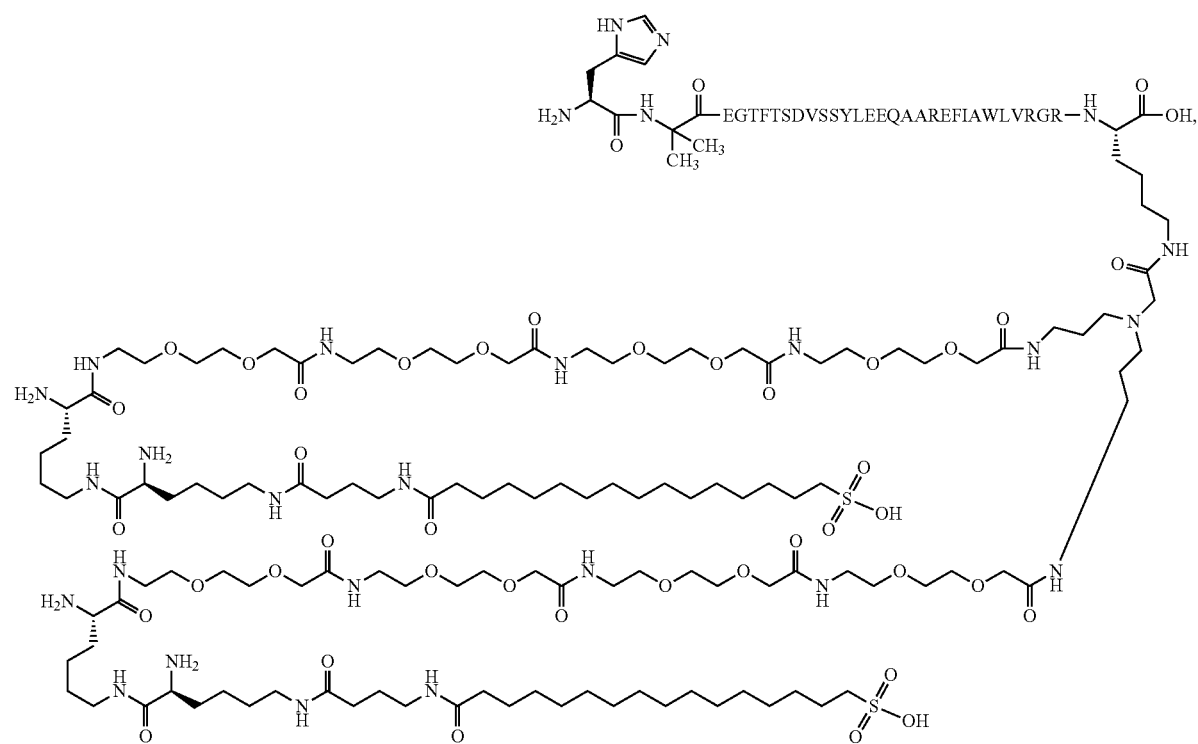

(SEQ ID NO: 2)
(SEQ ID NO: 2)
Chem. 35
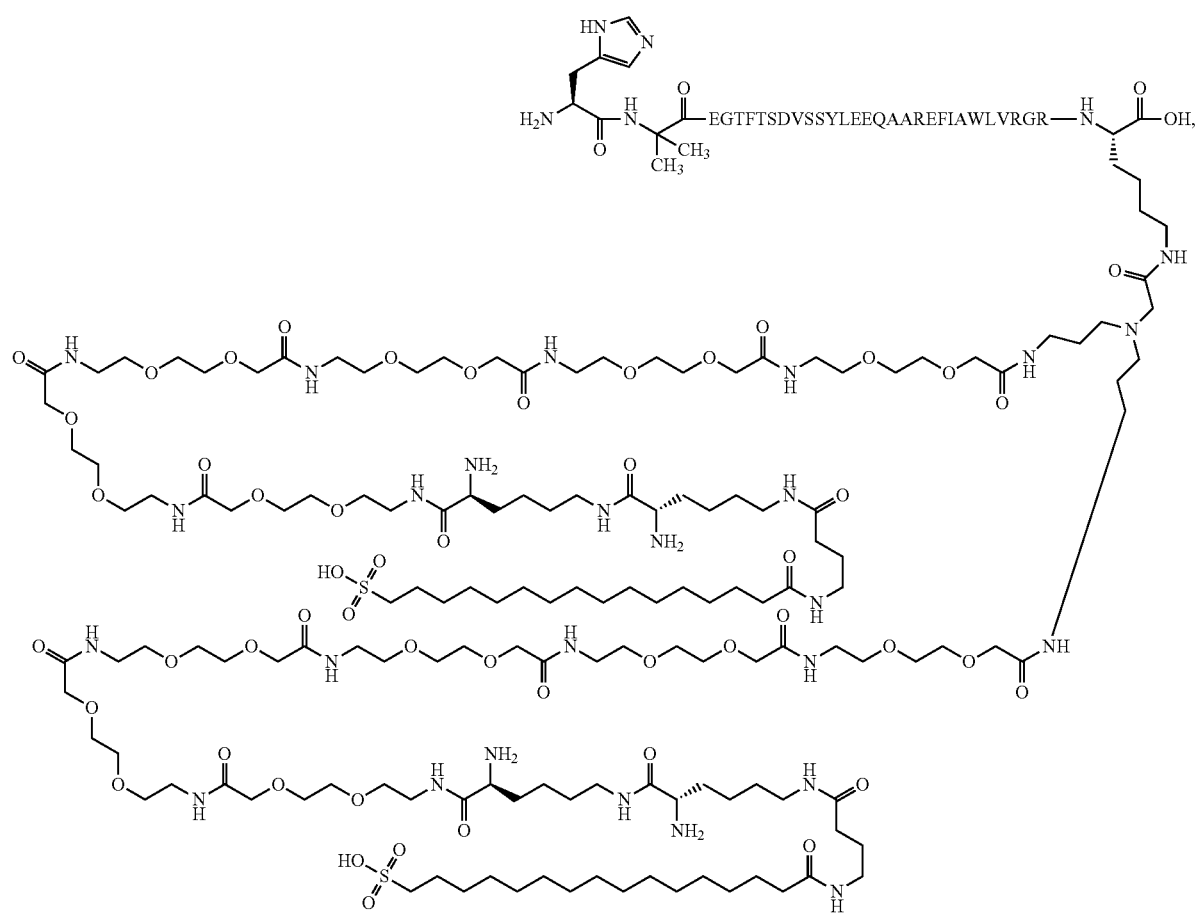

-continued
(SEQ ID NO: 2)
Chem. 36
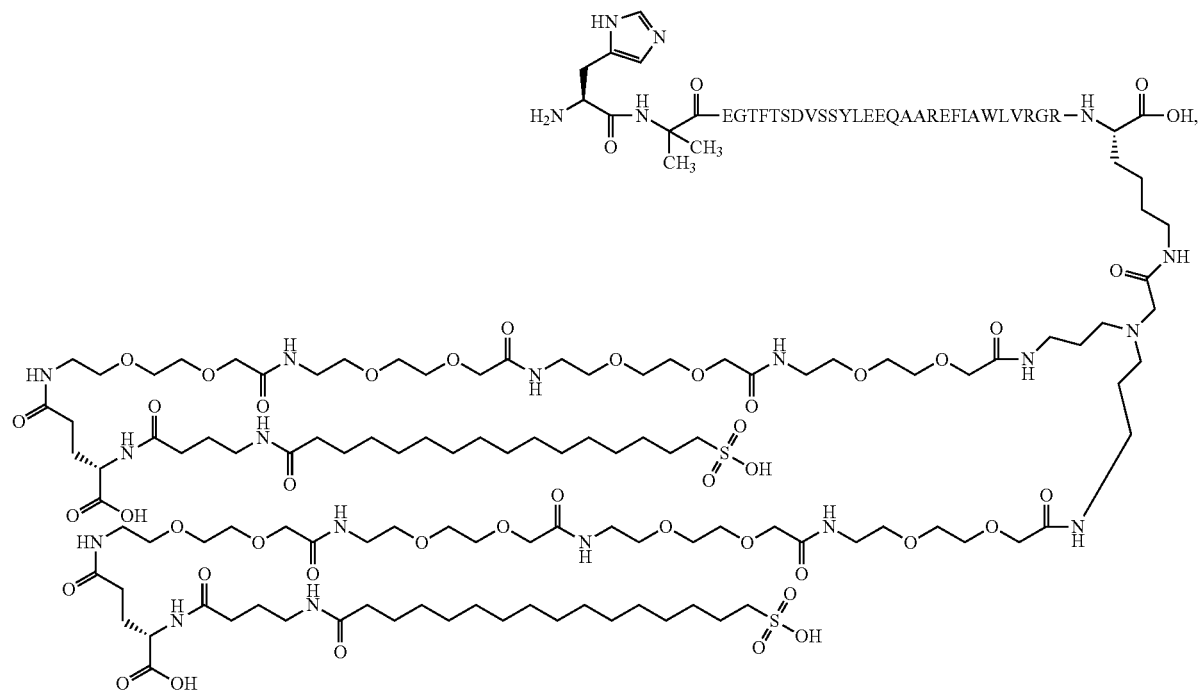
(SEQ NO ID: 2)
Chem. 37
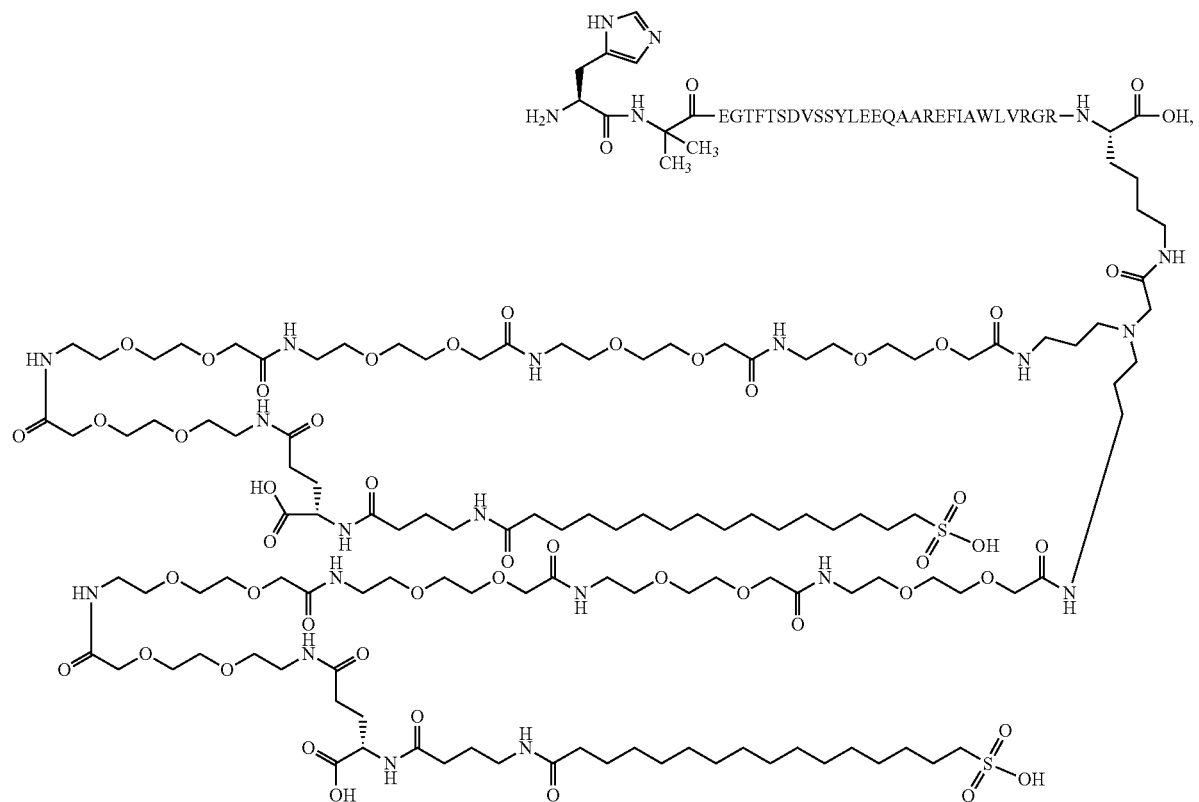

(SEQ NO ID: 2)
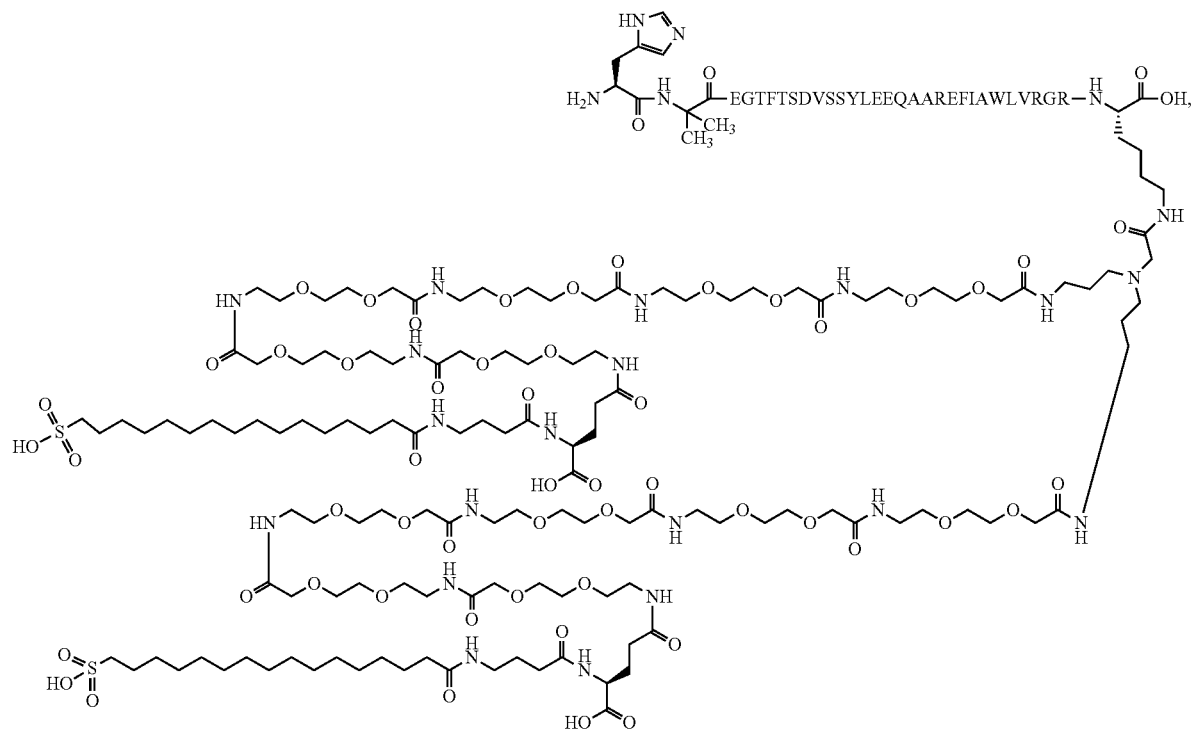
Chem. 38
(SEQ NO ID: 2)
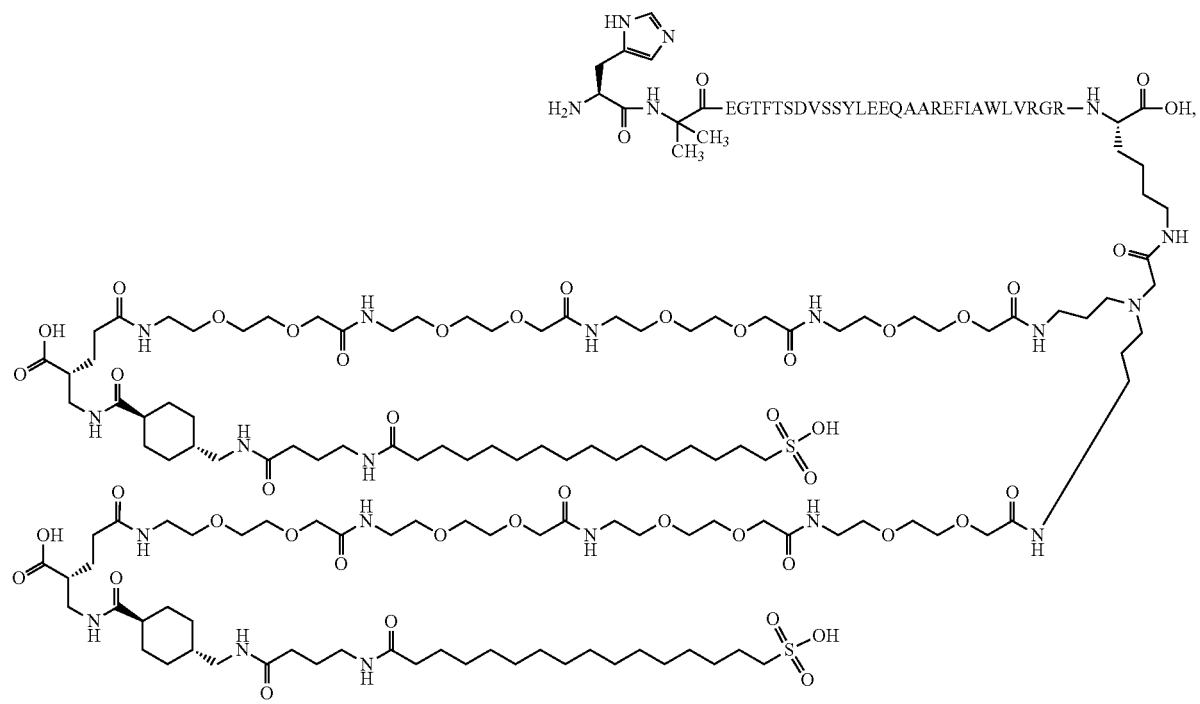
Chem. 39

(SEQ NO ID: 2)
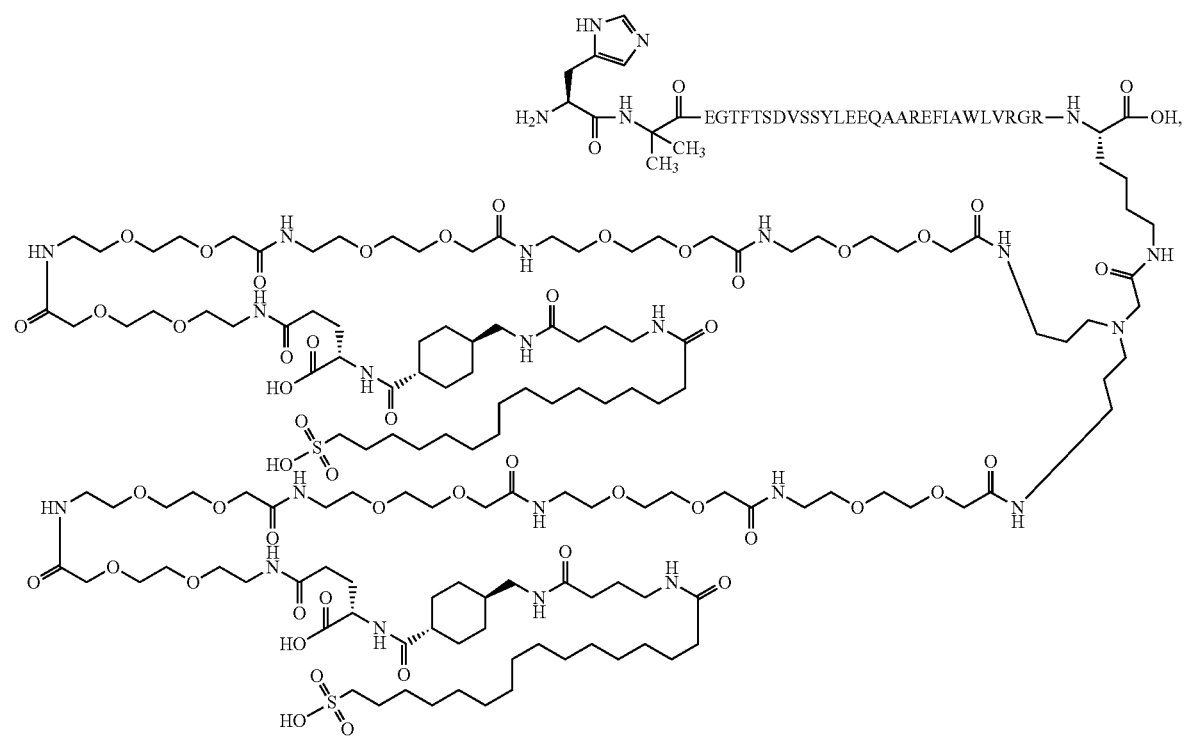
Chem. 40

(SEQ ID NO: 2)
Chem. 41
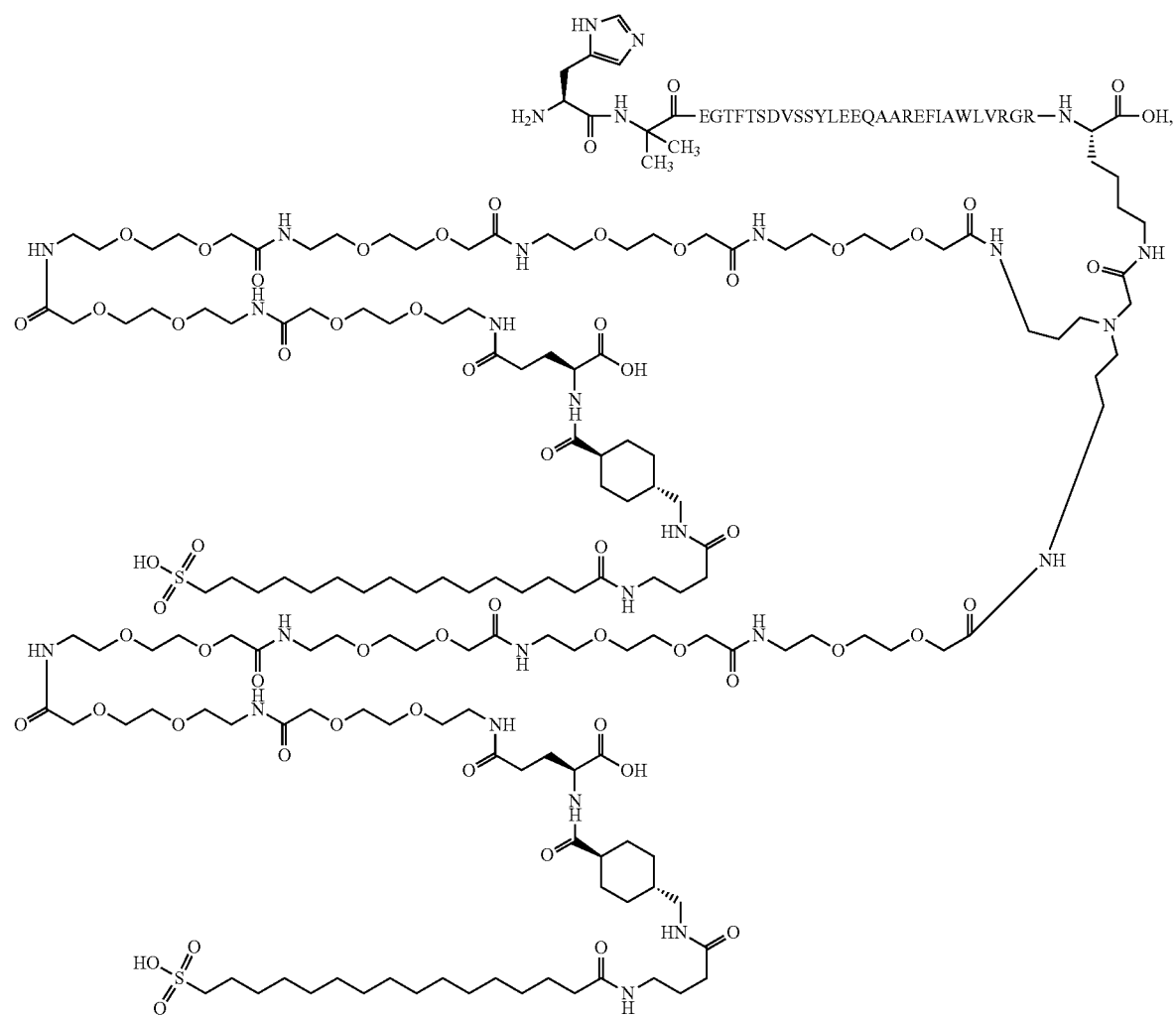

(SEQ ID NO: 2)
Chem. 42
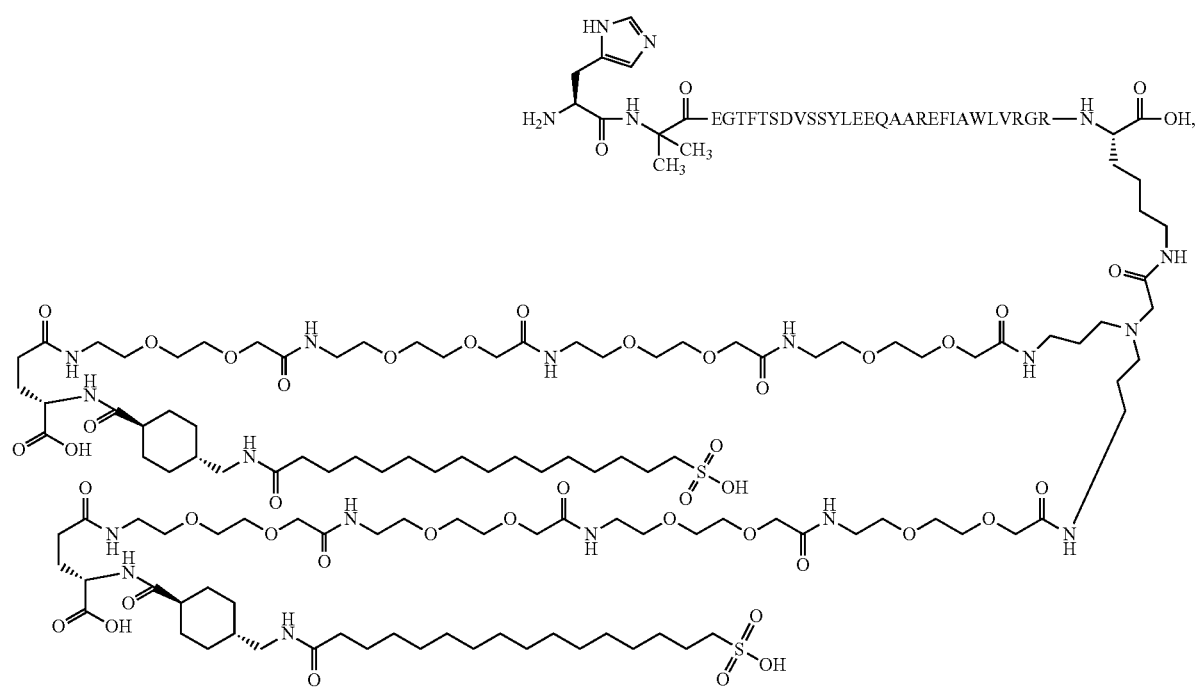

(SEQ NO ID: 2)
Chem. 43
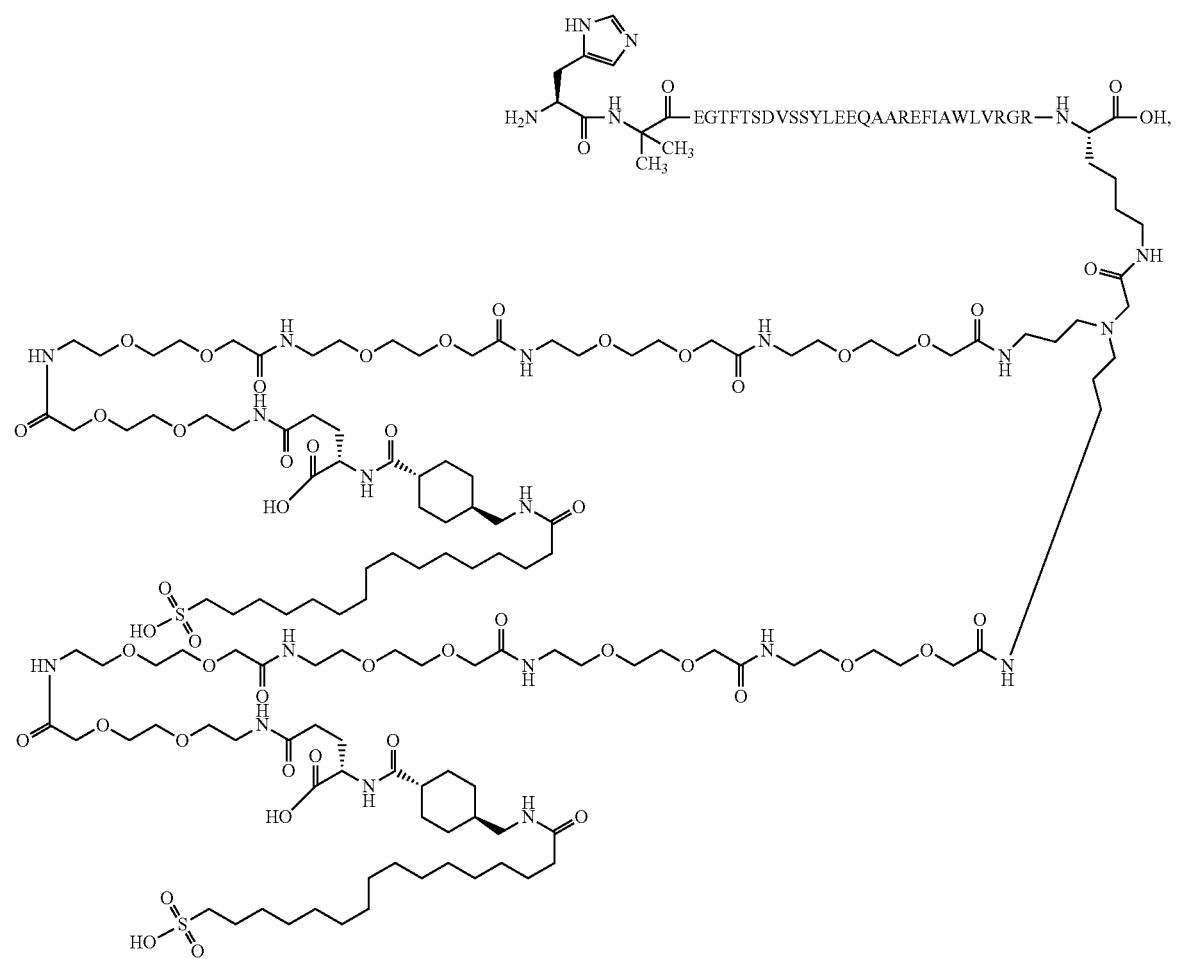

(SEQ ID NO: 2)
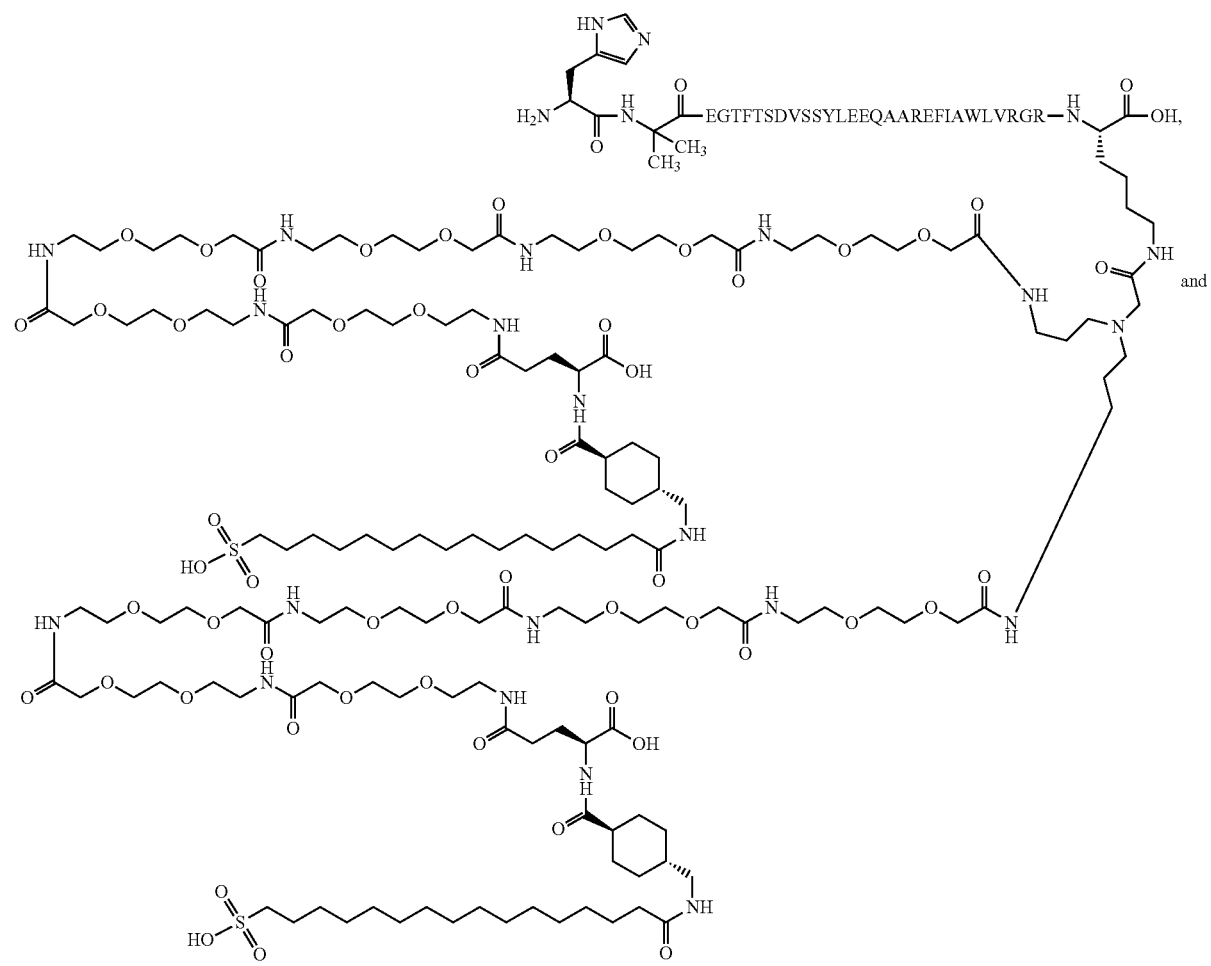
Chem. 44

(SEQ ID NO: 6)
Chem. 48
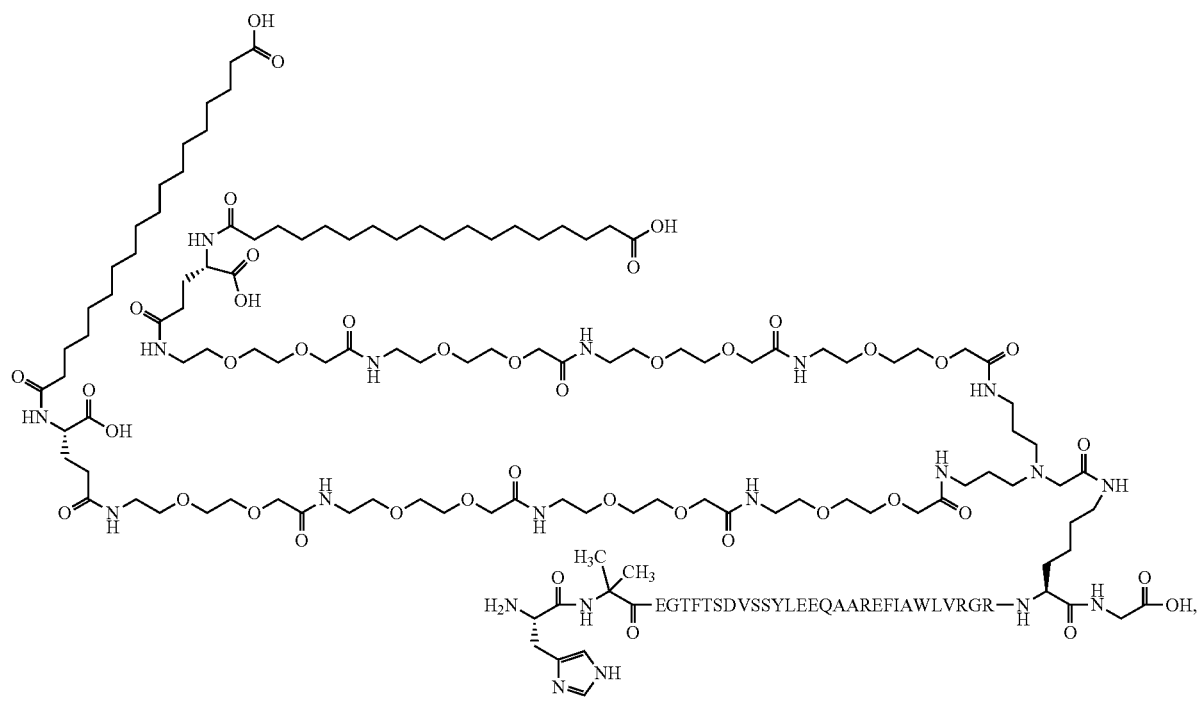
(SEQ ID NO: 6)
or a pharmaceutically acceptable salt, amide, or ester thereof.
2. A method for treating diabetes, said method comprising administering to a subject in need of such treatment a therapeutically effective amount of a pharmaceutical composition according to claim 1.
* * * * *

UNITED STATES PATENT AND TRADEMARK OFFICE
CERTIFICATE OF CORRECTION

| | | |
|---|---|---|
| PATENT NO. | : 11,572,398 B2 | Page 1 of 1 |
| APPLICATION NO. | : 15/531105 | |
| DATED | : February 7, 2023 | |
| INVENTOR(S) | : Sauerberg et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 93 days.

Signed and Sealed this
Seventh Day of January, 2025

Derrick Brent
*Acting Director of the United States Patent and Trademark Office*

SEQUENCE LISTING

<160> NUMBER OF SEQ ID NOS: 9

<210> SEQ ID NO 1
<211> LENGTH: 31
<212> TYPE: PRT
<213> ORGANISM: Homo sapiens

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 2
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 2

His Xaa Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Arg Lys
            20                  25                  30

<210> SEQ ID NO 3
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Imp (3-(Imidazol-5-yl)propanoic acid)
<220> FEATURE:
<221> NAME/KEY: MOD_RES
<222> LOCATION: (2)..(2)
<223> OTHER INFORMATION: Aib

<400> SEQUENCE: 3

Xaa Xaa Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Arg Lys
            20                  25                  30

<210> SEQ ID NO 4
<211> LENGTH: 32
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 4

His Xaa Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Arg Pro Lys
            20                  25                  30

```
<210> SEQ ID NO 5
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (29)..(29)
<223> OTHER INFORMATION: Aib
<220> FEATURE:
<221> NAME/KEY: MOD_RES
<222> LOCATION: (31)..(31)
<223> OTHER INFORMATION: AMIDATION

<400> SEQUENCE: 5

His Xaa Glu Gly Thr Phe Thr Ser Asp Val Ser Ser Tyr Leu Glu Xaa
1               5                   10                  15

Gln Ala Ala Lys Glu Phe Ile Ala Trp Leu Val Lys Xaa Arg Lys
            20                  25                  30

<210> SEQ ID NO 6
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 6

His Xaa Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Lys Gly
            20                  25                  30

<210> SEQ ID NO 7
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 7

His Xaa Glu Gly Thr Phe Thr Ser Asp Val Ser Ser Tyr Leu Glu Glu
1               5                   10                  15

Gln Ala Ala Arg Glu Phe Ile Glu Trp Leu Val Arg Gly Lys Gly
            20                  25                  30

<210> SEQ ID NO 8
<211> LENGTH: 31
<212> TYPE: PRT
<213> ORGANISM: Artificial Sequence
<220> FEATURE:
```

```
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 8

His Xaa Glu Gly Thr Phe Thr Ser Asp Val Ser Ser Tyr Leu Glu Glu
1               5                   10                  15

Gln Ala Ala Arg Glu Phe Ile Ala Trp Leu Val Lys Gly Arg Gly
                20                  25                  30

<210> SEQ ID NO 9
<211> LENGTH: 32
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: L-histidine,
      (S)-2-Hydroxy-3-(1H-imidazol-4-yl)-propionic acid,
      D-histidine, deamino-histidine, homohistidine, N
      alpha-acetyl-histidine, N alpha-formyl-histidine, N
      alpha-methyl-histidine, 3-pyridylalanine, 2-pyridylalanine,
<220> FEATURE:
<221> NAME/KEY: MISC_FEATURE
<222> LOCATION: (1)..(1)
<223> OTHER INFORMATION: or 4-pyridylalanine
<220> FEATURE:
<221> NAME/KEY: MISC_FEATURE
<222> LOCATION: (2)..(2)
<223> OTHER INFORMATION: Ala, Gly, Ser, Aib, (1-aminocyclopropyl)
      carboxylic acid, or (1-aminocyclobutyl) carboxylic acid
<220> FEATURE:
<221> NAME/KEY: MISC_FEATURE
<222> LOCATION: (6)..(6)
<223> OTHER INFORMATION: Phe or Leu
<220> FEATURE:
<221> NAME/KEY: MISC_FEATURE
<222> LOCATION: (10)..(10)
<223> OTHER INFORMATION: Val or Leu
<220> FEATURE:
<221> NAME/KEY: MISC_FEATURE
<222> LOCATION: (12)..(12)
<223> OTHER INFORMATION: Ser, Val, Arg, or Leu
<220> FEATURE:
<221> NAME/KEY: MISC_FEATURE
<222> LOCATION: (13)..(13)
<223> OTHER INFORMATION: Tyr or Gln
<220> FEATURE:
<221> NAME/KEY: MISC_FEATURE
<222> LOCATION: (14)..(14)
<223> OTHER INFORMATION: Leu or Met
```

```
<220> FEATURE:
<221> NAME/KEY: MISC_FEATURE
<222> LOCATION: (16)..(16)
<223> OTHER INFORMATION: Gly or Glu
<220> FEATURE:
<221> NAME/KEY: MISC_FEATURE
<222> LOCATION: (17)..(17)
<223> OTHER INFORMATION: Gln, Glu, or Arg
<220> FEATURE:
<221> NAME/KEY: MISC_FEATURE
<222> LOCATION: (19)..(19)
<223> OTHER INFORMATION: Ala or Val
<220> FEATURE:
<221> NAME/KEY: MISC_FEATURE
<222> LOCATION: (20)..(20)
<223> OTHER INFORMATION: Arg
<220> FEATURE:
<221> NAME/KEY: MISC_FEATURE
<222> LOCATION: (21)..(21)
<223> OTHER INFORMATION: Glu or Leu
<220> FEATURE:
<221> NAME/KEY: MISC_FEATURE
<222> LOCATION: (24)..(24)
<223> OTHER INFORMATION: Ala, Glu, or Arg
<220> FEATURE:
<221> NAME/KEY: MISC_FEATURE
<222> LOCATION: (25)..(25)
<223> OTHER INFORMATION: Trp or His
<220> FEATURE:
<221> NAME/KEY: MISC_FEATURE
<222> LOCATION: (27)..(27)
<223> OTHER INFORMATION: Val
<220> FEATURE:
<221> NAME/KEY: MISC_FEATURE
<222> LOCATION: (28)..(28)
<223> OTHER INFORMATION: Arg, His, Asn, Gln, or Lys
<220> FEATURE:
<221> NAME/KEY: MISC_FEATURE
<222> LOCATION: (29)..(29)
<223> OTHER INFORMATION: Gly, Ala, or Lys
<220> FEATURE:
<221> NAME/KEY: MISC_FEATURE
<222> LOCATION: (30)..(30)
<223> OTHER INFORMATION: Arg, Gly, or Lys
<220> FEATURE:
<221> NAME/KEY: MISC_FEATURE
<222> LOCATION: (31)..(31)
<223> OTHER INFORMATION: Gly, Pro, or Lys
<220> FEATURE:
<221> NAME/KEY: MISC_FEATURE
<222> LOCATION: (32)..(32)
<223> OTHER INFORMATION: Lys, or absent

<400> SEQUENCE: 9

Xaa Xaa Glu Gly Thr Xaa Thr Ser Asp Xaa Ser Xaa Xaa Xaa Glu Xaa
1               5                   10                  15

Xaa Ala Xaa Xaa Xaa Phe Ile Xaa Xaa Leu Xaa Xaa Xaa Xaa Xaa Xaa
            20                  25                  30
```